US009833497B2

(12) United States Patent
Song et al.

(10) Patent No.: US 9,833,497 B2
(45) Date of Patent: Dec. 5, 2017

(54) HUMAN ORIGINATED EGF DOMAIN PROTEINS AND USE OF THE SAME

(71) Applicant: CHENGDU SOURCEBIO LIMITED-LIABILITY COMPANY, Chengdu (CN)

(72) Inventors: Xu Song, Sichuan (CN); Ling Li, Sichuan (CN); Jinwu Chen, Sichuan (CN); Deng Jiao Ma, Sichuan (CN)

(73) Assignee: Chengdu Sourcebio Limited-Liability Company, Chengdu (CN)

( * ) Notice: Subject to any disclaimer, the term of this patent is extended or adjusted under 35 U.S.C. 154(b) by 0 days.

(21) Appl. No.: 14/894,417

(22) PCT Filed: May 19, 2014

(86) PCT No.: PCT/CN2014/077789
§ 371 (c)(1),
(2) Date: Nov. 27, 2015

(87) PCT Pub. No.: WO2014/190860
PCT Pub. Date: Dec. 4, 2014

(65) Prior Publication Data
US 2016/0184396 A1 Jun. 30, 2016

(30) Foreign Application Priority Data

May 29, 2013 (CN) .......................... 2013 1 0206726
Apr. 30, 2014 (CN) .......................... 2014 1 0182727

(51) Int. Cl.
| | |
|---|---|
| A61K 38/36 | (2006.01) |
| C07K 14/00 | (2006.01) |
| A61K 38/18 | (2006.01) |
| C07K 14/485 | (2006.01) |

(52) U.S. Cl.
CPC .......... *A61K 38/1808* (2013.01); *A61K 38/36* (2013.01); *C07K 14/485* (2013.01)

(58) Field of Classification Search
CPC ... A61K 38/1808; A61K 38/36; C07K 14/485
USPC .......... 514/2.8, 9.6; 435/252.1, 252.8, 253.3
See application file for complete search history.

(56) References Cited

U.S. PATENT DOCUMENTS

| | | | | |
|---|---|---|---|---|
| 2006/0234935 | A1* | 10/2006 | Blajchman | ....... C12Y 304/2102 514/14.3 |
| 2013/0202596 | A1* | 8/2013 | Salas | .................... C07K 14/745 424/134.1 |

FOREIGN PATENT DOCUMENTS

WO 2004108763 A2 12/2004

OTHER PUBLICATIONS

Gram Negative Bacteria from Merck Manual, pp. 1-4. Accessed Dec. 8, 2016.*
Introduction to Gram-negative Bacilli from Merck Manual, p. 1. Accessed Dec. 8, 2016.*
*Escherichia coli* Infections from Merck Manual, pp. 1-3. Accessed Dec. 8, 2016.*
Gram-negative Bacteria from www.niaid.nih.gov/research/gram-negative-bacteria. pp. 1-2. Accessed Dec. 8, 2016.*
Zhang et al., "Capability of the First Epidermal Growth Factor Domain of Rat Coagulation Factor VII in Vitro", Chinese Journal of Thrombosis and Hemostasis, 2007, vol. 12, No. 4, pp. 148-151.
Mei et al., "Binding of EGF1 Domain Peptide in Coagulation Factor VII with Tissue Factor and Its Implications for the Triggering of Coagulation", J Huazhong Univ Sci Technol 30(1), 2010, pp. 42-47.

\* cited by examiner

*Primary Examiner* — Julie Ha
(74) *Attorney, Agent, or Firm* — Calfee, Halter & Griswold LLP

(57) ABSTRACT

In the invention, the minimum inhibitory concentrations of human-originated EGF domain proteins against different Gram-negative bacteria are detected with the in vitro antibacterial activity. It has been shown that the human-originated EGF domain proteins have an obvious inhibitory effect on the Gram-negative bacteria, so as to develop a novel class of medicaments for treating Gram-negative bacteria infection. It has been demonstrated by silver staining that the human-originated EGF domain proteins have the effect on hydrolyzing and eliminating the endotoxin, which facilitates the development of a novel class of medicaments for treating endotoxemia. The amino acid sequences of the human-originated EGF domain proteins are the one described in SEQ ID NO: 1 in the sequence listing, or those having homology of over 50% to the amino acid sequence described in SEQ ID NO: 1.

18 Claims, 10 Drawing Sheets

HUMAN ORIGINATED EGF DOMAIN PROTEINS AND USE OF THE SAME

CROSS REFERENCE TO RELATED APPLICATIONS

This application is the U.S. national phase entry of PCT/CN2014/077789, with an international filing date of May 19, 2014, which claims priority to and any benefit of Chinese Patent Application No. 201310206726.6 filed May 29, 2013, and Chinese Patent Application No. 201410182727.6 filed Apr. 30, 2014, the entire contents of which are incorporated by reference in their entirety.

TECHNICAL FIELD

The present invention belongs to biomedical field, and especially relates to human-originated EGF domain proteins and use thereof in the pharmaceutical industry.

BACKGROUND

Gram-negative bacteria refer broadly to the bacteria which are stained in red in Gram's staining reaction, and they are different from the Gram-positive bacteria during the Gram's staining due to the difference in the structure of the cell wall (the positive bacteria being stained in violet). The Gram-negative bacteria are represented by *Escherichia coli*, as well as *Proteus, Shigella dysenteriae, Klebsiella pneumoniae, Brucella bacilli, Haemophilus influenzae, Haemophilus parainfluenzae, Moraxella catarrhalis, Acinetobacter* and so on. Pathogenicity of such bacteria is often associated with a particular component in their cell-walls, lipopolysaccharide (also known as endotoxin). In human's body, lipopolysaccharide will induce the body to produce a large amount of cytokines and to activate the immune system, eventually evoking innate immune responses against the pathogenic bacteria within the body. For instance, redness and swelling are the results of generation and release of a large amount of cytokines.

In addition to eliminating the focus of infection and a symptomatic and supportive treatment, antibiotics also need to be used during the treatment of a Gram-negative bacteria infection. At present, the antibiotics mainly used are aminoglycosides, beta-lactams, etc. These antibiotics have potent bactericidal effects on various Gram-negative bacteria, and moreover exhibit longer post-antibiotic effects on the common Gram-negative bacilli such as *Pseudomonas aeruginosa, Klebsiella pneumonia*, and *E. coli*. In addition to the antibiotics, the agents such as prostaglandin synthetase inhibitor, levamisole, and tuftsin are also useful in treatment of the Gram-negative bacteria infection. However, with the extensive application of antibiotics, the abuse of antibiotics in clinical medicine results in progression of the drug resistance of bacteria from single drug resistance into multi drug resistance, thus making many second-line antibiotics which would have been used effectively as alternatives ineffective. Secondly, the antibacterial drug may induce the generation of endotoxin while killing/inhibiting the bacteria, which increases the difficulty of treating the disease. Thus, while novel antibiotics with potent killing effect come out continuously and advanced supportive therapies occurs, treatment of the endotoxemia caused by Gram's negative bacteria infection is still a challenge in the clinical scenario, particularly with an unacceptable mortality rate of 20-30%. It has been reported that lipopolysaccharide is the major pathogenic factor which leads to a series of toxicity reaction occurring post the Gram-negative bacteria infection. Although antibiotics have a better effect of eliminating the bacteria, they have no effect on the lipopolysaccharide free in the blood and a wide variety of detrimental cytokines produced by target cells which are persistently stimulated with the free lipopolysaccharide. Therefore, when choosing an antibacterial drug clinically, a comprehensive consideration should be taken for the result of drug sensitive test and the feature of inducing release of the endotoxin. Thirdly, since lipopolysaccharide is located on the surface of the cell wall of Gram-negative bacteria, many early types of antibiotics are unable to inhibit such bacteria effectively. Based on these reasons, novel fields are being explored actively in treating Gram-negative bacteria infection in the recent years.

Antimicrobial peptides (AMPs) refer to short peptides having antibacterial activities, most of which have thermal stability, high alkalincity and broad-spectrum anti-bacterial activities. Currently, about more than or equal to 2000 of AMPs have already been identified from various organisms. These AMPs are synthesized after induction, play an important key role in an organism's resistance against the invasion of a pathogen, and are considered an important defensive constituent for the non-specific immunological function in an organism. Accordingly, it becomes a hot spot and a challenge to find out novel APMs against Gram-negative bacteria.

The EGF domain (the EGF-like domain, epidermal growth factor-like domain) is protein domains which is relatively conserved in evolution and has been designated due to first identification of the domain in epidermal growth factor. The EGF domain usually comprises 30-50 amino acid residues and has been currently identified in many animal proteins. E.g. human coagulation factor VII (human factor VII, hF VII). hF VII is a naturally-occurring protein in the human's body with molecular weight of about 50 kD. The molecule thereof comprises four domains: a membrane-bound N-terminal γ-carboxyglutamic acid domain (Gla domain), two EGF domains (EGF1 and EGF2), and a C-terminal serine protease domain. The human coagulation factor VII-EGF1 domain (hF VII-EGF1) has a molecular weight of about 3.9 kD. In human origin, there are also many analogues with the sequences similar to that of hF VII-EGF1, such as human-originated coagulation factor VII-EGF2 protein (hF VII-EGF2), human-originated coagulation factor IX-EGF1 protein (hF IX-EGF1), human-originated coagulation factor IX-EGF2 protein (hF IX-EGF2), human-originated coagulation factor X-EGF1 protein (hF X-EGF1), human-originated coagulation factor X-EGF2 protein (hF X-EGF2), etc. Up to now, there is no relevant report on treatment of a bacteria infection with a human-originated EGF domain protein as the antibacterial agent and no report on preparation of a medicament for treating endotoxemia caused by a Gram-negative bacterium.

SUMMARY OF THE INVENTION

One of the objectives of the present invention is to provide artificially-prepared human-originated EGF domain proteins. Another objective of the present invention is to prove that the human-originated EGF domain proteins have an inhibitory effect on the Gram-negative bacteria and that the human-originated EGF domain proteins can hydrolyze and thus eliminate endotoxin, so as to develop a novel class of medicaments for treating Gram-negative bacteria infection and medicaments for treating endotoxemia caused by the Gram-negative bacteria.

The human-originated EGF domain protein set forth in the present invention has the amino acid sequence described in SEQ ID NO: 1 in the sequence listing, or is the protein having homology of over 50% to the amino acid sequence described in SEQ ID NO: 1. The protein having homology of over 50% to the amino acid sequence of the protein described in SEQ ID NO: 1 has any of the amino acid sequences described in SEQ ID NO: 2 to SEQ ID NO: 1498 in the sequence listing.

The human-originated EGF domain proteins set forth in the present invention are designated as shown in Table 1.

TABLE 1

Designation of the human-originated EGF domain proteins set forth in the present invention

| No. in the sequence listing | Designation | Code in the invention |
|---|---|---|
| SEQ ID NO: 1 | human coagulation factor VII-EGF1 domain protein (hF VII-EGF1 protein) | PRT1 |
| SEQ ID NO: 2 | human coagulation factor VII-EGF2 domain protein (hF VII-EGF2 protein) | PRT2 |
| SEQ ID NO: 3 | human coagulation factor IX-EGF1 domain protein (hF IX-EGF1 protein) | PRT3 |
| SEQ ID NO: 4 | human coagulation factor IX-EGF2 domain protein (hF IX-EGF2 protein) | PRT4 |
| SEQ ID NO: 5 | human coagulation factor X-EGF1 domain protein (hF X-EGF1 protein) | PRT5 |
| SEQ ID NO: 6 | human coagulation factor X-EGF2 domain protein (hF X-EGF2 protein) | PRT6 |
| SEQ ID NO: 7 | human ADAM metallopeptidase domain 22-EGF1 protein | PRT7 |
| SEQ ID NO: 8 | human ADAM metallopeptidase domain 30-EGF1 protein | PRT8 |
| SEQ ID NO: 9 | human ADAM metallopeptidase domain 33, isoform CRA_g-EGF1 protein | PRT9 |
| SEQ ID NO: 10 | human ADAM8 protein-EGF1 protein | PRT10 |
| SEQ ID NO: 11 | human ADAM9 protein-EGF1 protein | PRT11 |
| SEQ ID NO: 12 | human ADAM9 protein-EGF2 protein | PRT12 |
| SEQ ID NO: 13 | human Aggrecan core protein-EGF1 protein | PRT13 |
| SEQ ID NO: 14 | human Agrin-EGF1 protein | PRT14 |
| SEQ ID NO: 15 | human Agrin-EGF2 protein | PRT15 |
| SEQ ID NO: 16 | human Agrin-EGF3 protein | PRT16 |
| SEQ ID NO: 17 | human Agrin-EGF4 protein | PRT17 |
| SEQ ID NO: 18 | human Agrin-EGF5 protein | PRT18 |
| SEQ ID NO: 19 | human Agrin-EGF6 protein | PRT19 |
| SEQ ID NO: 20 | human All-trans retinoic acid-induced differentiation factor-EGF1 protein | PRT20 |
| SEQ ID NO: 21 | human Alpha-tectorin-EGF1 protein | PRT21 |
| SEQ ID NO: 22 | human Alpha-tectorin-EGF2 protein | PRT22 |
| SEQ ID NO: 23 | human Amphiregulin-EGF1 protein | PRT23 |
| SEQ ID NO: 24 | human Anchor protein-EGF1 protein | PRT24 |
| SEQ ID NO: 25 | human Anchor protein-EGF2 protein | PRT25 |
| SEQ ID NO: 26 | human Anchor protein-EGF3 protein | PRT26 |
| SEQ ID NO: 27 | human Anchor protein-EGF4 protein | PRT27 |
| SEQ ID NO: 28 | human Anchor protein-EGF5 protein | PRT28 |
| SEQ ID NO: 29 | human Anchor protein-EGF6 protein | PRT29 |
| SEQ ID NO: 30 | human Anchor protein-EGF7 protein | PRT30 |
| SEQ ID NO: 31 | human Anchor protein-EGF8 protein | PRT31 |
| SEQ ID NO: 32 | human Angiopoietin-1 receptor-EGF1 protein | PRT32 |
| SEQ ID NO: 33 | human Angiopoietin-1 receptor-EGF2 protein | PRT33 |
| SEQ ID NO: 34 | human Angiopoietin-1 receptor-EGF3 protein | PRT34 |
| SEQ ID NO: 35 | human Astrotactin-1-EGF1 protein | PRT35 |
| SEQ ID NO: 36 | human Astrotactin-1-EGF2 protein | PRT36 |
| SEQ ID NO: 37 | human Astrotactin-1-EGF3 protein | PRT37 |
| SEQ ID NO: 38 | human Astrotactin-2-EGF1 protein | PRT38 |
| SEQ ID NO: 39 | human Astrotactin-2-EGF2 protein | PRT39 |
| SEQ ID NO: 40 | human Astrotactin-2-EGF3 protein | PRT40 |
| SEQ ID NO: 41 | human Attractin-EGF1 protein | PRT41 |
| SEQ ID NO: 42 | human Attractin-EGF2 protein | PRT42 |
| SEQ ID NO: 43 | human Attractin-EGF3 protein | PRT43 |
| SEQ ID NO: 44 | human Attractin-like protein 1-EGF1 protein | PRT44 |
| SEQ ID NO: 45 | human Attractin-like protein 1-EGF2 protein | PRT45 |
| SEQ ID NO: 46 | human Attractin-like protein 1-EGF3 protein | PRT46 |
| SEQ ID NO: 47 | human Attractin-like protein 1-EGF4 protein | PRT47 |
| SEQ ID NO: 48 | human Basement membrane-specific heparan sulfate proteoglycan core protein-EGF1 protein | PRT48 |
| SEQ ID NO: 49 | human Basement membrane-specific heparan sulfate proteoglycan core protein-EGF2 protein | PRT49 |
| SEQ ID NO: 50 | human Basement membrane-specific heparan sulfate proteoglycan core protein-EGF9 protein | PRT50 |
| SEQ ID NO: 51 | human Basement membrane-specific heparan sulfate proteoglycan core protein-EGF10 protein | PRT51 |
| SEQ ID NO: 52 | human Basement membrane-specific heparan sulfate proteoglycan core protein-EGF3 protein | PRT52 |

TABLE 1-continued

Designation of the human-originated EGF domain proteins set forth in the present invention

| No. in the sequence listing | Designation | Code in the invention |
|---|---|---|
| SEQ ID NO: 53 | human Basement membrane-specific heparan sulfate proteoglycan core protein-EGF4 protein | PRT53 |
| SEQ ID NO: 54 | human Basement membrane-specific heparan sulfate proteoglycan core protein-EGF5 protein | PRT54 |
| SEQ ID NO: 55 | human Basement membrane-specific heparan sulfate proteoglycan core protein-EGF6 protein | PRT55 |
| SEQ ID NO: 56 | human Basement membrane-specific heparan sulfate proteoglycan core protein-EGF7 protein | PRT56 |
| SEQ ID NO: 57 | human Basement membrane-specific heparan sulfate proteoglycan core protein-EGF8 protein | PRT57 |
| SEQ ID NO: 58 | human BMP/retinoic acid-inducible neural-specific protein 2-EGF1 protein | PRT58 |
| SEQ ID NO: 59 | human BMP/retinoic acid-inducible neural-specific protein 3-EGF1 protein | PRT59 |
| SEQ ID NO: 60 | human Bone morphogenetic protein 1-EGF1 protein | PRT60 |
| SEQ ID NO: 61 | human Bone morphogenetic protein 1-EGF2 protein | PRT61 |
| SEQ ID NO: 62 | human Brevican core protein-EGF1 protein | PRT62 |
| SEQ ID NO: 63 | human C1q receptor protein-EGF1 protein | PRT63 |
| SEQ ID NO: 64 | human C1q receptor protein-EGF2 protein | PRT64 |
| SEQ ID NO: 65 | human C5R protein-EGF1 protein | PRT65 |
| SEQ ID NO: 66 | human Cadherin EGF LAG seven-pass G-type receptor 1-EGF1 protein | PRT66 |
| SEQ ID NO: 67 | human Cadherin EGF LAG seven-pass G-type receptor 1-EGF2 protein | PRT67 |
| SEQ ID NO: 68 | human Cadherin EGF LAG seven-pass G-type receptor 1-EGF3 protein | PRT68 |
| SEQ ID NO: 69 | human Cadherin EGF LAG seven-pass G-type receptor 1-EGF4 protein | PRT69 |
| SEQ ID NO: 70 | human Cadherin EGF LAG seven-pass G-type receptor 1-EGF5 protein | PRT70 |
| SEQ ID NO: 71 | human Cadherin EGF LAG seven-pass G-type receptor 1-EGF6 protein | PRT71 |
| SEQ ID NO: 72 | human Cadherin EGF LAG seven-pass G-type receptor 1-EGF7 protein | PRT72 |
| SEQ ID NO: 73 | human Cadherin EGF LAG seven-pass G-type receptor 1-EGF8 protein | PRT73 |
| SEQ ID NO: 74 | human Cadherin EGF LAG seven-pass G-type receptor 1-EGF9 protein | PRT74 |
| SEQ ID NO: 75 | human Cadherin EGF LAG seven-pass G-type receptor 2-EGF1 protein | PRT75 |
| SEQ ID NO: 76 | human Cadherin EGF LAG seven-pass G-type receptor 2-EGF2 protein | PRT76 |
| SEQ ID NO: 77 | human Cadherin EGF LAG seven-pass G-type receptor 2-EGF3 protein | PRT77 |
| SEQ ID NO: 78 | human Cadherin EGF LAG seven-pass G-type receptor 2-EGF4 protein | PRT78 |
| SEQ ID NO: 79 | human Cadherin EGF LAG seven-pass G-type receptor 2-EGF5 protein | PRT79 |
| SEQ ID NO: 80 | human Cadherin EGF LAG seven-pass G-type receptor 2-EGF6 protein | PRT80 |
| SEQ ID NO: 81 | human Cadherin EGF LAG seven-pass G-type receptor 2-EGF7 protein | PRT81 |
| SEQ ID NO: 82 | human Cadherin EGF LAG seven-pass G-type receptor 2-EGF8 protein | PRT82 |
| SEQ ID NO: 83 | human Cadherin EGF LAG seven-pass G-type receptor 3-EGF1 protein | PRT83 |
| SEQ ID NO: 84 | human Cadherin EGF LAG seven-pass G-type receptor 3-EGF2 protein | PRT84 |
| SEQ ID NO: 85 | human Cadherin EGF LAG seven-pass G-type receptor 3-EGF3 protein | PRT85 |
| SEQ ID NO: 86 | human Cadherin EGF LAG seven-pass G-type receptor 3-EGF4 protein | PRT86 |
| SEQ ID NO: 87 | human Cadherin EGF LAG seven-pass G-type receptor 3-EGF5 protein | PRT87 |
| SEQ ID NO: 88 | human Cadherin EGF LAG seven-pass G-type receptor 3-EGF6 protein | PRT88 |
| SEQ ID NO: 89 | human Cadherin EGF LAG seven-pass G-type receptor 3-EGF7 protein | PRT89 |
| SEQ ID NO: 90 | human Cadherin EGF LAG seven-pass G-type receptor 3-EGF8 protein | PRT90 |
| SEQ ID NO: 91 | human Cartilage acidic protein 1-EGF1 protein | PRT91 |
| SEQ ID NO: 92 | human Cartilage matrix protein-EGF1 protein | PRT92 |
| SEQ ID NO: 93 | human Cartilage oligomeric matrix protein-EGF1 protein | PRT93 |
| SEQ ID NO: 94 | human Cartilage oligomeric matrix protein-EGF2 protein | PRT94 |
| SEQ ID NO: 95 | human Cartilage oligomeric matrix protein-EGF3 protein | PRT95 |

TABLE 1-continued

Designation of the human-originated EGF domain proteins set forth in the present invention

| No. in the sequence listing | Designation | Code in the invention |
|---|---|---|
| SEQ ID NO: 96 | human Cartilage oligomeric matrix protein-EGF4 protein | PRT96 |
| SEQ ID NO: 97 | human CD97 antigen-EGF1 protein | PRT97 |
| SEQ ID NO: 98 | human CD97 antigen-EGF2 protein | PRT98 |
| SEQ ID NO: 99 | human CD97 antigen-EGF3 protein | PRT99 |
| SEQ ID NO: 100 | human CD97 antigen-EGF4 protein | PRT100 |
| SEQ ID NO: 101 | human CD97 antigen-EGF5 protein | PRT101 |
| SEQ ID NO: 102 | human Cell recognition protein CASPR4-EGF1 protein | PRT102 |
| SEQ ID NO: 103 | human Cell recognition protein CASPR4-EGF2 protein | PRT103 |
| SEQ ID NO: 104 | human Chondroitin sulfate proteoglycan 2 (Versican) variant-EGF1 protein | PRT104 |
| SEQ ID NO: 105 | human Chondroitin sulfate proteoglycan 2 (Versican) variant-EGF2 protein | PRT105 |
| SEQ ID NO: 106 | human Chondroitin sulfate proteoglycan 5-EGF1 protein | PRT106 |
| SEQ ID NO: 107 | human CNTNAP3 protein-EGF1 protein | PRT107 |
| SEQ ID NO: 108 | human Coagulation factor XII-EGF1 protein | PRT108 |
| SEQ ID NO: 109 | human Coagulation factor XII-EGF2 protein | PRT109 |
| SEQ ID NO: 110 | human Collagen and calcium-binding EGF domain-containing protein 1-EGF1 protein | PRT110 |
| SEQ ID NO: 111 | human Complement C1r subcomponent-EGF1 protein | PRT111 |
| SEQ ID NO: 112 | human Complement C1s subcomponent-EGF1 protein | PRT112 |
| SEQ ID NO: 113 | human Complement component 1, r subcomponent, isoform CRA_a-EGF1 protein | PRT113 |
| SEQ ID NO: 114 | human Complement component C1q receptor-EGF1 protein | PRT114 |
| SEQ ID NO: 115 | human Complement component C1q receptor-EGF2 protein | PRT115 |
| SEQ ID NO: 116 | human Complement component C1q receptor-EGF3 protein | PRT116 |
| SEQ ID NO: 117 | human Complement component C1q receptor-EGF4 protein | PRT117 |
| SEQ ID NO: 118 | human Complement component C1q receptor-EGF5 protein | PRT118 |
| SEQ ID NO: 119 | human Complement component C6-EGF1 protein | PRT119 |
| SEQ ID NO: 120 | human Complement component C7-EGF1 protein | PRT120 |
| SEQ ID NO: 121 | human Complement component C8 alpha chain-EGF1 protein | PRT121 |
| SEQ ID NO: 122 | human Complement component C8 beta chain-EGF1 protein | PRT122 |
| SEQ ID NO: 123 | human Complement component C9-EGF1 protein | PRT123 |
| SEQ ID NO: 124 | human Contactin-associated protein 1-EGF1 protein | PRT124 |
| SEQ ID NO: 125 | human Contactin-associated protein 1-EGF2 protein | PRT125 |
| SEQ ID NO: 126 | human Contactin-associated protein-like 2-EGF1 protein | PRT126 |
| SEQ ID NO: 127 | human Contactin-associated protein-like 2-EGF2 protein | PRT127 |
| SEQ ID NO: 128 | human Contactin-associated protein-like 3-EGF1 protein | PRT128 |
| SEQ ID NO: 129 | human Contactin-associated protein-like 3-EGF2 protein | PRT129 |
| SEQ ID NO: 130 | human Contactin-associated protein-like 3B-EGF1 protein | PRT130 |
| SEQ ID NO: 131 | human Contactin-associated protein-like 3B-EGF2 protein | PRT131 |
| SEQ ID NO: 132 | human Contactin-associated protein-like 4-EGF1 protein | PRT132 |
| SEQ ID NO: 133 | human Contactin-associated protein-like 4-EGF2 protein | PRT133 |
| SEQ ID NO: 134 | human Contactin-associated protein-like 5-EGF1 protein | PRT134 |
| SEQ ID NO: 135 | human Contactin-associated protein-like 5-EGF2 protein | PRT135 |
| SEQ ID NO: 136 | human CPXV021 protein-EGF1 protein | PRT136 |
| SEQ ID NO: 137 | human Crumbs homolog 1 isoform II variant-EGF1 protein | PRT137 |
| SEQ ID NO: 138 | human Crumbs homolog 1 isoform II variant-EGF2 protein | PRT138 |
| SEQ ID NO: 139 | human Cryptic family protein 1B-EGF1 protein | PRT139 |
| SEQ ID NO: 140 | human Cryptic protein-EGF1 protein | PRT140 |
| SEQ ID NO: 141 | human CSPG3 variant protein-EGF1 protein | PRT141 |
| SEQ ID NO: 142 | human C-type lectin domain family 14 member A-EGF1 protein | PRT142 |
| SEQ ID NO: 143 | human C-type lectin domain family 18 member A-EGF1 protein | PRT143 |
| SEQ ID NO: 144 | human Cubilin-EGF1 protein | PRT144 |
| SEQ ID NO: 145 | human Cubilin-EGF2 protein | PRT145 |
| SEQ ID NO: 146 | human Cubilin-EGF3 protein | PRT146 |
| SEQ ID NO: 147 | human Cubilin-EGF4 protein | PRT147 |
| SEQ ID NO: 148 | human Cubilin-EGF5 protein | PRT148 |
| SEQ ID NO: 149 | human Cubilin-EGF6 protein | PRT149 |
| SEQ ID NO: 150 | human Cubilin-EGF7 protein | PRT150 |
| SEQ ID NO: 151 | human Cyritestin 2-EGF1 protein | PRT151 |
| SEQ ID NO: 152 | human Cysteine-rich with EGF-like domain protein 1-EGF1 protein | PRT152 |
| SEQ ID NO: 153 | human Cysteine-rich with EGF-like domain protein 2-EGF1 protein | PRT153 |
| SEQ ID NO: 154 | human Cysteine-rich with EGF-like domain protein 2-EGF2 protein | PRT154 |
| SEQ ID NO: 155 | human Delta and Notch-like epidermal growth factor-related-EGF1 protein | PRT155 |
| SEQ ID NO: 156 | human Delta and Notch-like epidermal growth factor-related-EGF10 protein | PRT156 |
| SEQ ID NO: 157 | human Delta and Notch-like epidermal growth factor-related-EGF2 protein | PRT157 |
| SEQ ID NO: 158 | human Delta and Notch-like epidermal growth factor-related-EGF3 protein | PRT158 |
| SEQ ID NO: 159 | human Delta and Notch-like epidermal growth factor-related-EGF4 protein | PRT159 |
| SEQ ID NO: 160 | human Delta and Notch-like epidermal growth factor-related-EGF5 protein | PRT160 |

TABLE 1-continued

Designation of the human-originated EGF domain proteins set forth in the present invention

| No. in the sequence listing | Designation | Code in the invention |
|---|---|---|
| SEQ ID NO: 161 | human Delta and Notch-like epidermal growth factor-related-EGF6 protein | PRT161 |
| SEQ ID NO: 162 | human Delta and Notch-like epidermal growth factor-related-EGF7 protein | PRT162 |
| SEQ ID NO: 163 | human Delta and Notch-like epidermal growth factor-related-EGF8 protein | PRT163 |
| SEQ ID NO: 164 | human Delta and Notch-like epidermal growth factor-related-EGF9 protein | PRT164 |
| SEQ ID NO: 165 | human Delta-like 1-EGF1 protein | PRT165 |
| SEQ ID NO: 166 | human Delta-like 1-EGF2 protein | PRT166 |
| SEQ ID NO: 167 | human Delta-like 1-EGF3 protein | PRT167 |
| SEQ ID NO: 168 | human Delta-like protein 1-EGF1 protein | PRT168 |
| SEQ ID NO: 169 | human Delta-like protein 1-EGF2 protein | PRT169 |
| SEQ ID NO: 170 | human Delta-like protein 1-EGF3 protein | PRT170 |
| SEQ ID NO: 171 | human Delta-like protein 1-EGF4 protein | PRT171 |
| SEQ ID NO: 172 | human Delta-like protein 1-EGF5 protein | PRT172 |
| SEQ ID NO: 173 | human Delta-like protein 1-EGF6 protein | PRT173 |
| SEQ ID NO: 174 | human Delta-like protein 1-EGF7 protein | PRT174 |
| SEQ ID NO: 175 | human Delta-like protein 1-EGF8 protein | PRT175 |
| SEQ ID NO: 176 | human Delta-like protein 3-EGF1 protein | PRT176 |
| SEQ ID NO: 177 | human Delta-like protein 3-EGF2 protein | PRT177 |
| SEQ ID NO: 178 | human Delta-like protein 3-EGF3 protein | PRT178 |
| SEQ ID NO: 179 | human Delta-like protein 3-EGF4 protein | PRT179 |
| SEQ ID NO: 180 | human Delta-like protein 3-EGF5 protein | PRT180 |
| SEQ ID NO: 181 | human Delta-like protein 3-EGF6 protein | PRT181 |
| SEQ ID NO: 182 | human Delta-like protein 4-EGF1 protein | PRT182 |
| SEQ ID NO: 183 | human Delta-like protein 4-EGF2 protein | PRT183 |
| SEQ ID NO: 184 | human Delta-like protein 4-EGF3 protein | PRT184 |
| SEQ ID NO: 185 | human Delta-like protein 4-EGF4 protein | PRT185 |
| SEQ ID NO: 186 | human Delta-like protein 4-EGF5 protein | PRT186 |
| SEQ ID NO: 187 | human Delta-like protein 4-EGF6 protein | PRT187 |
| SEQ ID NO: 188 | human Delta-like protein 4-EGF7 protein | PRT188 |
| SEQ ID NO: 189 | human Delta-like protein 4-EGF8 protein | PRT189 |
| SEQ ID NO: 190 | human DIET1-EGF1 protein | PRT190 |
| SEQ ID NO: 191 | human Diphtheria toxin receptor (Heparin-binding epidermal growth factor-like growth factor) variant-EGF1 protein | PRT191 |
| SEQ ID NO: 192 | human Disintegrin and metalloproteinase domain-containing protein 11-EGF1 protein | PRT192 |
| SEQ ID NO: 193 | human Disintegrin and metalloproteinase domain-containing protein 12-EGF1 protein | PRT193 |
| SEQ ID NO: 194 | human Disintegrin and metalloproteinase domain-containing protein 15-EGF1 protein | PRT194 |
| SEQ ID NO: 195 | human Disintegrin and metalloproteinase domain-containing protein 18-EGF1 protein | PRT195 |
| SEQ ID NO: 196 | human Disintegrin and metalloproteinase domain-containing protein 19-EGF1 protein | PRT196 |
| SEQ ID NO: 197 | human Disintegrin and metalloproteinase domain-containing protein 2-EGF1 protein | PRT197 |
| SEQ ID NO: 198 | human Disintegrin and metalloproteinase domain-containing protein 20-EGF1 protein | PRT198 |
| SEQ ID NO: 199 | human Disintegrin and metalloproteinase domain-containing protein 21-EGF1 protein | PRT199 |
| SEQ ID NO: 200 | human Disintegrin and metalloproteinase domain-containing protein 22-EGF1 protein | PRT200 |
| SEQ ID NO: 201 | human Disintegrin and metalloproteinase domain-containing protein 23-EGF1 protein | PRT201 |
| SEQ ID NO: 202 | human Disintegrin and metalloproteinase domain-containing protein 28-EGF1 protein | PRT202 |
| SEQ ID NO: 203 | human Disintegrin and metalloproteinase domain-containing protein 29-EGF1 protein | PRT203 |
| SEQ ID NO: 204 | human Disintegrin and metalloproteinase domain-containing protein 30-EGF1 protein | PRT204 |
| SEQ ID NO: 205 | human Disintegrin and metalloproteinase domain-containing protein 32-EGF1 protein | PRT205 |
| SEQ ID NO: 206 | human Disintegrin and metalloproteinase domain-containing protein 33-EGF1 protein | PRT206 |
| SEQ ID NO: 207 | human Disintegrin and metalloproteinase domain-containing protein 8-EGF1 protein | PRT207 |
| SEQ ID NO: 208 | human Disintegrin and metalloproteinase domain-containing protein 9-EGF1 protein | PRT208 |
| SEQ ID NO: 209 | human EFEMP2 protein-EGF1 protein | PRT209 |
| SEQ ID NO: 210 | human EFEMP2 protein-EGF2 protein | PRT210 |
| SEQ ID NO: 211 | human EFEMP2 protein-EGF3 protein | PRT211 |
| SEQ ID NO: 212 | human EFEMP2 protein-EGF4 protein | PRT212 |

TABLE 1-continued

Designation of the human-originated EGF domain proteins set forth in the present invention

| No. in the sequence listing | Designation | Code in the invention |
|---|---|---|
| SEQ ID NO: 213 | human EGF, latrophilin and seven transmembrane domain-containing protein 1-EGF1 protein | PRT213 |
| SEQ ID NO: 214 | human EGF, latrophilin and seven transmembrane domain-containing protein 1-EGF2 protein | PRT214 |
| SEQ ID NO: 215 | human EGF-containing fibulin-like extracellular matrix protein 1-EGF1 protein | PRT215 |
| SEQ ID NO: 216 | human EGF-containing fibulin-like extracellular matrix protein 1-EGF2 protein | PRT216 |
| SEQ ID NO: 217 | human EGF-containing fibulin-like extracellular matrix protein 1-EGF3 protein | PRT217 |
| SEQ ID NO: 218 | human EGF-containing fibulin-like extracellular matrix protein 1-EGF4 protein | PRT218 |
| SEQ ID NO: 219 | human EGF-containing fibulin-like extracellular matrix protein 1-EGF5 protein | PRT219 |
| SEQ ID NO: 220 | human EGF-containing fibulin-like extracellular matrix protein 1-EGF6 protein | PRT220 |
| SEQ ID NO: 221 | human EGF-containing fibulin-like extracellular matrix protein 2-EGF1 protein | PRT221 |
| SEQ ID NO: 222 | human EGF-containing fibulin-like extracellular matrix protein 2-EGF2 protein | PRT222 |
| SEQ ID NO: 223 | human EGF-containing fibulin-like extracellular matrix protein 2-EGF3 protein | PRT223 |
| SEQ ID NO: 224 | human EGF-containing fibulin-like extracellular matrix protein 2-EGF4 protein | PRT224 |
| SEQ ID NO: 225 | human EGF-containing fibulin-like extracellular matrix protein 2-EGF5 protein | PRT225 |
| SEQ ID NO: 226 | human EGF-containing fibulin-like extracellular matrix protein 2-EGF6 protein | PRT226 |
| SEQ ID NO: 227 | human EGF-like module-containing mucin-like hormone receptor-like 1-EGF1 protein | PRT227 |
| SEQ ID NO: 228 | human EGF-like module-containing mucin-like hormone receptor-like 1-EGF2 protein | PRT228 |
| SEQ ID NO: 229 | human EGF-like module-containing mucin-like hormone receptor-like 1-EGF3 protein | PRT229 |
| SEQ ID NO: 230 | human EGF-like module-containing mucin-like hormone receptor-like 1-EGF4 protein | PRT230 |
| SEQ ID NO: 231 | human EGF-like module-containing mucin-like hormone receptor-like 1-EGF5 protein | PRT231 |
| SEQ ID NO: 232 | human EGF-like module-containing mucin-like hormone receptor-like 1-EGF6 protein | PRT232 |
| SEQ ID NO: 233 | human EGF-like module-containing mucin-like hormone receptor-like 2-EGF1 protein | PRT233 |
| SEQ ID NO: 234 | human EGF-like module-containing mucin-like hormone receptor-like 2-EGF2 protein | PRT234 |
| SEQ ID NO: 235 | human EGF-like module-containing mucin-like hormone receptor-like 2-EGF3 protein | PRT235 |
| SEQ ID NO: 236 | human EGF-like module-containing mucin-like hormone receptor-like 3-EGF1 protein | PRT236 |
| SEQ ID NO: 237 | human EGF-like module-containing mucin-like hormone receptor-like 3-EGF2 protein | PRT237 |
| SEQ ID NO: 238 | human EGF-like repeat and discoidin I-like domain-containing protein 3-EGF1 protein | PRT238 |
| SEQ ID NO: 239 | human EGF-like repeat and discoidin I-like domain-containing protein 3-EGF2 protein | PRT239 |
| SEQ ID NO: 240 | human EGF-like repeat and discoidin I-like domain-containing protein 3-EGF3 protein | PRT240 |
| SEQ ID NO: 241 | human Endosialin-EGF1 protein | PRT241 |
| SEQ ID NO: 242 | human Epidermal growth factor-like protein 6-EGF1 protein | PRT242 |
| SEQ ID NO: 243 | human Epidermal growth factor-like protein 6-EGF2 protein | PRT243 |
| SEQ ID NO: 244 | human Epidermal growth factor-like protein 6-EGF3 protein | PRT244 |
| SEQ ID NO: 245 | human Epidermal growth factor-like protein 6-EGF4 protein | PRT245 |
| SEQ ID NO: 246 | human Epidermal growth factor-like protein 6-EGF5 protein | PRT246 |
| SEQ ID NO: 247 | human Epidermal growth factor-like protein 7-EGF1 protein | PRT247 |
| SEQ ID NO: 248 | human Epidermal growth factor-like protein 7-EGF2 protein | PRT248 |
| SEQ ID NO: 249 | human Epidermal growth factor-like protein 8-EGF1 protein | PRT249 |
| SEQ ID NO: 250 | human Epidermal growth factor-like protein 8-EGF2 protein | PRT250 |
| SEQ ID NO: 251 | human Epigen-EGF1 protein | PRT251 |
| SEQ ID NO: 252 | human E-selectin-EGF1 protein | PRT252 |
| SEQ ID NO: 253 | human FAT2 protein-EGF1 protein | PRT253 |
| SEQ ID NO: 254 | human FAT2 protein-EGF2 protein | PRT254 |
| SEQ ID NO: 255 | human FBLN7 protein-EGF1 protein | PRT255 |
| SEQ ID NO: 256 | human FEX1-EGF1 protein | PRT256 |
| SEQ ID NO: 257 | human FEX1-EGF10 protein | PRT257 |
| SEQ ID NO: 258 | human FEX1-EGF2 protein | PRT258 |
| SEQ ID NO: 259 | human FEX1-EGF3 protein | PRT259 |

TABLE 1-continued

Designation of the human-originated EGF domain proteins set forth in the present invention

| No. in the sequence listing | Designation | Code in the invention |
| --- | --- | --- |
| SEQ ID NO: 260 | human FEX1-EGF4 protein | PRT260 |
| SEQ ID NO: 261 | human FEX1-EGF5 protein | PRT261 |
| SEQ ID NO: 262 | human FEX1-EGF6 protein | PRT262 |
| SEQ ID NO: 263 | human FEX1-EGF7 protein | PRT263 |
| SEQ ID NO: 264 | human FEX1-EGF8 protein | PRT264 |
| SEQ ID NO: 265 | human FEX1-EGF9 protein | PRT265 |
| SEQ ID NO: 266 | human Fibrillin 15-EGF1 protein | PRT266 |
| SEQ ID NO: 267 | human Fibrillin 15-EGF2 protein | PRT267 |
| SEQ ID NO: 268 | human Fibrillin 15-EGF3 protein | PRT268 |
| SEQ ID NO: 269 | human Fibrillin 15-EGF4 protein | PRT269 |
| SEQ ID NO: 270 | human Fibrillin 15-EGF5 protein | PRT270 |
| SEQ ID NO: 271 | human Fibrillin 15-EGF6 protein | PRT271 |
| SEQ ID NO: 272 | human Fibrillin 15-EGF7 protein | PRT272 |
| SEQ ID NO: 273 | human Fibrillin 15-EGF8 protein | PRT273 |
| SEQ ID NO: 274 | human Fibrillin-1-EGF1 protein | PRT274 |
| SEQ ID NO: 275 | human Fibrillin-1-EGF10 protein | PRT275 |
| SEQ ID NO: 276 | human Fibrillin-1-EGF11 protein | PRT276 |
| SEQ ID NO: 277 | human Fibrillin-1-EGF12 protein | PRT277 |
| SEQ ID NO: 278 | human Fibrillin-1-EGF13 protein | PRT278 |
| SEQ ID NO: 279 | human Fibrillin-1-EGF14 protein | PRT279 |
| SEQ ID NO: 280 | human Fibrillin-1-EGF15 protein | PRT280 |
| SEQ ID NO: 281 | human Fibrillin-1-EGF16 protein | PRT281 |
| SEQ ID NO: 282 | human Fibrillin-1-EGF17 protein | PRT282 |
| SEQ ID NO: 283 | human Fibrillin-1-EGF18 protein | PRT283 |
| SEQ ID NO: 284 | human Fibrillin-1-EGF19 protein | PRT284 |
| SEQ ID NO: 285 | human Fibrillin-1-EGF2 protein | PRT285 |
| SEQ ID NO: 286 | human Fibrillin-1-EGF20 protein | PRT286 |
| SEQ ID NO: 287 | human Fibrillin-1-EGF21 protein | PRT287 |
| SEQ ID NO: 288 | human Fibrillin-1-EGF22 protein | PRT288 |
| SEQ ID NO: 289 | human Fibrillin-1-EGF23 protein | PRT289 |
| SEQ ID NO: 290 | human Fibrillin-1-EGF24 protein | PRT290 |
| SEQ ID NO: 291 | human Fibrillin-1-EGF25 protein | PRT291 |
| SEQ ID NO: 292 | human Fibrillin-1-EGF26 protein | PRT292 |
| SEQ ID NO: 293 | human Fibrillin-1-EGF27 protein | PRT293 |
| SEQ ID NO: 294 | human Fibrillin-1-EGF28 protein | PRT294 |
| SEQ ID NO: 295 | human Fibrillin-1-EGF29 protein | PRT295 |
| SEQ ID NO: 296 | human Fibrillin-1-EGF3 protein | PRT296 |
| SEQ ID NO: 297 | human Fibrillin-1-EGF30 protein | PRT297 |
| SEQ ID NO: 298 | human Fibrillin-1-EGF31 protein | PRT298 |
| SEQ ID NO: 299 | human Fibrillin-1-EGF32 protein | PRT299 |
| SEQ ID NO: 300 | human Fibrillin-1-EGF33 protein | PRT300 |
| SEQ ID NO: 301 | human Fibrillin-1-EGF34 protein | PRT301 |
| SEQ ID NO: 302 | human Fibrillin-1-EGF35 protein | PRT302 |
| SEQ ID NO: 303 | human Fibrillin-1-EGF36 protein | PRT303 |
| SEQ ID NO: 304 | human Fibrillin-1-EGF37 protein | PRT304 |
| SEQ ID NO: 305 | human Fibrillin-1-EGF38 protein | PRT305 |
| SEQ ID NO: 306 | human Fibrillin-1-EGF39 protein | PRT306 |
| SEQ ID NO: 307 | human Fibrillin-1-EGF4 protein | PRT307 |
| SEQ ID NO: 308 | human Fibrillin-1-EGF40 protein | PRT308 |
| SEQ ID NO: 309 | human Fibrillin-1-EGF41 protein | PRT309 |
| SEQ ID NO: 310 | human Fibrillin-1-EGF42 protein | PRT310 |
| SEQ ID NO: 311 | human Fibrillin-1-EGF43 protein | PRT311 |
| SEQ ID NO: 312 | human Fibrillin-1-EGF44 protein | PRT312 |
| SEQ ID NO: 313 | human Fibrillin-1-EGF45 protein | PRT313 |
| SEQ ID NO: 314 | human Fibrillin-1-EGF46 protein | PRT314 |
| SEQ ID NO: 315 | human Fibrillin-1-EGF47 protein | PRT315 |
| SEQ ID NO: 316 | human Fibrillin-1-EGF5 protein | PRT316 |
| SEQ ID NO: 317 | human Fibrillin-1-EGF6 protein | PRT317 |
| SEQ ID NO: 318 | human Fibrillin-1-EGF7 protein | PRT318 |
| SEQ ID NO: 319 | human Fibrillin-1-EGF8 protein | PRT319 |
| SEQ ID NO: 320 | human Fibrillin-1-EGF9 protein | PRT320 |
| SEQ ID NO: 321 | human Fibrillin-2-EGF1 protein | PRT321 |
| SEQ ID NO: 322 | human Fibrillin-2-EGF10 protein | PRT322 |
| SEQ ID NO: 323 | human Fibrillin-2-EGF11 protein | PRT323 |
| SEQ ID NO: 324 | human Fibrillin-2-EGF12 protein | PRT324 |
| SEQ ID NO: 325 | human Fibrillin-2-EGF13 protein | PRT325 |
| SEQ ID NO: 326 | human Fibrillin-2-EGF14 protein | PRT326 |
| SEQ ID NO: 327 | human Fibrillin-2-EGF15 protein | PRT327 |
| SEQ ID NO: 328 | human Fibrillin-2-EGF16 protein | PRT328 |
| SEQ ID NO: 329 | human Fibrillin-2-EGF17 protein | PRT329 |
| SEQ ID NO: 330 | human Fibrillin-2-EGF18 protein | PRT330 |
| SEQ ID NO: 331 | human Fibrillin-2-EGF19 protein | PRT331 |
| SEQ ID NO: 332 | human Fibrillin-2-EGF2 protein | PRT332 |
| SEQ ID NO: 333 | human Fibrillin-2-EGF20 protein | PRT333 |
| SEQ ID NO: 334 | human Fibrillin-2-EGF21 protein | PRT334 |

TABLE 1-continued

Designation of the human-originated EGF domain proteins set forth in the present invention

| No. in the sequence listing | Designation | Code in the invention |
|---|---|---|
| SEQ ID NO: 335 | human Fibrillin-2-EGF22 protein | PRT335 |
| SEQ ID NO: 336 | human Fibrillin-2-EGF23 protein | PRT336 |
| SEQ ID NO: 337 | human Fibrillin-2-EGF24 protein | PRT337 |
| SEQ ID NO: 338 | human Fibrillin-2-EGF25 protein | PRT338 |
| SEQ ID NO: 339 | human Fibrillin-2-EGF26 protein | PRT339 |
| SEQ ID NO: 340 | human Fibrillin-2-EGF27 protein | PRT340 |
| SEQ ID NO: 341 | human Fibrillin-2-EGF28 protein | PRT341 |
| SEQ ID NO: 342 | human Fibrillin-2-EGF29 protein | PRT342 |
| SEQ ID NO: 343 | human Fibrillin-2-EGF3 protein | PRT343 |
| SEQ ID NO: 344 | human Fibrillin-2-EGF30 protein | PRT344 |
| SEQ ID NO: 345 | human Fibrillin-2-EGF31 protein | PRT345 |
| SEQ ID NO: 346 | human Fibrillin-2-EGF32 protein | PRT346 |
| SEQ ID NO: 347 | human Fibrillin-2-EGF33 protein | PRT347 |
| SEQ ID NO: 348 | human Fibrillin-2-EGF34 protein | PRT348 |
| SEQ ID NO: 349 | human Fibrillin-2-EGF35 protein | PRT349 |
| SEQ ID NO: 350 | human Fibrillin-2-EGF36 protein | PRT350 |
| SEQ ID NO: 351 | human Fibrillin-2-EGF37 protein | PRT351 |
| SEQ ID NO: 352 | human Fibrillin-2-EGF38 protein | PRT352 |
| SEQ ID NO: 353 | human Fibrillin-2-EGF39 protein | PRT353 |
| SEQ ID NO: 354 | human Fibrillin-2-EGF4 protein | PRT354 |
| SEQ ID NO: 355 | human Fibrillin-2-EGF40 protein | PRT355 |
| SEQ ID NO: 356 | human Fibrillin-2-EGF41 protein | PRT356 |
| SEQ ID NO: 357 | human Fibrillin-2-EGF42 protein | PRT357 |
| SEQ ID NO: 358 | human Fibrillin-2-EGF43 protein | PRT358 |
| SEQ ID NO: 359 | human Fibrillin-2-EGF44 protein | PRT359 |
| SEQ ID NO: 360 | human Fibrillin-2-EGF45 protein | PRT360 |
| SEQ ID NO: 361 | human Fibrillin-2-EGF46 protein | PRT361 |
| SEQ ID NO: 362 | human Fibrillin-2-EGF47 protein | PRT362 |
| SEQ ID NO: 363 | human Fibrillin-2-EGF5 protein | PRT363 |
| SEQ ID NO: 364 | human Fibrillin-2-EGF6 protein | PRT364 |
| SEQ ID NO: 365 | human Fibrillin-2-EGF7 protein | PRT365 |
| SEQ ID NO: 366 | human Fibrillin-2-EGF8 protein | PRT366 |
| SEQ ID NO: 367 | human Fibrillin-2-EGF9 protein | PRT367 |
| SEQ ID NO: 368 | human Fibrillin-3-EGF1 protein | PRT368 |
| SEQ ID NO: 369 | human Fibrillin-3-EGF10 protein | PRT369 |
| SEQ ID NO: 370 | human Fibrillin-3-EGF11 protein | PRT370 |
| SEQ ID NO: 371 | human Fibrillin-3-EGF12 protein | PRT371 |
| SEQ ID NO: 372 | human Fibrillin-3-EGF13 protein | PRT372 |
| SEQ ID NO: 373 | human Fibrillin-3-EGF14 protein | PRT373 |
| SEQ ID NO: 374 | human Fibrillin-3-EGF15 protein | PRT374 |
| SEQ ID NO: 375 | human Fibrillin-3-EGF16 protein | PRT375 |
| SEQ ID NO: 376 | human Fibrillin-3-EGF17 protein | PRT376 |
| SEQ ID NO: 377 | human Fibrillin-3-EGF18 protein | PRT377 |
| SEQ ID NO: 378 | human Fibrillin-3-EGF19 protein | PRT378 |
| SEQ ID NO: 379 | human Fibrillin-3-EGF2 protein | PRT379 |
| SEQ ID NO: 380 | human Fibrillin-3-EGF20 protein | PRT380 |
| SEQ ID NO: 381 | human Fibrillin-3-EGF21 protein | PRT381 |
| SEQ ID NO: 382 | human Fibrillin-3-EGF22 protein | PRT382 |
| SEQ ID NO: 383 | human Fibrillin-3-EGF23 protein | PRT383 |
| SEQ ID NO: 384 | human Fibrillin-3-EGF24 protein | PRT384 |
| SEQ ID NO: 385 | human Fibrillin-3-EGF25 protein | PRT385 |
| SEQ ID NO: 386 | human Fibrillin-3-EGF26 protein | PRT386 |
| SEQ ID NO: 387 | human Fibrillin-3-EGF27 protein | PRT387 |
| SEQ ID NO: 388 | human Fibrillin-3-EGF28 protein | PRT388 |
| SEQ ID NO: 389 | human Fibrillin-3-EGF29 protein | PRT389 |
| SEQ ID NO: 390 | human Fibrillin-3-EGF3 protein | PRT390 |
| SEQ ID NO: 391 | human Fibrillin-3-EGF30 protein | PRT391 |
| SEQ ID NO: 392 | human Fibrillin-3-EGF31 protein | PRT392 |
| SEQ ID NO: 393 | human Fibrillin-3-EGF32 protein | PRT393 |
| SEQ ID NO: 394 | human Fibrillin-3-EGF33 protein | PRT394 |
| SEQ ID NO: 395 | human Fibrillin-3-EGF34 protein | PRT395 |
| SEQ ID NO: 396 | human Fibrillin-3-EGF35 protein | PRT396 |
| SEQ ID NO: 397 | human Fibrillin-3-EGF36 protein | PRT397 |
| SEQ ID NO: 398 | human Fibrillin-3-EGF37 protein | PRT398 |
| SEQ ID NO: 399 | human Fibrillin-3-EGF38 protein | PRT399 |
| SEQ ID NO: 400 | human Fibrillin-3-EGF39 protein | PRT400 |
| SEQ ID NO: 401 | human Fibrillin-3-EGF4 protein | PRT401 |
| SEQ ID NO: 402 | human Fibrillin-3-EGF40 protein | PRT402 |
| SEQ ID NO: 403 | human Fibrillin-3-EGF41 protein | PRT403 |
| SEQ ID NO: 404 | human Fibrillin-3-EGF42 protein | PRT404 |
| SEQ ID NO: 405 | human Fibrillin-3-EGF43 protein | PRT405 |
| SEQ ID NO: 406 | human Fibrillin-3-EGF44 protein | PRT406 |
| SEQ ID NO: 407 | human Fibrillin-3-EGF5 protein | PRT407 |
| SEQ ID NO: 408 | human Fibrillin-3-EGF6 protein | PRT408 |
| SEQ ID NO: 409 | human Fibrillin-3-EGF7 protein | PRT409 |

TABLE 1-continued

Designation of the human-originated EGF domain proteins set forth in the present invention

| No. in the sequence listing | Designation | Code in the invention |
|---|---|---|
| SEQ ID NO: 410 | human Fibrillin-3-EGF8 protein | PRT410 |
| SEQ ID NO: 411 | human Fibrillin-3-EGF9 protein | PRT411 |
| SEQ ID NO: 412 | human Fibulin-1-EGF1 protein | PRT412 |
| SEQ ID NO: 413 | human Fibulin-1-EGF2 protein | PRT413 |
| SEQ ID NO: 414 | human Fibulin-1-EGF3 protein | PRT414 |
| SEQ ID NO: 415 | human Fibulin-1-EGF4 protein | PRT415 |
| SEQ ID NO: 416 | human Fibulin-1-EGF5 protein | PRT416 |
| SEQ ID NO: 417 | human Fibulin-1-EGF6 protein | PRT417 |
| SEQ ID NO: 418 | human Fibulin-1-EGF7 protein | PRT418 |
| SEQ ID NO: 419 | human Fibulin-1-EGF8 protein | PRT419 |
| SEQ ID NO: 420 | human Fibulin-1-EGF9 protein | PRT420 |
| SEQ ID NO: 421 | human Fibulin-2-EGF1 protein | PRT421 |
| SEQ ID NO: 422 | human Fibulin-2-EGF10 protein | PRT422 |
| SEQ ID NO: 423 | human Fibulin-2-EGF2 protein | PRT423 |
| SEQ ID NO: 424 | human Fibulin-2-EGF3 protein | PRT424 |
| SEQ ID NO: 425 | human Fibulin-2-EGF4 protein | PRT425 |
| SEQ ID NO: 426 | human Fibulin-2-EGF5 protein | PRT426 |
| SEQ ID NO: 427 | human Fibulin-2-EGF6 protein | PRT427 |
| SEQ ID NO: 428 | human Fibulin-2-EGF7 protein | PRT428 |
| SEQ ID NO: 429 | human Fibulin-2-EGF8 protein | PRT429 |
| SEQ ID NO: 430 | human Fibulin-2-EGF9 protein | PRT430 |
| SEQ ID NO: 431 | human Fibulin-5-EGF1 protein | PRT431 |
| SEQ ID NO: 432 | human Fibulin-5-EGF2 protein | PRT432 |
| SEQ ID NO: 433 | human Fibulin-5-EGF3 protein | PRT433 |
| SEQ ID NO: 434 | human Fibulin-5-EGF4 protein | PRT434 |
| SEQ ID NO: 435 | human Fibulin-5-EGF5 protein | PRT435 |
| SEQ ID NO: 436 | human Fibulin-5-EGF6 protein | PRT436 |
| SEQ ID NO: 437 | human Fibulin-6-EGF1 protein | PRT437 |
| SEQ ID NO: 438 | human Fibulin-6-EGF2 protein | PRT438 |
| SEQ ID NO: 439 | human Fibulin-6-EGF3 protein | PRT439 |
| SEQ ID NO: 440 | human Fibulin-6-EGF4 protein | PRT440 |
| SEQ ID NO: 441 | human Fibulin-6-EGF5 protein | PRT441 |
| SEQ ID NO: 442 | human Fibulin-6-EGF6 protein | PRT442 |
| SEQ ID NO: 443 | human Fibulin-6-EGF7 protein | PRT443 |
| SEQ ID NO: 444 | human Fibulin-7-EGF1 protein | PRT444 |
| SEQ ID NO: 445 | human Fibulin-7-EGF2 protein | PRT445 |
| SEQ ID NO: 446 | human Fibulin-7-EGF3 protein | PRT446 |
| SEQ ID NO: 447 | human Fibulin-like extracellular matrix protein-EGF1 protein | PRT447 |
| SEQ ID NO: 448 | human Fibulin-like extracellular matrix protein-EGF2 protein | PRT448 |
| SEQ ID NO: 449 | human Fibulin-like extracellular matrix protein-EGF3 protein | PRT449 |
| SEQ ID NO: 450 | human Glycoprotein receptor gp330/megalin-EGF1 protein | PRT450 |
| SEQ ID NO: 451 | human Glycoprotein receptor gp330/megalin-EGF2 protein | PRT451 |
| SEQ ID NO: 452 | human Glycoprotein receptor gp330/megalin-EGF3 protein | PRT452 |
| SEQ ID NO: 453 | human Glycoprotein receptor gp330/megalin-EGF4 protein | PRT453 |
| SEQ ID NO: 454 | human Growth arrest-specific protein 6-EGF1 protein | PRT454 |
| SEQ ID NO: 455 | human Growth arrest-specific protein 6-EGF2 protein | PRT455 |
| SEQ ID NO: 456 | human Growth arrest-specific protein 6-EGF3 protein | PRT456 |
| SEQ ID NO: 457 | human Growth arrest-specific protein 6-EGF4 protein | PRT457 |
| SEQ ID NO: 458 | human Hedgehog-interacting protein-EGF1 protein | PRT458 |
| SEQ ID NO: 459 | human Hedgehog-interacting protein-EGF2 protein | PRT459 |
| SEQ ID NO: 460 | human Hemicentin-2-EGF1 protein | PRT460 |
| SEQ ID NO: 461 | human Hemicentin-2-EGF2 protein | PRT461 |
| SEQ ID NO: 462 | human Hemicentin-2-EGF3 protein | PRT462 |
| SEQ ID NO: 463 | human Hemicentin-2-EGF4 protein | PRT463 |
| SEQ ID NO: 464 | human Hemicentin-2-EGF5 protein | PRT464 |
| SEQ ID NO: 465 | human Hepatocyte growth factor activator-EGF1 protein | PRT465 |
| SEQ ID NO: 466 | human Hepatocyte growth factor activator-EGF2 protein | PRT466 |
| SEQ ID NO: 467 | human HMGA2ex3/WIF1ex3 fusion protein-EGF1 protein | PRT467 |
| SEQ ID NO: 468 | human HMGA2ex3/WIF1ex3 fusion protein-EGF2 protein | PRT468 |
| SEQ ID NO: 469 | human HMGA2ex3/WIF1ex3 fusion protein-EGF3 protein | PRT469 |
| SEQ ID NO: 470 | human HMGA2ex3/WIF1ex3 fusion protein-EGF4 protein | PRT470 |
| SEQ ID NO: 471 | human HMGA2ex3/WIF1ex3 fusion protein-EGF5 protein | PRT471 |
| SEQ ID NO: 472 | human HSPG2 protein-EGF1 protein | PRT472 |
| SEQ ID NO: 473 | human HSPG2 protein-EGF2 protein | PRT473 |
| SEQ ID NO: 474 | human Hyaluronan-binding protein 2-EGF1 protein | PRT474 |
| SEQ ID NO: 475 | human Hyaluronan-binding protein 2-EGF2 protein | PRT475 |
| SEQ ID NO: 476 | human Hyaluronan-binding protein 2-EGF3 protein | PRT476 |
| SEQ ID NO: 477 | human Hyaluronidase-1-EGF1 protein | PRT477 |
| SEQ ID NO: 478 | human Hyaluronidase-2-EGF1 protein | PRT478 |
| SEQ ID NO: 479 | human Hyaluronidase-3-EGF1 protein | PRT479 |
| SEQ ID NO: 480 | human Hyaluronidase-4-EGF1 protein | PRT480 |
| SEQ ID NO: 481 | human Inactive serine protease PAMR1-EGF1 protein | PRT481 |
| SEQ ID NO: 482 | human Integrin beta-like protein 1-EGF1 protein | PRT482 |
| SEQ ID NO: 483 | human Integrin beta-like protein 1-EGF2 protein | PRT483 |
| SEQ ID NO: 484 | human Integrin beta-like protein 1-EGF3 protein | PRT484 |

TABLE 1-continued

Designation of the human-originated EGF domain proteins set forth in the present invention

| No. in the sequence listing | Designation | Code in the invention |
|---|---|---|
| SEQ ID NO: 485 | human Interphotoreceptor matrix proteoglycan 1, isoform CRA_a-EGF1 protein | PRT485 |
| SEQ ID NO: 486 | human Interphotoreceptor matrix proteoglycan 2-EGF1 protein | PRT486 |
| SEQ ID NO: 487 | human Interphotoreceptor matrix proteoglycan 2-EGF2 protein | PRT487 |
| SEQ ID NO: 488 | human Intestinal mucin-EGF1 protein | PRT488 |
| SEQ ID NO: 489 | human Intestinal mucin-EGF2 protein | PRT489 |
| SEQ ID NO: 490 | human KIAA0921 splice variant 1-EGF1 protein | PRT490 |
| SEQ ID NO: 491 | human Lactadherin-EGF1 protein | PRT491 |
| SEQ ID NO: 492 | human Laminin subunit alpha-1-EGF1 protein | PRT492 |
| SEQ ID NO: 493 | human Laminin subunit alpha-1-EGF10 protein | PRT493 |
| SEQ ID NO: 494 | human Laminin subunit alpha-1-EGF11 protein | PRT494 |
| SEQ ID NO: 495 | human Laminin subunit alpha-1-EGF12 protein | PRT495 |
| SEQ ID NO: 496 | human Laminin subunit alpha-1-EGF13 protein | PRT496 |
| SEQ ID NO: 497 | human Laminin subunit alpha-1-EGF14 protein | PRT497 |
| SEQ ID NO: 498 | human Laminin subunit alpha-1-EGF15 protein | PRT498 |
| SEQ ID NO: 499 | human Laminin subunit alpha-1-EGF2 protein | PRT499 |
| SEQ ID NO: 500 | human Laminin subunit alpha-1-EGF3 protein | PRT500 |
| SEQ ID NO: 501 | human Laminin subunit alpha-1-EGF4 protein | PRT501 |
| SEQ ID NO: 502 | human Laminin subunit alpha-1-EGF5 protein | PRT502 |
| SEQ ID NO: 503 | human Laminin subunit alpha-1-EGF6 protein | PRT503 |
| SEQ ID NO: 504 | human Laminin subunit alpha-1-EGF7 protein | PRT504 |
| SEQ ID NO: 505 | human Laminin subunit alpha-1-EGF8 protein | PRT505 |
| SEQ ID NO: 506 | human Laminin subunit alpha-1-EGF9 protein | PRT506 |
| SEQ ID NO: 507 | human Laminin subunit alpha-2-EGF1 protein | PRT507 |
| SEQ ID NO: 508 | human Laminin subunit alpha-2-EGF10 protein | PRT508 |
| SEQ ID NO: 509 | human Laminin subunit alpha-2-EGF11 protein | PRT509 |
| SEQ ID NO: 510 | human Laminin subunit alpha-2-EGF12 protein | PRT510 |
| SEQ ID NO: 511 | human Laminin subunit alpha-2-EGF13 protein | PRT511 |
| SEQ ID NO: 512 | human Laminin subunit alpha-2-EGF14 protein | PRT512 |
| SEQ ID NO: 513 | human Laminin subunit alpha-2-EGF15 protein | PRT513 |
| SEQ ID NO: 514 | human Laminin subunit alpha-2-EGF2 protein | PRT514 |
| SEQ ID NO: 515 | human Laminin subunit alpha-2-EGF3 protein | PRT515 |
| SEQ ID NO: 516 | human Laminin subunit alpha-2-EGF4 protein | PRT516 |
| SEQ ID NO: 517 | human Laminin subunit alpha-2-EGF5 protein | PRT517 |
| SEQ ID NO: 518 | human Laminin subunit alpha-2-EGF6 protein | PRT518 |
| SEQ ID NO: 519 | human Laminin subunit alpha-2-EGF7 protein | PRT519 |
| SEQ ID NO: 520 | human Laminin subunit alpha-2-EGF8 protein | PRT520 |
| SEQ ID NO: 521 | human Laminin subunit alpha-2-EGF9 protein | PRT521 |
| SEQ ID NO: 522 | human Laminin subunit alpha-3-EGF1 protein | PRT522 |
| SEQ ID NO: 523 | human Laminin subunit alpha-3-EGF10 protein | PRT523 |
| SEQ ID NO: 524 | human Laminin subunit alpha-3-EGF11 protein | PRT524 |
| SEQ ID NO: 525 | human Laminin subunit alpha-3-EGF12 protein | PRT525 |
| SEQ ID NO: 526 | human Laminin subunit alpha-3-EGF13 protein | PRT526 |
| SEQ ID NO: 527 | human Laminin subunit alpha-3-EGF14 protein | PRT527 |
| SEQ ID NO: 528 | human Laminin subunit alpha-3-EGF15 protein | PRT528 |
| SEQ ID NO: 529 | human Laminin subunit alpha-3-EGF2 protein | PRT529 |
| SEQ ID NO: 530 | human Laminin subunit alpha-3-EGF3 protein | PRT530 |
| SEQ ID NO: 531 | human Laminin subunit alpha-3-EGF4 protein | PRT531 |
| SEQ ID NO: 532 | human Laminin subunit alpha-3-EGF5 protein | PRT532 |
| SEQ ID NO: 533 | human Laminin subunit alpha-3-EGF6 protein | PRT533 |
| SEQ ID NO: 534 | human Laminin subunit alpha-3-EGF7 protein | PRT534 |
| SEQ ID NO: 535 | human Laminin subunit alpha-3-EGF8 protein | PRT535 |
| SEQ ID NO: 536 | human Laminin subunit alpha-3-EGF9 protein | PRT536 |
| SEQ ID NO: 537 | human Laminin subunit alpha-4-EGF1 protein | PRT537 |
| SEQ ID NO: 538 | human Laminin subunit alpha-4-EGF2 protein | PRT538 |
| SEQ ID NO: 539 | human Laminin subunit alpha-4-EGF3 protein | PRT539 |
| SEQ ID NO: 540 | human Laminin subunit alpha-5-EGF1 protein | PRT540 |
| SEQ ID NO: 541 | human Laminin subunit alpha-5-EGF10 protein | PRT541 |
| SEQ ID NO: 542 | human Laminin subunit alpha-5-EGF11 protein | PRT542 |
| SEQ ID NO: 543 | human Laminin subunit alpha-5-EGF12 protein | PRT543 |
| SEQ ID NO: 544 | human Laminin subunit alpha-5-EGF13 protein | PRT544 |
| SEQ ID NO: 545 | human Laminin subunit alpha-5-EGF14 protein | PRT545 |
| SEQ ID NO: 546 | human Laminin subunit alpha-5-EGF15 protein | PRT546 |
| SEQ ID NO: 547 | human Laminin subunit alpha-5-EGF16 protein | PRT547 |
| SEQ ID NO: 548 | human Laminin subunit alpha-5-EGF17 protein | PRT548 |
| SEQ ID NO: 549 | human Laminin subunit alpha-5-EGF18 protein | PRT549 |
| SEQ ID NO: 550 | human Laminin subunit alpha-5-EGF19 protein | PRT550 |
| SEQ ID NO: 551 | human Laminin subunit alpha-5-EGF2 protein | PRT551 |
| SEQ ID NO: 552 | human Laminin subunit alpha-5-EGF20 protein | PRT552 |
| SEQ ID NO: 553 | human Laminin subunit alpha-5-EGF21 protein | PRT553 |
| SEQ ID NO: 554 | human Laminin subunit alpha-5-EGF3 protein | PRT554 |
| SEQ ID NO: 555 | human Laminin subunit alpha-5-EGF4 protein | PRT555 |
| SEQ ID NO: 556 | human Laminin subunit alpha-5-EGF5 protein | PRT556 |
| SEQ ID NO: 557 | human Laminin subunit alpha-5-EGF6 protein | PRT557 |
| SEQ ID NO: 558 | human Laminin subunit alpha-5-EGF7 protein | PRT558 |

TABLE 1-continued

Designation of the human-originated EGF domain proteins set forth in the present invention

| No. in the sequence listing | Designation | Code in the invention |
|---|---|---|
| SEQ ID NO: 559 | human Laminin subunit alpha-5-EGF8 protein | PRT559 |
| SEQ ID NO: 560 | human Laminin subunit alpha-5-EGF9 protein | PRT560 |
| SEQ ID NO: 561 | human Laminin subunit beta-1-EGF1 protein | PRT561 |
| SEQ ID NO: 562 | human Laminin subunit beta-1-EGF10 protein | PRT562 |
| SEQ ID NO: 563 | human Laminin subunit beta-1-EGF11 protein | PRT563 |
| SEQ ID NO: 564 | human Laminin subunit beta-1-EGF12 protein | PRT564 |
| SEQ ID NO: 565 | human Laminin subunit beta-1-EGF13 protein | PRT565 |
| SEQ ID NO: 566 | human Laminin subunit beta-1-EGF2 protein | PRT566 |
| SEQ ID NO: 567 | human Laminin subunit beta-1-EGF3 protein | PRT567 |
| SEQ ID NO: 568 | human Laminin subunit beta-1-EGF4 protein | PRT568 |
| SEQ ID NO: 569 | human Laminin subunit beta-1-EGF5 protein | PRT569 |
| SEQ ID NO: 570 | human Laminin subunit beta-1-EGF6 protein | PRT570 |
| SEQ ID NO: 571 | human Laminin subunit beta-1-EGF7 protein | PRT571 |
| SEQ ID NO: 572 | human Laminin subunit beta-1-EGF8 protein | PRT572 |
| SEQ ID NO: 573 | human Laminin subunit beta-1-EGF9 protein | PRT573 |
| SEQ ID NO: 574 | human Laminin subunit beta-2-EGF1 protein | PRT574 |
| SEQ ID NO: 575 | human Laminin subunit beta-2-EGF10 protein | PRT575 |
| SEQ ID NO: 576 | human Laminin subunit beta-2-EGF11 protein | PRT576 |
| SEQ ID NO: 577 | human Laminin subunit beta-2-EGF12 protein | PRT577 |
| SEQ ID NO: 578 | human Laminin subunit beta-2-EGF13 protein | PRT578 |
| SEQ ID NO: 579 | human Laminin subunit beta-2-EGF2 protein | PRT579 |
| SEQ ID NO: 580 | human Laminin subunit beta-2-EGF3 protein | PRT580 |
| SEQ ID NO: 581 | human Laminin subunit beta-2-EGF4 protein | PRT581 |
| SEQ ID NO: 582 | human Laminin subunit beta-2-EGF5 protein | PRT582 |
| SEQ ID NO: 583 | human Laminin subunit beta-2-EGF6 protein | PRT583 |
| SEQ ID NO: 584 | human Laminin subunit beta-2-EGF7 protein | PRT584 |
| SEQ ID NO: 585 | human Laminin subunit beta-2-EGF8 protein | PRT585 |
| SEQ ID NO: 586 | human Laminin subunit beta-2-EGF9 protein | PRT586 |
| SEQ ID NO: 587 | human Laminin subunit beta-3-EGF1 protein | PRT587 |
| SEQ ID NO: 588 | human Laminin subunit beta-3-EGF2 protein | PRT588 |
| SEQ ID NO: 589 | human Laminin subunit beta-3-EGF3 protein | PRT589 |
| SEQ ID NO: 590 | human Laminin subunit beta-3-EGF4 protein | PRT590 |
| SEQ ID NO: 591 | human Laminin subunit beta-3-EGF5 protein | PRT591 |
| SEQ ID NO: 592 | human Laminin subunit beta-3-EGF6 protein | PRT592 |
| SEQ ID NO: 593 | human Laminin subunit beta-4-EGF1 protein | PRT593 |
| SEQ ID NO: 594 | human Laminin subunit beta-4-EGF10 protein | PRT594 |
| SEQ ID NO: 595 | human Laminin subunit beta-4-EGF11 protein | PRT595 |
| SEQ ID NO: 596 | human Laminin subunit beta-4-EGF12 protein | PRT596 |
| SEQ ID NO: 597 | human Laminin subunit beta-4-EGF13 protein | PRT597 |
| SEQ ID NO: 598 | human Laminin subunit beta-4-EGF2 protein | PRT598 |
| SEQ ID NO: 599 | human Laminin subunit beta-4-EGF3 protein | PRT599 |
| SEQ ID NO: 600 | human Laminin subunit beta-4-EGF4 protein | PRT600 |
| SEQ ID NO: 601 | human Laminin subunit beta-4-EGF5 protein | PRT601 |
| SEQ ID NO: 602 | human Laminin subunit beta-4-EGF6 protein | PRT602 |
| SEQ ID NO: 603 | human Laminin subunit beta-4-EGF7 protein | PRT603 |
| SEQ ID NO: 604 | human Laminin subunit beta-4-EGF8 protein | PRT604 |
| SEQ ID NO: 605 | human Laminin subunit beta-4-EGF9 protein | PRT605 |
| SEQ ID NO: 606 | human Laminin subunit gamma-1-EGF1 protein | PRT606 |
| SEQ ID NO: 607 | human Laminin subunit gamma-1-EGF10 protein | PRT607 |
| SEQ ID NO: 608 | human Laminin subunit gamma-1-EGF2 protein | PRT608 |
| SEQ ID NO: 609 | human Laminin subunit gamma-1-EGF3 protein | PRT609 |
| SEQ ID NO: 610 | human Laminin subunit gamma-1-EGF4 protein | PRT610 |
| SEQ ID NO: 611 | human Laminin subunit gamma-1-EGF5 protein | PRT611 |
| SEQ ID NO: 612 | human Laminin subunit gamma-1-EGF6 protein | PRT612 |
| SEQ ID NO: 613 | human Laminin subunit gamma-1-EGF7 protein | PRT613 |
| SEQ ID NO: 614 | human Laminin subunit gamma-1-EGF8 protein | PRT614 |
| SEQ ID NO: 615 | human Laminin subunit gamma-1-EGF9 protein | PRT615 |
| SEQ ID NO: 616 | human Laminin subunit gamma-2-EGF1 protein | PRT616 |
| SEQ ID NO: 617 | human Laminin subunit gamma-2-EGF2 protein | PRT617 |
| SEQ ID NO: 618 | human Laminin subunit gamma-2-EGF3 protein | PRT618 |
| SEQ ID NO: 619 | human Laminin subunit gamma-2-EGF4 protein | PRT619 |
| SEQ ID NO: 620 | human Laminin subunit gamma-2-EGF5 protein | PRT620 |
| SEQ ID NO: 621 | human Laminin subunit gamma-2-EGF6 protein | PRT621 |
| SEQ ID NO: 622 | human Laminin subunit gamma-2-EGF7 protein | PRT622 |
| SEQ ID NO: 623 | human Laminin subunit gamma-3-EGF1 protein | PRT623 |
| SEQ ID NO: 624 | human Laminin subunit gamma-3-EGF10 protein | PRT624 |
| SEQ ID NO: 625 | human Laminin subunit gamma-3-EGF2 protein | PRT625 |
| SEQ ID NO: 626 | human Laminin subunit gamma-3-EGF3 protein | PRT626 |
| SEQ ID NO: 627 | human Laminin subunit gamma-3-EGF4 protein | PRT627 |
| SEQ ID NO: 628 | human Laminin subunit gamma-3-EGF5 protein | PRT628 |
| SEQ ID NO: 629 | human Laminin subunit gamma-3-EGF6 protein | PRT629 |
| SEQ ID NO: 630 | human Laminin subunit gamma-3-EGF7 protein | PRT630 |
| SEQ ID NO: 631 | human Laminin subunit gamma-3-EGF8 protein | PRT631 |
| SEQ ID NO: 632 | human Laminin subunit gamma-3-EGF9 protein | PRT632 |

TABLE 1-continued

Designation of the human-originated EGF domain proteins set forth in the present invention

| No. in the sequence listing | Designation | Code in the invention |
|---|---|---|
| SEQ ID NO: 633 | human Latent-transforming growth factor beta-binding protein 1-EGF1 protein | PRT633 |
| SEQ ID NO: 634 | human Latent-transforming growth factor beta-binding protein 1-EGF10 protein | PRT634 |
| SEQ ID NO: 635 | human Latent-transforming growth factor beta-binding protein 1-EGF11 protein | PRT635 |
| SEQ ID NO: 636 | human Latent-transforming growth factor beta-binding protein 1-EGF12 protein | PRT636 |
| SEQ ID NO: 637 | human Latent-transforming growth factor beta-binding protein 1-EGF13 protein | PRT637 |
| SEQ ID NO: 638 | human Latent-transforming growth factor beta-binding protein 1-EGF14 protein | PRT638 |
| SEQ ID NO: 639 | human Latent-transforming growth factor beta-binding protein 1-EGF15 protein | PRT639 |
| SEQ ID NO: 640 | human Latent-transforming growth factor beta-binding protein 1-EGF16 protein | PRT640 |
| SEQ ID NO: 641 | human Latent-transforming growth factor beta-binding protein 1-EGF17 protein | PRT641 |
| SEQ ID NO: 642 | human Latent-transforming growth factor beta-binding protein 1-EGF18 protein | PRT642 |
| SEQ ID NO: 643 | human Latent-transforming growth factor beta-binding protein 1-EGF2 protein | PRT643 |
| SEQ ID NO: 644 | human Latent-transforming growth factor beta-binding protein 1-EGF3 protein | PRT644 |
| SEQ ID NO: 645 | human Latent-transforming growth factor beta-binding protein 1-EGF4 protein | PRT645 |
| SEQ ID NO: 646 | human Latent-transforming growth factor beta-binding protein 1-EGF5 protein | PRT646 |
| SEQ ID NO: 647 | human Latent-transforming growth factor beta-binding protein 1-EGF6 protein | PRT647 |
| SEQ ID NO: 648 | human Latent-transforming growth factor beta-binding protein 1-EGF7 protein | PRT648 |
| SEQ ID NO: 649 | human Latent-transforming growth factor beta-binding protein 1-EGF8 protein | PRT649 |
| SEQ ID NO: 650 | human Latent-transforming growth factor beta-binding protein 1-EGF9 protein | PRT650 |
| SEQ ID NO: 651 | human Latent-transforming growth factor beta-binding protein 2-EGF1 protein | PRT651 |
| SEQ ID NO: 652 | human Latent-transforming growth factor beta-binding protein 2-EGF10 protein | PRT652 |
| SEQ ID NO: 653 | human Latent-transforming growth factor beta-binding protein 2-EGF11 protein | PRT653 |
| SEQ ID NO: 654 | human Latent-transforming growth factor beta-binding protein 2-EGF12 protein | PRT654 |
| SEQ ID NO: 655 | human Latent-transforming growth factor beta-binding protein 2-EGF13 protein | PRT655 |
| SEQ ID NO: 656 | human Latent-transforming growth factor beta-binding protein 2-EGF14 protein | PRT656 |
| SEQ ID NO: 657 | human Latent-transforming growth factor beta-binding protein 2-EGF15 protein | PRT657 |
| SEQ ID NO: 658 | human Latent-transforming growth factor beta-binding protein 2-EGF16 protein | PRT658 |
| SEQ ID NO: 659 | human Latent-transforming growth factor beta-binding protein 2-EGF17 protein | PRT659 |
| SEQ ID NO: 660 | human Latent-transforming growth factor beta-binding protein 2-EGF18 protein | PRT660 |
| SEQ ID NO: 661 | human Latent-transforming growth factor beta-binding protein 2-EGF19 protein | PRT661 |
| SEQ ID NO: 662 | human Latent-transforming growth factor beta-binding protein 2-EGF2 protein | PRT662 |
| SEQ ID NO: 663 | human Latent-transforming growth factor beta-binding protein 2-EGF20 protein | PRT663 |
| SEQ ID NO: 664 | human Latent-transforming growth factor beta-binding protein 2-EGF3 protein | PRT664 |
| SEQ ID NO: 665 | human Latent-transforming growth factor beta-binding protein 2-EGF4 protein | PRT665 |
| SEQ ID NO: 666 | human Latent-transforming growth factor beta-binding protein 2-EGF5 protein | PRT666 |
| SEQ ID NO: 667 | human Latent-transforming growth factor beta-binding protein 2-EGF6 protein | PRT667 |
| SEQ ID NO: 668 | human Latent-transforming growth factor beta-binding protein 2-EGF7 protein | PRT668 |
| SEQ ID NO: 669 | human Latent-transforming growth factor beta-binding protein 2-EGF8 protein | PRT669 |

TABLE 1-continued

Designation of the human-originated EGF domain proteins set forth in the present invention

| No. in the sequence listing | Designation | Code in the invention |
|---|---|---|
| SEQ ID NO: 670 | human Latent-transforming growth factor beta-binding protein 2-EGF9 protein | PRT670 |
| SEQ ID NO: 671 | human Latent-transforming growth factor beta-binding protein 3-EGF1 protein | PRT671 |
| SEQ ID NO: 672 | human Latent-transforming growth factor beta-binding protein 3-EGF10 protein | PRT672 |
| SEQ ID NO: 673 | human Latent-transforming growth factor beta-binding protein 3-EGF11 protein | PRT673 |
| SEQ ID NO: 674 | human Latent-transforming growth factor beta-binding protein 3-EGF12 protein | PRT674 |
| SEQ ID NO: 675 | human Latent-transforming growth factor beta-binding protein 3-EGF13 protein | PRT675 |
| SEQ ID NO: 676 | human Latent-transforming growth factor beta-binding protein 3-EGF2 protein | PRT676 |
| SEQ ID NO: 677 | human Latent-transforming growth factor beta-binding protein 3-EGF3 protein | PRT677 |
| SEQ ID NO: 678 | human Latent-transforming growth factor beta-binding protein 3-EGF4 protein | PRT678 |
| SEQ ID NO: 679 | human Latent-transforming growth factor beta-binding protein 3-EGF5 protein | PRT679 |
| SEQ ID NO: 680 | human Latent-transforming growth factor beta-binding protein 3-EGF6 protein | PRT680 |
| SEQ ID NO: 681 | human Latent-transforming growth factor beta-binding protein 3-EGF7 protein | PRT681 |
| SEQ ID NO: 682 | human Latent-transforming growth factor beta-binding protein 3-EGF8 protein | PRT682 |
| SEQ ID NO: 683 | human Latent-transforming growth factor beta-binding protein 3-EGF9 protein | PRT683 |
| SEQ ID NO: 684 | human Latent-transforming growth factor beta-binding protein 4-EGF1 protein | PRT684 |
| SEQ ID NO: 685 | human Latent-transforming growth factor beta-binding protein 4-EGF10 protein | PRT685 |
| SEQ ID NO: 686 | human Latent-transforming growth factor beta-binding protein 4-EGF11 protein | PRT686 |
| SEQ ID NO: 687 | human Latent-transforming growth factor beta-binding protein 4-EGF12 protein | PRT687 |
| SEQ ID NO: 688 | human Latent-transforming growth factor beta-binding protein 4-EGF13 protein | PRT688 |
| SEQ ID NO: 689 | human Latent-transforming growth factor beta-binding protein 4-EGF14 protein | PRT689 |
| SEQ ID NO: 690 | human Latent-transforming growth factor beta-binding protein 4-EGF15 protein | PRT690 |
| SEQ ID NO: 691 | human Latent-transforming growth factor beta-binding protein 4-EGF16 protein | PRT691 |
| SEQ ID NO: 692 | human Latent-transforming growth factor beta-binding protein 4-EGF2 protein | PRT692 |
| SEQ ID NO: 693 | human Latent-transforming growth factor beta-binding protein 4-EGF3 protein | PRT693 |
| SEQ ID NO: 694 | human Latent-transforming growth factor beta-binding protein 4-EGF4 protein | PRT694 |
| SEQ ID NO: 695 | human Latent-transforming growth factor beta-binding protein 4-EGF5 protein | PRT695 |
| SEQ ID NO: 696 | human Latent-transforming growth factor beta-binding protein 4-EGF6 protein | PRT696 |
| SEQ ID NO: 697 | human Latent-transforming growth factor beta-binding protein 4-EGF7 protein | PRT697 |
| SEQ ID NO: 698 | human Latent-transforming growth factor beta-binding protein 4-EGF8 protein | PRT698 |
| SEQ ID NO: 699 | human Latent-transforming growth factor beta-binding protein 4-EGF9 protein | PRT699 |
| SEQ ID NO: 700 | human Low-density lipoprotein receptor-EGF1 protein | PRT700 |
| SEQ ID NO: 701 | human Low-density lipoprotein receptor-EGF2 protein | PRT701 |
| SEQ ID NO: 702 | human Low-density lipoprotein receptor-EGF3 protein | PRT702 |
| SEQ ID NO: 703 | human Low-density lipoprotein receptor-related protein 1-EGF1 protein | PRT703 |
| SEQ ID NO: 704 | human Low-density lipoprotein receptor-related protein 1B-EGF1 protein | PRT704 |
| SEQ ID NO: 705 | human Low-density lipoprotein receptor-related protein 1B-EGF10 protein | PRT705 |
| SEQ ID NO: 706 | human Low-density lipoprotein receptor-related protein 1B-EGF11 protein | PRT706 |
| SEQ ID NO: 707 | human Low-density lipoprotein receptor-related protein 1B-EGF12 protein | PRT707 |
| SEQ ID NO: 708 | human Low-density lipoprotein receptor-related protein 1B-EGF13 protein | PRT708 |

TABLE 1-continued

Designation of the human-originated EGF domain proteins set forth in the present invention

| No. in the sequence listing | Designation | Code in the invention |
|---|---|---|
| SEQ ID NO: 709 | human Low-density lipoprotein receptor-related protein 1B-EGF14 protein | PRT709 |
| SEQ ID NO: 710 | human Low-density lipoprotein receptor-related protein 1B-EGF2 protein | PRT710 |
| SEQ ID NO: 711 | human Low-density lipoprotein receptor-related protein 1B-EGF3 protein | PRT711 |
| SEQ ID NO: 712 | human Low-density lipoprotein receptor-related protein 1B-EGF4 protein | PRT712 |
| SEQ ID NO: 713 | human Low-density lipoprotein receptor-related protein 1B-EGF5 protein | PRT713 |
| SEQ ID NO: 714 | human Low-density lipoprotein receptor-related protein 1B-EGF6 protein | PRT714 |
| SEQ ID NO: 715 | human Low-density lipoprotein receptor-related protein 1B-EGF7 protein | PRT715 |
| SEQ ID NO: 716 | human Low-density lipoprotein receptor-related protein 1B-EGF8 protein | PRT716 |
| SEQ ID NO: 717 | human Low-density lipoprotein receptor-related protein 1B-EGF9 protein | PRT717 |
| SEQ ID NO: 718 | human Low-density lipoprotein receptor-related protein 2-EGF1 protein | PRT718 |
| SEQ ID NO: 719 | human Low-density lipoprotein receptor-related protein 2-EGF10 protein | PRT719 |
| SEQ ID NO: 720 | human Low-density lipoprotein receptor-related protein 2-EGF11 protein | PRT720 |
| SEQ ID NO: 721 | human Low-density lipoprotein receptor-related protein 2-EGF12 protein | PRT721 |
| SEQ ID NO: 722 | human Low-density lipoprotein receptor-related protein 2-EGF13 protein | PRT722 |
| SEQ ID NO: 723 | human Low-density lipoprotein receptor-related protein 2-EGF14 protein | PRT723 |
| SEQ ID NO: 724 | human Low-density lipoprotein receptor-related protein 2-EGF15 protein | PRT724 |
| SEQ ID NO: 725 | human Low-density lipoprotein receptor-related protein 2-EGF16 protein | PRT725 |
| SEQ ID NO: 726 | human Low-density lipoprotein receptor-related protein 2-EGF17 protein | PRT726 |
| SEQ ID NO: 727 | human Low-density lipoprotein receptor-related protein 2-EGF2 protein | PRT727 |
| SEQ ID NO: 728 | human Low-density lipoprotein receptor-related protein 2-EGF3 protein | PRT728 |
| SEQ ID NO: 729 | human Low-density lipoprotein receptor-related protein 2-EGF4 protein | PRT729 |
| SEQ ID NO: 730 | human Low-density lipoprotein receptor-related protein 2-EGF5 protein | PRT730 |
| SEQ ID NO: 731 | human Low-density lipoprotein receptor-related protein 2-EGF6 protein | PRT731 |
| SEQ ID NO: 732 | human Low-density lipoprotein receptor-related protein 2-EGF7 protein | PRT732 |
| SEQ ID NO: 733 | human Low-density lipoprotein receptor-related protein 2-EGF8 protein | PRT733 |
| SEQ ID NO: 734 | human Low-density lipoprotein receptor-related protein 2-EGF9 protein | PRT734 |
| SEQ ID NO: 735 | human Low-density lipoprotein receptor-related protein 4-EGF1 protein | PRT735 |
| SEQ ID NO: 736 | human Low-density lipoprotein receptor-related protein 4-EGF2 protein | PRT736 |
| SEQ ID NO: 737 | human Low-density lipoprotein receptor-related protein 4-EGF3 protein | PRT737 |
| SEQ ID NO: 738 | human Low-density lipoprotein receptor-related protein 5-EGF1 protein | PRT738 |
| SEQ ID NO: 739 | human Low-density lipoprotein receptor-related protein 5-EGF2 protein | PRT739 |
| SEQ ID NO: 740 | human Low-density lipoprotein receptor-related protein 5-EGF3 protein | PRT740 |
| SEQ ID NO: 741 | human Low-density lipoprotein receptor-related protein 5-EGF4 protein | PRT741 |
| SEQ ID NO: 742 | human Low-density lipoprotein receptor-related protein 6-EGF1 protein | PRT742 |
| SEQ ID NO: 743 | human Low-density lipoprotein receptor-related protein 6-EGF2 protein | PRT743 |
| SEQ ID NO: 744 | human Low-density lipoprotein receptor-related protein 6-EGF3 protein | PRT744 |
| SEQ ID NO: 745 | human Low-density lipoprotein receptor-related protein 6-EGF4 protein | PRT745 |

TABLE 1-continued

Designation of the human-originated EGF domain proteins set forth in the present invention

| No. in the sequence listing | Designation | Code in the invention |
|---|---|---|
| SEQ ID NO: 746 | human Low-density lipoprotein receptor-related protein 8-EGF1 protein | PRT746 |
| SEQ ID NO: 747 | human Low-density lipoprotein receptor-related protein 8-EGF2 protein | PRT747 |
| SEQ ID NO: 748 | human L-selectin-EGF1 protein | PRT748 |
| SEQ ID NO: 749 | human Mannan-binding lectin serine protease 1-EGF1 protein | PRT749 |
| SEQ ID NO: 750 | human Mannan-binding lectin serine protease 2-EGF1 protein | PRT750 |
| SEQ ID NO: 751 | human MATN1 protein-EGF1 protein | PRT751 |
| SEQ ID NO: 752 | human Matrilin-2-EGF1 protein | PRT752 |
| SEQ ID NO: 753 | human Matrilin-2-EGF10 protein | PRT753 |
| SEQ ID NO: 754 | human Matrilin-2-EGF2 protein | PRT754 |
| SEQ ID NO: 755 | human Matrilin-2-EGF3 protein | PRT755 |
| SEQ ID NO: 756 | human Matrilin-2-EGF4 protein | PRT756 |
| SEQ ID NO: 757 | human Matrilin-2-EGF5 protein | PRT757 |
| SEQ ID NO: 758 | human Matrilin-2-EGF6 protein | PRT758 |
| SEQ ID NO: 759 | human Matrilin-2-EGF7 protein | PRT759 |
| SEQ ID NO: 760 | human Matrilin-2-EGF8 protein | PRT760 |
| SEQ ID NO: 761 | human Matrilin-2-EGF9 protein | PRT761 |
| SEQ ID NO: 762 | human Matrilin-3-EGF1 protein | PRT762 |
| SEQ ID NO: 763 | human Matrilin-3-EGF2 protein | PRT763 |
| SEQ ID NO: 764 | human Matrilin-3-EGF3 protein | PRT764 |
| SEQ ID NO: 765 | human Matrilin-3-EGF4 protein | PRT765 |
| SEQ ID NO: 766 | human Matrilin-4-EGF1 protein | PRT766 |
| SEQ ID NO: 767 | human Matrilin-4-EGF2 protein | PRT767 |
| SEQ ID NO: 768 | human Matrilin-4-EGF3 protein | PRT768 |
| SEQ ID NO: 769 | human Matrilin-4-EGF4 protein | PRT769 |
| SEQ ID NO: 770 | human Meprin A subunit alpha-EGF1 protein | PRT770 |
| SEQ ID NO: 771 | human Meprin A subunit beta-EGF1 protein | PRT771 |
| SEQ ID NO: 772 | human Mucin-12-EGF1 protein | PRT772 |
| SEQ ID NO: 773 | human Mucin-13-EGF1 protein | PRT773 |
| SEQ ID NO: 774 | human Mucin-13-EGF2 protein | PRT774 |
| SEQ ID NO: 775 | human Mucin-13-EGF3 protein | PRT775 |
| SEQ ID NO: 776 | human Mucin-17-EGF1 protein | PRT776 |
| SEQ ID NO: 777 | human Mucin-3A-EGF1 protein | PRT777 |
| SEQ ID NO: 778 | human Mucin-4-EGF1 protein | PRT778 |
| SEQ ID NO: 779 | human Mucin-4-EGF2 protein | PRT779 |
| SEQ ID NO: 780 | human Multimerin-1-EGF1 protein | PRT780 |
| SEQ ID NO: 781 | human Multiple epidermal growth factor-like domains protein 10-EGF1 protein | PRT781 |
| SEQ ID NO: 782 | human Multiple epidermal growth factor-like domains protein 10-EGF10 protein | PRT782 |
| SEQ ID NO: 783 | human Multiple epidermal growth factor-like domains protein 10-EGF11 protein | PRT783 |
| SEQ ID NO: 784 | human Multiple epidermal growth factor-like domains protein 10-EGF12 protein | PRT784 |
| SEQ ID NO: 785 | human Multiple epidermal growth factor-like domains protein 10-EGF13 protein | PRT785 |
| SEQ ID NO: 786 | human Multiple epidermal growth factor-like domains protein 10-EGF14 protein | PRT786 |
| SEQ ID NO: 787 | human Multiple epidermal growth factor-like domains protein 10-EGF15 protein | PRT787 |
| SEQ ID NO: 788 | human Multiple epidermal growth factor-like domains protein 10-EGF2 protein | PRT788 |
| SEQ ID NO: 789 | human Multiple epidermal growth factor-like domains protein 10-EGF3 protein | PRT789 |
| SEQ ID NO: 790 | human Multiple epidermal growth factor-like domains protein 10-EGF4 protein | PRT790 |
| SEQ ID NO: 791 | human Multiple epidermal growth factor-like domains protein 10-EGF5 protein | PRT791 |
| SEQ ID NO: 792 | human Multiple epidermal growth factor-like domains protein 10-EGF6 protein | PRT792 |
| SEQ ID NO: 793 | human Multiple epidermal growth factor-like domains protein 10-EGF7 protein | PRT793 |
| SEQ ID NO: 794 | human Multiple epidermal growth factor-like domains protein 10-EGF8 protein | PRT794 |
| SEQ ID NO: 795 | human Multiple epidermal growth factor-like domains protein 10-EGF9 protein | PRT795 |
| SEQ ID NO: 796 | human Multiple epidermal growth factor-like domains protein 11-EGF1 protein | PRT796 |
| SEQ ID NO: 797 | human Multiple epidermal growth factor-like domains protein 11-EGF10 protein | PRT797 |
| SEQ ID NO: 798 | human Multiple epidermal growth factor-like domains protein 11-EGF11 protein | PRT798 |
| SEQ ID NO: 799 | human Multiple epidermal growth factor-like domains protein 11-EGF12 protein | PRT799 |

TABLE 1-continued

Designation of the human-originated EGF domain proteins set forth in the present invention

| No. in the sequence listing | Designation | Code in the invention |
|---|---|---|
| SEQ ID NO: 800 | human Multiple epidermal growth factor-like domains protein 11-EGF13 protein | PRT800 |
| SEQ ID NO: 801 | human Multiple epidermal growth factor-like domains protein 11-EGF14 protein | PRT801 |
| SEQ ID NO: 802 | human Multiple epidermal growth factor-like domains protein 11-EGF2 protein | PRT802 |
| SEQ ID NO: 803 | human Multiple epidermal growth factor-like domains protein 11-EGF3 protein | PRT803 |
| SEQ ID NO: 804 | human Multiple epidermal growth factor-like domains protein 11-EGF4 protein | PRT804 |
| SEQ ID NO: 805 | human Multiple epidermal growth factor-like domains protein 11-EGF5 protein | PRT805 |
| SEQ ID NO: 806 | human Multiple epidermal growth factor-like domains protein 11-EGF6 protein | PRT806 |
| SEQ ID NO: 807 | human Multiple epidermal growth factor-like domains protein 11-EGF7 protein | PRT807 |
| SEQ ID NO: 808 | human Multiple epidermal growth factor-like domains protein 11-EGF8 protein | PRT808 |
| SEQ ID NO: 809 | human Multiple epidermal growth factor-like domains protein 11-EGF9 protein | PRT809 |
| SEQ ID NO: 810 | human Multiple epidermal growth factor-like domains protein 6-EGF1 protein | PRT810 |
| SEQ ID NO: 811 | human Multiple epidermal growth factor-like domains protein 6-EGF10 protein | PRT811 |
| SEQ ID NO: 812 | human Multiple epidermal growth factor-like domains protein 6-EGF11 protein | PRT812 |
| SEQ ID NO: 813 | human Multiple epidermal growth factor-like domains protein 6-EGF12 protein | PRT813 |
| SEQ ID NO: 814 | human Multiple epidermal growth factor-like domains protein 6-EGF13 protein | PRT814 |
| SEQ ID NO: 815 | human Multiple epidermal growth factor-like domains protein 6-EGF14 protein | PRT815 |
| SEQ ID NO: 816 | human Multiple epidermal growth factor-like domains protein 6-EGF15 protein | PRT816 |
| SEQ ID NO: 817 | human Multiple epidermal growth factor-like domains protein 6-EGF16 protein | PRT817 |
| SEQ ID NO: 818 | human Multiple epidermal growth factor-like domains protein 6-EGF17 protein | PRT818 |
| SEQ ID NO: 819 | human Multiple epidermal growth factor-like domains protein 6-EGF18 protein | PRT819 |
| SEQ ID NO: 820 | human Multiple epidermal growth factor-like domains protein 6-EGF19 protein | PRT820 |
| SEQ ID NO: 821 | human Multiple epidermal growth factor-like domains protein 6-EGF2 protein | PRT821 |
| SEQ ID NO: 822 | human Multiple epidermal growth factor-like domains protein 6-EGF20 protein | PRT822 |
| SEQ ID NO: 823 | human Multiple epidermal growth factor-like domains protein 6-EGF21 protein | PRT823 |
| SEQ ID NO: 824 | human Multiple epidermal growth factor-like domains protein 6-EGF22 protein | PRT824 |
| SEQ ID NO: 825 | human Multiple epidermal growth factor-like domains protein 6-EGF23 protein | PRT825 |
| SEQ ID NO: 826 | human Multiple epidermal growth factor-like domains protein 6-EGF24 protein | PRT826 |
| SEQ ID NO: 827 | human Multiple epidermal growth factor-like domains protein 6-EGF25 protein | PRT827 |
| SEQ ID NO: 828 | human Multiple epidermal growth factor-like domains protein 6-EGF26 protein | PRT828 |
| SEQ ID NO: 829 | human Multiple epidermal growth factor-like domains protein 6-EGF27 protein | PRT829 |
| SEQ ID NO: 830 | human Multiple epidermal growth factor-like domains protein 6-EGF3 protein | PRT830 |
| SEQ ID NO: 831 | human Multiple epidermal growth factor-like domains protein 6-EGF4 protein | PRT831 |
| SEQ ID NO: 832 | human Multiple epidermal growth factor-like domains protein 6-EGF5 protein | PRT832 |
| SEQ ID NO: 833 | human Multiple epidermal growth factor-like domains protein 6-EGF6 protein | PRT833 |
| SEQ ID NO: 834 | human Multiple epidermal growth factor-like domains protein 6-EGF7 protein | PRT834 |
| SEQ ID NO: 835 | human Multiple epidermal growth factor-like domains protein 6-EGF8 protein | PRT835 |
| SEQ ID NO: 836 | human Multiple epidermal growth factor-like domains protein 6-EGF9 protein | PRT836 |

TABLE 1-continued

Designation of the human-originated EGF domain proteins set forth in the present invention

| No. in the sequence listing | Designation | Code in the invention |
|---|---|---|
| SEQ ID NO: 837 | human Multiple epidermal growth factor-like domains protein 8-EGF1 protein | PRT837 |
| SEQ ID NO: 838 | human Multiple epidermal growth factor-like domains protein 8-EGF2 protein | PRT838 |
| SEQ ID NO: 839 | human Multiple epidermal growth factor-like domains protein 8-EGF3 protein | PRT839 |
| SEQ ID NO: 840 | human Multiple epidermal growth factor-like domains protein 8-EGF4 protein | PRT840 |
| SEQ ID NO: 841 | human Multiple epidermal growth factor-like domains protein 8-EGF5 protein | PRT841 |
| SEQ ID NO: 842 | human Multiple epidermal growth factor-like domains protein 8-EGF6 protein | PRT842 |
| SEQ ID NO: 843 | human Multiple epidermal growth factor-like domains protein 8-EGF7 protein | PRT843 |
| SEQ ID NO: 844 | human Multiple epidermal growth factor-like domains protein 8-EGF8 protein | PRT844 |
| SEQ ID NO: 845 | human Multiple epidermal growth factor-like domains protein 8-EGF9 protein | PRT845 |
| SEQ ID NO: 846 | human Multiple epidermal growth factor-like domains protein 9-EGF1 protein | PRT846 |
| SEQ ID NO: 847 | human Multiple epidermal growth factor-like domains protein 9-EGF2 protein | PRT847 |
| SEQ ID NO: 848 | human Multiple epidermal growth factor-like domains protein 9-EGF3 protein | PRT848 |
| SEQ ID NO: 849 | human Multiple epidermal growth factor-like domains protein 9-EGF4 protein | PRT849 |
| SEQ ID NO: 850 | human Multiple epidermal growth factor-like domains protein 9-EGF5 protein | PRT850 |
| SEQ ID NO: 851 | human N-acetylglucosamine-1-phosphodiester alpha-N-acetylglucosaminidase-EGF1 protein | PRT851 |
| SEQ ID NO: 852 | human Nephronectin-EGF1 protein | PRT852 |
| SEQ ID NO: 853 | human Nephronectin-EGF2 protein | PRT853 |
| SEQ ID NO: 854 | human Nephronectin-EGF3 protein | PRT854 |
| SEQ ID NO: 855 | human Nephronectin-EGF4 protein | PRT855 |
| SEQ ID NO: 856 | human Nephronectin-EGF5 protein | PRT856 |
| SEQ ID NO: 857 | human Netrin-1-EGF1 protein | PRT857 |
| SEQ ID NO: 858 | human Netrin-1-EGF2 protein | PRT858 |
| SEQ ID NO: 859 | human Netrin-1-EGF3 protein | PRT859 |
| SEQ ID NO: 860 | human Netrin-3-EGF1 protein | PRT860 |
| SEQ ID NO: 861 | human Netrin-3-EGF2 protein | PRT861 |
| SEQ ID NO: 862 | human Netrin-3-EGF3 protein | PRT862 |
| SEQ ID NO: 863 | human Netrin-4-EGF1 protein | PRT863 |
| SEQ ID NO: 864 | human Netrin-4-EGF2 protein | PRT864 |
| SEQ ID NO: 865 | human Netrin-4-EGF3 protein | PRT865 |
| SEQ ID NO: 866 | human Netrin-5-EGF1 protein | PRT866 |
| SEQ ID NO: 867 | human Netrin-5-EGF2 protein | PRT867 |
| SEQ ID NO: 868 | human Netrin-5-EGF3 protein | PRT868 |
| SEQ ID NO: 869 | human Netrin-G1-EGF1 protein | PRT869 |
| SEQ ID NO: 870 | human Netrin-G1-EGF2 protein | PRT870 |
| SEQ ID NO: 871 | human Netrin-G1-EGF3 protein | PRT871 |
| SEQ ID NO: 872 | human Netrin-G2-EGF1 protein | PRT872 |
| SEQ ID NO: 873 | human Netrin-G2-EGF2 protein | PRT873 |
| SEQ ID NO: 874 | human Netrin-G2-EGF3 protein | PRT874 |
| SEQ ID NO: 875 | human Neurexin-1-EGF1 protein | PRT875 |
| SEQ ID NO: 876 | human Neurexin-1-EGF2 protein | PRT876 |
| SEQ ID NO: 877 | human Neurexin-1-EGF3 protein | PRT877 |
| SEQ ID NO: 878 | human Neurexin-2-EGF1 protein | PRT878 |
| SEQ ID NO: 879 | human Neurexin-2-EGF2 protein | PRT879 |
| SEQ ID NO: 880 | human Neurexin-2-EGF3 protein | PRT880 |
| SEQ ID NO: 881 | human Neurexin-3-EGF1 protein | PRT881 |
| SEQ ID NO: 882 | human Neurexin-3-EGF2 protein | PRT882 |
| SEQ ID NO: 883 | human Neurexin-3-EGF3 protein | PRT883 |
| SEQ ID NO: 884 | human Neurocan core protein-EGF1 protein | PRT884 |
| SEQ ID NO: 885 | human Neurocan core protein-EGF2 protein | PRT885 |
| SEQ ID NO: 886 | human Neurogenic locus notch homolog protein 1-EGF1 protein | PRT886 |
| SEQ ID NO: 887 | human Neurogenic locus notch homolog protein 1-EGF10 protein | PRT887 |
| SEQ ID NO: 888 | human Neurogenic locus notch homolog protein 1-EGF11 protein | PRT888 |
| SEQ ID NO: 889 | human Neurogenic locus notch homolog protein 1-EGF12 protein | PRT889 |
| SEQ ID NO: 890 | human Neurogenic locus notch homolog protein 1-EGF13 protein | PRT890 |
| SEQ ID NO: 891 | human Neurogenic locus notch homolog protein 1-EGF14 protein | PRT891 |
| SEQ ID NO: 892 | human Neurogenic locus notch homolog protein 1-EGF15 protein | PRT892 |
| SEQ ID NO: 893 | human Neurogenic locus notch homolog protein 1-EGF16 protein | PRT893 |
| SEQ ID NO: 894 | human Neurogenic locus notch homolog protein 1-EGF17 protein | PRT894 |
| SEQ ID NO: 895 | human Neurogenic locus notch homolog protein 1-EGF18 protein | PRT895 |
| SEQ ID NO: 896 | human Neurogenic locus notch homolog protein 1-EGF19 protein | PRT896 |

TABLE 1-continued

Designation of the human-originated EGF domain proteins set forth in the present invention

| No. in the sequence listing | Designation | Code in the invention |
|---|---|---|
| SEQ ID NO: 897 | human Neurogenic locus notch homolog protein 1-EGF2 protein | PRT897 |
| SEQ ID NO: 898 | human Neurogenic locus notch homolog protein 1-EGF20 protein | PRT898 |
| SEQ ID NO: 899 | human Neurogenic locus notch homolog protein 1-EGF21 protein | PRT899 |
| SEQ ID NO: 900 | human Neurogenic locus notch homolog protein 1-EGF22 protein | PRT900 |
| SEQ ID NO: 901 | human Neurogenic locus notch homolog protein 1-EGF23 protein | PRT901 |
| SEQ ID NO: 902 | human Neurogenic locus notch homolog protein 1-EGF24 protein | PRT902 |
| SEQ ID NO: 903 | human Neurogenic locus notch homolog protein 1-EGF25 protein | PRT903 |
| SEQ ID NO: 904 | human Neurogenic locus notch homolog protein 1-EGF26 protein | PRT904 |
| SEQ ID NO: 905 | human Neurogenic locus notch homolog protein 1-EGF27 protein | PRT905 |
| SEQ ID NO: 906 | human Neurogenic locus notch homolog protein 1-EGF28 protein | PRT906 |
| SEQ ID NO: 907 | human Neurogenic locus notch homolog protein 1-EGF29 protein | PRT907 |
| SEQ ID NO: 908 | human Neurogenic locus notch homolog protein 1-EGF3 protein | PRT908 |
| SEQ ID NO: 909 | human Neurogenic locus notch homolog protein 1-EGF30 protein | PRT909 |
| SEQ ID NO: 910 | human Neurogenic locus notch homolog protein 1-EGF31 protein | PRT910 |
| SEQ ID NO: 911 | human Neurogenic locus notch homolog protein 1-EGF32 protein | PRT911 |
| SEQ ID NO: 912 | human Neurogenic locus notch homolog protein 1-EGF33 protein | PRT912 |
| SEQ ID NO: 913 | human Neurogenic locus notch homolog protein 1-EGF34 protein | PRT913 |
| SEQ ID NO: 914 | human Neurogenic locus notch homolog protein 1-EGF35 protein | PRT914 |
| SEQ ID NO: 915 | human Neurogenic locus notch homolog protein 1-EGF36 protein | PRT915 |
| SEQ ID NO: 916 | human Neurogenic locus notch homolog protein 1-EGF4 protein | PRT916 |
| SEQ ID NO: 917 | human Neurogenic locus notch homolog protein 1-EGF5 protein | PRT917 |
| SEQ ID NO: 918 | human Neurogenic locus notch homolog protein 1-EGF6 protein | PRT918 |
| SEQ ID NO: 919 | human Neurogenic locus notch homolog protein 1-EGF7 protein | PRT919 |
| SEQ ID NO: 920 | human Neurogenic locus notch homolog protein 1-EGF8 protein | PRT920 |
| SEQ ID NO: 921 | human Neurogenic locus notch homolog protein 1-EGF9 protein | PRT921 |
| SEQ ID NO: 922 | human Neurogenic locus notch homolog protein 2-EGF1 protein | PRT922 |
| SEQ ID NO: 923 | human Neurogenic locus notch homolog protein 2-EGF10 protein | PRT923 |
| SEQ ID NO: 924 | human Neurogenic locus notch homolog protein 2-EGF11 protein | PRT924 |
| SEQ ID NO: 925 | human Neurogenic locus notch homolog protein 2-EGF12 protein | PRT925 |
| SEQ ID NO: 926 | human Neurogenic locus notch homolog protein 2-EGF13 protein | PRT926 |
| SEQ ID NO: 927 | human Neurogenic locus notch homolog protein 2-EGF14 protein | PRT927 |
| SEQ ID NO: 928 | human Neurogenic locus notch homolog protein 2-EGF15 protein | PRT928 |
| SEQ ID NO: 929 | human Neurogenic locus notch homolog protein 2-EGF16 protein | PRT929 |
| SEQ ID NO: 930 | human Neurogenic locus notch homolog protein 2-EGF17 protein | PRT930 |
| SEQ ID NO: 931 | human Neurogenic locus notch homolog protein 2-EGF18 protein | PRT931 |
| SEQ ID NO: 932 | human Neurogenic locus notch homolog protein 2-EGF19 protein | PRT932 |
| SEQ ID NO: 933 | human Neurogenic locus notch homolog protein 2-EGF2 protein | PRT933 |
| SEQ ID NO: 934 | human Neurogenic locus notch homolog protein 2-EGF20 protein | PRT934 |
| SEQ ID NO: 935 | human Neurogenic locus notch homolog protein 2-EGF21 protein | PRT935 |
| SEQ ID NO: 936 | human Neurogenic locus notch homolog protein 2-EGF22 protein | PRT936 |
| SEQ ID NO: 937 | human Neurogenic locus notch homolog protein 2-EGF23 protein | PRT937 |
| SEQ ID NO: 938 | human Neurogenic locus notch homolog protein 2-EGF24 protein | PRT938 |
| SEQ ID NO: 939 | human Neurogenic locus notch homolog protein 2-EGF25 protein | PRT939 |
| SEQ ID NO: 940 | human Neurogenic locus notch homolog protein 2-EGF26 protein | PRT940 |
| SEQ ID NO: 941 | human Neurogenic locus notch homolog protein 2-EGF27 protein | PRT941 |
| SEQ ID NO: 942 | human Neurogenic locus notch homolog protein 2-EGF28 protein | PRT942 |
| SEQ ID NO: 943 | human Neurogenic locus notch homolog protein 2-EGF29 protein | PRT943 |
| SEQ ID NO: 944 | human Neurogenic locus notch homolog protein 2-EGF3 protein | PRT944 |
| SEQ ID NO: 945 | human Neurogenic locus notch homolog protein 2-EGF30 protein | PRT945 |
| SEQ ID NO: 946 | human Neurogenic locus notch homolog protein 2-EGF31 protein | PRT946 |
| SEQ ID NO: 947 | human Neurogenic locus notch homolog protein 2-EGF32 protein | PRT947 |
| SEQ ID NO: 948 | human Neurogenic locus notch homolog protein 2-EGF33 protein | PRT948 |
| SEQ ID NO: 949 | human Neurogenic locus notch homolog protein 2-EGF34 protein | PRT949 |
| SEQ ID NO: 950 | human Neurogenic locus notch homolog protein 2-EGF35 protein | PRT950 |
| SEQ ID NO: 951 | human Neurogenic locus notch homolog protein 2-EGF4 protein | PRT951 |
| SEQ ID NO: 952 | human Neurogenic locus notch homolog protein 2-EGF5 protein | PRT952 |
| SEQ ID NO: 953 | human Neurogenic locus notch homolog protein 2-EGF6 protein | PRT953 |
| SEQ ID NO: 954 | human Neurogenic locus notch homolog protein 2-EGF7 protein | PRT954 |
| SEQ ID NO: 955 | human Neurogenic locus notch homolog protein 2-EGF8 protein | PRT955 |
| SEQ ID NO: 956 | human Neurogenic locus notch homolog protein 2-EGF9 protein | PRT956 |
| SEQ ID NO: 957 | human Neurogenic locus notch homolog protein 3-EGF1 protein | PRT957 |
| SEQ ID NO: 958 | human Neurogenic locus notch homolog protein 3-EGF10 protein | PRT958 |
| SEQ ID NO: 959 | human Neurogenic locus notch homolog protein 3-EGF11 protein | PRT959 |
| SEQ ID NO: 960 | human Neurogenic locus notch homolog protein 3-EGF12 protein | PRT960 |
| SEQ ID NO: 961 | human Neurogenic locus notch homolog protein 3-EGF13 protein | PRT961 |
| SEQ ID NO: 962 | human Neurogenic locus notch homolog protein 3-EGF14 protein | PRT962 |
| SEQ ID NO: 963 | human Neurogenic locus notch homolog protein 3-EGF15 protein | PRT963 |
| SEQ ID NO: 964 | human Neurogenic locus notch homolog protein 3-EGF16 protein | PRT964 |
| SEQ ID NO: 965 | human Neurogenic locus notch homolog protein 3-EGF17 protein | PRT965 |
| SEQ ID NO: 966 | human Neurogenic locus notch homolog protein 3-EGF18 protein | PRT966 |
| SEQ ID NO: 967 | human Neurogenic locus notch homolog protein 3-EGF19 protein | PRT967 |
| SEQ ID NO: 968 | human Neurogenic locus notch homolog protein 3-EGF2 protein | PRT968 |
| SEQ ID NO: 969 | human Neurogenic locus notch homolog protein 3-EGF20 protein | PRT969 |
| SEQ ID NO: 970 | human Neurogenic locus notch homolog protein 3-EGF21 protein | PRT970 |
| SEQ ID NO: 971 | human Neurogenic locus notch homolog protein 3-EGF22 protein | PRT971 |

TABLE 1-continued

Designation of the human-originated EGF domain proteins set forth in the present invention

| No. in the sequence listing | Designation | Code in the invention |
|---|---|---|
| SEQ ID NO: 972 | human Neurogenic locus notch homolog protein 3-EGF23 protein | PRT972 |
| SEQ ID NO: 973 | human Neurogenic locus notch homolog protein 3-EGF24 protein | PRT973 |
| SEQ ID NO: 974 | human Neurogenic locus notch homolog protein 3-EGF25 protein | PRT974 |
| SEQ ID NO: 975 | human Neurogenic locus notch homolog protein 3-EGF26 protein | PRT975 |
| SEQ ID NO: 976 | human Neurogenic locus notch homolog protein 3-EGF27 protein | PRT976 |
| SEQ ID NO: 977 | human Neurogenic locus notch homolog protein 3-EGF28 protein | PRT977 |
| SEQ ID NO: 978 | human Neurogenic locus notch homolog protein 3-EGF29 protein | PRT978 |
| SEQ ID NO: 979 | human Neurogenic locus notch homolog protein 3-EGF3 protein | PRT979 |
| SEQ ID NO: 980 | human Neurogenic locus notch homolog protein 3-EGF30 protein | PRT980 |
| SEQ ID NO: 981 | human Neurogenic locus notch homolog protein 3-EGF31 protein | PRT981 |
| SEQ ID NO: 982 | human Neurogenic locus notch homolog protein 3-EGF32 protein | PRT982 |
| SEQ ID NO: 983 | human Neurogenic locus notch homolog protein 3-EGF33 protein | PRT983 |
| SEQ ID NO: 984 | human Neurogenic locus notch homolog protein 3-EGF34 protein | PRT984 |
| SEQ ID NO: 985 | human Neurogenic locus notch homolog protein 3-EGF4 protein | PRT985 |
| SEQ ID NO: 986 | human Neurogenic locus notch homolog protein 3-EGF5 protein | PRT986 |
| SEQ ID NO: 987 | human Neurogenic locus notch homolog protein 3-EGF6 protein | PRT987 |
| SEQ ID NO: 988 | human Neurogenic locus notch homolog protein 3-EGF7 protein | PRT988 |
| SEQ ID NO: 989 | human Neurogenic locus notch homolog protein 3-EGF8 protein | PRT989 |
| SEQ ID NO: 990 | human Neurogenic locus notch homolog protein 3-EGF9 protein | PRT990 |
| SEQ ID NO: 991 | human Neurogenic locus notch homolog protein 4-EGF1 protein | PRT991 |
| SEQ ID NO: 992 | human Neurogenic locus notch homolog protein 4-EGF10 protein | PRT992 |
| SEQ ID NO: 993 | human Neurogenic locus notch homolog protein 4-EGF11 protein | PRT993 |
| SEQ ID NO: 994 | human Neurogenic locus notch homolog protein 4-EGF12 protein | PRT994 |
| SEQ ID NO: 995 | human Neurogenic locus notch homolog protein 4-EGF13 protein | PRT995 |
| SEQ ID NO: 996 | human Neurogenic locus notch homolog protein 4-EGF14 protein | PRT996 |
| SEQ ID NO: 997 | human Neurogenic locus notch homolog protein 4-EGF15 protein | PRT997 |
| SEQ ID NO: 998 | human Neurogenic locus notch homolog protein 4-EGF16 protein | PRT998 |
| SEQ ID NO: 999 | human Neurogenic locus notch homolog protein 4-EGF17 protein | PRT999 |
| SEQ ID NO: 1000 | human Neurogenic locus notch homolog protein 4-EGF18 protein | PRT1000 |
| SEQ ID NO: 1001 | human Neurogenic locus notch homolog protein 4-EGF19 protein | PRT1001 |
| SEQ ID NO: 1002 | human Neurogenic locus notch homolog protein 4-EGF2 protein | PRT1002 |
| SEQ ID NO: 1003 | human Neurogenic locus notch homolog protein 4-EGF20 protein | PRT1003 |
| SEQ ID NO: 1004 | human Neurogenic locus notch homolog protein 4-EGF21 protein | PRT1004 |
| SEQ ID NO: 1005 | human Neurogenic locus notch homolog protein 4-EGF22 protein | PRT1005 |
| SEQ ID NO: 1006 | human Neurogenic locus notch homolog protein 4-EGF23 protein | PRT1006 |
| SEQ ID NO: 1007 | human Neurogenic locus notch homolog protein 4-EGF24 protein | PRT1007 |
| SEQ ID NO: 1008 | human Neurogenic locus notch homolog protein 4-EGF25 protein | PRT1008 |
| SEQ ID NO: 1009 | human Neurogenic locus notch homolog protein 4-EGF26 protein | PRT1009 |
| SEQ ID NO: 1010 | human Neurogenic locus notch homolog protein 4-EGF27 protein | PRT1010 |
| SEQ ID NO: 1011 | human Neurogenic locus notch homolog protein 4-EGF28 protein | PRT1011 |
| SEQ ID NO: 1012 | human Neurogenic locus notch homolog protein 4-EGF29 protein | PRT1012 |
| SEQ ID NO: 1013 | human Neurogenic locus notch homolog protein 4-EGF3 protein | PRT1013 |
| SEQ ID NO: 1014 | human Neurogenic locus notch homolog protein 4-EGF4 protein | PRT1014 |
| SEQ ID NO: 1015 | human Neurogenic locus notch homolog protein 4-EGF5 protein | PRT1015 |
| SEQ ID NO: 1016 | human Neurogenic locus notch homolog protein 4-EGF6 protein | PRT1016 |
| SEQ ID NO: 1017 | human Neurogenic locus notch homolog protein 4-EGF7 protein | PRT1017 |
| SEQ ID NO: 1018 | human Neurogenic locus notch homolog protein 4-EGF8 protein | PRT1018 |
| SEQ ID NO: 1019 | human Neurogenic locus notch homolog protein 4-EGF9 protein | PRT1019 |
| SEQ ID NO: 1020 | human Nidogen-1-EGF1 protein | PRT1020 |
| SEQ ID NO: 1021 | human Nidogen-1-EGF2 protein | PRT1021 |
| SEQ ID NO: 1022 | human Nidogen-1-EGF3 protein | PRT1022 |
| SEQ ID NO: 1023 | human Nidogen-1-EGF4 protein | PRT1023 |
| SEQ ID NO: 1024 | human Nidogen-1-EGF5 protein | PRT1024 |
| SEQ ID NO: 1025 | human Nidogen-1-EGF6 protein | PRT1025 |
| SEQ ID NO: 1026 | human Nidogen-2-EGF1 protein | PRT1026 |
| SEQ ID NO: 1027 | human Nidogen-2-EGF2 protein | PRT1027 |
| SEQ ID NO: 1028 | human Nidogen-2-EGF3 protein | PRT1028 |
| SEQ ID NO: 1029 | human Nidogen-2-EGF4 protein | PRT1029 |
| SEQ ID NO: 1030 | human Nidogen-2-EGF5 protein | PRT1030 |
| SEQ ID NO: 1031 | human Notch homolog 2 N-terminal-like protein-EGF1 protein | PRT1031 |
| SEQ ID NO: 1032 | human Notch homolog 2 N-terminal-like protein-EGF2 protein | PRT1032 |
| SEQ ID NO: 1033 | human Notch homolog 2 N-terminal-like protein-EGF3 protein | PRT1033 |
| SEQ ID NO: 1034 | human Oncoprotein-induced transcript 3 protein-EGF1 protein | PRT1034 |
| SEQ ID NO: 1035 | human Otogelin-EGF1 protein | PRT1035 |
| SEQ ID NO: 1036 | human Pancreatic secretory granule membrane major glycoprotein GP2-EGF1 protein | PRT1036 |
| SEQ ID NO: 1037 | human Perforin-1-EGF1 protein | PRT1037 |
| SEQ ID NO: 1038 | human Pikachurin-EGF1 protein | PRT1038 |
| SEQ ID NO: 1039 | human Pikachurin-EGF2 protein | PRT1039 |
| SEQ ID NO: 1040 | human Pikachurin-EGF3 protein | PRT1040 |
| SEQ ID NO: 1041 | human Platelet endothelial aggregation receptor 1-EGF1 protein | PRT1041 |
| SEQ ID NO: 1042 | human Platelet endothelial aggregation receptor 1-EGF2 protein | PRT1042 |
| SEQ ID NO: 1043 | human Platelet endothelial aggregation receptor 1-EGF3 protein | PRT1043 |
| SEQ ID NO: 1044 | human Platelet endothelial aggregation receptor 1-EGF4 protein | PRT1044 |
| SEQ ID NO: 1045 | human Platelet endothelial aggregation receptor 1-EGF5 protein | PRT1045 |

TABLE 1-continued

Designation of the human-originated EGF domain proteins set forth in the present invention

| No. in the sequence listing | Designation | Code in the invention |
|---|---|---|
| SEQ ID NO: 1046 | human Platelet endothelial aggregation receptor 1-EGF6 protein | PRT1046 |
| SEQ ID NO: 1047 | human Platelet endothelial aggregation receptor 1-EGF7 protein | PRT1047 |
| SEQ ID NO: 1048 | human Platelet endothelial aggregation receptor 1-EGF8 protein | PRT1048 |
| SEQ ID NO: 1049 | human Platelet endothelial aggregation receptor 1-EGF9 protein | PRT1049 |
| SEQ ID NO: 1050 | human Probetacellulin-EGF1 protein | PRT1050 |
| SEQ ID NO: 1051 | human Pro-epidermal growth factor-EGF1 protein | PRT1051 |
| SEQ ID NO: 1052 | human Pro-epidermal growth factor-EGF2 protein | PRT1052 |
| SEQ ID NO: 1053 | human Pro-epidermal growth factor-EGF3 protein | PRT1053 |
| SEQ ID NO: 1054 | human Pro-epidermal growth factor-EGF4 protein | PRT1054 |
| SEQ ID NO: 1055 | human Pro-epidermal growth factor-EGF5 protein | PRT1055 |
| SEQ ID NO: 1056 | human Pro-epidermal growth factor-EGF6 protein | PRT1056 |
| SEQ ID NO: 1057 | human Pro-epidermal growth factor-EGF7 protein | PRT1057 |
| SEQ ID NO: 1058 | human Pro-epidermal growth factor-EGF8 protein | PRT1058 |
| SEQ ID NO: 1059 | human Pro-epidermal growth factor-EGF9 protein | PRT1059 |
| SEQ ID NO: 1060 | human Proepiregulin-EGF1 protein | PRT1060 |
| SEQ ID NO: 1061 | human Proheparin-binding EGF-like growth factor-EGF1 protein | PRT1061 |
| SEQ ID NO: 1062 | human Prolow-density lipoprotein receptor-related protein 1-EGF1 protein | PRT1062 |
| SEQ ID NO: 1063 | human Prolow-density lipoprotein receptor-related protein 1-EGF10 protein | PRT1063 |
| SEQ ID NO: 1064 | human Prolow-density lipoprotein receptor-related protein 1-EGF11 protein | PRT1064 |
| SEQ ID NO: 1065 | human Prolow-density lipoprotein receptor-related protein 1-EGF12 protein | PRT1065 |
| SEQ ID NO: 1066 | human Prolow-density lipoprotein receptor-related protein 1-EGF13 protein | PRT1066 |
| SEQ ID NO: 1067 | human Prolow-density lipoprotein receptor-related protein 1-EGF14 protein | PRT1067 |
| SEQ ID NO: 1068 | human Prolow-density lipoprotein receptor-related protein 1-EGF15 protein | PRT1068 |
| SEQ ID NO: 1069 | human Prolow-density lipoprotein receptor-related protein 1-EGF16 protein | PRT1069 |
| SEQ ID NO: 1070 | human Prolow-density lipoprotein receptor-related protein 1-EGF17 protein | PRT1070 |
| SEQ ID NO: 1071 | human Prolow-density lipoprotein receptor-related protein 1-EGF18 protein | PRT1071 |
| SEQ ID NO: 1072 | human Prolow-density lipoprotein receptor-related protein 1-EGF19 protein | PRT1072 |
| SEQ ID NO: 1073 | human Prolow-density lipoprotein receptor-related protein 1-EGF2 protein | PRT1073 |
| SEQ ID NO: 1074 | human Prolow-density lipoprotein receptor-related protein 1-EGF20 protein | PRT1074 |
| SEQ ID NO: 1075 | human Prolow-density lipoprotein receptor-related protein 1-EGF21 protein | PRT1075 |
| SEQ ID NO: 1076 | human Prolow-density lipoprotein receptor-related protein 1-EGF22 protein | PRT1076 |
| SEQ ID NO: 1077 | human Prolow-density lipoprotein receptor-related protein 1-EGF3 protein | PRT1077 |
| SEQ ID NO: 1078 | human Prolow-density lipoprotein receptor-related protein 1-EGF4 protein | PRT1078 |
| SEQ ID NO: 1079 | human Prolow-density lipoprotein receptor-related protein 1-EGF5 protein | PRT1079 |
| SEQ ID NO: 1080 | human Prolow-density lipoprotein receptor-related protein 1-EGF6 protein | PRT1080 |
| SEQ ID NO: 1081 | human Prolow-density lipoprotein receptor-related protein 1-EGF7 protein | PRT1081 |
| SEQ ID NO: 1082 | human Prolow-density lipoprotein receptor-related protein 1-EGF8 protein | PRT1082 |
| SEQ ID NO: 1083 | human Prolow-density lipoprotein receptor-related protein 1-EGF9 protein | PRT1083 |
| SEQ ID NO: 1084 | human Pro-neuregulin-1, membrane-bound isoform-EGF1 protein | PRT1084 |
| SEQ ID NO: 1085 | human Pro-neuregulin-2, membrane-bound isoform-EGF1 protein | PRT1085 |
| SEQ ID NO: 1086 | human Pro-neuregulin-3, membrane-bound isoform-EGF1 protein | PRT1086 |
| SEQ ID NO: 1087 | human Pro-neuregulin-4, membrane-bound isoform-EGF1 protein | PRT1087 |
| SEQ ID NO: 1088 | human Prostaglandin G/H synthase 1-EGF1 protein | PRT1088 |
| SEQ ID NO: 1089 | human Prostaglandin G/H synthase 2-EGF1 protein | PRT1089 |
| SEQ ID NO: 1090 | human Protein crumbs homolog 1-EGF10 protein | PRT1090 |
| SEQ ID NO: 1091 | human Protein crumbs homolog 1-EGF11 protein | PRT1091 |
| SEQ ID NO: 1092 | human Protein crumbs homolog 1-EGF12 protein | PRT1092 |
| SEQ ID NO: 1093 | human Protein crumbs homolog 1-EGF13 protein | PRT1093 |
| SEQ ID NO: 1094 | human Protein crumbs homolog 1-EGF14 protein | PRT1094 |
| SEQ ID NO: 1095 | human Protein crumbs homolog 1-EGF15 protein | PRT1095 |
| SEQ ID NO: 1096 | human Protein crumbs homolog 1-EGF16 protein | PRT1096 |
| SEQ ID NO: 1097 | human Protein crumbs homolog 1-EGF17 protein | PRT1097 |
| SEQ ID NO: 1098 | human Protein crumbs homolog 1-EGF18 protein | PRT1098 |

TABLE 1-continued

Designation of the human-originated EGF domain proteins set forth in the present invention

| No. in the sequence listing | Designation | Code in the invention |
|---|---|---|
| SEQ ID NO: 1099 | human Protein crumbs homolog 1-EGF19 protein | PRT1099 |
| SEQ ID NO: 1100 | human Protein crumbs homolog 1-EGF20 protein | PRT1100 |
| SEQ ID NO: 1101 | human Protein crumbs homolog 1-EGF2 protein | PRT1101 |
| SEQ ID NO: 1102 | human Protein crumbs homolog 1-EGF3 protein | PRT1102 |
| SEQ ID NO: 1103 | human Protein crumbs homolog 1-EGF4 protein | PRT1103 |
| SEQ ID NO: 1104 | human Protein crumbs homolog 1-EGF5 protein | PRT1104 |
| SEQ ID NO: 1105 | human Protein crumbs homolog 1-EGF6 protein | PRT1105 |
| SEQ ID NO: 1106 | human Protein crumbs homolog 1-EGF7 protein | PRT1106 |
| SEQ ID NO: 1107 | human Protein crumbs homolog 1-EGF8 protein | PRT1107 |
| SEQ ID NO: 1108 | human Protein crumbs homolog 1-EGF9 protein | PRT1108 |
| SEQ ID NO: 1109 | human Protein crumbs homolog 2-EGF1 protein | PRT1109 |
| SEQ ID NO: 1110 | human Protein crumbs homolog 2-EGF10 protein | PRT1110 |
| SEQ ID NO: 1111 | human Protein crumbs homolog 2-EGF11 protein | PRT1111 |
| SEQ ID NO: 1112 | human Protein crumbs homolog 2-EGF12 protein | PRT1112 |
| SEQ ID NO: 1113 | human Protein crumbs homolog 2-EGF13 protein | PRT1113 |
| SEQ ID NO: 1114 | human Protein crumbs homolog 2-EGF14 protein | PRT1114 |
| SEQ ID NO: 1115 | human Protein crumbs homolog 2-EGF15 protein | PRT1115 |
| SEQ ID NO: 1116 | human Protein crumbs homolog 2-EGF2 protein | PRT1116 |
| SEQ ID NO: 1117 | human Protein crumbs homolog 2-EGF3 protein | PRT1117 |
| SEQ ID NO: 1118 | human Protein crumbs homolog 2-EGF4 protein | PRT1118 |
| SEQ ID NO: 1119 | human Protein crumbs homolog 2-EGF5 protein | PRT1119 |
| SEQ ID NO: 1120 | human Protein crumbs homolog 2-EGF6 protein | PRT1120 |
| SEQ ID NO: 1121 | human Protein crumbs homolog 2-EGF7 protein | PRT1121 |
| SEQ ID NO: 1122 | human Protein crumbs homolog 2-EGF8 protein | PRT1122 |
| SEQ ID NO: 1123 | human Protein crumbs homolog 2-EGF9 protein | PRT1123 |
| SEQ ID NO: 1124 | human Protein delta homolog 1-EGF1 protein | PRT1124 |
| SEQ ID NO: 1125 | human Protein delta homolog 1-EGF2 protein | PRT1125 |
| SEQ ID NO: 1126 | human Protein delta homolog 1-EGF3 protein | PRT1126 |
| SEQ ID NO: 1127 | human Protein delta homolog 1-EGF4 protein | PRT1127 |
| SEQ ID NO: 1128 | human Protein delta homolog 1-EGF5 protein | PRT1128 |
| SEQ ID NO: 1129 | human Protein delta homolog 1-EGF6 protein | PRT1129 |
| SEQ ID NO: 1130 | human Protein delta homolog 2-EGF1 protein | PRT1130 |
| SEQ ID NO: 1131 | human Protein delta homolog 2-EGF2 protein | PRT1131 |
| SEQ ID NO: 1132 | human Protein delta homolog 2-EGF3 protein | PRT1132 |
| SEQ ID NO: 1133 | human Protein delta homolog 2-EGF4 protein | PRT1133 |
| SEQ ID NO: 1134 | human Protein delta homolog 2-EGF5 protein | PRT1134 |
| SEQ ID NO: 1135 | human Protein delta homolog 2-EGF6 protein | PRT1135 |
| SEQ ID NO: 1136 | human Protein eyes shut homolog-EGF1 protein | PRT1136 |
| SEQ ID NO: 1137 | human Protein eyes shut homolog-EGF10 protein | PRT1137 |
| SEQ ID NO: 1138 | human Protein eyes shut homolog-EGF11 protein | PRT1138 |
| SEQ ID NO: 1139 | human Protein eyes shut homolog-EGF12 protein | PRT1139 |
| SEQ ID NO: 1140 | human Protein eyes shut homolog-EGF13 protein | PRT1140 |
| SEQ ID NO: 1141 | human Protein eyes shut homolog-EGF14 protein | PRT1141 |
| SEQ ID NO: 1142 | human Protein eyes shut homolog-EGF15 protein | PRT1142 |
| SEQ ID NO: 1143 | human Protein eyes shut homolog-EGF16 protein | PRT1143 |
| SEQ ID NO: 1144 | human Protein eyes shut homolog-EGF17 protein | PRT1144 |
| SEQ ID NO: 1145 | human Protein eyes shut homolog-EGF18 protein | PRT1145 |
| SEQ ID NO: 1146 | human Protein eyes shut homolog-EGF19 protein | PRT1146 |
| SEQ ID NO: 1147 | human Protein eyes shut homolog-EGF2 protein | PRT1147 |
| SEQ ID NO: 1148 | human Protein eyes shut homolog-EGF20 protein | PRT1148 |
| SEQ ID NO: 1149 | human Protein eyes shut homolog-EGF21 protein | PRT1149 |
| SEQ ID NO: 1150 | human Protein eyes shut homolog-EGF22 protein | PRT1150 |
| SEQ ID NO: 1151 | human Protein eyes shut homolog-EGF23 protein | PRT1151 |
| SEQ ID NO: 1152 | human Protein eyes shut homolog-EGF24 protein | PRT1152 |
| SEQ ID NO: 1153 | human Protein eyes shut homolog-EGF25 protein | PRT1153 |
| SEQ ID NO: 1154 | human Protein eyes shut homolog-EGF26 protein | PRT1154 |
| SEQ ID NO: 1155 | human Protein eyes shut homolog-EGF27 protein | PRT1155 |
| SEQ ID NO: 1156 | human Protein eyes shut homolog-EGF3 protein | PRT1156 |
| SEQ ID NO: 1157 | human Protein eyes shut homolog-EGF4 protein | PRT1157 |
| SEQ ID NO: 1158 | human Protein eyes shut homolog-EGF5 protein | PRT1158 |
| SEQ ID NO: 1159 | human Protein eyes shut homolog-EGF6 protein | PRT1159 |
| SEQ ID NO: 1160 | human Protein eyes shut homolog-EGF7 protein | PRT1160 |
| SEQ ID NO: 1161 | human Protein eyes shut homolog-EGF8 protein | PRT1161 |
| SEQ ID NO: 1162 | human Protein eyes shut homolog-EGF9 protein | PRT1162 |
| SEQ ID NO: 1163 | human Protein HEG homolog 1-EGF1 protein | PRT1163 |
| SEQ ID NO: 1164 | human Protein HEG homolog 1-EGF2 protein | PRT1164 |
| SEQ ID NO: 1165 | human Protein jagged-1-EGF1 protein | PRT1165 |
| SEQ ID NO: 1166 | human Protein jagged-1-EGF10 protein | PRT1166 |
| SEQ ID NO: 1167 | human Protein jagged-1-EGF11 protein | PRT1167 |
| SEQ ID NO: 1168 | human Protein jagged-1-EGF12 protein | PRT1168 |
| SEQ ID NO: 1169 | human Protein jagged-1-EGF13 protein | PRT1169 |
| SEQ ID NO: 1170 | human Protein jagged-1-EGF14 protein | PRT1170 |
| SEQ ID NO: 1171 | human Protein jagged-1-EGF15 protein | PRT1171 |
| SEQ ID NO: 1172 | human Protein jagged-1-EGF16 protein | PRT1172 |
| SEQ ID NO: 1173 | human Protein jagged-1-EGF2 protein | PRT1173 |

TABLE 1-continued

Designation of the human-originated EGF domain proteins set forth in the present invention

| No. in the sequence listing | Designation | Code in the invention |
| --- | --- | --- |
| SEQ ID NO: 1174 | human Protein jagged-1-EGF3 protein | PRT1174 |
| SEQ ID NO: 1175 | human Protein jagged-1-EGF4 protein | PRT1175 |
| SEQ ID NO: 1176 | human Protein jagged-1-EGF5 protein | PRT1176 |
| SEQ ID NO: 1177 | human Protein jagged-1-EGF6 protein | PRT1177 |
| SEQ ID NO: 1178 | human Protein jagged-1-EGF7 protein | PRT1178 |
| SEQ ID NO: 1179 | human Protein jagged-1-EGF8 protein | PRT1179 |
| SEQ ID NO: 1180 | human Protein jagged-1-EGF9 protein | PRT1180 |
| SEQ ID NO: 1181 | human Protein jagged-2-EGF1 protein | PRT1181 |
| SEQ ID NO: 1182 | human Protein jagged-2-EGF10 protein | PRT1182 |
| SEQ ID NO: 1183 | human Protein jagged-2-EGF11 protein | PRT1183 |
| SEQ ID NO: 1184 | human Protein jagged-2-EGF12 protein | PRT1184 |
| SEQ ID NO: 1185 | human Protein jagged-2-EGF13 protein | PRT1185 |
| SEQ ID NO: 1186 | human Protein jagged-2-EGF14 protein | PRT1186 |
| SEQ ID NO: 1187 | human Protein jagged-2-EGF15 protein | PRT1187 |
| SEQ ID NO: 1188 | human Protein jagged-2-EGF16 protein | PRT1188 |
| SEQ ID NO: 1189 | human Protein jagged-2-EGF2 protein | PRT1189 |
| SEQ ID NO: 1190 | human Protein jagged-2-EGF3 protein | PRT1190 |
| SEQ ID NO: 1191 | human Protein jagged-2-EGF4 protein | PRT1191 |
| SEQ ID NO: 1192 | human Protein jagged-2-EGF5 protein | PRT1192 |
| SEQ ID NO: 1193 | human Protein jagged-2-EGF6 protein | PRT1193 |
| SEQ ID NO: 1194 | human Protein jagged-2-EGF7 protein | PRT1194 |
| SEQ ID NO: 1195 | human Protein jagged-2-EGF8 protein | PRT1195 |
| SEQ ID NO: 1196 | human Protein jagged-2-EGF9 protein | PRT1196 |
| SEQ ID NO: 1197 | human Protein kinase C-binding protein NELL1-EGF1 protein | PRT1197 |
| SEQ ID NO: 1198 | human Protein kinase C-binding protein NELL1-EGF2 protein | PRT1198 |
| SEQ ID NO: 1199 | human Protein kinase C-binding protein NELL1-EGF3 protein | PRT1199 |
| SEQ ID NO: 1200 | human Protein kinase C-binding protein NELL1-EGF4 protein | PRT1200 |
| SEQ ID NO: 1201 | human Protein kinase C-binding protein NELL1-EGF5 protein | PRT1201 |
| SEQ ID NO: 1202 | human Protein kinase C-binding protein NELL2-EGF1 protein | PRT1202 |
| SEQ ID NO: 1203 | human Protein kinase C-binding protein NELL2-EGF2 protein | PRT1203 |
| SEQ ID NO: 1204 | human Protein kinase C-binding protein NELL2-EGF3 protein | PRT1204 |
| SEQ ID NO: 1205 | human Protein kinase C-binding protein NELL2-EGF4 protein | PRT1205 |
| SEQ ID NO: 1206 | human Protein kinase C-binding protein NELL2-EGF5 protein | PRT1206 |
| SEQ ID NO: 1207 | human Protein kinase C-binding protein NELL2-EGF6 protein | PRT1207 |
| SEQ ID NO: 1208 | human Protocadherin Fat 1-EGF1 protein | PRT1208 |
| SEQ ID NO: 1209 | human Protocadherin Fat 1-EGF2 protein | PRT1209 |
| SEQ ID NO: 1210 | human Protocadherin Fat 1-EGF3 protein | PRT1210 |
| SEQ ID NO: 1211 | human Protocadherin Fat 1-EGF4 protein | PRT1211 |
| SEQ ID NO: 1212 | human Protocadherin Fat 1-EGF5 protein | PRT1212 |
| SEQ ID NO: 1213 | human Protocadherin Fat 2-EGF1 protein | PRT1213 |
| SEQ ID NO: 1214 | human Protocadherin Fat 2-EGF2 protein | PRT1214 |
| SEQ ID NO: 1215 | human Protocadherin Fat 3-EGF1 protein | PRT1215 |
| SEQ ID NO: 1216 | human Protocadherin Fat 3-EGF2 protein | PRT1216 |
| SEQ ID NO: 1217 | human Protocadherin Fat 3-EGF3 protein | PRT1217 |
| SEQ ID NO: 1218 | human Protocadherin Fat 3-EGF4 protein | PRT1218 |
| SEQ ID NO: 1219 | human Protocadherin Fat 4-EGF1 protein | PRT1219 |
| SEQ ID NO: 1220 | human Protocadherin Fat 4-EGF2 protein | PRT1220 |
| SEQ ID NO: 1221 | human Protocadherin Fat 4-EGF3 protein | PRT1221 |
| SEQ ID NO: 1222 | human Protocadherin Fat 4-EGF4 protein | PRT1222 |
| SEQ ID NO: 1223 | human Protocadherin Fat 4-EGF5 protein | PRT1223 |
| SEQ ID NO: 1224 | human Protocadherin Fat 4-EGF6 protein | PRT1224 |
| SEQ ID NO: 1225 | human Protransforming growth factor alpha-EGF1 protein | PRT1225 |
| SEQ ID NO: 1226 | human P-selectin-EGF1 protein | PRT1226 |
| SEQ ID NO: 1227 | human Putative disintegrin and metalloproteinase domain-containing protein 5-EGF1 protein | PRT1227 |
| SEQ ID NO: 1228 | human Putative EGF-like module-containing mucin-like hormone receptor-like 4-EGF1 protein | PRT1228 |
| SEQ ID NO: 1229 | human Putative EGF-like module-containing mucin-like hormone receptor-like 4-EGF2 protein | PRT1229 |
| SEQ ID NO: 1230 | human Putative teratocarcinoma-derived growth factor 3-EGF1 protein | PRT1230 |
| SEQ ID NO: 1231 | human Reelin-EGF1 protein | PRT1231 |
| SEQ ID NO: 1232 | human Reelin-EGF2 protein | PRT1232 |
| SEQ ID NO: 1233 | human Reelin-EGF3 protein | PRT1233 |
| SEQ ID NO: 1234 | human Reelin-EGF4 protein | PRT1234 |
| SEQ ID NO: 1235 | human Reelin-EGF5 protein | PRT1235 |
| SEQ ID NO: 1236 | human Reelin-EGF6 protein | PRT1236 |
| SEQ ID NO: 1237 | human Reelin-EGF7 protein | PRT1237 |
| SEQ ID NO: 1238 | human Reelin-EGF8 protein | PRT1238 |
| SEQ ID NO: 1239 | human Scavenger receptor class F member 1-EGF1 protein | PRT1239 |
| SEQ ID NO: 1240 | human Scavenger receptor class F member 1-EGF2 protein | PRT1240 |
| SEQ ID NO: 1241 | human Scavenger receptor class F member 1-EGF3 protein | PRT1241 |
| SEQ ID NO: 1242 | human Scavenger receptor class F member 1-EGF4 protein | PRT1242 |
| SEQ ID NO: 1243 | human Scavenger receptor class F member 1-EGF5 protein | PRT1243 |
| SEQ ID NO: 1244 | human Scavenger receptor class F member 1-EGF6 protein | PRT1244 |

TABLE 1-continued

Designation of the human-originated EGF domain proteins set forth in the present invention

| No. in the sequence listing | Designation | Code in the invention |
|---|---|---|
| SEQ ID NO: 1245 | human Scavenger receptor class F member 2-EGF1 protein | PRT1245 |
| SEQ ID NO: 1246 | human Scavenger receptor class F member 2-EGF2 protein | PRT1246 |
| SEQ ID NO: 1247 | human Scavenger receptor class F member 2-EGF3 protein | PRT1247 |
| SEQ ID NO: 1248 | human Scavenger receptor class F member 2-EGF4 protein | PRT1248 |
| SEQ ID NO: 1249 | human Scavenger receptor class F member 2-EGF5 protein | PRT1249 |
| SEQ ID NO: 1250 | human Scavenger receptor class F member 2-EGF6 protein | PRT1250 |
| SEQ ID NO: 1251 | human Scavenger receptor class F member 2-EGF7 protein | PRT1251 |
| SEQ ID NO: 1252 | human SCO-spondin-EGF1 protein | PRT1252 |
| SEQ ID NO: 1253 | human SCO-spondin-EGF2 protein | PRT1253 |
| SEQ ID NO: 1254 | human Signal peptide, CUB and EGF-like domain-containing protein 1-EGF1 protein | PRT1254 |
| SEQ ID NO: 1255 | human Signal peptide, CUB and EGF-like domain-containing protein 1-EGF2 protein | PRT1255 |
| SEQ ID NO: 1256 | human Signal peptide, CUB and EGF-like domain-containing protein 1-EGF3 protein | PRT1256 |
| SEQ ID NO: 1257 | human Signal peptide, CUB and EGF-like domain-containing protein 1-EGF4 protein | PRT1257 |
| SEQ ID NO: 1258 | human Signal peptide, CUB and EGF-like domain-containing protein 1-EGF5 protein | PRT1258 |
| SEQ ID NO: 1259 | human Signal peptide, CUB and EGF-like domain-containing protein 1-EGF6 protein | PRT1259 |
| SEQ ID NO: 1260 | human Signal peptide, CUB and EGF-like domain-containing protein 1-EGF7 protein | PRT1260 |
| SEQ ID NO: 1261 | human Signal peptide, CUB and EGF-like domain-containing protein 1-EGF8 protein | PRT1261 |
| SEQ ID NO: 1262 | human Signal peptide, CUB and EGF-like domain-containing protein 1-EGF9 protein | PRT1262 |
| SEQ ID NO: 1263 | human Signal peptide, CUB and EGF-like domain-containing protein 2-EGF1 protein | PRT1263 |
| SEQ ID NO: 1264 | human Signal peptide, CUB and EGF-like domain-containing protein 2-EGF2 protein | PRT1264 |
| SEQ ID NO: 1265 | human Signal peptide, CUB and EGF-like domain-containing protein 2-EGF3 protein | PRT1265 |
| SEQ ID NO: 1266 | human Signal peptide, CUB and EGF-like domain-containing protein 2-EGF4 protein | PRT1266 |
| SEQ ID NO: 1267 | human Signal peptide, CUB and EGF-like domain-containing protein 2-EGF5 protein | PRT1267 |
| SEQ ID NO: 1268 | human Signal peptide, CUB and EGF-like domain-containing protein 2-EGF6 protein | PRT1268 |
| SEQ ID NO: 1269 | human Signal peptide, CUB and EGF-like domain-containing protein 2-EGF7 protein | PRT1269 |
| SEQ ID NO: 1270 | human Signal peptide, CUB and EGF-like domain-containing protein 2-EGF8 protein | PRT1270 |
| SEQ ID NO: 1271 | human Signal peptide, CUB and EGF-like domain-containing protein 2-EGF9 protein | PRT1271 |
| SEQ ID NO: 1272 | human Signal peptide, CUB and EGF-like domain-containing protein 3-EGF1 protein | PRT1272 |
| SEQ ID NO: 1273 | human Signal peptide, CUB and EGF-like domain-containing protein 3-EGF2 protein | PRT1273 |
| SEQ ID NO: 1274 | human Signal peptide, CUB and EGF-like domain-containing protein 3-EGF3 protein | PRT1274 |
| SEQ ID NO: 1275 | human Signal peptide, CUB and EGF-like domain-containing protein 3-EGF4 protein | PRT1275 |
| SEQ ID NO: 1276 | human Signal peptide, CUB and EGF-like domain-containing protein 3-EGF5 protein | PRT1276 |
| SEQ ID NO: 1277 | human Signal peptide, CUB and EGF-like domain-containing protein 3-EGF6 protein | PRT1277 |
| SEQ ID NO: 1278 | human Signal peptide, CUB and EGF-like domain-containing protein 3-EGF7 protein | PRT1278 |
| SEQ ID NO: 1279 | human Signal peptide, CUB and EGF-like domain-containing protein 3-EGF8 protein | PRT1279 |
| SEQ ID NO: 1280 | human Signal peptide, CUB and EGF-like domain-containing protein 3-EGF9 protein | PRT1280 |
| SEQ ID NO: 1281 | human Slit homolog 1 protein-EGF1 protein | PRT1281 |
| SEQ ID NO: 1282 | human Slit homolog 1 protein-EGF2 protein | PRT1282 |
| SEQ ID NO: 1283 | human Slit homolog 1 protein-EGF3 protein | PRT1283 |
| SEQ ID NO: 1284 | human Slit homolog 1 protein-EGF4 protein | PRT1284 |
| SEQ ID NO: 1285 | human Slit homolog 1 protein-EGF5 protein | PRT1285 |
| SEQ ID NO: 1286 | human Slit homolog 1 protein-EGF6 protein | PRT1286 |
| SEQ ID NO: 1287 | human Slit homolog 1 protein-EGF7 protein | PRT1287 |
| SEQ ID NO: 1288 | human Slit homolog 1 protein-EGF8 protein | PRT1288 |
| SEQ ID NO: 1289 | human Slit homolog 1 protein-EGF9 protein | PRT1289 |
| SEQ ID NO: 1290 | human Slit homolog 2 protein-EGF1 protein | PRT1290 |
| SEQ ID NO: 1291 | human Slit homolog 2 protein-EGF2 protein | PRT1291 |
| SEQ ID NO: 1292 | human Slit homolog 2 protein-EGF3 protein | PRT1292 |

TABLE 1-continued

Designation of the human-originated EGF domain proteins set forth in the present invention

| No. in the sequence listing | Designation | Code in the invention |
|---|---|---|
| SEQ ID NO: 1293 | human Slit homolog 2 protein-EGF4 protein | PRT1293 |
| SEQ ID NO: 1294 | human Slit homolog 2 protein-EGF5 protein | PRT1294 |
| SEQ ID NO: 1295 | human Slit homolog 2 protein-EGF6 protein | PRT1295 |
| SEQ ID NO: 1296 | human Slit homolog 2 protein-EGF7 protein | PRT1296 |
| SEQ ID NO: 1297 | human Slit homolog 3 protein-EGF1 protein | PRT1297 |
| SEQ ID NO: 1298 | human Slit homolog 3 protein-EGF2 protein | PRT1298 |
| SEQ ID NO: 1299 | human Slit homolog 3 protein-EGF3 protein | PRT1299 |
| SEQ ID NO: 1300 | human Slit homolog 3 protein-EGF4 protein | PRT1300 |
| SEQ ID NO: 1301 | human Slit homolog 3 protein-EGF5 protein | PRT1301 |
| SEQ ID NO: 1302 | human Slit homolog 3 protein-EGF6 protein | PRT1302 |
| SEQ ID NO: 1303 | human Slit homolog 3 protein-EGF7 protein | PRT1303 |
| SEQ ID NO: 1304 | human Slit homolog 3 protein-EGF8 protein | PRT1304 |
| SEQ ID NO: 1305 | human Slit homolog 3 protein-EGF9 protein | PRT1305 |
| SEQ ID NO: 1306 | human Sortilin-related receptor-EGF1 protein | PRT1306 |
| SEQ ID NO: 1307 | human Stabilin-1-EGF1 protein | PRT1307 |
| SEQ ID NO: 1308 | human Stabilin-1-EGF10 protein | PRT1308 |
| SEQ ID NO: 1309 | human Stabilin-1-EGF11 protein | PRT1309 |
| SEQ ID NO: 1310 | human Stabilin-1-EGF12 protein | PRT1310 |
| SEQ ID NO: 1311 | human Stabilin-1-EGF13 protein | PRT1311 |
| SEQ ID NO: 1312 | human Stabilin-1-EGF14 protein | PRT1312 |
| SEQ ID NO: 1313 | human Stabilin-1-EGF15 protein | PRT1313 |
| SEQ ID NO: 1314 | human Stabilin-1-EGF16 protein | PRT1314 |
| SEQ ID NO: 1315 | human Stabilin-1-EGF2 protein | PRT1315 |
| SEQ ID NO: 1316 | human Stabilin-1-EGF3 protein | PRT1316 |
| SEQ ID NO: 1317 | human Stabilin-1-EGF4 protein | PRT1317 |
| SEQ ID NO: 1318 | human Stabilin-1-EGF5 protein | PRT1318 |
| SEQ ID NO: 1319 | human Stabilin-1-EGF6 protein | PRT1319 |
| SEQ ID NO: 1320 | human Stabilin-1-EGF7 protein | PRT1320 |
| SEQ ID NO: 1321 | human Stabilin-1-EGF8 protein | PRT1321 |
| SEQ ID NO: 1322 | human Stabilin-1-EGF9 protein | PRT1322 |
| SEQ ID NO: 1323 | human Stabilin-2-EGF1 protein | PRT1323 |
| SEQ ID NO: 1324 | human Stabilin-2-EGF10 protein | PRT1324 |
| SEQ ID NO: 1325 | human Stabilin-2-EGF11 protein | PRT1325 |
| SEQ ID NO: 1326 | human Stabilin-2-EGF12 protein | PRT1326 |
| SEQ ID NO: 1327 | human Stabilin-2-EGF13 protein | PRT1327 |
| SEQ ID NO: 1328 | human Stabilin-2-EGF14 protein | PRT1328 |
| SEQ ID NO: 1329 | human Stabilin-2-EGF15 protein | PRT1329 |
| SEQ ID NO: 1330 | human Stabilin-2-EGF16 protein | PRT1330 |
| SEQ ID NO: 1331 | human Stabilin-2-EGF17 protein | PRT1331 |
| SEQ ID NO: 1332 | human Stabilin-2-EGF2 protein | PRT1332 |
| SEQ ID NO: 1333 | human Stabilin-2-EGF3 protein | PRT1333 |
| SEQ ID NO: 1334 | human Stabilin-2-EGF4 protein | PRT1334 |
| SEQ ID NO: 1335 | human Stabilin-2-EGF5 protein | PRT1335 |
| SEQ ID NO: 1336 | human Stabilin-2-EGF6 protein | PRT1336 |
| SEQ ID NO: 1337 | human Stabilin-2-EGF7 protein | PRT1337 |
| SEQ ID NO: 1338 | human Stabilin-2-EGF8 protein | PRT1338 |
| SEQ ID NO: 1339 | human Stabilin-2-EGF9 protein | PRT1339 |
| SEQ ID NO: 1340 | human Sushi domain-containing protein 1-EGF1 protein | PRT1340 |
| SEQ ID NO: 1341 | human Sushi domain-containing protein 1-EGF2 protein | PRT1341 |
| SEQ ID NO: 1342 | human Sushi domain-containing protein 1-EGF3 protein | PRT1342 |
| SEQ ID NO: 1343 | human Sushi, von Willebrand factor type A, EGF and pentraxin domain-containing protein 1-EGF1 protein | PRT1343 |
| SEQ ID NO: 1344 | human Sushi, von Willebrand factor type A, EGF and pentraxin domain-containing protein 1-EGF2 protein | PRT1344 |
| SEQ ID NO: 1345 | human Sushi, von Willebrand factor type A, EGF and pentraxin domain-containing protein 1-EGF3 protein | PRT1345 |
| SEQ ID NO: 1346 | human Sushi, von Willebrand factor type A, EGF and pentraxin domain-containing protein 1-EGF4 protein | PRT1346 |
| SEQ ID NO: 1347 | human Sushi, von Willebrand factor type A, EGF and pentraxin domain-containing protein 1-EGF5 protein | PRT1347 |
| SEQ ID NO: 1348 | human Sushi, von Willebrand factor type A, EGF and pentraxin domain-containing protein 1-EGF6 protein | PRT1348 |
| SEQ ID NO: 1349 | human Sushi, von Willebrand factor type A, EGF and pentraxin domain-containing protein 1-EGF7 protein | PRT1349 |
| SEQ ID NO: 1350 | human Sushi, von Willebrand factor type A, EGF and pentraxin domain-containing protein 1-EGF8 protein | PRT1350 |
| SEQ ID NO: 1351 | human Sushi, von Willebrand factor type A, EGF and pentraxin domain-containing protein 1-EGF9 protein | PRT1351 |
| SEQ ID NO: 1352 | human Tenascin-EGF1 protein | PRT1352 |
| SEQ ID NO: 1353 | human Tenascin-EGF10 protein | PRT1353 |
| SEQ ID NO: 1354 | human Tenascin-EGF11 protein | PRT1354 |
| SEQ ID NO: 1355 | human Tenascin-EGF12 protein | PRT1355 |
| SEQ ID NO: 1356 | human Tenascin-EGF13 protein | PRT1356 |
| SEQ ID NO: 1357 | human Tenascin-EGF14 protein | PRT1357 |
| SEQ ID NO: 1358 | human Tenascin-EGF2 protein | PRT1358 |

TABLE 1-continued

Designation of the human-originated EGF domain proteins set forth in the present invention

| No. in the sequence listing | Designation | Code in the invention |
|---|---|---|
| SEQ ID NO: 1359 | human Tenascin-EGF3 protein | PRT1359 |
| SEQ ID NO: 1360 | human Tenascin-EGF4 protein | PRT1360 |
| SEQ ID NO: 1361 | human Tenascin-EGF5 protein | PRT1361 |
| SEQ ID NO: 1362 | human Tenascin-EGF6 protein | PRT1362 |
| SEQ ID NO: 1363 | human Tenascin-EGF7 protein | PRT1363 |
| SEQ ID NO: 1364 | human Tenascin-EGF8 protein | PRT1364 |
| SEQ ID NO: 1365 | human Tenascin-EGF9 protein | PRT1365 |
| SEQ ID NO: 1366 | human Tenascin-N-EGF1 protein | PRT1366 |
| SEQ ID NO: 1367 | human Tenascin-N-EGF2 protein | PRT1367 |
| SEQ ID NO: 1368 | human Tenascin-N-EGF3 protein | PRT1368 |
| SEQ ID NO: 1369 | human Tenascin-X-EGF1 protein | PRT1369 |
| SEQ ID NO: 1370 | human Tenascin-X-EGF10 protein | PRT1370 |
| SEQ ID NO: 1371 | human Tenascin-X-EGF11 protein | PRT1371 |
| SEQ ID NO: 1372 | human Tenascin-X-EGF12 protein | PRT1372 |
| SEQ ID NO: 1373 | human Tenascin-X-EGF13 protein | PRT1373 |
| SEQ ID NO: 1374 | human Tenascin-X-EGF14 protein | PRT1374 |
| SEQ ID NO: 1375 | human Tenascin-X-EGF15 protein | PRT1375 |
| SEQ ID NO: 1376 | human Tenascin-X-EGF16 protein | PRT1376 |
| SEQ ID NO: 1377 | human Tenascin-X-EGF17 protein | PRT1377 |
| SEQ ID NO: 1378 | human Tenascin-X-EGF18 protein | PRT1378 |
| SEQ ID NO: 1379 | human Tenascin-X-EGF2 protein | PRT1379 |
| SEQ ID NO: 1380 | human Tenascin-X-EGF3 protein | PRT1380 |
| SEQ ID NO: 1381 | human Tenascin-X-EGF4 protein | PRT1381 |
| SEQ ID NO: 1382 | human Tenascin-X-EGF5 protein | PRT1382 |
| SEQ ID NO: 1383 | human Tenascin-X-EGF6 protein | PRT1383 |
| SEQ ID NO: 1384 | human Tenascin-X-EGF7 protein | PRT1384 |
| SEQ ID NO: 1385 | human Tenascin-X-EGF8 protein | PRT1385 |
| SEQ ID NO: 1386 | human Tenascin-X-EGF9 protein | PRT1386 |
| SEQ ID NO: 1387 | human Teneurin-1-EGF1 protein | PRT1387 |
| SEQ ID NO: 1388 | human Teneurin-1-EGF2 protein | PRT1388 |
| SEQ ID NO: 1389 | human Teneurin-1-EGF3 protein | PRT1389 |
| SEQ ID NO: 1390 | human Teneurin-1-EGF4 protein | PRT1390 |
| SEQ ID NO: 1391 | human Teneurin-1-EGF5 protein | PRT1391 |
| SEQ ID NO: 1392 | human Teneurin-1-EGF6 protein | PRT1392 |
| SEQ ID NO: 1393 | human Teneurin-1-EGF7 protein | PRT1393 |
| SEQ ID NO: 1394 | human Teneurin-1-EGF8 protein | PRT1394 |
| SEQ ID NO: 1395 | human Teneurin-2-EGF1 protein | PRT1395 |
| SEQ ID NO: 1396 | human Teneurin-2-EGF2 protein | PRT1396 |
| SEQ ID NO: 1397 | human Teneurin-2-EGF3 protein | PRT1397 |
| SEQ ID NO: 1398 | human Teneurin-2-EGF4 protein | PRT1398 |
| SEQ ID NO: 1399 | human Teneurin-2-EGF5 protein | PRT1399 |
| SEQ ID NO: 1400 | human Teneurin-2-EGF6 protein | PRT1400 |
| SEQ ID NO: 1401 | human Teneurin-2-EGF7 protein | PRT1401 |
| SEQ ID NO: 1402 | human Teneurin-2-EGF8 protein | PRT1402 |
| SEQ ID NO: 1403 | human Teneurin-3-EGF1 protein | PRT1403 |
| SEQ ID NO: 1404 | human Teneurin-3-EGF2 protein | PRT1404 |
| SEQ ID NO: 1405 | human Teneurin-3-EGF3 protein | PRT1405 |
| SEQ ID NO: 1406 | human Teneurin-3-EGF4 protein | PRT1406 |
| SEQ ID NO: 1407 | human Teneurin-3-EGF5 protein | PRT1407 |
| SEQ ID NO: 1408 | human Teneurin-3-EGF6 protein | PRT1408 |
| SEQ ID NO: 1409 | human Teneurin-3-EGF7 protein | PRT1409 |
| SEQ ID NO: 1410 | human Teneurin-3-EGF8 protein | PRT1410 |
| SEQ ID NO: 1411 | human Teneurin-4-EGF1 protein | PRT1411 |
| SEQ ID NO: 1412 | human Teneurin-4-EGF2 protein | PRT1412 |
| SEQ ID NO: 1413 | human Teneurin-4-EGF3 protein | PRT1413 |
| SEQ ID NO: 1414 | human Teneurin-4-EGF4 protein | PRT1414 |
| SEQ ID NO: 1415 | human Teneurin-4-EGF5 protein | PRT1415 |
| SEQ ID NO: 1416 | human Teneurin-4-EGF6 protein | PRT1416 |
| SEQ ID NO: 1417 | human Teneurin-4-EGF7 protein | PRT1417 |
| SEQ ID NO: 1418 | human Teneurin-4-EGF8 protein | PRT1418 |
| SEQ ID NO: 1419 | human Teratocarcinoma-derived growth factor 1-EGF1 protein | PRT1419 |
| SEQ ID NO: 1420 | human Thrombomodulin-EGF1 protein | PRT1420 |
| SEQ ID NO: 1421 | human Thrombomodulin-EGF2 protein | PRT1421 |
| SEQ ID NO: 1422 | human Thrombomodulin-EGF3 protein | PRT1422 |
| SEQ ID NO: 1423 | human Thrombomodulin-EGF4 protein | PRT1423 |
| SEQ ID NO: 1424 | human Thrombomodulin-EGF5 protein | PRT1424 |
| SEQ ID NO: 1425 | human Thrombomodulin-EGF6 protein | PRT1425 |
| SEQ ID NO: 1426 | human Thrombospondin-1-EGF1 protein | PRT1426 |
| SEQ ID NO: 1427 | human Thrombospondin-1-EGF2 protein | PRT1427 |
| SEQ ID NO: 1428 | human Thrombospondin-2-EGF1 protein | PRT1428 |
| SEQ ID NO: 1429 | human Thrombospondin-2-EGF2 protein | PRT1429 |
| SEQ ID NO: 1430 | human Thrombospondin-3-EGF1 protein | PRT1430 |
| SEQ ID NO: 1431 | human Thrombospondin-3-EGF2 protein | PRT1431 |
| SEQ ID NO: 1432 | human Thrombospondin-3-EGF3 protein | PRT1432 |
| SEQ ID NO: 1433 | human Thrombospondin-4-EGF1 protein | PRT1433 |

TABLE 1-continued

Designation of the human-originated EGF domain proteins set forth in the present invention

| No. in the sequence listing | Designation | Code in the invention |
|---|---|---|
| SEQ ID NO: 1434 | human Thrombospondin-4-EGF2 protein | PRT1434 |
| SEQ ID NO: 1435 | human Thrombospondin-4-EGF3 protein | PRT1435 |
| SEQ ID NO: 1436 | human Thrombospondin-4-EGF4 protein | PRT1436 |
| SEQ ID NO: 1437 | human Thyroid peroxidase-EGF1 protein | PRT1437 |
| SEQ ID NO: 1438 | human Tissue-type plasminogen activator-EGF1 protein | PRT1438 |
| SEQ ID NO: 1439 | human Tolloid-like protein 1-EGF1 protein | PRT1439 |
| SEQ ID NO: 1440 | human Tolloid-like protein 1-EGF2 protein | PRT1440 |
| SEQ ID NO: 1441 | human Tolloid-like protein 2-EGF1 protein | PRT1441 |
| SEQ ID NO: 1442 | human Tolloid-like protein 2-EGF2 protein | PRT1442 |
| SEQ ID NO: 1443 | human Tomoregulin-1-EGF1 protein | PRT1443 |
| SEQ ID NO: 1444 | human Tomoregulin-2-EGF1 protein | PRT1444 |
| SEQ ID NO: 1445 | human Transmembrane protein 8A-EGF1 protein | PRT1445 |
| SEQ ID NO: 1446 | human Transmembrane protein 8B-EGF1 protein | PRT1446 |
| SEQ ID NO: 1447 | human Tyrosine-protein kinase receptor Tie-1-EGF1 protein | PRT1447 |
| SEQ ID NO: 1448 | human Tyrosine-protein kinase receptor Tie-1-EGF2 protein | PRT1448 |
| SEQ ID NO: 1449 | human Tyrosine-protein kinase receptor Tie-1-EGF3 protein | PRT1449 |
| SEQ ID NO: 1450 | human Urokinase-type plasminogen activator-EGF1 protein | PRT1450 |
| SEQ ID NO: 1451 | human Uromodulin-EGF1 protein | PRT1451 |
| SEQ ID NO: 1452 | human Uromodulin-EGF2 protein | PRT1452 |
| SEQ ID NO: 1453 | human Uromodulin-EGF3 protein | PRT1453 |
| SEQ ID NO: 1454 | human Uromodulin-like 1-EGF1 protein | PRT1454 |
| SEQ ID NO: 1455 | human Uromodulin-like 1-EGF2 protein | PRT1455 |
| SEQ ID NO: 1456 | human Uromodulin-like 1-EGF3 protein | PRT1456 |
| SEQ ID NO: 1457 | human Usherin-EGF1 protein | PRT1457 |
| SEQ ID NO: 1458 | human Usherin-EGF10 protein | PRT1458 |
| SEQ ID NO: 1459 | human Usherin-EGF2 protein | PRT1459 |
| SEQ ID NO: 1460 | human Usherin-EGF3 protein | PRT1460 |
| SEQ ID NO: 1461 | human Usherin-EGF4 protein | PRT1461 |
| SEQ ID NO: 1462 | human Usherin-EGF5 protein | PRT1462 |
| SEQ ID NO: 1463 | human Usherin-EGF6 protein | PRT1463 |
| SEQ ID NO: 1464 | human Usherin-EGF7 protein | PRT1464 |
| SEQ ID NO: 1465 | human Usherin-EGF8 protein | PRT1465 |
| SEQ ID NO: 1466 | human Usherin-EGF9 protein | PRT1466 |
| SEQ ID NO: 1467 | human Vasorin-EGF1 protein | PRT1467 |
| SEQ ID NO: 1468 | human Versican core protein-EGF1 protein | PRT1468 |
| SEQ ID NO: 1469 | human Very low-density lipoprotein receptor-EGF1 protein | PRT1469 |
| SEQ ID NO: 1470 | human Very low-density lipoprotein receptor-EGF2 protein | PRT1470 |
| SEQ ID NO: 1471 | human Very low-density lipoprotein receptor-EGF3 protein | PRT1471 |
| SEQ ID NO: 1472 | human Vitamin K-dependent protein C-EGF1 protein | PRT1472 |
| SEQ ID NO: 1473 | human Vitamin K-dependent protein C-EGF2 protein | PRT1473 |
| SEQ ID NO: 1474 | human Vitamin K-dependent protein S-EGF1 protein | PRT1474 |
| SEQ ID NO: 1475 | human Vitamin K-dependent protein S-EGF2 protein | PRT1475 |
| SEQ ID NO: 1476 | human Vitamin K-dependent protein S-EGF3 protein | PRT1476 |
| SEQ ID NO: 1477 | human Vitamin K-dependent protein S-EGF4 protein | PRT1477 |
| SEQ ID NO: 1478 | human Vitamin K-dependent protein Z-EGF1 protein | PRT1478 |
| SEQ ID NO: 1479 | human Vitamin K-dependent protein Z-EGF2 protein | PRT1479 |
| SEQ ID NO: 1480 | human von Willebrand factor A domain-containing protein 2-EGF1 protein | PRT1480 |
| SEQ ID NO: 1481 | human von Willebrand factor A domain-containing protein 2-EGF2 protein | PRT1481 |
| SEQ ID NO: 1482 | human von Willebrand factor C and EGF domain-containing protein-EGF1 protein | PRT1482 |
| SEQ ID NO: 1483 | human von Willebrand factor C and EGF domain-containing protein-EGF2 protein | PRT1483 |
| SEQ ID NO: 1484 | human von Willebrand factor C and EGF domain-containing protein-EGF3 protein | PRT1484 |
| SEQ ID NO: 1485 | human von Willebrand factor C and EGF domain-containing protein-EGF4 protein | PRT1485 |
| SEQ ID NO: 1486 | human von Willebrand factor D and EGF domain-containing protein-EGF1 protein | PRT1486 |
| SEQ ID NO: 1487 | human von Willebrand factor D and EGF domain-containing protein-EGF2 protein | PRT1487 |
| SEQ ID NO: 1488 | human von Willebrand factor D and EGF domain-containing protein-EGF3 protein | PRT1488 |
| SEQ ID NO: 1489 | human von Willebrand factor D and EGF domain-containing protein-EGF4 protein | PRT1489 |
| SEQ ID NO: 1490 | human von Willebrand factor D and EGF domain-containing protein-EGF5 protein | PRT1490 |
| SEQ ID NO: 1491 | human von Willebrand factor D and EGF domain-containing protein-EGF6 protein | PRT1491 |
| SEQ ID NO: 1492 | human von Willebrand factor D and EGF domain-containing protein-EGF7 protein | PRT1492 |
| SEQ ID NO: 1493 | human Wnt inhibitory factor 1-EGF1 protein | PRT1493 |
| SEQ ID NO: 1494 | human Wnt inhibitory factor 1-EGF2 protein | PRT1494 |
| SEQ ID NO: 1495 | human Wnt inhibitory factor 1-EGF3 protein | PRT1495 |

TABLE 1-continued

Designation of the human-originated EGF domain proteins set forth in the present invention

| No. in the sequence listing | Designation | Code in the invention |
|---|---|---|
| SEQ ID NO: 1496 | human Wnt inhibitory factor 1-EGF4 protein | PRT1496 |
| SEQ ID NO: 1497 | human Wnt inhibitory factor 1-EGF5 protein | PRT1497 |
| SEQ ID NO: 1498 | human Zonadhesin-EGF1 protein | PRT1498 |

The human-originated EGF domain proteins mentioned above are expressed from a prokaryotic or eukaryotic recombinant plasmid or prepared by chemical synthesis.

The steps used in the present invention are as follows:

(1) obtain a gene encoding the human-originated EGF domain protein hF VII-EGF1 or a gene having homology of more than 50% thereto, as well as a gene coding for a fluorescent protein by PCR amplification or artificial synthesis; and obtain a fusion gene encoding for the RFP fusion protein, RFP-hF VII-EGF1 human-originated EGF domain protein, or a gene for a fusion protein having homology of more than 50% to the aforementioned fusion protein through overlapping PCR amplification reaction;

(2) insert the individual gene fragments mentioned above encoding for the recombinant fusion proteins respectively into a prokaryotic or eukaryotic vector to construct the recombinant prokaryotic or eukaryotic plasmid, followed by transformation of the resultant recombinant plasmid into competent bacteria to be cultured, and then screen the recombinant plasmid comprising the correctly inserted fragments by sequencing;

(3) transform the recombinant prokaryotic plasmids with the correct sequencing result into an engineering bacterium to be expressed; isolate and purify the expressed protein to obtain the fusion protein RFP-hF VII-EGF1 or the protein having homology of more than 50% to the fusion protein; or transfect the resultant recombinant eukaryotic plasmids with the correct sequencing result into mammalian cells to be cultured, establish a stable cell line for eukaryotic expression, isolate and purify the expressed protein to obtain the fusion protein RFP-hF VII-EGF1 or the protein having homology of more than 50% to the fusion protein;

(4) release the recombination protein hF VII-EGF1 or the protein having homology of more than 50% thereto by enzymatic digestion with rTEV enzyme, and purify the protein;

(5) analyze the antibacterial activity of the recombination protein hF VII-EGF1 or the protein having homology of more than 50% thereto;

(6) analyze the hydrolysis of the lipopolysaccharide by the recombination protein hF VII-EGF1 or the protein having homology of more than 50% thereto by silver staining;

where the prokaryotic vector is the pET plasmid system which includes the prokaryotic expression plasmids such as pET-14b, pET-19b, pET-21a (+), pET-28a (+), pET-42a (+), etc; and the eukaryotic vector is pcDNA3.1 (+), pcDNA3.1 (−), etc.

Chemical synthesis of the human-originated EGF domain proteins is usually outsourced to professional companies.

It has been demonstrated experimentally that: 1498 of the human-originated EGF domain proteins (PRT1 to PRT1498 in Table 1) set forth in the present invention such as hF VII-EGF1 protein are able to hydrolyze the lipopolysaccharide of Gram-negative bacteria (also known as endotoxin, a major component in the outer-membrane of a Gram-negative bacterium) and disrupt the stability of cellular structure, thereby exerting the bactericidal action. Meanwhile, the human-originated EGF domain proteins such as hF VII-EGF1, hF VII-EGF2, hF IX-EGF1, hF IX-EGF2, hF X-EGF1, and hF X-EGF2, have very strong binding to the tissue factor. When the body is injured, the tissue factor will be exposed at the wound in a large amount, which allows such EGF domain-containing proteins to aggregate accordingly at the wound, exerting a targeted bacteriostatic effect. Assays on the antibacterial activity demonstrate that 1498 of the human-originated EGF domain proteins (PRT1 to PRT1498 in Table 1) such as hF VII-EGF1 protein can inhibit the Gram-negative bacteria significantly. The minimum inhibitory concentrations (MICs) of the abovementioned recombinant proteins for *E. coli* DH5α, *E. coli* BL21, *Pseudomonas aeruginosa, Klebsiella pneumonia, Enterobacter cloacae, Aeromonas hydrophila, Citrobacter diversus, Moraxella catarrhalis, Proteus mirabilis, Proteus vulgaris, Serratia marcescens* are shown in Tables 2 and 3 in the Examples below.

1498 of the human-originated EGF domain proteins (PRT1 to PRT1498 in Table 1) set forth in the present invention such as hF VII-EGF1 protein can hydrolyze the lipopolysaccharide of Gram-negative bacteria (also known as endotoxin, seen in Example 17) and lipopolysaccharide is the major pathogenic factor causing endotoxemia. Therefore, 1498 of the human-originated EGF domain proteins (PRT1 to PRT1498 in Table 1) set forth in the present invention such as hF VII-EGF1 protein can be used in preparing a medicament for treating endotoxemia caused by the Gram-negative bacteria.

The present invention has the following advantageous effects:

1. 1498 of the artificially-prepared human-originated EGF domain proteins (PRT1 to PRT1498 in Table 1) provided in the present invention such as hF VII-EGF1 protein are able to hydrolyze the outer membrane of the Gram-negative bacteria and has been shown experimentally to have significant inhibitory effects on the Gram-negative bacteria, thereby providing a novel class of therapeutic drugs for treating diseases caused by the Gram-negative bacteria infection.

2. 1498 of the artificially-prepared human-originated EGF domain proteins (PRT1 to PRT1498 in Table 1) provided in the present invention such as hF VII-EGF1 protein are able to hydrolyze the lipopolysaccharide (also known as endotoxin) of the Gram-negative bacteria, thereby providing a novel class of therapeutic drugs for treating endotoxemia caused by the Gram-negative bacteria.

3. Six human-originated EGF domain proteins provided in the present invention which are artificially prepared, i.e. hF VII-EGF1, hF VII-EGF2, hF IX-EGF1, hF IX-EGF2, hF X-EGF1, and hF X-EGF2, can exhibit an excellent targeted bactericidal effect on Gram-negative bacteria at the wound site by targeted localization at the wound site via binding to tissue factor, and be prospective to be used in preparation of a novel targeted antibacterial drug.

4. 1498 of the human-originated EGF domain proteins (PRT1 to PRT1498 in Table 1) such as hF VII-EGF1 protein are natural and intrinsic components in the human body, and use of the EGF domain proteins as the bacteriostatic domain in the present invention can reduce the immunogenicity of the medicament effectively.

5. Since 1498 of the recombinant human-originated EGF domain proteins (PRT1 to PRT1498 in Table 1) such as hF VII-EGF1 protein could be expressed properly in cells of *E. coli* directly through the genetic engineering techniques, the production cost is lower, suitable for industrial production.

BRIEF DESCRIPTION OF ACCOMPANYING DRAWINGS

FIG. 1 is the electrophoregram of PCR amplification of the gene sequence encoding the recombinant protein hF VII-EGF1 in Example 1, wherein Lane 1 is the DNA molecular weight marker (Marker 1, purchased from TIANGEN BIOTECH Co. Ltd.) and Lane 2 is PCR amplification of the sequence encoding hF VII-EGF1. The arrowhead is directed toward the amplified fragment of interest.

Figure 4:
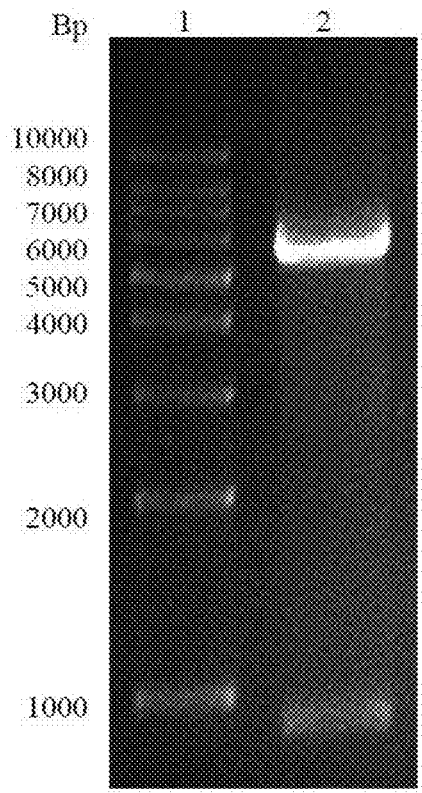

FIG. 4 is the electrophoregram for identification of the restriction-endonuclease digested fragments of the recombinant plasmid pET19bRFP-hF VII-EGF1 in Example 2, wherein Lane 1 is the DNA molecular weight marker (1 kb Marker, purchased from TIANGEN BIOTECH Co. Ltd.) and Lane 2 is the pET19b vector fragment and the DNA fragment encoding the recombinant protein RFP-hF VII-EGF1 which are obtained after restriction-endonuclease double digestion of the recombinant plasmid pET19bRFP-hF VII-EGF1.

Figure 5:
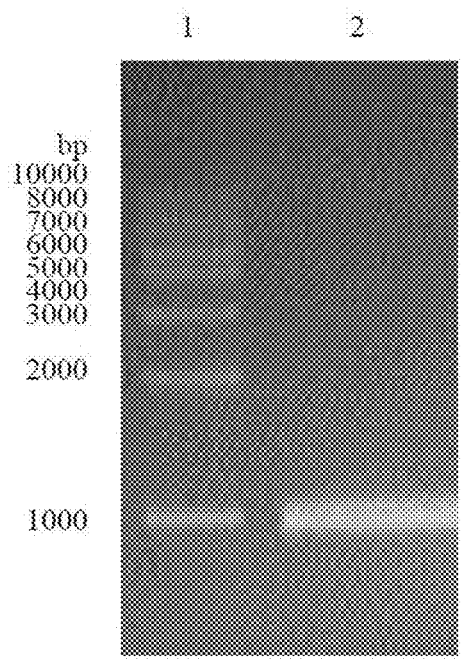

FIG. 5 is the electrophoregram of PCR amplification of the gene sequence encoding the fusion protein RFP-hF VII-EGF2 in Example 3, wherein Lane 1 is the DNA molecular weight marker (1 kb Marker, purchased from TIANGEN BIOTECH Co. Ltd.) and Lane 2 is PCR amplification of the sequence encoding RFP-hF VII-EGF2.

Figure 6:
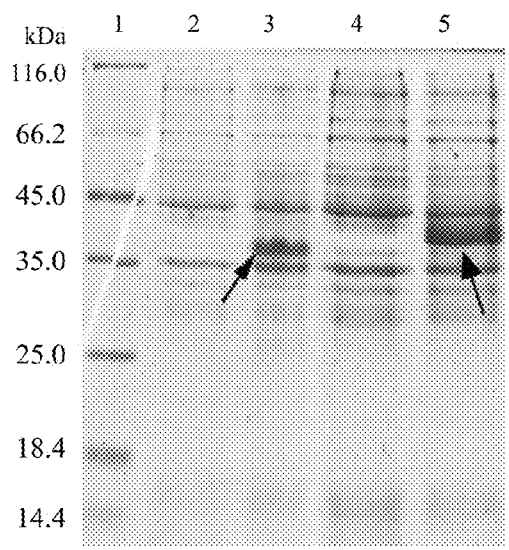

FIG. 6 is the SDS-PAGE analysis of inducible expression of the fusion proteins RFP-hF VII-EGF1 and RFP-hF VII-EGF2 from the recombinant plasmids pET19bRFP-hF VII-EGF1 and pET19bRFP-FVII-EGF2 in *E. coli* in Examples 5 and 8, wherein Lane 1 is the protein molecular weight marker (Unst. Protein Marker, purchased from Thermo Scientific); Lane 2 is the total protein of the *E. coli* without expressing the fusion protein RFP-hF VII-EGF1 before induction; Lane 3 is the total protein of the *E. coli* after expressing the fusion protein RFP-hF VII-EGF1 by induction; Lane 4 is the total protein of the *E. coli* without expressing the fusion protein RFP-hF VII-EGF2 before induction; and Lane 5 is the total protein of the *E. coli* after expressing the fusion protein RFP-hF VII-EGF2 by induction. The arrowheads indicate the expressed fusion proteins.

Figure 7:
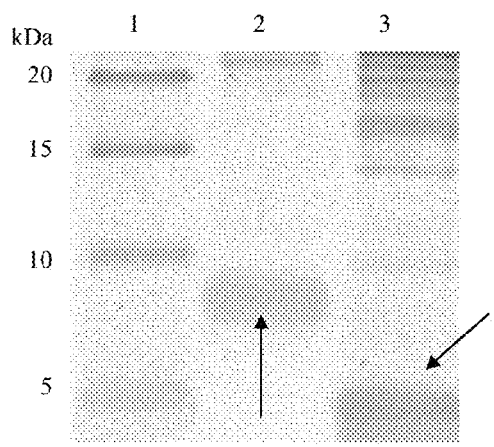

FIG. 7 is picture of Tricien gel analysis for identifying the recombination proteins hF VII-EGF1 and hF VII-EGF2 obtained after enzymatic digestion of the fusion proteins RFP-hF VII-EGF1 and RFP-hF VII-EGF2 with rTEV in Examples 7 and 8, in which Lane 1 is the lower molecular weight protein marker (PageRuler Unstained Low Range Protein Ladder, purchased from Thermo Scientific); Lane 2 is the recombination protein hF VII-EGF2 obtained after rTEV enzymatic digestion; Lane 3 is the recombination protein hF VII-EGF1 obtained after rTEV enzymatic digestion; and the arrowheads indicate the proteins of interest after enzymatic digestion.

Figure 8:
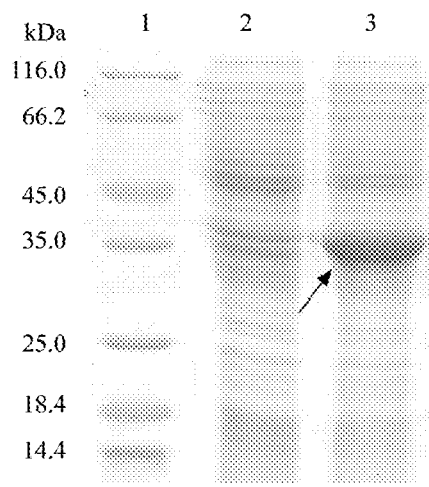

FIG. 8 is the SDS-PAGE analysis of inducible expression of the fusion protein RFP-hF IX-EGF1 from the recombinant plasmid pET21ahF IX-EGF1-RFP in *E. coli* in Example 8, wherein Lane 1 is the protein molecular weight marker (Unst. Protein Marker, purchased from Thermo Scientific); Lane 2 is the total protein of the *E. coli* without expressing the fusion protein RFP-hF IX-EGF1 before induction; and Lane 3 is the total protein of the *E. coli* after expressing the fusion protein RFP-hF IX-EGF1 by induction. The arrowhead indicates the expressed fusion protein.

Figure 9:
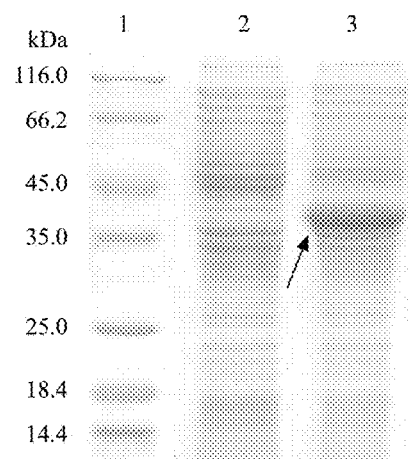

FIG. 9 is the SDS-PAGE analysis of inducible expression of the fusion protein RFP-hF IX-EGF2 from the recombinant plasmid pET21ahF IX-EGF2-RFP in *E. coli* in Example 8, wherein Lane 1 is the protein molecular weight marker (Unst. Protein Marker, purchased from Thermo Scientific); Lane 2 is the total protein of the *E. coli* without expressing the fusion protein RFP-hF IX-EGF2 before induction; and Lane 3 is the total protein of the *E. coli* after expressing the fusion protein RFP-hF IX-EGF2 by induction. The arrowhead indicates the expressed fusion protein.

Figure 10:
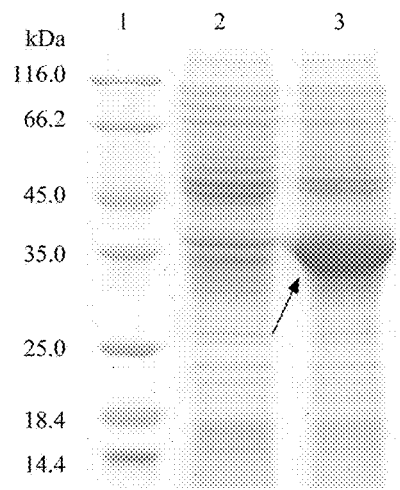

FIG. 10 is the SDS-PAGE analysis of inducible expression of the fusion protein RFP-hF X-EGF1 from the recombinant plasmid pET21ahF X-EGF1-RFP in *E. coli* in Example 8, wherein Lane 1 is the protein molecular weight marker (Unst. Protein Marker, purchased from Thermo Scientific); Lane 2 is the total protein of the *E. coli* without expressing the fusion protein RFP-hF X-EGF1 before induction; and Lane 3 is the total protein of the *E. coli* after expressing the fusion protein RFP-hF X-EGF1 by induction. The arrowhead indicates the expressed fusion protein.

Figure 11:
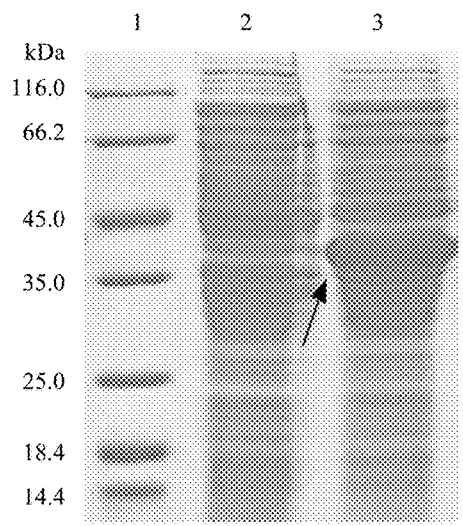

FIG. 11 is the SDS-PAGE analysis of inducible expression of the fusion protein RFP-hF X-EGF2 from the recombinant plasmid pET21ahF X-EGF2-RFP in *E. coli* in Example 8, wherein Lane 1 is the protein molecular weight marker (Unst. Protein Marker, purchased from Thermo Scientific); Lane 2 is the total protein of the *E. coli* without expressing the fusion protein RFP-hF X-EGF2 before induction; and Lane 3 is the total protein of the *E. coli* after expressing the fusion protein RFP-hF X-EGF2 by induction. The arrowhead indicates the expressed fusion protein.

Figure 12:
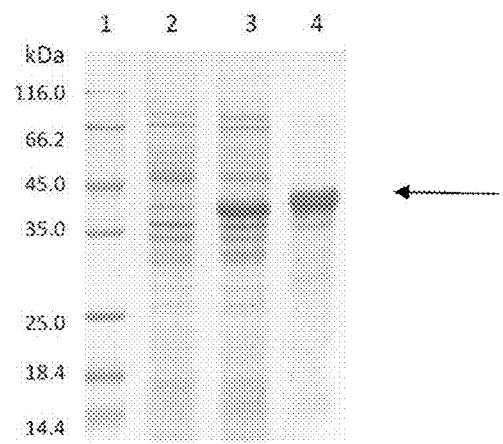

FIG. 12 is the SDS-PAGE analysis of inducible expression of the fusion protein RFP-Delta and Notch-like epidermal growth factor-related-EGF1 from the recombinant plasmid pET21ahDelta and Notch-like epidermal growth factor-related-EGF1-RFP in *E. coli* in Example 8, wherein Lane 1 is the protein molecular weight marker (Unst. Protein Marker, purchased from Thermo Scientific); Lane 2 is the total protein of the *E. coli* without expressing the fusion protein RFP-Delta and Notch-like epidermal growth factor-related-EGF1 before induction; and Lane 3 is the total protein of the *E. coli* after expressing the fusion protein RFP-Delta and Notch-like epidermal growth factor-related-EGF1 by induction; and Lane 4 is the purified fusion protein RFP-Delta and Notch-like epidermal growth factor-related-EGF1. The arrowhead indicates the expressed fusion protein.

Figure 13:
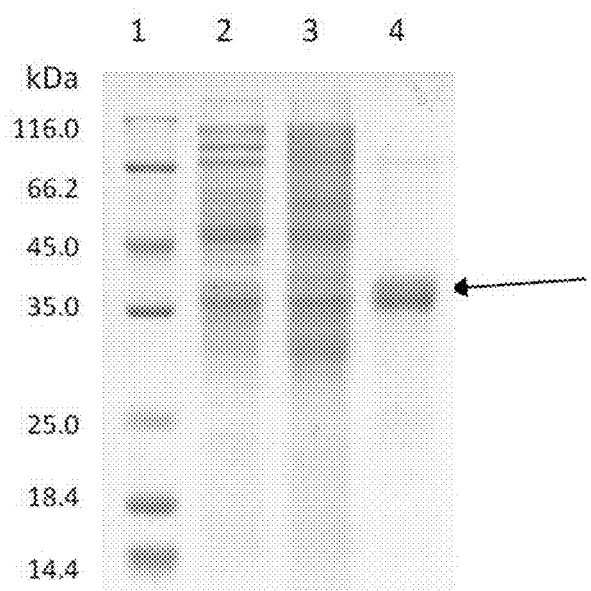

FIG. 13 is the SDS-PAGE analysis of inducible expression of the fusion protein RFP-Zonadhesin-EGF1 from the recombinant plasmid pET21ahZonadhesin-EGF1-RFP in *E. coli* in Example 8, wherein Lane 1 is the protein molecular weight marker (Unst. Protein Marker, purchased from Thermo Scientific); Lane 2 is the total protein of the *E. coli* without expressing the fusion protein RFP-Zonadhesin-EGF1 before induction; and Lane 3 is the total protein of the *E. coli* after expressing the fusion protein RFP-Zonadhesin-EGF1 by induction; and Lane 4 is the purified fusion protein RFP-Zonadhesin-EGF1. The arrowhead indicates the expressed fusion protein.

Figure 14:
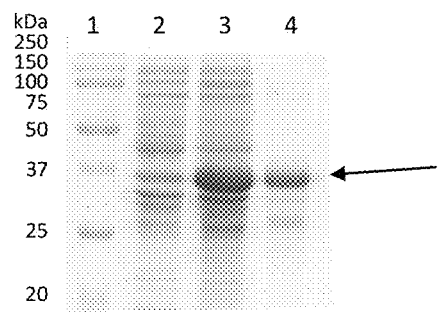

FIG. 14 is the SDS-PAGE analysis of inducible expression of the fusion protein RFP-EGF, latrophilin and seven transmembrane domain-containing protein 1-EGF2 from the recombinant plasmid pET21ahEGF-latrophilin and seven transmembrane domain-containing protein 1-EGF2-RFP in *E. coli* in Example 8, wherein Lane 1 is the protein molecular weight marker (Precision Plus Protein Standards, purchased from BIO-RAD); Lane 2 is the total protein of the *E. coli* without expressing the fusion protein RFP-EGF, latrophilin and seven transmembrane domain-containing protein 1-EGF2 before induction; and Lane 3 is the total protein of the *E. coli* after expressing the fusion protein RFP-EGF, latrophilin and seven transmembrane domain-containing protein 1-EGF2 by induction; and Lane 4 is the purified fusion protein RFP-EGF, latrophilin and seven transmembrane domain-containing protein 1-EGF2. The arrowhead indicates the expressed fusion protein.

Figure 15:
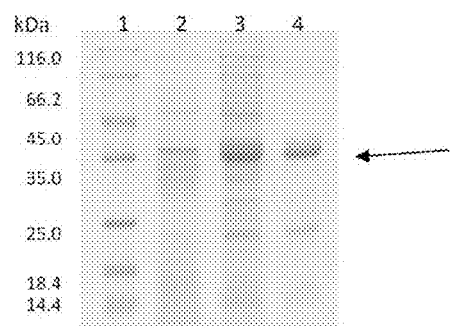

FIG. 15 is the SDS-PAGE analysis of inducible expression of the fusion protein RFP-Prostaglandin G/H synthase 1-EGF1 from the recombinant plasmid pET21ahProstaglandin G/H synthase 1-EGF1-RFP in *E. coli* in Example 8, wherein Lane 1 is the protein molecular weight marker (Unst. Protein Marker, purchased from Thermo Scientific); Lane 2 is the total protein of the *E. coli* without expressing the fusion protein RFP-Prostaglandin G/H synthase 1-EGF1 before induction; and Lane 3 is the total protein of the *E. coli* after expressing the fusion protein RFP-Prostaglandin G/H synthase 1-EGF1 by induction; and Lane 4 is the purified fusion protein RFP-Prostaglandin G/H synthase 1-EGF1. The arrowhead indicates the expressed fusion protein.

Figure 16:
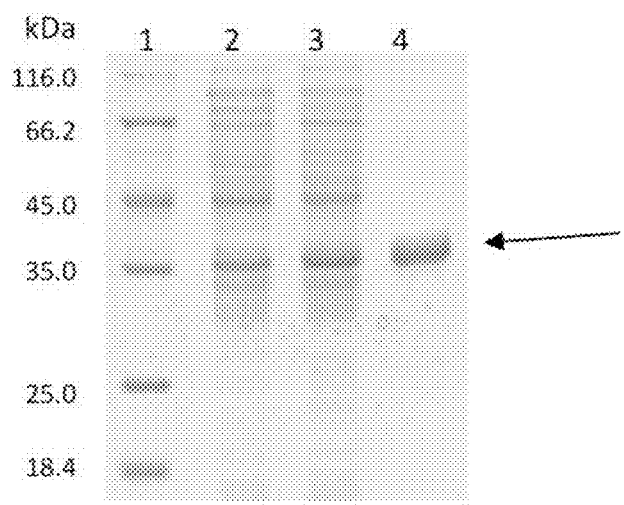

FIG. 16 is the SDS-PAGE analysis of inducible expression of the fusion protein RFP-Neurexin-1-EGF1 from the recombinant plasmid pET21ahNeurexin-1-EGF1-RFP in *E. coli* in Example 8, wherein Lane 1 is the protein molecular weight marker (Unst. Protein Marker, purchased from Thermo Scientific); Lane 2 is the total protein of the *E. coli* without expressing the fusion protein RFP-Neurexin-1-EGF1 before induction; and Lane 3 is the total protein of the *E. coli* after expressing the fusion protein RFP-Neurexin-1-EGF1 by induction; and Lane 4 is the purified fusion protein RFP-Neurexin-1-EGF1. The arrowhead indicates the expressed fusion protein.

Figure 17:
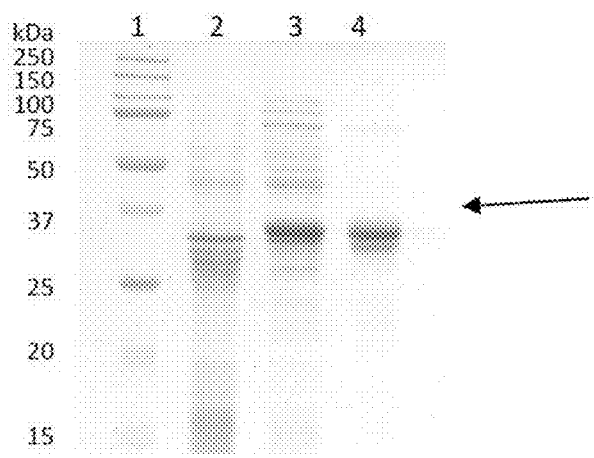

FIG. 17 is the SDS-PAGE analysis of inducible expression of the fusion protein RFP-EGF-containing fibulin-like extracellular matrix protein 1-EGF1 from the recombinant plasmid pET21ahEGF-containing fibulin-like extracellular matrix protein 1-EGF1-RFP in *E. coli* in Example 8, wherein Lane 1 is the protein molecular weight marker (Precision Plus Protein Standards, purchased from BIO-RAD); Lane 2 is the total protein of the *E. coli* without expressing the fusion protein RFP-EGF-containing fibulin-like extracellular matrix protein 1-EGF1 before induction; and Lane 3 is the total protein of the *E. coli* after expressing the fusion protein RFP-EGF-containing fibulin-like extracellular matrix protein 1-EGF1 by induction; and Lane 4 is the purified fusion protein RFP-EGF-containing fibulin-like extracellular matrix protein 1-EGF1. The arrowhead indicates the expressed fusion protein.

Figure 18:
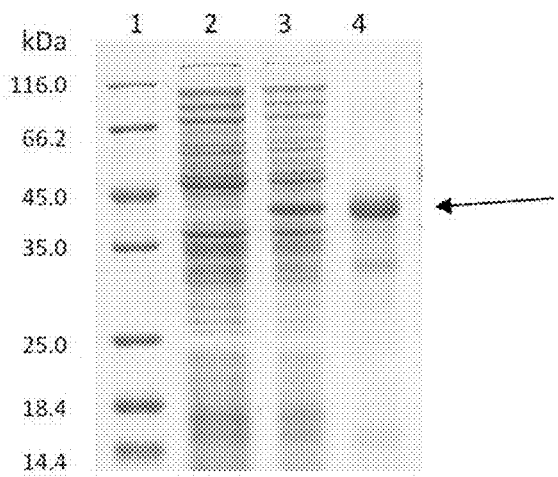

FIG. 18 is the SDS-PAGE analysis of inducible expression of the fusion protein RFP-Netrin-3-EGF1 from the recombinant plasmid pET21ahNetrin-3-EGF1-RFP in *E. coli* in Example 8, wherein Lane 1 is the protein molecular weight marker (Unst. Protein Marker, purchased from Thermo Scientific); Lane 2 is the total protein of the *E. coli* without expressing the fusion protein RFP-Netrin-3-EGF1 before induction; and Lane 3 is the total protein of the *E. coli* after expressing the fusion protein RFP-Netrin-3-EGF1 by induction; and Lane 4 is the purified fusion protein RFP-Netrin-3-EGF1. The arrowhead indicates the expressed fusion protein.

Figure 19:
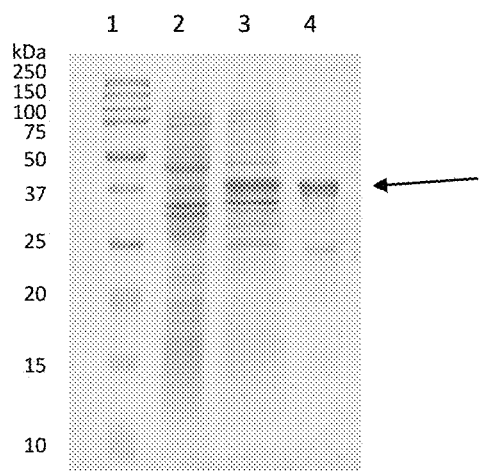

FIG. 19 is the SDS-PAGE analysis of inducible expression of the fusion protein RFP-Putative EGF-like module-containing mucin-like hormone receptor-like 4-EGF2 from the recombinant plasmid pET21ahPutative EGF-like module-containing mucin-like hormone receptor-like 4-EGF2-RFP in *E. coli* in Example 8, wherein Lane 1 is the protein molecular weight marker (Precision Plus Protein Standards, purchased from BIO-RAD); Lane 2 is the total protein of the *E. coli* without expressing the fusion protein RFP-Putative EGF-like module-containing mucin-like hormone receptor-like 4-EGF2 before induction; and Lane 3 is the total protein of the *E. coli* after expressing the fusion protein RFP-Putative EGF-like module-containing mucin-like hormone receptor-like 4-EGF2 by induction; and Lane 4 is the purified fusion protein RFP-Putative EGF-like module-containing mucin-like hormone receptor-like 4-EGF2. The arrowhead indicates the expressed fusion protein.

Figure 20:
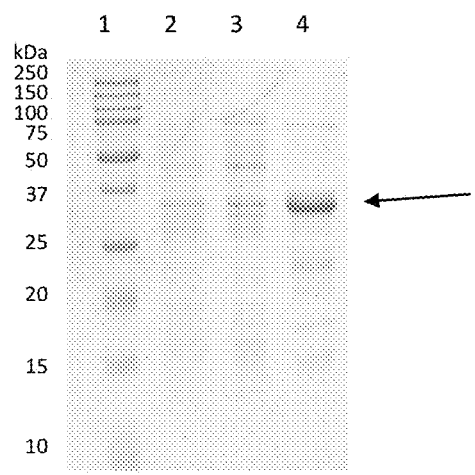

FIG. 20 is the SDS-PAGE analysis of inducible expression of the fusion protein RFP-Protransforming growth factor alpha-EGF1 from the recombinant plasmid pET21ahProtransforming growth factor alpha-EGF1-RFP in *E. coli* in Example 8, wherein Lane 1 is the protein molecular weight marker (Precision Plus Protein Standards, purchased from BIO-RAD); Lane 2 is the total protein of the *E. coli* without expressing the fusion protein RFP-Protransforming growth factor alpha-EGF1 before induction; and Lane 3 is the total protein of the *E. coli* after expressing the fusion protein RFP-Protransforming growth factor alpha-EGF1 by induction; and Lane 4 is the purified fusion protein RFP-Protransforming growth factor alpha-EGF1. The arrowhead indicates the expressed fusion protein.

Figure 21:
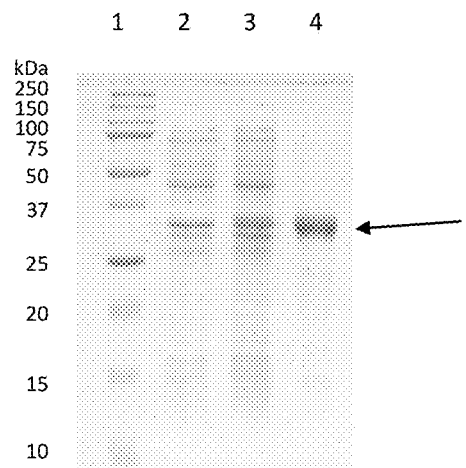

FIG. 21 is the SDS-PAGE analysis of inducible expression of the fusion protein RFP-Delta-like protein 4-EGF2 from the recombinant plasmid pET21ahDelta-like protein 4-EGF2-RFP in *E. coli* in Example 8, wherein Lane 1 is the protein molecular weight marker (Precision Plus Protein Standards, purchased from BIO-RAD); Lane 2 is the total protein of the *E. coli* without expressing the fusion protein RFP-Delta-like protein 4-EGF2 before induction; and Lane 3 is the total protein of the *E. coli* after expressing the fusion protein RFP-Delta-like protein 4-EGF2 by induction; and Lane 4 is the purified fusion protein RFP-Delta-like protein 4-EGF2. The arrowhead indicates the expressed fusion protein.

Figure 22:
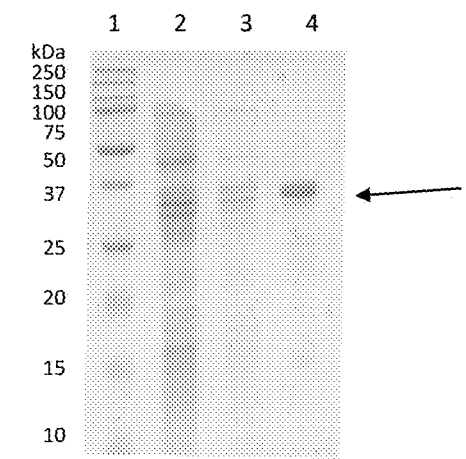

FIG. 22 is the SDS-PAGE analysis of inducible expression of the fusion protein RFP-Nidogen-1-EGF1 from the recombinant plasmid pET21ahNidogen-1-EGF1-RFP in *E. coli* in Example 8, wherein Lane 1 is the protein molecular weight marker (Precision Plus Protein Standards, purchased from BIO-RAD); Lane 2 is the total protein of the *E. coli* without expressing the fusion protein RFP-Nidogen-1-EGF1 before induction; and Lane 3 is the total protein of the *E. coli* after expressing the fusion protein RFP-Nidogen-1-EGF1 by induction; and Lane 4 is the purified fusion protein RFP-Nidogen-1-EGF1. The arrowhead indicates the expressed fusion protein.

Figure 23:
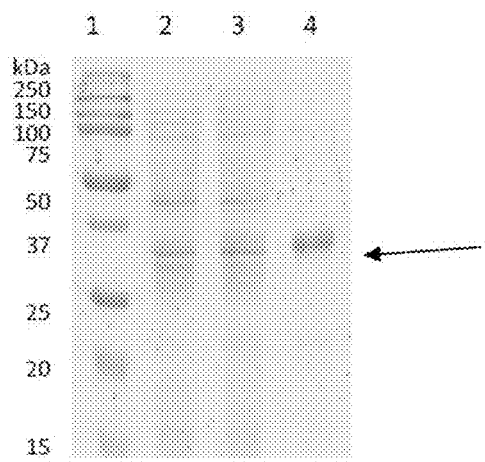

FIG. 23 is the SDS-PAGE analysis of inducible expression of the fusion protein RFP-Uromodulin-like 1-EGF3 from the recombinant plasmid pET21ahNidogen-1-EGF1-RFP in *E. coli* in Example 8, wherein Lane 1 is the protein molecular weight marker (Precision Plus Protein Standards, purchased from BIO-RAD); Lane 2 is the total protein of the *E. coli* without expressing the fusion protein RFP-Uromodulin-like 1-EGF3 before induction; and Lane 3 is the total protein of the *E. coli* after expressing the fusion protein RFP-Uromodulin-like 1-EGF3 by induction; and Lane 4 is the purified fusion protein RFP-Uromodulin-like 1-EGF3. The arrowhead indicates the expressed fusion protein.

Figure 24:
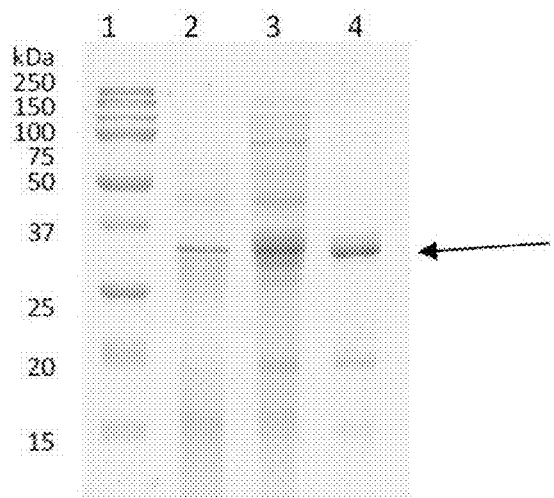

FIG. 24 is the SDS-PAGE analysis of inducible expression of the fusion protein RFP-Sushi, von Willebrand factor type A-EGF and pentraxin domain-containing protein 1-EGF2 from the recombinant plasmid pET21 ahSushi, von Willebrand factor type A-EGF and pentraxin domain-containing protein 1-EGF2-RFP in *E. coli* in Example 8, wherein Lane 1 is the protein molecular weight marker (Precision Plus Protein Standards, purchased from BIO-RAD); Lane 2 is the total protein of the *E. coli* without expressing the fusion protein RFP-Sushi, von Willebrand factor type A-EGF and pentraxin domain-containing protein 1-EGF2 before induction; and Lane 3 is the total protein of the *E. coli* after expressing the fusion protein RFP-Sushi, von Willebrand factor type A-EGF and pentraxin domain-containing protein 1-EGF2 by induction; and Lane 4 is the purified fusion protein RFP-Sushi, von Willebrand factor type A-EGF and pentraxin domain-containing protein 1-EGF2. The arrowhead indicates the expressed fusion protein.

Figure 25:
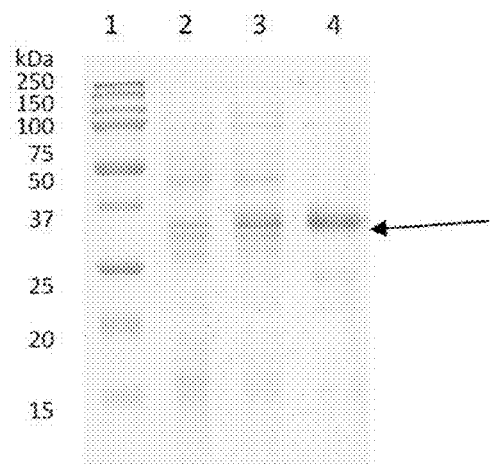

FIG. 25 is the SDS-PAGE analysis of inducible expression of the fusion protein RFP-Protocadherin Fat 2-EGF1 from the recombinant plasmid pET21ahProtocadherin Fat 2-EGF1-RFP in *E. coli* in Example 8, wherein Lane 1 is the protein molecular weight marker (Precision Plus Protein Standards, purchased from BIO-RAD); Lane 2 is the total protein of the *E. coli* without expressing the fusion protein RFP-Protocadherin Fat 2-EGF1 before induction; and Lane 3 is the total protein of the *E. coli* after expressing the fusion protein RFP-Protocadherin Fat 2-EGF1 by induction; and Lane 4 is the purified fusion protein RFP-Protocadherin Fat 2-EGF1. The arrowhead indicates the expressed fusion protein.

Figure 26:
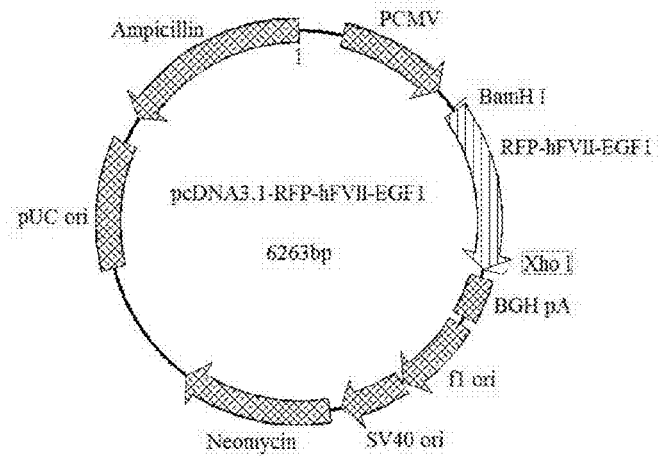

FIG. 26 is the schematic representation of the recombinant eukaryotic plasmid pcDNA3.1-RFP-hF VII-EGF1 in Example 9, wherein the counterclockwise sequence is the forward gene fragment and the clockwise one is the reverse gene fragment.

Figure 27:
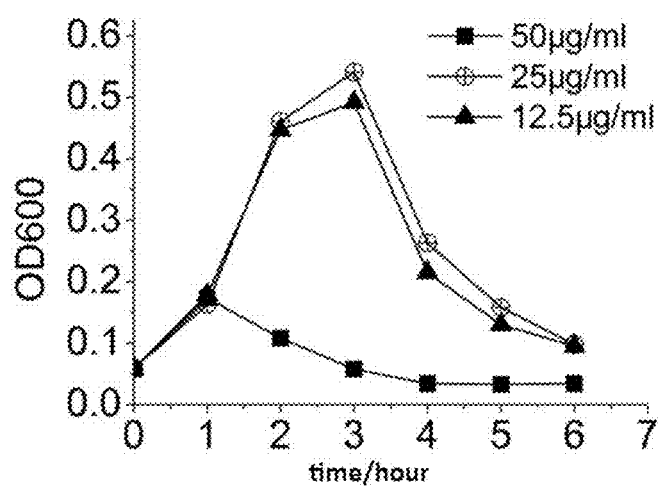

FIG. 27 is the growth curve of *E. coli* DH5α treated with the recombinant protein hF VII-EGF1 in Example 14.

Figure 28:
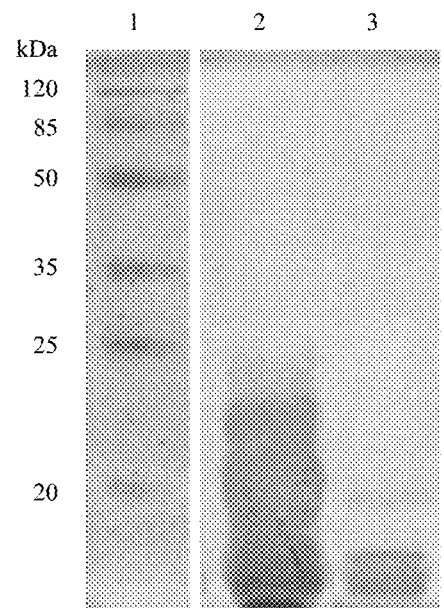

FIG. 28 is a silver staining image for hydrolysis of *E. coli* EH100 LPS by the recombinant protein hF VII-EGF1 in Example 17, in which Lane 1 is the prestained protein marker; Lane 2 is the *E. coli* EH100 LPS untreated; and Lane 3 is the *E. coli* EH100 LPS treated with hF VII-EGF1.

DETAILED DESCRIPTION

The present invention will be further illustrated below in connection with the Examples. In the Examples described hereinafter, where the particular experiment conditions are not otherwise noted, they will follow the conventional conditions well known to the person of skill in the art, such as the conditions and experimental steps described in Molecular Cloning: A Laboratory Manual, Sambrook et al (Ed.), New York, Cold Spring Harbor Laboratory Press, 1989, An Conventional Manual for Laboratory Animals (National Center for Standard Laboratory Animals, November, 2004), and a Manual of Basic Technique, 5$^{th}$ Edition (John Wiley & Sons, Inc., 2005), or follow the conditions and experimental steps recommended by the manufacture. The particular experimental methods in the Examples are exemplified by the protein hF VH-EGF1, and the experimental methods for other human-originated. EGF domain proteins (PRT2 to PRT1498 in Table 1) are performed with reference to those for the protein hF VII-EGF1. Nucleotide sequences for the expressed proteins of interest can be obtained from the databases on the web www.uniprot.org/or www.ncbi.nlm.nih.gov/).

Example 1: Acquisition of the Gene for the Fusion Protein RFP-hF VII-EGF1 with a Red Fluorescent Protein (RFP) Tag 1. The primers for PCR amplification as shown below were synthesized (by Invitrogen Biological Technology Co. Ltd.):

```
Primer 1:
                                    SEQ ID NO: 1499
5'-TAACATATGGTGAGCAAGGGCGAGGAGGATA-3'
     Nde I Primer 2:
                                    SEQ ID NO: 1500
5'-GAAAACCTGTACTTCCAGGGTCAATTCGAAGATGGGGACCAGTGTGC
CTC-3'
                       Bsp119 I
The enzymatic cleavage site for
the recombinant protease (rTEV)

Primer 3:
                                    SEQ ID NO: 1501
5'-CCTGGAAGTACAGGTTTTCCTTGTACAGCTCGTC-3'

Primer 4:
                                    SEQ ID NO: 1502
5'-TATGGATCCTTACTCACAGTTCCGGCCCTCGAA-3'
     BamH I
```

2. Obtaining the coding sequences for hF VII-EGF1 and RFP by PCR amplification (1) Obtaining the DNA Fragment Encoding for hF VII-EGF1

The PCR amplification was performed with Primers 2 and 4 using a plasmid comprising the hF VII CDS region (FulenGen Co. Ltd., Guangzhou) as the template. A BamH I restriction site introduced into the sequence of Primer 4, and an enzymatic cleavage site for the recombinant tobacco mosaic virus proteinase (rTEV) and a restriction site for Bsp119 I were introduced into the sequence of Primer 2, in order to facilitate replacement with the expressible sequences for expressing other human-originated EGF domain proteins (PRT2 to PRT1498 in Table 1). The PCR reaction system (50 μL) was as follows:

| | |
|---|---:|
| Deionized water: | 31.5 μL |
| 5 × Reaction buffer: | 10 μL |
| dNTP Mix: | 4 μL |

-continued

| | |
|---|---|
| Primer 2 (10 mM): | 1 µL |
| Primer 4 (10 mM): | 1 µL |
| Plasmid comprising the hF VII CDS region (100 ng/µL) | 2 µL |
| PrimeStar DNA polymerase: | 0.5 µL |

The reaction condition for the PCR amplification was set with reference to the instruction of PrimeStar DNA polymerase (purchased from Takara): pre-denaturation at 98° C. for 2 min, 30 cycles of denaturation at 98° C. for 10 sec, annealing at 55° C. for 15 sec, and elongation at 72° C. for 30 sec, followed by elongation at 72° C. for 4 min.

Figure 1:
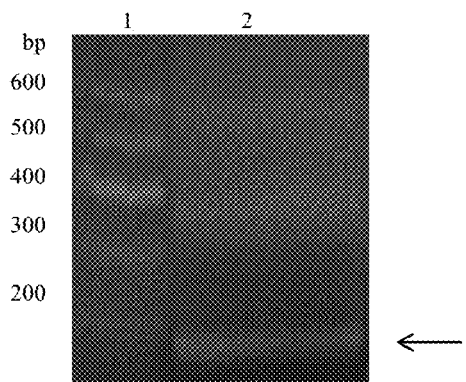

The amplified products were analyzed with 2% agarose gel electrophoresis, the DNA fragments comprising the coding sequence for hF VII-EGF1 was obtained (see FIG. 1), and the fragments of interest was recovered according to the instruction of a gel recovery kit (purchased from Omega).

(2) Obtaining the DNA Fragment Encoding for the Protein Tag RFP

The PCR amplification was performed with Primers 1 and 3 using a plasmid comprising the coding sequence of the gene for the RFP protein (purchased from Takara) as the template. An Nde I restriction site was introduced into the sequence of Primer 1. The reaction system was set up with reference to that for obtaining the DNA fragment encoding for hF VII-EGF1.

The reaction condition for the PCR amplification was set up with reference to the instruction of PrimeStar DNA polymerase: pre-denaturation at 98° C. for 2 min, 30 cycles of denaturation at 98° C. for 10 sec, annealing at 55° C. for 15 sec, and elongation at 72° C. for 1 min, followed by elongation at 72° C. for 4 min.

The amplified products were analyzed with 2% agarose gel electrophoresis, the DNA fragment comprising the coding sequence for RFP was obtained, and the fragment of interest was recovered according to the instruction of a gel recovery kit (purchased from Omega).

3. Amplification of the gene encoding for the fusion protein RFP-hF VII-EGF1 by overlapping PCR.

A overlapping PCR amplification was performed with Primers 1 and 4 using the DNA fragment obtained from the two PCR amplifications mentioned above as templates, yielding a fusion gene fragment RFP-hF VII-EGF1 which comprises a coding sequence for the RFP-TEV enzymatic cleavage site and the human coagulation factor VII-EGF1 protein. The PCR reaction system (50 µL) was as follows:

| | |
|---|---|
| Deionized water: | 31.5 µL |
| 5 × Reaction buffer: | 10 µL |
| dNTP Mix: | 4 µL |
| Primer 1: | 1 µL |
| Primer 4: | 1 µL |
| the hF VII-EGF1-encoding DNA fragment obtained by the first PCR amplification (100 ng/µL): | 1 µL |
| the RFP-encoding DNA fragment obtained by the second PCR amplification (100 ng/µL): | 1 µL |
| PrimeStar DNA polymerase: | 0.5 µL |

The reaction condition for the PCR amplification was set up with reference to the instruction of PrimeStar DNA polymerase: pre-denaturation at 98° C. for 2 min, 30 cycles of denaturation at 98° C. for 10 sec, annealing at 55° C. for 15 sec, and elongation at 72° C. for 1.5 min, followed by elongation at 72° C. for 4 min.

Figure 2:
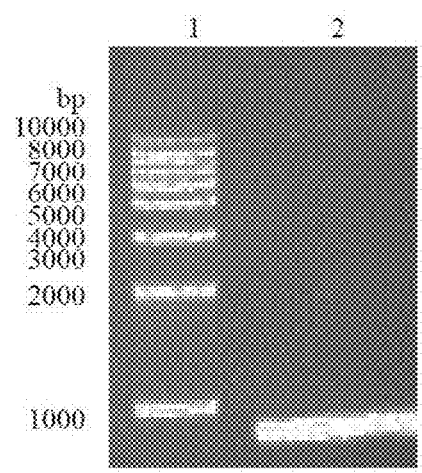
FIG. 2 is the electrophoregram of PCR amplification of the gene sequence encoding the fusion protein RFP-hF VII-EGF1 in Example 1, wherein Lane 1 is the DNA molecular weight marker (1 kb Marker, purchased from TIANGEN BIOTECH Co. Ltd.) and Lane 2 is PCR amplification of the sequence encoding RFP-hF VII-EGF1.

The amplified products were analyzed with 2% agarose gel electrophoresis, the fragment comprising the sequence encoding for RFP-hF VII-EGF1 was obtained (see FIG. 2), and the fragment of interest was recovered according to the instruction of a gel recovery kit (purchased from Omega).

Example 2: Construction of the Recombinant Prokaryotic Plasmid for Expressing the Fusion Protein RFP-hF VII-EGF1

1. Pre-Treatment of the RFP-hF VII-EGF1 gene and the prokaryotic expression vector pET19b The RFP-hF VII-EGF1 gene fragment obtained in Example 1 and the prokaryotic expression vector pET19b (the product from Novagen, the plasmid had been modified to carry a gene encoding for a red fluorescent protein) were individually double digested with the restriction endonucleases Nde I and BamH I (both purchased from TaKaRa or Fermentas) at 37° C. overnight, and the reaction systems were established as follows:

| Reagent | RFP-hF VII-EGF1 (µL) | pET19b (µL) |
|---|---|---|
| DNA | 20 | 20 |
| Nde I | 1 | 1 |
| BamH I/Xho I | 1 | 1 |
| 10 × Buffer | 6 | 6 |
| Double distilled water | 2 | 2 |
| Total volume | 30 | 30 |

After completion of the double digestion, the reaction products were analyzed with 1% agarose gel electrophoresis and the fragments of interest were recovered under the ultraviolet lamp of a gel imaging system according to the instruction of a gel recovery kit (purchased from Omega).

2. Ligation of the RFP-hF VII-EGF1 gene to the prokaryotic expression vector pET19b and transformation (1) The gene fragment RFP-hF VII-EGF1 and the prokaryotic vector fragment obtained in the above steps were quantified approximately and then subjected to ligation according to the ligation reaction principle where a ratio of the molecule number of the gene fragment to the molecule number of the prokaryotic vector is 3:1. The ligation reaction system was set up as follows:

| Reagent | Volume (µL) |
|---|---|
| pET19b DNA | 1.5 |
| RFP-hF VII-EGF1 | 7 |
| T4 ligase | 0.5 |
| 10 × buffer | 1 |
| Total volume | 10 |

Figure 3:
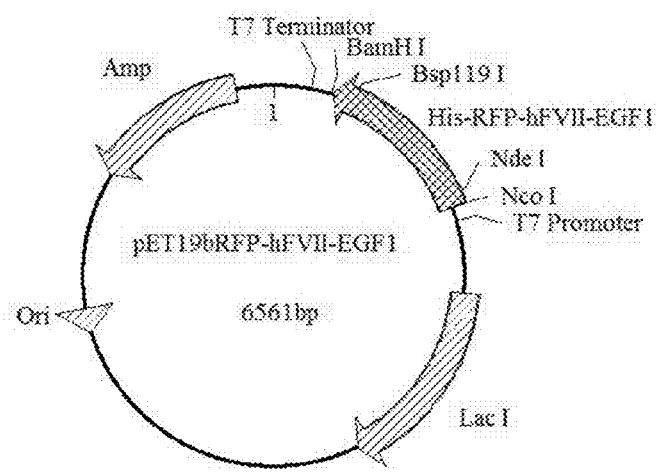
FIG. 3 is the schematic representation of the recombinant prokaryotic plasmid pET19bRFP-hF VII-EGF1 in Example 2, wherein the counterclockwise sequence is the forward gene fragment and the clockwise one is the reverse gene fragment.

(2) The entire ligation reaction was proceeded at 16° C. overnight treated with T4 DNA ligase (purchased from Fermentas). The gene fragment RFP-hF VII-EGF1 amplified above was inserted into the prokaryotic expression vector pET19b and the construction of the recombinant prokaryotic plasmid was schematically shown in FIG. 3.

(3) The ligation product was transformed into the competent cells (prepared according to Molecular Cloning: a Laboratory Manual) of E. coli Top10 (purchased from Invitrogen company). The main steps of the procedure for transforming the ligation product were as follows:

1) 5 µl of the ligation product was pipetted into 100 µL of the competent cells of *E. coli* Top10 placed in a 1.5 mL Eppendorf tube, and the negative control is 100 µl of the competent cells of *E. coli* Top10 placed in a 1.5 mL Eppendorf tube;

2) the tubes were placed on ice for 30 min;

3) the competent cells were shocked in a metal bath at 42° C. for 90 s;

4) the tubes were transferred rapidly into an ice-bath to be cooled for 2 min;

5) 900 µL of SOC medium (10 g peptone, 5 g yeast extract, 0.5 g NaCl, 0.186 g KCl, 0.95 g $MgCl_2$, dissolved with $ddH_2O$ and made up to a volume of 980 mL, autoclaved, cooled to room temperature and then 20 mL of sterile 20% aqueous glucose solution was added) was added, and placed on ice;

6) the tubes were incubated at 37° C. for 1 h with shaking at 180 rpm;

7) the bacterial suspension was centrifuged at 4000×g for 3 min, and the excessive medium was removed except 200 µL supernatant was kept. 200 µL of the remaining supernatant was used to resuspend the bacteria;

8) the resuspended transformants were plated uniformly onto the solid LB medium containing 0.1 g/mL of ampicillin and incubated in a constant-temperature incubator at 37° C. overnight.

3. Identification of the recombinant plasmid

The single clone of the transformed *E. coli* Top 10 mentioned above was picked, cultured in a small quantity and subjected to plasmid extraction with a plasmid extraction kit (purchased from OMEGA), followed by double digestion set forth in the steps of the present Example step 1. The result of the double digested product resolved by gel-electrophoresis is shown in FIG. 4. The sizes of the two bands produced by the enzymatic digestion are consistent with those of the expected products, demonstrating the success of construction of the plasmid of interest.

The plasmids which had been identified by double digestion to be correct ones were send to Beijing Genomics Institute for sequencing of the inserted fusion gene fragment. Finally, the recombinant prokaryotic plasmid comprising the RFP-hF VII-EGF1 gene with the correct sequencing result was designated as pET19bRFP-hF VII-EGF1.

Example 3: Obtaining the Fusion Genes for the RFP Fusion Proteins of Other Human-Originated EGF Domain Proteins (PRT2 to PRT1498 in Table 1) with a Red Fluorescent Protein (RFP) Tag Since all of the expressed sequences of the human-originated EGF domain proteins (PRT1 to PRT1498 in Table 1) set forth in the present invention have been published, the expressible nucleotide sequences can be obtained directly by artificial synthesis. In this Example, synthesis of the gene fragments was outsourced respectively to the commercial companies such as Beijing Genomics Institute, GENEWIZ (Beijing) Co. Ltd., etc. When synthesized, a Bsp119 I restriction site was introduced upstream of all these gene fragments, to facilitated construction of prokaryotic expression plasmids. Electrophoresis of an overlapping PCR amplification of the gene sequence encoding for the fusion protein RFP-hF VII-EGF2 is shown in FIG. 5.

Example 4: Construction of the Prokaryotic Recombinant Plasmids for Expression of the RFP Fusion Proteins of Other Human-Originated EGF Domain Proteins (PRT2 to PRT1498 in Table 1)

1. Pre-Treatment of the genes and the prokaryotic expression vector pET19b

The gene fragments for other human-originated EGF domain proteins and the recombinant plasmid pET19bRFP-hF VII-EGF1 constructed in Example 2 were double digested with the restriction endonucleases Bsp119 I and BamH I (both purchased from TaKaRa or Fermentas) at 37° C. overnight.

2. Other steps for ligation of the expression genes to the plasmid and identification were performed with reference to Example 2.

Example 5: Expression from the Recombinant Plasmid pET19bRFP-hF VII-EGF1

1. The recombinant plasmid pET19bRFP-hF VII-EGF1 constructed in Example 2 was transformed into *E. coli* BL21(DE3) (purchased from Invitrogen); the single clone was picked into the LB medium containing 0.1 g/mL ampicillin and incubated at 37° C. with shaking at 185 rpm to $OD_{600}$ of about 0.6, and 1 mL of the bacterial suspension was taken and frozen at −20° C. Then, IPTG (isopropyl-β-D-thiogalactoside) was added to the remaining bacterial suspension at a final concentration of 0.8 mM. The incubation proceeded for 6 h and 1 mL of the bacterial suspension was taken and frozen at −20° C.

2. The above-mentioned samples before and after IPTG induction were assayed by SDS-PAGE electrophoresis with 5% of the stacking gel and 12% of the separating gel, in order to analyze expression of the protein of interest (see FIG. 6). The result indicated that the protein was expressed normally.

Example 6: Purification of the Fusion Protein RFP-hF VII-EGF1 by Affinity Chromatography 1. The bacterium RFP-hF VII-EGF1-pET19bBL21-(DE3) was cultured on a large scale according to the method in Example 5, induced by addition of IPTG, and cultured overnight at 18° C., with shaking at 175 rpm.

2. The above-mentioned bacterial suspension was centrifuged at 4000×g for 3 min to collect the bacteria. The bacterial pellet was washed by resuspension in the EW buffer (20 mM sodium phosphate, 500 mM NaCl, 1 mM DTT, 0.1 mM PMSF, pH 7.4). The bacterial suspension was centrifuged at 4000×g for 3 min, and the supernatant was discarded. Again, the bacterial pellet was resuspended with 10 mL of the EW buffer.

3. The bacteria were disrupted by sonication (power: 300 W; duration for sonication: 10 s; interval: 10 s; total time for sonication: 3 min; performed in ice-bath). After completion of the sonication, the bacterial suspension was centrifuged at 48,400×g at 4° C. for 1 h. The supernatant was collected and placed on ice.

4. The chromatographic column was preloaded according to the instruction of $Co^{2+}$ purification system (Talon Metal Affinity Resin, Clontech company product), and the sample was loaded. The column was washed twice with 10 mL EW buffer and the protein impurities were washed out with 10 mM imidazole solution. Finally, the protein was eluted with 100 mM imidazole.

5. The eluent comprising the proteins of interest was ultrafiltrated with Tris-Cl buffer (pH 7.4), for buffer exchange and concentration. After ultrafiltration, the high concentration of the fusion protein RFP-hF VII-EGF1 can be obtained. It was shown by protein quantitation that about 15 mg of the proteins of interest with more than 95% of purity can be obtained per liter of the expressing bacterium suspension.

Example 7: Enzymatic Cleavage of the Fusion Protein RFP-hF VII-EGF1 and Purification of the Recombination Protein hF VII-EGF1

1. The Reasin Ni column (Ni column purchased from GE) was treated as follows: 200 µL of the Ni column mix was pipetted into a 1.5 mL EP tube (AxyGEN) and centrifuged at 700×g for 2 min, the preservative solution for the Reasin Ni column (20% ethanol) was discarded, then, the Ni column was washed twice with 1 mL deionised water, followed by equilibration of the Ni column with 1 mL binding buffer (0.5 M NaCl, 20 mM phosphate buffer, pH 7.4).

2. 450 µA of 3 µg/µL fusion proteins were mixed individually with the treated Ni column to homogeneity after equilibration of the Ni column, co-incubated at 4° C. for 1 h on a vertical rotary mixer.

3. After completion of incubation, the mixture was centrifuged at 4° C. at 700×g for 3 min After completion of centrifugation, Ni beads obtained by centrifugation were washed twice with 500 µA of binding buffer. Ni beads were collected after completion of washing.

4. The beads were resuspended with 423 µl of binding buffer. After resuspending and mixing well, the resultant mixture was subjected to cleavage at 4° C. with the rTEV proteinase (purchased from Shanghai Sangon). The mixture was placed on a vertical rotary mixer overnight with the time of period limited to 10 h. After completion of the enzymatic cleavage, the mixture was centrifuged at 700×g at 4° C. for 5 min. After completion of centrifugation, the supernatant was collected as the recombination protein hF VII-EGF1. The picture of Tricien gel analysis for identifying the recombination protein hF VII-EGF1 obtained after enzymatic cleavage of the fusion protein RFP-hF VII-EGF1 with rTEV is seen in FIG. 7. The enzymatic cleavage system was set up as follows:

| 20 × TEV buffer | 22.5 µL |
| 0.1M DTT | 1.5 µL |
| Protein beads | 420 µL |
| rTEV enzyme | 3 µL |

Example 8: Prokaryotic Expression of the Other Recombination Human-Originated EGF Domain Proteins (PRT2 to PRT1498 in Table 1) and Purification of the Same The other human-originated EGF domain proteins (PRT2 to PRT1498 in Table 1) can be expressed prokaryotically and then purified with the same methods as those in Examples 5-7. Partial profiles are shown in FIGS. 6 to 25.

Example 9: Construction of the Recombinant Eukaryotic Plasmid for Expressing the Fusion Protein RFP-hF VII-EGF1

1. The primers for PCR amplification as shown below were synthesized (by Invitrogen Biological Technology Co. Ltd.):

```
Primer 1:
                                    SEQ ID NO: 1503
TAAGGATCCTGCAGAGATTTCATCATGCATCATCATCAT
   BamH I    Kozak Primer 2:
                                    SEQ ID NO: 1504
TATCTCGAGTTACTCACAGTTCCGG
   Xho I
```

2. PCR Amplification System

The PCR amplification was performed with Primers 1 and 2 using the plasmid pET19bRFP-hF VII-EGF1 constructed in Example 2 as the template. A BamH I restriction enzyme cutting site and a Kozak sequence were introduced into the sequence of Primer 1, and an Xho I restriction enzyme cutting site was introduced into the sequence of Primer 2. The PCR reaction was performed with reference to Example 1.

3. Construction of the recombinant plasmid for eukaryotic expression of the fusion protein RFP-hF VII-EGF1

The cloned gene fragment RFP-hF VII-EGF1 and the eukaryotic expression vector pcDNA3.1 (+) (the product from Novagen) were double digested with the restriction endonucleases BamH I and Xho I (both purchased from TaKaRa or Fermentas), and the reaction systems were set up with reference to Example 2. The steps for ligating the gene fragment to the eukaryotic expression vector and for transforming and identifying the recombinant plasmid were performed with reference to Example 2.

Finally, the recombinant plasmid comprising the RFP-hF VII-EGF1 gene with the correct sequencing result was designated as pcDNA3.1-RFP-hF VII-EGF1. The plasmid map of the recombinant plasmid is seen in FIG. 26.

Example 10: Construction of a Stable Cell Line for Expressing the Fusion Protein RFP-hF VII-EGF1

1. Cell preparation

DG44 cells (purchased from ATCC) were cultured in the α-MEM complete culture medium (containing L-glutamine, ribonucleic acid and deoxyribonucleic acid, purchased from Hiclony) supplemented with 10% FBS (fetal bovine serum, purchased from Hiclony). On the day before transfection, DG44 cells were seeded in a 6-well plate at 4×10$^5$ cells/mL with 2 mL per well.

2. Cell transfection

Cells were transfected by using liposome method following the instruction of Lipofectamine™ 2000 kit (purchased from Invitrogen). The detailed steps are as follows:

1) The cell culture medium was replaced with serum-free α-MEM medium, 2 mL/well.

2) 4.0 µg of the recombinant eukaryotic expression plasmid pcDNA3.1-RFP-hF VII-EGF1 constructed in Example 9 was mixed with 250 µL Opti-MEM, while 10 µL of Lipofectamine™ 2000 was mixed with 250 µL of Opti-MEM and incubated for 5 min.

3) The two solutions were mixed well and incubated for 20 min. The liposome complexes were added into the well with cells, gently mixed, placed into an incubator and cultured at 37° C.

4) After 5 h, the medium was replaced with the α-MEM complete culture medium supplemented with 10% FBS.

3. Screening and expanding of the positive cell clones

After 24 h of transfection with the recombinant plasmid, the cells were transferred into 100 mm petri dishes at a ratio of 1:2000. G418 (purchased from Gibco) was added at a final concentration of 800 μg/mL for screening. Cells transfected with an empty vector or not transfected were used as controls. After 15 days, the single clones were picked into and cultured in 24-well plates, and sequentially transferred into 6-well plates and into 100 mm petri-dishes for expanding culture once cellular confluence was reached. When the cell confluency was 90%, cells were frozen at a rate of 1:4 in FBS with 10% DMSO (purchased from Gibco).

4. Identification of the positive cell clones

The picked positive cell clones were identified by the genomic PCR and RT-PCR. The fragment of interest could be amplified by both of the techniques, which demonstrated that the fusion gene has been integrated into the genome of the cell and a functional mRNA is transcribed. The stable cell line obtained was designated as DG44-RFP-hF VII-EGF1.

Example 11: Collection of the Eukaryotically Expressed Fusion Protein RFP-hF VII-EGF1

1. The DG44-RFP-hF VII-EGF1 cells were cultured in the α-MEM complete culture medium containing 10% FBS supplemented with 400 μg/mL G418, and passaged into 10 plates.

2. When the cell confluency in each plate reached to more than 90%, the α-MEM complete culture medium containing 10% FBS was replaced with CHO serum-free medium, and supplemented with Vitamin K (Sigma) to a final concentration of 1 μg/mL.

3. After 3 days of cultivation, the cellular pellet was collected and disrupted. Then, the supernatant was obtained by centrifugation, purified by cobalt ion affinity chromatography and identified by SDS-PAGE plus Western Blot. The steps were referred to those in Example 6.

Example 12: Enzymatic Cleavage of the Eukaryotically Expressed Fusion Protein RFP-hF VII-EGF1 and Recovery of hF VII-EGF1

The experimental method followed that in Example 7.

Example 13: Eukaryotic Expression of the Other Human-Originated EGF Domain Proteins (PRT2 to PRT1498 in Table 1) and Purification of the Same According to the methods of Examples 9-10, the eukaryotic expression plasmids for the RFP fusion proteins of other human-originated EGF domain proteins (PRT2 to PRT1498 in Table 1) were constructed and the cell lines stably expressing these fusion proteins were established.

According to the methods of Examples 11-12, the eukaryotically expressed fusion proteins were collected and subjected to enzymatic cleavage, and the other human-originated EGF domain proteins (PRT2 to PRT1498 in Table 1) were finally obtained.

Example 14: Determination of the Antibacterial Activity of the Recombinant Protein hF VII-EGF1

1. *E. coli* DH5α was exemplified. *E. coli* DH5α was streaked and cultured on LB solid medium. Then, a typical clone was picked and inoculated into common LB liquid medium, cultured at 37° C. with shaking at 185 rpm until the logarithmic growth phase was reached ($OD_{600}$ of about 0.5). The bacterial culture was centrifuged at 4000×g for 3 min, the supernatant was discarded, and the thalli were resuspended with fresh LB medium.

2. The above-mentioned bacterial suspension was diluted and inoculated into a 96-well plate with the total volume of 100 μL per well and a bacterial count of $5 \times 10^5$ CFU/mL.

3. The recombinant protein hF VII-EGF1 was added to the above-mentioned wells with the final protein concentration in the well of the highest protein concentration being 50 μg/mL. Basing on this final concentration, a two-fold serial dilution was performed till a protein concentration gradient consisting of 50, 25, and 12.5 μg/mL was set up. Three parallel wells were set up for each concentration in the gradient.

4. The above-mentioned 96-well plate was placed and cultured at 37° C. in shaking incubator shaking at 175 rpm. Samples were taken every 30 min, the absorbance values were determined at 600 nm wavelength under a ultra violet spectrophotometer, and an inhibition curve was plotted. Judgement on MIC: After 8 h of cultivation, the growth was observed with naked eyes or judged under the ultra violet spectrophotometer at a wavelength of 600 nm. The minimal inhibitory concentration MIC is defined as the lowest concentration of the recombinant protein at which there is no growth of the bacteria.

The growth curve of *E. coli* DH5α treated with the recombinant protein hF VII-EGF1 is seen in FIG. 27. The curve indicates that the recombinant protein hF VII-EGF1 exhibits a significant inhibitory effect on the growth of *E. coli* DH5α, with the MIC being 12.5 μg/mL.

Example 15: Determination of Antibacterial Activities of the Other Human-Originated EGF Domain Proteins (PRT2 to PRT1498 in Table 1)

According to the experimental procedures in Example 14, the minimal inhibitory concentrations (MIC, μg/mL) of the other human-originated EGF domain proteins (PRT2 to PRT1498 in Table 1) for *E. coli* DH5α were determined. The results are shown in Table 2:

TABLE 2

| MIC (μg/mL) of the human-originated EGF domain proteins against *E. coli* DH5α ||
| Protein | MIC |
| --- | --- |
| PRT1 | 12.5 |
| PRT2 | 25 |
| PRT3 | 12.5 |
| PRT4 | 25 |
| PRT5 | 12.5 |
| PRT6 | 50 |
| PRT7 | 12.5 |
| PRT8 | 25 |
| PRT9 | 12.5 |
| PRT10 | 25 |
| PRT11 | 12.5 |
| PRT12 | 12.5 |
| PRT13 | 25 |
| PRT14 | 25 |
| PRT15 | 25 |
| PRT16 | 12.5 |
| PRT17 | 12.5 |
| PRT18 | 12.5 |
| PRT19 | 25 |
| PRT20 | 12.5 |

TABLE 2-continued

MIC (μg/mL) of the human-originated EGF domain proteins against *E. coli* DH5α

| Protein | MIC |
|---|---|
| PRT21 | 25 |
| PRT22 | 50 |
| PRT23 | 12.5 |
| PRT24 | 12.5 |
| PRT25 | 50 |
| PRT26 | 25 |
| PRT27 | 12.5 |
| PRT28 | 50 |
| PRT29 | 25 |
| PRT30 | 25 |
| PRT31 | 25 |
| PRT32 | 12.5 |
| PRT33 | 12.5 |
| PRT34 | 100 |
| PRT35 | 12.5 |
| PRT36 | 12.5 |
| PRT37 | 25 |
| PRT38 | 50 |
| PRT39 | 50 |
| PRT40 | 25 |
| PRT41 | 25 |
| PRT42 | 25 |
| PRT43 | 12.5 |
| PRT44 | 12.5 |
| PRT45 | 50 |
| PRT46 | 25 |
| PRT47 | 12.5 |
| PRT48 | 12.5 |
| PRT49 | 12.5 |
| PRT50 | 25 |
| PRT51 | 25 |
| PRT52 | 12.5 |
| PRT53 | 12.5 |
| PRT54 | 12.5 |
| PRT55 | 25 |
| PRT56 | 25 |
| PRT57 | 12.5 |
| PRT58 | 12.5 |
| PRT59 | 25 |
| PRT60 | 12.5 |
| PRT61 | 12.5 |
| PRT62 | 12.5 |
| PRT63 | 12.5 |
| PRT64 | 12.5 |
| PRT65 | 25 |
| PRT66 | 12.5 |
| PRT67 | 12.5 |
| PRT68 | 12.5 |
| PRT69 | 12.5 |
| PRT70 | 12.5 |
| PRT71 | 50 |
| PRT72 | 12.5 |
| PRT73 | 25 |
| PRT74 | 50 |
| PRT75 | 50 |
| PRT76 | 25 |
| PRT77 | 25 |
| PRT78 | 50 |
| PRT79 | 50 |
| PRT80 | 12.5 |
| PRT81 | 12.5 |
| PRT82 | 25 |
| PRT83 | 12.5 |
| PRT84 | 12.5 |
| PRT85 | 12.5 |
| PRT86 | 50 |
| PRT87 | 12.5 |
| PRT88 | 25 |
| PRT89 | 25 |
| PRT90 | 50 |
| PRT91 | 12.5 |
| PRT92 | 50 |
| PRT93 | 50 |
| PRT94 | 12.5 |
| PRT95 | 25 |
| PRT96 | 12.5 |
| PRT97 | 25 |
| PRT98 | 12.5 |
| PRT99 | 12.5 |
| PRT100 | 12.5 |
| PRT101 | 25 |
| PRT102 | 12.5 |
| PRT103 | 50 |
| PRT104 | 12.5 |
| PRT105 | 12.5 |
| PRT106 | 12.5 |
| PRT107 | 12.5 |
| PRT108 | 50 |
| PRT109 | 12.5 |
| PRT110 | 25 |
| PRT111 | 12.5 |
| PRT112 | 50 |
| PRT113 | 12.5 |
| PRT114 | 12.5 |
| PRT115 | 12.5 |
| PRT116 | 25 |
| PRT117 | 12.5 |
| PRT118 | 12.5 |
| PRT119 | 12.5 |
| PRT120 | 12.5 |
| PRT121 | 25 |
| PRT122 | 12.5 |
| PRT123 | 25 |
| PRT124 | 12.5 |
| PRT125 | 100 |
| PRT126 | 12.5 |
| PRT127 | 12.5 |
| PRT128 | 12.5 |
| PRT129 | 50 |
| PRT130 | 12.5 |
| PRT131 | 50 |
| PRT132 | 25 |
| PRT133 | 50 |
| PRT134 | 12.5 |
| PRT135 | 25 |
| PRT136 | 12.5 |
| PRT137 | 25 |
| PRT138 | 12.5 |
| PRT139 | 12.5 |
| PRT140 | 12.5 |
| PRT141 | 12.5 |
| PRT142 | 12.5 |
| PRT143 | 12.5 |
| PRT144 | 25 |
| PRT145 | 12.5 |
| PRT146 | 12.5 |
| PRT147 | 12.5 |
| PRT148 | 25 |
| PRT149 | 12.5 |
| PRT150 | 25 |
| PRT151 | 12.5 |
| PRT152 | 12.5 |
| PRT153 | 12.5 |
| PRT154 | 12.5 |
| PRT155 | 12.5 |
| PRT156 | 25 |
| PRT157 | 12.5 |
| PRT158 | 12.5 |
| PRT159 | 25 |
| PRT160 | 12.5 |
| PRT161 | 12.5 |
| PRT162 | 12.5 |
| PRT163 | 12.5 |
| PRT164 | 25 |
| PRT165 | 12.5 |
| PRT166 | 12.5 |
| PRT167 | 12.5 |
| PRT168 | 25 |
| PRT169 | 50 |
| PRT170 | 50 |

TABLE 2-continued

MIC (µg/mL) of the human-originated EGF domain proteins against *E. coli* DH5α

| Protein | MIC |
|---|---|
| PRT171 | 25 |
| PRT172 | 12.5 |
| PRT173 | 12.5 |
| PRT174 | 50 |
| PRT175 | 12.5 |
| PRT176 | 25 |
| PRT177 | 50 |
| PRT178 | 25 |
| PRT179 | 50 |
| PRT180 | 12.5 |
| PRT181 | 25 |
| PRT182 | 12.5 |
| PRT183 | 12.5 |
| PRT184 | 25 |
| PRT185 | 50 |
| PRT186 | 12.5 |
| PRT187 | 25 |
| PRT188 | 12.5 |
| PRT189 | 25 |
| PRT190 | 12.5 |
| PRT191 | 12.5 |
| PRT192 | 25 |
| PRT193 | 50 |
| PRT194 | 12.5 |
| PRT195 | 25 |
| PRT196 | 50 |
| PRT197 | 50 |
| PRT198 | 12.5 |
| PRT199 | 25 |
| PRT200 | 12.5 |
| PRT201 | 50 |
| PRT202 | 25 |
| PRT203 | 12.5 |
| PRT204 | 25 |
| PRT205 | 12.5 |
| PRT206 | 25 |
| PRT207 | 12.5 |
| PRT208 | 25 |
| PRT209 | 12.5 |
| PRT210 | 50 |
| PRT211 | 25 |
| PRT212 | 12.5 |
| PRT213 | 12.5 |
| PRT214 | 12.5 |
| PRT215 | 25 |
| PRT216 | 12.5 |
| PRT217 | 12.5 |
| PRT218 | 100 |
| PRT219 | 12.5 |
| PRT220 | 25 |
| PRT221 | 12.5 |
| PRT222 | 50 |
| PRT223 | 12.5 |
| PRT224 | 25 |
| PRT225 | 12.5 |
| PRT226 | 50 |
| PRT227 | 12.5 |
| PRT228 | 25 |
| PRT229 | 50 |
| PRT230 | 25 |
| PRT231 | 12.5 |
| PRT232 | 25 |
| PRT233 | 12.5 |
| PRT234 | 25 |
| PRT235 | 12.5 |
| PRT236 | 12.5 |
| PRT237 | 25 |
| PRT238 | 25 |
| PRT239 | 25 |
| PRT240 | 25 |
| PRT241 | 12.5 |
| PRT242 | 12.5 |
| PRT243 | 12.5 |
| PRT244 | 50 |
| PRT245 | 12.5 |
| PRT246 | 12.5 |
| PRT247 | 12.5 |
| PRT248 | 12.5 |
| PRT249 | 25 |
| PRT250 | 12.5 |
| PRT251 | 25 |
| PRT252 | 25 |
| PRT253 | 12.5 |
| PRT254 | 25 |
| PRT255 | 12.5 |
| PRT256 | 25 |
| PRT257 | 12.5 |
| PRT258 | 50 |
| PRT259 | 12.5 |
| PRT260 | 12.5 |
| PRT261 | 12.5 |
| PRT262 | 12.5 |
| PRT263 | 25 |
| PRT264 | 12.5 |
| PRT265 | 25 |
| PRT266 | 12.5 |
| PRT267 | 50 |
| PRT268 | 12.5 |
| PRT269 | 12.5 |
| PRT270 | 12.5 |
| PRT271 | 12.5 |
| PRT272 | 25 |
| PRT273 | 12.5 |
| PRT274 | 12.5 |
| PRT275 | 50 |
| PRT276 | 100 |
| PRT277 | 12.5 |
| PRT278 | 50 |
| PRT279 | 12.5 |
| PRT280 | 12.5 |
| PRT281 | 50 |
| PRT282 | 12.5 |
| PRT283 | 12.5 |
| PRT284 | 50 |
| PRT285 | 50 |
| PRT286 | 12.5 |
| PRT287 | 12.5 |
| PRT288 | 12.5 |
| PRT289 | 50 |
| PRT290 | 50 |
| PRT291 | 12.5 |
| PRT292 | 50 |
| PRT293 | 12.5 |
| PRT294 | 12.5 |
| PRT295 | 12.5 |
| PRT296 | 50 |
| PRT297 | 25 |
| PRT298 | 25 |
| PRT299 | 25 |
| PRT300 | 12.5 |
| PRT301 | 50 |
| PRT302 | 12.5 |
| PRT303 | 50 |
| PRT304 | 12.5 |
| PRT305 | 12.5 |
| PRT306 | 50 |
| PRT307 | 25 |
| PRT308 | 12.5 |
| PRT309 | 25 |
| PRT310 | 50 |
| PRT311 | 12.5 |
| PRT312 | 50 |
| PRT313 | 25 |
| PRT314 | 12.5 |
| PRT315 | 12.5 |
| PRT316 | 50 |
| PRT317 | 12.5 |
| PRT318 | 12.5 |
| PRT319 | 25 |
| PRT320 | 50 |

TABLE 2-continued

MIC (µg/mL) of the human-originated EGF domain proteins against *E. coli* DH5α

| Protein | MIC |
|---|---|
| PRT321 | 50 |
| PRT322 | 25 |
| PRT323 | 25 |
| PRT324 | 25 |
| PRT325 | 12.5 |
| PRT326 | 50 |
| PRT327 | 50 |
| PRT328 | 12.5 |
| PRT329 | 25 |
| PRT330 | 12.5 |
| PRT331 | 50 |
| PRT332 | 25 |
| PRT333 | 12.5 |
| PRT334 | 50 |
| PRT335 | 12.5 |
| PRT336 | 50 |
| PRT337 | 50 |
| PRT338 | 50 |
| PRT339 | 50 |
| PRT340 | 25 |
| PRT341 | 50 |
| PRT342 | 50 |
| PRT343 | 25 |
| PRT344 | 50 |
| PRT345 | 12.5 |
| PRT346 | 50 |
| PRT347 | 12.5 |
| PRT348 | 25 |
| PRT349 | 12.5 |
| PRT350 | 25 |
| PRT351 | 12.5 |
| PRT352 | 25 |
| PRT353 | 12.5 |
| PRT354 | 50 |
| PRT355 | 25 |
| PRT356 | 25 |
| PRT357 | 50 |
| PRT358 | 5 |
| PRT359 | 12.5 |
| PRT360 | 50 |
| PRT361 | 25 |
| PRT362 | 25 |
| PRT363 | 25 |
| PRT364 | 12.5 |
| PRT365 | 12.5 |
| PRT366 | 12.5 |
| PRT367 | 25 |
| PRT368 | 12.5 |
| PRT369 | 50 |
| PRT370 | 50 |
| PRT371 | 50 |
| PRT372 | 12.5 |
| PRT373 | 50 |
| PRT374 | 25 |
| PRT375 | 12.5 |
| PRT376 | 50 |
| PRT377 | 12.5 |
| PRT378 | 50 |
| PRT379 | 12.5 |
| PRT380 | 50 |
| PRT381 | 12.5 |
| PRT382 | 50 |
| PRT383 | 25 |
| PRT384 | 50 |
| PRT385 | 25 |
| PRT386 | 25 |
| PRT387 | 12.5 |
| PRT388 | 12.5 |
| PRT389 | 12.5 |
| PRT390 | 12.5 |
| PRT391 | 50 |
| PRT392 | 12.5 |
| PRT393 | 50 |
| PRT394 | 12.5 |
| PRT395 | 25 |
| PRT396 | 50 |
| PRT397 | 12.5 |
| PRT398 | 50 |
| PRT399 | 12.5 |
| PRT400 | 50 |
| PRT401 | 50 |
| PRT402 | 12.5 |
| PRT403 | 12.5 |
| PRT404 | 25 |
| PRT405 | 12.5 |
| PRT406 | 50 |
| PRT407 | 25 |
| PRT408 | 12.5 |
| PRT409 | 50 |
| PRT410 | 12.5 |
| PRT411 | 25 |
| PRT412 | 12.5 |
| PRT413 | 12.5 |
| PRT414 | 12.5 |
| PRT415 | 25 |
| PRT416 | 50 |
| PRT417 | 25 |
| PRT418 | 12.5 |
| PRT419 | 25 |
| PRT420 | 50 |
| PRT421 | 12.5 |
| PRT422 | 12.5 |
| PRT423 | 12.5 |
| PRT424 | 25 |
| PRT425 | 12.5 |
| PRT426 | 12.5 |
| PRT427 | 25 |
| PRT428 | 50 |
| PRT429 | 12.5 |
| PRT430 | 12.5 |
| PRT431 | 50 |
| PRT432 | 25 |
| PRT433 | 12.5 |
| PRT434 | 12.5 |
| PRT435 | 12.5 |
| PRT436 | 12.5 |
| PRT437 | 50 |
| PRT438 | 25 |
| PRT439 | 25 |
| PRT440 | 50 |
| PRT441 | 12.5 |
| PRT442 | 12.5 |
| PRT443 | 12.5 |
| PRT444 | 25 |
| PRT445 | 50 |
| PRT446 | 12.5 |
| PRT447 | 50 |
| PRT448 | 12.5 |
| PRT449 | 50 |
| PRT450 | 12.5 |
| PRT451 | 25 |
| PRT452 | 12.5 |
| PRT453 | 25 |
| PRT454 | 50 |
| PRT455 | 50 |
| PRT456 | 25 |
| PRT457 | 50 |
| PRT458 | 50 |
| PRT459 | 25 |
| PRT460 | 50 |
| PRT461 | 50 |
| PRT462 | 12.5 |
| PRT463 | 50 |
| PRT464 | 12.5 |
| PRT465 | 50 |
| PRT466 | 12.5 |
| PRT467 | 12.5 |
| PRT468 | 25 |
| PRT469 | 12.5 |
| PRT470 | 50 |

TABLE 2-continued

MIC (μg/mL) of the human-originated EGF domain proteins against *E. coli* DH5α

| Protein | MIC |
|---|---|
| PRT471 | 100 |
| PRT472 | 25 |
| PRT473 | 50 |
| PRT474 | 12.5 |
| PRT475 | 50 |
| PRT476 | 12.5 |
| PRT477 | 12.5 |
| PRT478 | 50 |
| PRT479 | 25 |
| PRT480 | 12.5 |
| PRT481 | 25 |
| PRT482 | 50 |
| PRT483 | 12.5 |
| PRT484 | 25 |
| PRT485 | 50 |
| PRT486 | 12.5 |
| PRT487 | 12.5 |
| PRT488 | 50 |
| PRT489 | 12.5 |
| PRT490 | 25 |
| PRT491 | 12.5 |
| PRT492 | 25 |
| PRT493 | 12.5 |
| PRT494 | 50 |
| PRT495 | 25 |
| PRT496 | 12.5 |
| PRT497 | 12.5 |
| PRT498 | 12.5 |
| PRT499 | 12.5 |
| PRT500 | 25 |
| PRT501 | 12.5 |
| PRT502 | 25 |
| PRT503 | 12.5 |
| PRT504 | 12.5 |
| PRT505 | 50 |
| PRT506 | 25 |
| PRT507 | 12.5 |
| PRT508 | 12.5 |
| PRT509 | 12.5 |
| PRT510 | 50 |
| PRT511 | 50 |
| PRT512 | 50 |
| PRT513 | 50 |
| PRT514 | 50 |
| PRT515 | 25 |
| PRT516 | 12.5 |
| PRT517 | 25 |
| PRT518 | 50 |
| PRT519 | 25 |
| PRT520 | 25 |
| PRT521 | 50 |
| PRT522 | 25 |
| PRT523 | 12.5 |
| PRT524 | 12.5 |
| PRT525 | 25 |
| PRT526 | 50 |
| PRT527 | 50 |
| PRT528 | 12.5 |
| PRT529 | 25 |
| PRT530 | 50 |
| PRT531 | 50 |
| PRT532 | 12.5 |
| PRT533 | 50 |
| PRT534 | 50 |
| PRT535 | 12.5 |
| PRT536 | 12.5 |
| PRT537 | 50 |
| PRT538 | 25 |
| PRT539 | 12.5 |
| PRT540 | 12.5 |
| PRT541 | 12.5 |
| PRT542 | 25 |
| PRT543 | 12.5 |
| PRT544 | 12.5 |
| PRT545 | 12.5 |
| PRT546 | 12.5 |
| PRT547 | 25 |
| PRT548 | 12.5 |
| PRT549 | 12.5 |
| PRT550 | 25 |
| PRT551 | 12.5 |
| PRT552 | 25 |
| PRT553 | 25 |
| PRT554 | 12.5 |
| PRT555 | 50 |
| PRT556 | 25 |
| PRT557 | 12.5 |
| PRT558 | 12.5 |
| PRT559 | 25 |
| PRT560 | 12.5 |
| PRT561 | 50 |
| PRT562 | 50 |
| PRT563 | 25 |
| PRT564 | 50 |
| PRT565 | 50 |
| PRT566 | 50 |
| PRT567 | 50 |
| PRT568 | 12.5 |
| PRT569 | 25 |
| PRT570 | 25 |
| PRT571 | 12.5 |
| PRT572 | 12.5 |
| PRT573 | 25 |
| PRT574 | 50 |
| PRT575 | 50 |
| PRT576 | 12.5 |
| PRT577 | 12.5 |
| PRT578 | 12.5 |
| PRT579 | 12.5 |
| PRT580 | 12.5 |
| PRT581 | 50 |
| PRT582 | 12.5 |
| PRT583 | 25 |
| PRT584 | 50 |
| PRT585 | 50 |
| PRT586 | 12.5 |
| PRT587 | 25 |
| PRT588 | 12.5 |
| PRT589 | 12.5 |
| PRT590 | 50 |
| PRT591 | 25 |
| PRT592 | 50 |
| PRT593 | 25 |
| PRT594 | 12.5 |
| PRT595 | 12.5 |
| PRT596 | 12.5 |
| PRT597 | 25 |
| PRT598 | 25 |
| PRT599 | 12.5 |
| PRT600 | 25 |
| PRT601 | 50 |
| PRT602 | 50 |
| PRT603 | 25 |
| PRT604 | 50 |
| PRT605 | 12.5 |
| PRT606 | 25 |
| PRT607 | 50 |
| PRT608 | 12.5 |
| PRT609 | 50 |
| PRT610 | 50 |
| PRT611 | 12.5 |
| PRT612 | 25 |
| PRT613 | 50 |
| PRT614 | 50 |
| PRT615 | 12.5 |
| PRT616 | 25 |
| PRT617 | 25 |
| PRT618 | 50 |
| PRT619 | 12.5 |
| PRT620 | 25 |

TABLE 2-continued

MIC (µg/mL) of the human-originated EGF domain proteins against *E. coli* DH5α

| Protein | MIC |
|---|---|
| PRT621 | 50 |
| PRT622 | 25 |
| PRT623 | 12.5 |
| PRT624 | 25 |
| PRT625 | 12.5 |
| PRT626 | 25 |
| PRT627 | 12.5 |
| PRT628 | 12.5 |
| PRT629 | 12.5 |
| PRT630 | 50 |
| PRT631 | 25 |
| PRT632 | 12.5 |
| PRT633 | 12.5 |
| PRT634 | 12.5 |
| PRT635 | 12.5 |
| PRT636 | 12.5 |
| PRT637 | 25 |
| PRT638 | 25 |
| PRT639 | 12.5 |
| PRT640 | 12.5 |
| PRT641 | 50 |
| PRT642 | 12.5 |
| PRT643 | 12.5 |
| PRT644 | 25 |
| PRT645 | 50 |
| PRT646 | 12.5 |
| PRT647 | 25 |
| PRT648 | 12.5 |
| PRT649 | 50 |
| PRT650 | 12.5 |
| PRT651 | 12.5 |
| PRT652 | 12.5 |
| PRT653 | 25 |
| PRT654 | 12.5 |
| PRT655 | 25 |
| PRT656 | 50 |
| PRT657 | 12.5 |
| PRT658 | 12.5 |
| PRT659 | 25 |
| PRT660 | 12.5 |
| PRT661 | 50 |
| PRT662 | 25 |
| PRT663 | 100 |
| PRT664 | 25 |
| PRT665 | 25 |
| PRT666 | 12.5 |
| PRT667 | 50 |
| PRT668 | 12.5 |
| PRT669 | 25 |
| PRT670 | 25 |
| PRT671 | 50 |
| PRT672 | 12.5 |
| PRT673 | 50 |
| PRT674 | 12.5 |
| PRT675 | 12.5 |
| PRT676 | 25 |
| PRT677 | 50 |
| PRT678 | 25 |
| PRT679 | 12.5 |
| PRT680 | 12.5 |
| PRT681 | 12.5 |
| PRT682 | 25 |
| PRT683 | 12.5 |
| PRT684 | 12.5 |
| PRT685 | 50 |
| PRT686 | 50 |
| PRT687 | 50 |
| PRT688 | 25 |
| PRT689 | 100 |
| PRT690 | 25 |
| PRT691 | 25 |
| PRT692 | 50 |
| PRT693 | 25 |
| PRT694 | 50 |
| PRT695 | 25 |
| PRT696 | 50 |
| PRT697 | 25 |
| PRT698 | 50 |
| PRT699 | 50 |
| PRT700 | 25 |
| PRT701 | 50 |
| PRT702 | 25 |
| PRT703 | 25 |
| PRT704 | 50 |
| PRT705 | 25 |
| PRT706 | 25 |
| PRT707 | 50 |
| PRT708 | 50 |
| PRT709 | 50 |
| PRT710 | 25 |
| PRT711 | 25 |
| PRT712 | 25 |
| PRT713 | 50 |
| PRT714 | 12.5 |
| PRT715 | 50 |
| PRT716 | 25 |
| PRT717 | 50 |
| PRT718 | 12.5 |
| PRT719 | 50 |
| PRT720 | 50 |
| PRT721 | 25 |
| PRT722 | 12.5 |
| PRT723 | 25 |
| PRT724 | 12.5 |
| PRT725 | 25 |
| PRT726 | 12.5 |
| PRT727 | 12.5 |
| PRT728 | 25 |
| PRT729 | 12.5 |
| PRT730 | 25 |
| PRT731 | 50 |
| PRT732 | 12.5 |
| PRT733 | 50 |
| PRT734 | 50 |
| PRT735 | 12.5 |
| PRT736 | 12.5 |
| PRT737 | 12.5 |
| PRT738 | 50 |
| PRT739 | 12.5 |
| PRT740 | 12.5 |
| PRT741 | 12.5 |
| PRT742 | 50 |
| PRT743 | 12.5 |
| PRT744 | 12.5 |
| PRT745 | 50 |
| PRT746 | 12.5 |
| PRT747 | 50 |
| PRT748 | 50 |
| PRT749 | 50 |
| PRT750 | 25 |
| PRT751 | 12.5 |
| PRT752 | 50 |
| PRT753 | 25 |
| PRT754 | 25 |
| PRT755 | 12.5 |
| PRT756 | 12.5 |
| PRT757 | 50 |
| PRT758 | 12.5 |
| PRT759 | 25 |
| PRT760 | 50 |
| PRT761 | 50 |
| PRT762 | 50 |
| PRT763 | 25 |
| PRT764 | 12.5 |
| PRT765 | 12.5 |
| PRT766 | 25 |
| PRT767 | 25 |
| PRT768 | 12.5 |
| PRT769 | 12.5 |
| PRT770 | 50 |

TABLE 2-continued

MIC (μg/mL) of the human-originated EGF domain proteins against *E. coli* DH5α

| Protein | MIC |
|---|---|
| PRT771 | 25 |
| PRT772 | 12.5 |
| PRT773 | 50 |
| PRT774 | 50 |
| PRT775 | 12.5 |
| PRT776 | 12.5 |
| PRT777 | 50 |
| PRT778 | 50 |
| PRT779 | 12.5 |
| PRT780 | 12.5 |
| PRT781 | 25 |
| PRT782 | 50 |
| PRT783 | 25 |
| PRT784 | 50 |
| PRT785 | 25 |
| PRT786 | 50 |
| PRT787 | 12.5 |
| PRT788 | 50 |
| PRT789 | 25 |
| PRT790 | 25 |
| PRT791 | 50 |
| PRT792 | 12.5 |
| PRT793 | 25 |
| PRT794 | 50 |
| PRT795 | 50 |
| PRT796 | 25 |
| PRT797 | 50 |
| PRT798 | 12.5 |
| PRT799 | 25 |
| PRT800 | 25 |
| PRT801 | 25 |
| PRT802 | 12.5 |
| PRT803 | 50 |
| PRT804 | 12.5 |
| PRT805 | 12.5 |
| PRT806 | 12.5 |
| PRT807 | 25 |
| PRT808 | 25 |
| PRT809 | 25 |
| PRT810 | 25 |
| PRT811 | 12.5 |
| PRT812 | 12.5 |
| PRT813 | 50 |
| PRT814 | 25 |
| PRT815 | 25 |
| PRT816 | 25 |
| PRT817 | 50 |
| PRT818 | 25 |
| PRT819 | 12.5 |
| PRT820 | 12.5 |
| PRT821 | 12.5 |
| PRT822 | 12.5 |
| PRT823 | 25 |
| PRT824 | 12.5 |
| PRT825 | 25 |
| PRT826 | 12.5 |
| PRT827 | 12.5 |
| PRT828 | 12.5 |
| PRT829 | 50 |
| PRT830 | 12.5 |
| PRT831 | 25 |
| PRT832 | 50 |
| PRT833 | 12.5 |
| PRT834 | 50 |
| PRT835 | 25 |
| PRT836 | 50 |
| PRT837 | 25 |
| PRT838 | 50 |
| PRT839 | 12.5 |
| PRT840 | 25 |
| PRT841 | 12.5 |
| PRT842 | 12.5 |
| PRT843 | 25 |
| PRT844 | 12.5 |
| PRT845 | 25 |
| PRT846 | 25 |
| PRT847 | 12.5 |
| PRT848 | 25 |
| PRT849 | 12.5 |
| PRT850 | 50 |
| PRT851 | 25 |
| PRT852 | 12.5 |
| PRT853 | 25 |
| PRT854 | 12.5 |
| PRT855 | 50 |
| PRT856 | 25 |
| PRT857 | 25 |
| PRT858 | 12.5 |
| PRT859 | 50 |
| PRT860 | 25 |
| PRT861 | 12.5 |
| PRT862 | 12.5 |
| PRT863 | 50 |
| PRT864 | 12.5 |
| PRT865 | 25 |
| PRT866 | 25 |
| PRT867 | 50 |
| PRT868 | 12.5 |
| PRT869 | 12.5 |
| PRT870 | 12.5 |
| PRT871 | 12.5 |
| PRT872 | 25 |
| PRT873 | 12.5 |
| PRT874 | 12.5 |
| PRT875 | 25 |
| PRT876 | 12.5 |
| PRT877 | 25 |
| PRT878 | 50 |
| PRT879 | 25 |
| PRT880 | 25 |
| PRT881 | 12.5 |
| PRT882 | 25 |
| PRT883 | 12.5 |
| PRT884 | 12.5 |
| PRT885 | 25 |
| PRT886 | 25 |
| PRT887 | 12.5 |
| PRT888 | 12.5 |
| PRT889 | 25 |
| PRT890 | 50 |
| PRT891 | 12.5 |
| PRT892 | 25 |
| PRT893 | 12.5 |
| PRT894 | 12.5 |
| PRT895 | 50 |
| PRT896 | 25 |
| PRT897 | 50 |
| PRT898 | 25 |
| PRT899 | 12.5 |
| PRT900 | 12.5 |
| PRT901 | 25 |
| PRT902 | 50 |
| PRT903 | 12.5 |
| PRT904 | 50 |
| PRT905 | 25 |
| PRT906 | 50 |
| PRT907 | 25 |
| PRT908 | 50 |
| PRT909 | 50 |
| PRT910 | 50 |
| PRT911 | 12.5 |
| PRT912 | 25 |
| PRT913 | 12.5 |
| PRT914 | 12.5 |
| PRT915 | 25 |
| PRT916 | 25 |
| PRT917 | 25 |
| PRT918 | 12.5 |
| PRT919 | 50 |
| PRT920 | 12.5 |

TABLE 2-continued

MIC (µg/mL) of the human-originated EGF domain proteins against *E. coli* DH5α

| Protein | MIC |
|---|---|
| PRT921 | 12.5 |
| PRT922 | 12.5 |
| PRT923 | 25 |
| PRT924 | 12.5 |
| PRT925 | 12.5 |
| PRT926 | 25 |
| PRT927 | 25 |
| PRT928 | 25 |
| PRT929 | 100 |
| PRT930 | 50 |
| PRT931 | 12.5 |
| PRT932 | 25 |
| PRT933 | 12.5 |
| PRT934 | 12.5 |
| PRT935 | 12.5 |
| PRT936 | 25 |
| PRT937 | 25 |
| PRT938 | 12.5 |
| PRT939 | 50 |
| PRT940 | 12.5 |
| PRT941 | 25 |
| PRT942 | 25 |
| PRT943 | 12.5 |
| PRT944 | 12.5 |
| PRT945 | 25 |
| PRT946 | 50 |
| PRT947 | 12.5 |
| PRT948 | 50 |
| PRT949 | 12.5 |
| PRT950 | 50 |
| PRT951 | 25 |
| PRT952 | 50 |
| PRT953 | 12.5 |
| PRT954 | 50 |
| PRT955 | 50 |
| PRT956 | 12.5 |
| PRT957 | 12.5 |
| PRT958 | 50 |
| PRT959 | 25 |
| PRT960 | 12.5 |
| PRT961 | 12.5 |
| PRT962 | 25 |
| PRT963 | 25 |
| PRT964 | 12.5 |
| PRT965 | 12.5 |
| PRT966 | 50 |
| PRT967 | 50 |
| PRT968 | 25 |
| PRT969 | 50 |
| PRT970 | 50 |
| PRT971 | 50 |
| PRT972 | 50 |
| PRT973 | 12.5 |
| PRT974 | 25 |
| PRT975 | 25 |
| PRT976 | 50 |
| PRT977 | 12.5 |
| PRT978 | 12.5 |
| PRT979 | 50 |
| PRT980 | 12.5 |
| PRT981 | 25 |
| PRT982 | 50 |
| PRT983 | 25 |
| PRT984 | 50 |
| PRT985 | 50 |
| PRT986 | 12.5 |
| PRT987 | 25 |
| PRT988 | 12.5 |
| PRT989 | 50 |
| PRT990 | 12.5 |
| PRT991 | 50 |
| PRT992 | 12.5 |
| PRT993 | 12.5 |
| PRT994 | 50 |
| PRT995 | 12.5 |
| PRT996 | 25 |
| PRT997 | 12.5 |
| PRT998 | 12.5 |
| PRT999 | 12.5 |
| PRT1000 | 50 |
| PRT1001 | 12.5 |
| PRT1002 | 25 |
| PRT1003 | 50 |
| PRT1004 | 50 |
| PRT1005 | 50 |
| PRT1006 | 12.5 |
| PRT1007 | 25 |
| PRT1008 | 50 |
| PRT1009 | 25 |
| PRT1010 | 50 |
| PRT1011 | 12.5 |
| PRT1012 | 12.5 |
| PRT1013 | 12.5 |
| PRT1014 | 12.5 |
| PRT1015 | 12.5 |
| PRT1016 | 12.5 |
| PRT1017 | 50 |
| PRT1018 | 25 |
| PRT1019 | 12.5 |
| PRT1020 | 12.5 |
| PRT1021 | 25 |
| PRT1022 | 12.5 |
| PRT1023 | 25 |
| PRT1024 | 50 |
| PRT1025 | 50 |
| PRT1026 | 12.5 |
| PRT1027 | 12.5 |
| PRT1028 | 12.5 |
| PRT1029 | 12.5 |
| PRT1030 | 25 |
| PRT1031 | 12.5 |
| PRT1032 | 50 |
| PRT1033 | 50 |
| PRT1034 | 25 |
| PRT1035 | 12.5 |
| PRT1036 | 25 |
| PRT1037 | 12.5 |
| PRT1038 | 50 |
| PRT1039 | 50 |
| PRT1040 | 12.5 |
| PRT1041 | 12.5 |
| PRT1042 | 25 |
| PRT1043 | 50 |
| PRT1044 | 100 |
| PRT1045 | 25 |
| PRT1046 | 50 |
| PRT1047 | 50 |
| PRT1048 | 12.5 |
| PRT1049 | 12.5 |
| PRT1050 | 25 |
| PRT1051 | 50 |
| PRT1052 | 12.5 |
| PRT1053 | 12.5 |
| PRT1054 | 25 |
| PRT1055 | 12.5 |
| PRT1056 | 50 |
| PRT1057 | 25 |
| PRT1058 | 12.5 |
| PRT1059 | 50 |
| PRT1060 | 12.5 |
| PRT1061 | 12.5 |
| PRT1062 | 25 |
| PRT1063 | 12.5 |
| PRT1064 | 25 |
| PRT1065 | 50 |
| PRT1066 | 12.5 |
| PRT1067 | 25 |
| PRT1068 | 12.5 |
| PRT1069 | 12.5 |
| PRT1070 | 25 |

TABLE 2-continued

MIC (µg/mL) of the human-originated EGF domain proteins against *E. coli* DH5α

| Protein | MIC |
|---|---|
| PRT1071 | 50 |
| PRT1072 | 50 |
| PRT1073 | 25 |
| PRT1074 | 50 |
| PRT1075 | 25 |
| PRT1076 | 12.5 |
| PRT1077 | 12.5 |
| PRT1078 | 25 |
| PRT1079 | 50 |
| PRT1080 | 50 |
| PRT1081 | 25 |
| PRT1082 | 50 |
| PRT1083 | 50 |
| PRT1084 | 50 |
| PRT1085 | 25 |
| PRT1086 | 12.5 |
| PRT1087 | 50 |
| PRT1088 | 25 |
| PRT1089 | 50 |
| PRT1090 | 25 |
| PRT1091 | 12.5 |
| PRT1092 | 25 |
| PRT1093 | 12.5 |
| PRT1094 | 25 |
| PRT1095 | 50 |
| PRT1096 | 12.5 |
| PRT1097 | 25 |
| PRT1098 | 12.5 |
| PRT1099 | 12.5 |
| PRT1100 | 12.5 |
| PRT1101 | 25 |
| PRT1102 | 12.5 |
| PRT1103 | 12.5 |
| PRT1104 | 50 |
| PRT1105 | 12.5 |
| PRT1106 | 25 |
| PRT1107 | 12.5 |
| PRT1108 | 50 |
| PRT1109 | 12.5 |
| PRT1110 | 25 |
| PRT1111 | 12.5 |
| PRT1112 | 50 |
| PRT1113 | 12.5 |
| PRT1114 | 25 |
| PRT1115 | 50 |
| PRT1116 | 25 |
| PRT1117 | 50 |
| PRT1118 | 25 |
| PRT1119 | 100 |
| PRT1120 | 25 |
| PRT1121 | 12.5 |
| PRT1122 | 50 |
| PRT1123 | 25 |
| PRT1124 | 25 |
| PRT1125 | 25 |
| PRT1126 | 25 |
| PRT1127 | 12.5 |
| PRT1128 | 12.5 |
| PRT1129 | 50 |
| PRT1130 | 12.5 |
| PRT1131 | 50 |
| PRT1132 | 50 |
| PRT1133 | 12.5 |
| PRT1134 | 12.5 |
| PRT1135 | 25 |
| PRT1136 | 50 |
| PRT1137 | 25 |
| PRT1138 | 25 |
| PRT1139 | 12.5 |
| PRT1140 | 25 |
| PRT1141 | 50 |
| PRT1142 | 25 |
| PRT1143 | 12.5 |
| PRT1144 | 50 |
| PRT1145 | 12.5 |
| PRT1146 | 50 |
| PRT1147 | 50 |
| PRT1148 | 12.5 |
| PRT1149 | 25 |
| PRT1150 | 12.5 |
| PRT1151 | 25 |
| PRT1152 | 12.5 |
| PRT1153 | 12.5 |
| PRT1154 | 50 |
| PRT1155 | 25 |
| PRT1156 | 50 |
| PRT1157 | 12.5 |
| PRT1158 | 25 |
| PRT1159 | 12.5 |
| PRT1160 | 12.5 |
| PRT1161 | 25 |
| PRT1162 | 12.5 |
| PRT1163 | 12.5 |
| PRT1164 | 12.5 |
| PRT1165 | 50 |
| PRT1166 | 50 |
| PRT1167 | 50 |
| PRT1168 | 25 |
| PRT1169 | 50 |
| PRT1170 | 25 |
| PRT1171 | 12.5 |
| PRT1172 | 12.5 |
| PRT1173 | 12.5 |
| PRT1174 | 12.5 |
| PRT1175 | 12.5 |
| PRT1176 | 12.5 |
| PRT1177 | 50 |
| PRT1178 | 50 |
| PRT1179 | 12.5 |
| PRT1180 | 50 |
| PRT1181 | 12.5 |
| PRT1182 | 12.5 |
| PRT1183 | 25 |
| PRT1184 | 50 |
| PRT1185 | 50 |
| PRT1186 | 50 |
| PRT1187 | 50 |
| PRT1188 | 25 |
| PRT1189 | 50 |
| PRT1190 | 50 |
| PRT1191 | 12.5 |
| PRT1192 | 25 |
| PRT1193 | 12.5 |
| PRT1194 | 50 |
| PRT1195 | 25 |
| PRT1196 | 12.5 |
| PRT1197 | 25 |
| PRT1198 | 25 |
| PRT1199 | 50 |
| PRT1200 | 12.5 |
| PRT1201 | 12.5 |
| PRT1202 | 50 |
| PRT1203 | 25 |
| PRT1204 | 100 |
| PRT1205 | 25 |
| PRT1206 | 50 |
| PRT1207 | 12.5 |
| PRT1208 | 12.5 |
| PRT1209 | 50 |
| PRT1210 | 25 |
| PRT1211 | 50 |
| PRT1212 | 50 |
| PRT1213 | 25 |
| PRT1214 | 25 |
| PRT1215 | 25 |
| PRT1216 | 50 |
| PRT1217 | 50 |
| PRT1218 | 12.5 |
| PRT1219 | 12.5 |
| PRT1220 | 12.5 |

TABLE 2-continued

MIC (µg/mL) of the human-originated EGF domain proteins against *E. coli* DH5α

| Protein | MIC |
|---|---|
| PRT1221 | 25 |
| PRT1222 | 12.5 |
| PRT1223 | 50 |
| PRT1224 | 25 |
| PRT1225 | 25 |
| PRT1226 | 25 |
| PRT1227 | 50 |
| PRT1228 | 12.5 |
| PRT1229 | 25 |
| PRT1230 | 12.5 |
| PRT1231 | 12.5 |
| PRT1232 | 50 |
| PRT1233 | 25 |
| PRT1234 | 25 |
| PRT1235 | 12.5 |
| PRT1236 | 50 |
| PRT1237 | 12.5 |
| PRT1238 | 25 |
| PRT1239 | 25 |
| PRT1240 | 12.5 |
| PRT1241 | 50 |
| PRT1242 | 25 |
| PRT1243 | 12.5 |
| PRT1244 | 50 |
| PRT1245 | 50 |
| PRT1246 | 50 |
| PRT1247 | 50 |
| PRT1248 | 25 |
| PRT1249 | 12.5 |
| PRT1250 | 12.5 |
| PRT1251 | 100 |
| PRT1252 | 12.5 |
| PRT1253 | 50 |
| PRT1254 | 12.5 |
| PRT1255 | 12.5 |
| PRT1256 | 25 |
| PRT1257 | 12.5 |
| PRT1258 | 12.5 |
| PRT1259 | 25 |
| PRT1260 | 25 |
| PRT1261 | 12.5 |
| PRT1262 | 12.5 |
| PRT1263 | 100 |
| PRT1264 | 12.5 |
| PRT1265 | 25 |
| PRT1266 | 50 |
| PRT1267 | 12.5 |
| PRT1268 | 50 |
| PRT1269 | 12.5 |
| PRT1270 | 50 |
| PRT1271 | 25 |
| PRT1272 | 25 |
| PRT1273 | 12.5 |
| PRT1274 | 12.5 |
| PRT1275 | 12.5 |
| PRT1276 | 50 |
| PRT1277 | 12.5 |
| PRT1278 | 25 |
| PRT1279 | 50 |
| PRT1280 | 25 |
| PRT1281 | 50 |
| PRT1282 | 12.5 |
| PRT1283 | 12.5 |
| PRT1284 | 25 |
| PRT1285 | 12.5 |
| PRT1286 | 12.5 |
| PRT1287 | 50 |
| PRT1288 | 50 |
| PRT1289 | 12.5 |
| PRT1290 | 50 |
| PRT1291 | 50 |
| PRT1292 | 12.5 |
| PRT1293 | 25 |
| PRT1294 | 50 |
| PRT1295 | 12.5 |
| PRT1296 | 50 |
| PRT1297 | 12.5 |
| PRT1298 | 12.5 |
| PRT1299 | 25 |
| PRT1300 | 12.5 |
| PRT1301 | 12.5 |
| PRT1302 | 12.5 |
| PRT1303 | 12.5 |
| PRT1304 | 25 |
| PRT1305 | 12.5 |
| PRT1306 | 25 |
| PRT1307 | 12.5 |
| PRT1308 | 50 |
| PRT1309 | 12.5 |
| PRT1310 | 12.5 |
| PRT1311 | 50 |
| PRT1312 | 50 |
| PRT1313 | 12.5 |
| PRT1314 | 12.5 |
| PRT1315 | 25 |
| PRT1316 | 50 |
| PRT1317 | 50 |
| PRT1318 | 25 |
| PRT1319 | 12.5 |
| PRT1320 | 25 |
| PRT1321 | 50 |
| PRT1322 | 12.5 |
| PRT1323 | 12.5 |
| PRT1324 | 12.5 |
| PRT1325 | 12.5 |
| PRT1326 | 50 |
| PRT1327 | 25 |
| PRT1328 | 12.5 |
| PRT1329 | 12.5 |
| PRT1330 | 12.5 |
| PRT1331 | 25 |
| PRT1332 | 50 |
| PRT1333 | 25 |
| PRT1334 | 12.5 |
| PRT1335 | 50 |
| PRT1336 | 12.5 |
| PRT1337 | 12.5 |
| PRT1338 | 50 |
| PRT1339 | 25 |
| PRT1340 | 12.5 |
| PRT1341 | 12.5 |
| PRT1342 | 25 |
| PRT1343 | 12.5 |
| PRT1344 | 12.5 |
| PRT1345 | 12.5 |
| PRT1346 | 12.5 |
| PRT1347 | 25 |
| PRT1348 | 12.5 |
| PRT1349 | 50 |
| PRT1350 | 50 |
| PRT1351 | 25 |
| PRT1352 | 12.5 |
| PRT1353 | 12.5 |
| PRT1354 | 25 |
| PRT1355 | 50 |
| PRT1356 | 12.5 |
| PRT1357 | 50 |
| PRT1358 | 50 |
| PRT1359 | 25 |
| PRT1360 | 12.5 |
| PRT1361 | 25 |
| PRT1362 | 12.5 |
| PRT1363 | 12.5 |
| PRT1364 | 25 |
| PRT1365 | 12.5 |
| PRT1366 | 12.5 |
| PRT1367 | 25 |
| PRT1368 | 12.5 |
| PRT1369 | 12.5 |
| PRT1370 | 25 |

TABLE 2-continued

MIC (µg/mL) of the human-originated EGF domain proteins against *E. coli* DH5α

| Protein | MIC |
|---|---|
| PRT1371 | 50 |
| PRT1372 | 12.5 |
| PRT1373 | 25 |
| PRT1374 | 50 |
| PRT1375 | 12.5 |
| PRT1376 | 50 |
| PRT1377 | 25 |
| PRT1378 | 50 |
| PRT1379 | 50 |
| PRT1380 | 25 |
| PRT1381 | 12.5 |
| PRT1382 | 25 |
| PRT1383 | 12.5 |
| PRT1384 | 25 |
| PRT1385 | 12.5 |
| PRT1386 | 25 |
| PRT1387 | 12.5 |
| PRT1388 | 100 |
| PRT1389 | 25 |
| PRT1390 | 12.5 |
| PRT1391 | 12.5 |
| PRT1392 | 12.5 |
| PRT1393 | 25 |
| PRT1394 | 50 |
| PRT1395 | 12.5 |
| PRT1396 | 12.5 |
| PRT1397 | 50 |
| PRT1398 | 25 |
| PRT1399 | 12.5 |
| PRT1400 | 50 |
| PRT1401 | 12.5 |
| PRT1402 | 25 |
| PRT1403 | 50 |
| PRT1404 | 12.5 |
| PRT1405 | 12.5 |
| PRT1406 | 25 |
| PRT1407 | 50 |
| PRT1408 | 25 |
| PRT1409 | 12.5 |
| PRT1410 | 25 |
| PRT1411 | 12.5 |
| PRT1412 | 25 |
| PRT1413 | 12.5 |
| PRT1414 | 50 |
| PRT1415 | 25 |
| PRT1416 | 25 |
| PRT1417 | 25 |
| PRT1418 | 25 |
| PRT1419 | 12.5 |
| PRT1420 | 12.5 |
| PRT1421 | 12.5 |
| PRT1422 | 12.5 |
| PRT1423 | 50 |
| PRT1424 | 50 |
| PRT1425 | 12.5 |
| PRT1426 | 12.5 |
| PRT1427 | 25 |
| PRT1428 | 12.5 |
| PRT1429 | 25 |
| PRT1430 | 25 |
| PRT1431 | 12.5 |
| PRT1432 | 25 |
| PRT1433 | 12.5 |
| PRT1434 | 25 |
| PRT1435 | 50 |
| PRT1436 | 12.5 |
| PRT1437 | 12.5 |
| PRT1438 | 12.5 |
| PRT1439 | 50 |
| PRT1440 | 12.5 |
| PRT1441 | 25 |
| PRT1442 | 12.5 |
| PRT1443 | 25 |
| PRT1444 | 12.5 |
| PRT1445 | 50 |
| PRT1446 | 12.5 |
| PRT1447 | 100 |
| PRT1448 | 25 |
| PRT1449 | 50 |
| PRT1450 | 12.5 |
| PRT1451 | 25 |
| PRT1452 | 12.5 |
| PRT1453 | 25 |
| PRT1454 | 25 |
| PRT1455 | 25 |
| PRT1456 | 12.5 |
| PRT1457 | 12.5 |
| PRT1458 | 12.5 |
| PRT1459 | 12.5 |
| PRT1460 | 12.5 |
| PRT1461 | 25 |
| PRT1462 | 12.5 |
| PRT1463 | 50 |
| PRT1464 | 12.5 |
| PRT1465 | 12.5 |
| PRT1466 | 50 |
| PRT1467 | 25 |
| PRT1468 | 50 |
| PRT1469 | 25 |
| PRT1470 | 50 |
| PRT1471 | 12.5 |
| PRT1472 | 50 |
| PRT1473 | 12.5 |
| PRT1474 | 50 |
| PRT1475 | 25 |
| PRT1476 | 12.5 |
| PRT1477 | 50 |
| PRT1478 | 50 |
| PRT1479 | 50 |
| PRT1480 | 50 |
| PRT1481 | 12.5 |
| PRT1482 | 12.5 |
| PRT1483 | 12.5 |
| PRT1484 | 50 |
| PRT1485 | 12.5 |
| PRT1486 | 12.5 |
| PRT1487 | 25 |
| PRT1488 | 25 |
| PRT1489 | 25 |
| PRT1490 | 12.5 |
| PRT1491 | 25 |
| PRT1492 | 25 |
| PRT1493 | 100 |
| PRT1494 | 25 |
| PRT1495 | 25 |
| PRT1496 | 50 |
| PRT1497 | 50 |
| PRT1498 | 50 |

It can be known from the above table that: all of the human-originated EGF domain proteins (PRT1 to PRT1498 in Table 1) have an inhibitory effect on *E. coli* DH5α.

Example 16: Effect of the Human-Originated EGF Domain Proteins (PRT1 to PRT1498 in Table 1) Such as the Recombination Protein hF VII-EGF1, Etc on the Growth of Various Gram-Negative Bacteria 1. Gram-negative bacteria, such as *E. coli* BL21, *Pseudomonas aeruginosa*, *Klebsiella pneumonia*, *Enterobacter cloacae*, *Aeromonas hydrophila*, *Citrobacter diversus*, *Moraxella catarrhalis*, *Proteus mirabilis*, *Proteus vulgaris*, *Serratia marcescens*, etc were streaked on solid LB medium and cultured respectively. Then, typical clones were picked, inoculated into common liquid LB medium respectively, and cultured at 37° C. with shaking at 185 rpm until the McFarland specific turbidity was 0.5. The bacterial culture of each of Gram-negative bacteria was centrifuged at 4000×g for 3 min, the supernatant was discarded, and the thalli were resuspended with fresh LB medium.

2. The above-mentioned bacterial suspensions were diluted and inoculated into 96-well plates with the final concentration of the bacterial suspension being $5×10^5$ CFU/mL per well.

3. Each of the purified human-originated EGF domain proteins (PRT1 to PRT1498 in Table 1) was added to each of the above wells and subjected to two-fold serial dilution in concentration. Three parallel wells were set up for each concentration in the gradient.

4. The above-mentioned 96-well plates were placed and cultured at 37° C. in shaking incubator shaking at 175 rpm. Judgement on MIC: After 10 h of cultivation, the growth was observed with naked eyes or judged under the ultra violet spectrophotometer at a wavelength of 600 nm. The minimal inhibitory concentration MIC is defined as the lowest concentration of the recombinant protein at which there is no growth of the bacteria. The results are shown in Table 3:

TABLE 3

MIC (µg/mL) of the human-originated EGF domain proteins against various Gram-negative bacteria

| | MIC (µg/mL) | | | | | | | | | |
|---|---|---|---|---|---|---|---|---|---|---|
| Protein | E. coli BL21 | P. aeruginosa | K. pneumonia | E. cloacae | A. hydrophila | C. diversus | M. catarrhalis | P. mirabilis | P. vulgaris | S. marcescens |
| PRT1 | 12.5 | 25 | 25 | 12.5 | 12.5 | 12.5 | 25 | 25 | 12.5 | 12.5 |
| PRT2 | 50 | 50 | 50 | 25 | 25 | 25 | 12.5 | 25 | 12.5 | 12.5 |
| PRT3 | 25 | 25 | 12.5 | 12.5 | 25 | 25 | 12.5 | 12.5 | 25 | 12.5 |
| PRT4 | 50 | 25 | 25 | 12.5 | 25 | 12.5 | 25 | 25 | 50 | 25 |
| PRT5 | 12.5 | 25 | 25 | 25 | 12.5 | 25 | 25 | 12.5 | 12.5 | 25 |
| PRT6 | 50 | 25 | 50 | 25 | 12.5 | 25 | 25 | 12.5 | 25 | 25 |
| PRT7 | 25 | 25 | 12.5 | 12.5 | 50 | 12.5 | 25 | 50 | 50 | 12.5 |
| PRT8 | 50 | 12.5 | 25 | 50 | 12.5 | 50 | 12.5 | 12.5 | 25 | 12.5 |
| PRT9 | 25 | 12.5 | 12.5 | 12.5 | 25 | 12.5 | 12.5 | 12.5 | 50 | 12.5 |
| PRT10 | 50 | 12.5 | 50 | 12.5 | 50 | 25 | 12.5 | 12.5 | 25 | 12.5 |
| PRT11 | 25 | 12.5 | 25 | 12.5 | 25 | 50 | 25 | 12.5 | 50 | 25 |
| PRT12 | 25 | 50 | 12.5 | 25 | 12.5 | 12.5 | 12.5 | 25 | 12.5 | 12.5 |
| PRT13 | 12.5 | 12.5 | 25 | 12.5 | 12.5 | 25 | 12.5 | 50 | 25 | 12.5 |
| PRT14 | 50 | 25 | 12.5 | 25 | 50 | 25 | 12.5 | 25 | 50 | 12.5 |
| PRT15 | 50 | 25 | 12.5 | 50 | 12.5 | 25 | 12.5 | 12.5 | 12.5 | 25 |
| PRT16 | 12.5 | 25 | 12.5 | 12.5 | 50 | 25 | 12.5 | 50 | 25 | 25 |
| PRT17 | 12.5 | 12.5 | 25 | 50 | 12.5 | 50 | 25 | 12.5 | 50 | 25 |
| PRT18 | 50 | 25 | 100 | 50 | 25 | 12.5 | 12.5 | 25 | 12.5 | 12.5 |
| PRT19 | 12.5 | 12.5 | 25 | 50 | 12.5 | 25 | 50 | 12.5 | 25 | 50 |
| PRT20 | 25 | 50 | 25 | 12.5 | 50 | 25 | 12.5 | 50 | 25 | 12.5 |
| PRT21 | 50 | 12.5 | 25 | 50 | 12.5 | 25 | 12.5 | 50 | 25 | 50 |
| PRT22 | 50 | 25 | 12.5 | 12.5 | 25 | 12.5 | 25 | 12.5 | 12.5 | 25 |
| PRT23 | 25 | 12.5 | 12.5 | 25 | 12.5 | 50 | 25 | 50 | 25 | 50 |
| PRT24 | 25 | 12.5 | 25 | 12.5 | 12.5 | 25 | 12.5 | 25 | 12.5 | 25 |
| PRT25 | 50 | 25 | 50 | 25 | 12.5 | 100 | 25 | 12.5 | 25 | 12.5 |
| PRT26 | 12.5 | 25 | 12.5 | 25 | 12.5 | 25 | 12.5 | 25 | 12.5 | 25 |
| PRT27 | 25 | 50 | 25 | 12.5 | 25 | 50 | 12.5 | 25 | 50 | 100 |
| PRT28 | 25 | 12.5 | 50 | 25 | 12.5 | 25 | 50 | 12.5 | 25 | 50 |
| PRT29 | 25 | 12.5 | 25 | 50 | 25 | 25 | 12.5 | 25 | 50 | 12.5 |
| PRT30 | 50 | 12.5 | 25 | 50 | 12.5 | 25 | 50 | 12.5 | 25 | 12.5 |
| PRT31 | 12.5 | 12.5 | 25 | 12.5 | 25 | 12.5 | 12.5 | 25 | 50 | 25 |
| PRT32 | 50 | 12.5 | 12.5 | 25 | 50 | 12.5 | 50 | 12.5 | 25 | 50 |
| PRT33 | 50 | 12.5 | 12.5 | 25 | 12.5 | 12.5 | 12.5 | 25 | 25 | 12.5 |
| PRT34 | 25 | 25 | 12.5 | 12.5 | 25 | 25 | 12.5 | 12.5 | 25 | 12.5 |
| PRT35 | 50 | 25 | 12.5 | 50 | 25 | 12.5 | 50 | 12.5 | 25 | 12.5 |
| PRT36 | 25 | 12.5 | 12.5 | 25 | 25 | 50 | 25 | 25 | 12.5 | 25 |
| PRT37 | 50 | 25 | 25 | 12.5 | 12.5 | 25 | 12.5 | 12.5 | 25 | 12.5 |
| PRT38 | 25 | 12.5 | 50 | 25 | 100 | 50 | 12.5 | 25 | 50 | 50 |
| PRT39 | 25 | 50 | 50 | 25 | 50 | 50 | 12.5 | 25 | 12.5 | 12.5 |
| PRT40 | 12.5 | 25 | 12.5 | 25 | 50 | 25 | 12.5 | 12.5 | 25 | 12.5 |
| PRT41 | 12.5 | 25 | 12.5 | 25 | 12.5 | 25 | 12.5 | 25 | 12.5 | 50 |
| PRT42 | 12.5 | 25 | 12.5 | 25 | 12.5 | 25 | 12.5 | 25 | 100 | 50 |
| PRT43 | 25 | 12.5 | 25 | 12.5 | 25 | 12.5 | 25 | 12.5 | 25 | 12.5 |
| PRT44 | 12.5 | 25 | 12.5 | 12.5 | 25 | 25 | 25 | 50 | 25 | 12.5 |
| PRT45 | 25 | 12.5 | 25 | 50 | 25 | 25 | 12.5 | 50 | 12.5 | 50 |
| PRT46 | 12.5 | 50 | 12.5 | 25 | 12.5 | 12.5 | 12.5 | 25 | 12.5 | 100 |
| PRT47 | 25 | 12.5 | 12.5 | 25 | 12.5 | 50 | 25 | 25 | 50 | 12.5 |
| PRT48 | 25 | 12.5 | 50 | 12.5 | 25 | 50 | 12.5 | 25 | 12.5 | 12.5 |
| PRT49 | 25 | 25 | 12.5 | 25 | 25 | 12.5 | 25 | 12.5 | 25 | 100 |
| PRT50 | 12.5 | 25 | 12.5 | 12.5 | 25 | 50 | 25 | 12.5 | 25 | 50 |
| PRT51 | 12.5 | 50 | 25 | 12.5 | 12.5 | 12.5 | 25 | 12.5 | 12.5 | 25 |
| PRT52 | 12.5 | 25 | 12.5 | 25 | 12.5 | 25 | 12.5 | 25 | 50 | 25 |
| PRT53 | 25 | 50 | 12.5 | 50 | 12.5 | 50 | 25 | 12.5 | 100 | 12.5 |
| PRT54 | 12.5 | 25 | 12.5 | 12.5 | 12.5 | 12.5 | 25 | 50 | 25 | 12.5 |
| PRT55 | 50 | 12.5 | 50 | 100 | 12.5 | 12.5 | 25 | 12.5 | 12.5 | 12.5 |
| PRT56 | 12.5 | 12.5 | 100 | 12.5 | 25 | 12.5 | 50 | 25 | 25 | 50 |
| PRT57 | 50 | 12.5 | 50 | 25 | 12.5 | 50 | 12.5 | 25 | 12.5 | 25 |

TABLE 3-continued

MIC (μg/mL) of the human-originated EGF domain proteins against various Gram-negative bacteria

| | MIC (μg/mL) | | | | | | | | | |
|---|---|---|---|---|---|---|---|---|---|---|
| Protein | E. coli BL21 | P. aeruginosa | K. pneumonia | E. cloacae | A. hydrophila | C. diversus | M. catarrhalis | P. mirabilis | P. vulgaris | S. marcescens |
| PRT58 | 25 | 12.5 | 12.5 | 12.5 | 12.5 | 12.5 | 25 | 100 | 25 | 50 |
| PRT59 | 12.5 | 25 | 50 | 25 | 12.5 | 25 | 12.5 | 25 | 12.5 | 12.5 |
| PRT60 | 12.5 | 12.5 | 12.5 | 12.5 | 12.5 | 12.5 | 25 | 50 | 12.5 | 50 |
| PRT61 | 50 | 12.5 | 12.5 | 12.5 | 12.5 | 25 | 25 | 25 | 12.5 | 25 |
| PRT62 | 100 | 12.5 | 12.5 | 12.5 | 25 | 12.5 | 25 | 12.5 | 12.5 | 25 |
| PRT63 | 25 | 12.5 | 25 | 12.5 | 25 | 12.5 | 25 | 12.5 | 25 | 12.5 |
| PRT64 | 12.5 | 50 | 25 | 12.5 | 25 | 50 | 25 | 25 | 25 | 25 |
| PRT65 | 25 | 25 | 25 | 12.5 | 25 | 12.5 | 25 | 12.5 | 25 | 100 |
| PRT66 | 12.5 | 12.5 | 12.5 | 12.5 | 12.5 | 25 | 12.5 | 25 | 12.5 | 25 |
| PRT67 | 50 | 12.5 | 25 | 50 | 25 | 12.5 | 25 | 50 | 12.5 | 50 |
| PRT68 | 25 | 12.5 | 25 | 12.5 | 12.5 | 12.5 | 12.5 | 12.5 | 12.5 | 100 |
| PRT69 | 12.5 | 25 | 12.5 | 25 | 12.5 | 25 | 12.5 | 12.5 | 12.5 | 12.5 |
| PRT70 | 12.5 | 12.5 | 25 | 12.5 | 25 | 12.5 | 12.5 | 50 | 12.5 | 25 |
| PRT71 | 25 | 12.5 | 25 | 50 | 25 | 12.5 | 50 | 12.5 | 12.5 | 12.5 |
| PRT72 | 12.5 | 25 | 12.5 | 25 | 12.5 | 12.5 | 12.5 | 12.5 | 25 | 100 |
| PRT73 | 50 | 25 | 100 | 25 | 50 | 12.5 | 50 | 12.5 | 50 | 12.5 |
| PRT74 | 12.5 | 25 | 50 | 25 | 12.5 | 12.5 | 12.5 | 12.5 | 12.5 | 25 |
| PRT75 | 25 | 12.5 | 25 | 50 | 12.5 | 12.5 | 12.5 | 12.5 | 12.5 | 12.5 |
| PRT76 | 12.5 | 25 | 12.5 | 25 | 12.5 | 25 | 100 | 12.5 | 12.5 | 50 |
| PRT77 | 12.5 | 25 | 50 | 25 | 12.5 | 50 | 12.5 | 50 | 50 | 50 |
| PRT78 | 25 | 50 | 25 | 50 | 25 | 50 | 50 | 50 | 50 | 12.5 |
| PRT79 | 25 | 12.5 | 25 | 12.5 | 25 | 12.5 | 12.5 | 50 | 12.5 | 50 |
| PRT80 | 50 | 12.5 | 25 | 12.5 | 25 | 12.5 | 25 | 12.5 | 12.5 | 12.5 |
| PRT81 | 12.5 | 12.5 | 25 | 12.5 | 25 | 12.5 | 50 | 12.5 | 25 | 50 |
| PRT82 | 12.5 | 25 | 50 | 25 | 12.5 | 50 | 100 | 12.5 | 12.5 | 12.5 |
| PRT83 | 12.5 | 25 | 12.5 | 25 | 12.5 | 25 | 12.5 | 12.5 | 12.5 | 12.5 |
| PRT84 | 25 | 12.5 | 25 | 12.5 | 25 | 12.5 | 25 | 12.5 | 25 | 12.5 |
| PRT85 | 12.5 | 12.5 | 12.5 | 25 | 12.5 | 25 | 50 | 50 | 12.5 | 50 |
| PRT86 | 12.5 | 25 | 12.5 | 25 | 12.5 | 25 | 12.5 | 25 | 12.5 | 12.5 |
| PRT87 | 12.5 | 12.5 | 50 | 12.5 | 25 | 50 | 25 | 12.5 | 25 | 50 |
| PRT88 | 12.5 | 50 | 100 | 12.5 | 12.5 | 12.5 | 12.5 | 50 | 25 | 12.5 |
| PRT89 | 50 | 12.5 | 12.5 | 25 | 50 | 25 | 12.5 | 25 | 50 | 12.5 |
| PRT90 | 12.5 | 12.5 | 12.5 | 12.5 | 12.5 | 25 | 12.5 | 25 | 12.5 | 12.5 |
| PRT91 | 12.5 | 12.5 | 12.5 | 12.5 | 25 | 12.5 | 25 | 12.5 | 50 | 12.5 |
| PRT92 | 12.5 | 50 | 12.5 | 50 | 25 | 12.5 | 25 | 50 | 25 | 12.5 |
| PRT93 | 12.5 | 50 | 12.5 | 12.5 | 25 | 100 | 25 | 12.5 | 12.5 | 12.5 |
| PRT94 | 12.5 | 12.5 | 12.5 | 50 | 12.5 | 50 | 25 | 12.5 | 25 | 50 |
| PRT95 | 12.5 | 50 | 12.5 | 50 | 12.5 | 50 | 12.5 | 25 | 50 | 25 |
| PRT96 | 25 | 12.5 | 12.5 | 12.5 | 12.5 | 12.5 | 12.5 | 12.5 | 25 | 12.5 |
| PRT97 | 12.5 | 25 | 12.5 | 12.5 | 12.5 | 50 | 100 | 50 | 12.5 | 50 |
| PRT98 | 50 | 25 | 12.5 | 25 | 50 | 25 | 100 | 50 | 12.5 | 50 |
| PRT99 | 50 | 12.5 | 50 | 25 | 50 | 25 | 50 | 25 | 50 | 12.5 |
| PRT100 | 12.5 | 12.5 | 12.5 | 12.5 | 12.5 | 12.5 | 12.5 | 12.5 | 25 | 12.5 |
| PRT101 | 50 | 25 | 50 | 25 | 50 | 50 | 50 | 12.5 | 12.5 | 12.5 |
| PRT102 | 12.5 | 12.5 | 12.5 | 12.5 | 12.5 | 25 | 12.5 | 25 | 12.5 | 25 |
| PRT103 | 12.5 | 50 | 12.5 | 12.5 | 12.5 | 12.5 | 12.5 | 25 | 12.5 | 25 |
| PRT104 | 25 | 100 | 12.5 | 12.5 | 12.5 | 12.5 | 12.5 | 12.5 | 12.5 | 25 |
| PRT105 | 25 | 12.5 | 25 | 12.5 | 25 | 50 | 12.5 | 50 | 12.5 | 50 |
| PRT106 | 50 | 12.5 | 50 | 25 | 12.5 | 25 | 12.5 | 12.5 | 12.5 | 12.5 |
| PRT107 | 12.5 | 12.5 | 12.5 | 12.5 | 50 | 25 | 12.5 | 25 | 50 | 12.5 |
| PRT108 | 12.5 | 25 | 50 | 25 | 12.5 | 25 | 50 | 12.5 | 12.5 | 12.5 |
| PRT109 | 12.5 | 12.5 | 12.5 | 12.5 | 12.5 | 12.5 | 25 | 12.5 | 25 | 50 |
| PRT110 | 12.5 | 25 | 50 | 12.5 | 50 | 12.5 | 50 | 12.5 | 12.5 | 12.5 |
| PRT111 | 12.5 | 12.5 | 12.5 | 50 | 25 | 12.5 | 25 | 50 | 25 | 12.5 |
| PRT112 | 12.5 | 50 | 12.5 | 12.5 | 12.5 | 12.5 | 12.5 | 50 | 12.5 | 50 |
| PRT113 | 50 | 25 | 12.5 | 25 | 50 | 12.5 | 50 | 12.5 | 12.5 | 100 |
| PRT114 | 12.5 | 12.5 | 25 | 12.5 | 25 | 12.5 | 12.5 | 12.5 | 12.5 | 12.5 |
| PRT115 | 50 | 12.5 | 50 | 25 | 12.5 | 25 | 50 | 12.5 | 12.5 | 12.5 |
| PRT116 | 12.5 | 25 | 12.5 | 12.5 | 12.5 | 12.5 | 12.5 | 12.5 | 12.5 | 12.5 |
| PRT117 | 12.5 | 25 | 12.5 | 25 | 12.5 | 25 | 12.5 | 25 | 12.5 | 12.5 |
| PRT118 | 12.5 | 12.5 | 12.5 | 12.5 | 12.5 | 12.5 | 25 | 12.5 | 25 | 12.5 |
| PRT119 | 50 | 12.5 | 50 | 25 | 12.5 | 25 | 50 | 25 | 12.5 | 12.5 |
| PRT120 | 12.5 | 12.5 | 12.5 | 12.5 | 12.5 | 12.5 | 100 | 12.5 | 25 | 12.5 |
| PRT121 | 12.5 | 25 | 12.5 | 50 | 12.5 | 50 | 12.5 | 25 | 50 | 25 |
| PRT122 | 12.5 | 12.5 | 12.5 | 12.5 | 12.5 | 12.5 | 25 | 12.5 | 25 | 12.5 |
| PRT123 | 12.5 | 12.5 | 12.5 | 12.5 | 12.5 | 12.5 | 12.5 | 50 | 12.5 | 50 |
| PRT124 | 50 | 12.5 | 50 | 12.5 | 12.5 | 12.5 | 12.5 | 12.5 | 12.5 | 12.5 |
| PRT125 | 12.5 | 12.5 | 12.5 | 12.5 | 50 | 25 | 12.5 | 25 | 50 | 25 |
| PRT126 | 50 | 12.5 | 50 | 12.5 | 12.5 | 12.5 | 100 | 25 | 12.5 | 25 |
| PRT127 | 12.5 | 12.5 | 25 | 12.5 | 25 | 12.5 | 12.5 | 12.5 | 12.5 | 12.5 |
| PRT128 | 25 | 12.5 | 25 | 12.5 | 12.5 | 12.5 | 12.5 | 12.5 | 12.5 | 50 |
| PRT129 | 12.5 | 50 | 12.5 | 50 | 25 | 12.5 | 25 | 25 | 12.5 | 12.5 |
| PRT130 | 25 | 12.5 | 25 | 12.5 | 25 | 50 | 25 | 12.5 | 50 | 12.5 |

TABLE 3-continued

MIC (µg/mL) of the human-originated EGF domain proteins against various Gram-negative bacteria

| Protein | E. coli BL21 | P. aeruginosa | K. pneumonia | E. cloacae | A. hydrophila | C. diversus | M. catarrhalis | P. mirabilis | P. vulgaris | S. marcescens |
|---|---|---|---|---|---|---|---|---|---|---|
| PRT131 | 12.5 | 12.5 | 12.5 | 12.5 | 12.5 | 12.5 | 25 | 100 | 25 | 12.5 |
| PRT132 | 12.5 | 12.5 | 12.5 | 25 | 50 | 25 | 12.5 | 25 | 50 | 12.5 |
| PRT133 | 12.5 | 50 | 25 | 12.5 | 25 | 50 | 25 | 12.5 | 50 | 12.5 |
| PRT134 | 12.5 | 12.5 | 25 | 12.5 | 25 | 25 | 12.5 | 100 | 25 | 12.5 |
| PRT135 | 12.5 | 25 | 12.5 | 25 | 12.5 | 25 | 50 | 25 | 12.5 | 50 |
| PRT136 | 50 | 12.5 | 25 | 25 | 50 | 12.5 | 12.5 | 25 | 12.5 | 25 |
| PRT137 | 12.5 | 25 | 12.5 | 25 | 12.5 | 25 | 12.5 | 25 | 12.5 | 50 |
| PRT138 | 50 | 12.5 | 25 | 50 | 25 | 12.5 | 100 | 12.5 | 12.5 | 25 |
| PRT139 | 25 | 12.5 | 25 | 12.5 | 12.5 | 12.5 | 50 | 12.5 | 50 | 12.5 |
| PRT140 | 25 | 12.5 | 25 | 12.5 | 25 | 12.5 | 12.5 | 12.5 | 12.5 | 12.5 |
| PRT141 | 25 | 12.5 | 25 | 12.5 | 25 | 50 | 12.5 | 50 | 12.5 | 50 |
| PRT142 | 12.5 | 25 | 12.5 | 25 | 25 | 12.5 | 25 | 12.5 | 25 | 12.5 |
| PRT143 | 12.5 | 12.5 | 12.5 | 12.5 | 12.5 | 12.5 | 50 | 25 | 12.5 | 25 |
| PRT144 | 50 | 12.5 | 50 | 12.5 | 50 | 25 | 12.5 | 25 | 50 | 12.5 |
| PRT145 | 12.5 | 12.5 | 12.5 | 12.5 | 12.5 | 12.5 | 12.5 | 25 | 12.5 | 25 |
| PRT146 | 50 | 12.5 | 50 | 12.5 | 12.5 | 25 | 12.5 | 25 | 12.5 | 25 |
| PRT147 | 12.5 | 12.5 | 12.5 | 12.5 | 12.5 | 12.5 | 12.5 | 12.5 | 25 | 12.5 |
| PRT148 | 50 | 25 | 12.5 | 50 | 12.5 | 50 | 12.5 | 50 | 12.5 | 50 |
| PRT149 | 12.5 | 12.5 | 25 | 12.5 | 25 | 12.5 | 25 | 12.5 | 12.5 | 12.5 |
| PRT150 | 12.5 | 25 | 25 | 12.5 | 50 | 25 | 12.5 | 25 | 25 | 50 |
| PRT151 | 50 | 12.5 | 50 | 12.5 | 50 | 25 | 12.5 | 25 | 50 | 12.5 |
| PRT152 | 12.5 | 12.5 | 12.5 | 12.5 | 12.5 | 25 | 12.5 | 25 | 12.5 | 12.5 |
| PRT153 | 100 | 50 | 12.5 | 25 | 50 | 25 | 12.5 | 50 | 12.5 | 50 |
| PRT154 | 50 | 12.5 | 25 | 50 | 12.5 | 25 | 50 | 25 | 12.5 | 25 |
| PRT155 | 25 | 12.5 | 25 | 12.5 | 25 | 12.5 | 25 | 12.5 | 25 | 12.5 |
| PRT156 | 12.5 | 12.5 | 25 | 12.5 | 25 | 12.5 | 50 | 12.5 | 50 | 50 |
| PRT157 | 50 | 25 | 12.5 | 25 | 12.5 | 12.5 | 12.5 | 12.5 | 12.5 | 12.5 |
| PRT158 | 12.5 | 50 | 12.5 | 50 | 25 | 12.5 | 25 | 50 | 25 | 12.5 |
| PRT159 | 50 | 25 | 12.5 | 12.5 | 12.5 | 12.5 | 12.5 | 25 | 12.5 | 25 |
| PRT160 | 25 | 12.5 | 25 | 25 | 25 | 12.5 | 25 | 12.5 | 25 | 12.5 |
| PRT161 | 12.5 | 25 | 12.5 | 25 | 50 | 25 | 12.5 | 25 | 50 | 25 |
| PRT162 | 25 | 12.5 | 25 | 12.5 | 25 | 12.5 | 12.5 | 100 | 12.5 | 25 |
| PRT163 | 25 | 12.5 | 25 | 12.5 | 25 | 12.5 | 25 | 50 | 25 | 12.5 |
| PRT164 | 50 | 25 | 12.5 | 25 | 50 | 12.5 | 50 | 12.5 | 50 | 12.5 |
| PRT165 | 12.5 | 25 | 12.5 | 25 | 25 | 25 | 25 | 12.5 | 25 | 12.5 |
| PRT166 | 25 | 12.5 | 25 | 12.5 | 12.5 | 12.5 | 12.5 | 12.5 | 12.5 | 50 |
| PRT167 | 50 | 12.5 | 50 | 12.5 | 12.5 | 25 | 12.5 | 25 | 25 | 12.5 |
| PRT168 | 25 | 12.5 | 25 | 12.5 | 50 | 12.5 | 50 | 12.5 | 50 | 12.5 |
| PRT169 | 12.5 | 50 | 100 | 50 | 25 | 12.5 | 25 | 50 | 25 | 12.5 |
| PRT170 | 25 | 12.5 | 25 | 50 | 25 | 12.5 | 25 | 50 | 25 | 12.5 |
| PRT171 | 50 | 25 | 12.5 | 25 | 50 | 25 | 12.5 | 25 | 50 | 25 |
| PRT172 | 25 | 50 | 25 | 12.5 | 12.5 | 12.5 | 12.5 | 12.5 | 12.5 | 12.5 |
| PRT173 | 50 | 12.5 | 50 | 25 | 12.5 | 25 | 50 | 25 | 12.5 | 25 |
| PRT174 | 12.5 | 25 | 50 | 25 | 12.5 | 25 | 50 | 12.5 | 50 | 12.5 |
| PRT175 | 12.5 | 12.5 | 12.5 | 12.5 | 25 | 12.5 | 25 | 12.5 | 25 | 12.5 |
| PRT176 | 12.5 | 25 | 12.5 | 25 | 12.5 | 25 | 50 | 25 | 12.5 | 25 |
| PRT177 | 25 | 12.5 | 25 | 50 | 25 | 12.5 | 25 | 50 | 25 | 12.5 |
| PRT178 | 50 | 25 | 12.5 | 50 | 12.5 | 50 | 12.5 | 50 | 12.5 | 25 |
| PRT179 | 25 | 12.5 | 25 | 50 | 12.5 | 25 | 12.5 | 25 | 12.5 | 12.5 |
| PRT180 | 12.5 | 12.5 | 12.5 | 50 | 25 | 12.5 | 25 | 50 | 25 | 12.5 |
| PRT181 | 50 | 25 | 12.5 | 25 | 50 | 25 | 12.5 | 25 | 50 | 25 |
| PRT182 | 12.5 | 25 | 12.5 | 25 | 12.5 | 25 | 100 | 25 | 12.5 | 25 |
| PRT183 | 12.5 | 12.5 | 25 | 12.5 | 25 | 12.5 | 25 | 12.5 | 25 | 12.5 |
| PRT184 | 12.5 | 25 | 50 | 25 | 12.5 | 25 | 50 | 25 | 12.5 | 25 |
| PRT185 | 25 | 12.5 | 25 | 50 | 25 | 12.5 | 50 | 12.5 | 12.5 | 50 |
| PRT186 | 50 | 12.5 | 25 | 50 | 25 | 12.5 | 25 | 12.5 | 25 | 12.5 |
| PRT187 | 12.5 | 25 | 12.5 | 25 | 12.5 | 25 | 12.5 | 25 | 12.5 | 25 |
| PRT188 | 12.5 | 50 | 12.5 | 50 | 12.5 | 12.5 | 25 | 12.5 | 25 | 12.5 |
| PRT189 | 12.5 | 25 | 12.5 | 25 | 50 | 25 | 12.5 | 25 | 50 | 25 |
| PRT190 | 25 | 50 | 25 | 12.5 | 25 | 12.5 | 12.5 | 12.5 | 12.5 | 12.5 |
| PRT191 | 12.5 | 12.5 | 12.5 | 25 | 12.5 | 25 | 12.5 | 12.5 | 50 | 12.5 |
| PRT192 | 50 | 25 | 12.5 | 25 | 50 | 25 | 12.5 | 25 | 50 | 12.5 |
| PRT193 | 100 | 50 | 12.5 | 12.5 | 12.5 | 25 | 12.5 | 25 | 12.5 | 25 |
| PRT194 | 25 | 12.5 | 25 | 12.5 | 12.5 | 12.5 | 100 | 100 | 25 | 12.5 |
| PRT195 | 12.5 | 50 | 50 | 12.5 | 50 | 12.5 | 25 | 50 | 25 | 12.5 |
| PRT196 | 12.5 | 25 | 12.5 | 25 | 12.5 | 25 | 50 | 25 | 12.5 | 25 |
| PRT197 | 12.5 | 50 | 12.5 | 50 | 12.5 | 12.5 | 12.5 | 12.5 | 12.5 | 12.5 |
| PRT198 | 12.5 | 12.5 | 50 | 12.5 | 25 | 50 | 25 | 12.5 | 25 | 50 |
| PRT199 | 12.5 | 12.5 | 12.5 | 12.5 | 12.5 | 12.5 | 12.5 | 12.5 | 12.5 | 25 |
| PRT200 | 25 | 50 | 25 | 12.5 | 25 | 50 | 25 | 12.5 | 50 | 12.5 |
| PRT201 | 12.5 | 50 | 12.5 | 50 | 12.5 | 50 | 12.5 | 25 | 50 | 25 |
| PRT202 | 12.5 | 12.5 | 12.5 | 12.5 | 12.5 | 12.5 | 12.5 | 25 | 12.5 | 25 |
| PRT203 | 25 | 12.5 | 25 | 12.5 | 25 | 50 | 25 | 50 | 25 | 50 |

TABLE 3-continued

MIC (μg/mL) of the human-originated EGF domain proteins against various Gram-negative bacteria

| Protein | E. coli BL21 | P. aeruginosa | K. pneumonia | E. cloacae | A. hydrophila | C. diversus | M. catarrhalis | P. mirabilis | P. vulgaris | S. marcescens |
|---|---|---|---|---|---|---|---|---|---|---|
| PRT204 | 12.5 | 50 | 50 | 50 | 12.5 | 12.5 | 12.5 | 12.5 | 12.5 | 12.5 |
| PRT205 | 12.5 | 12.5 | 25 | 12.5 | 25 | 12.5 | 25 | 12.5 | 25 | 12.5 |
| PRT206 | 50 | 25 | 12.5 | 25 | 50 | 25 | 12.5 | 50 | 12.5 | 50 |
| PRT207 | 50 | 12.5 | 50 | 12.5 | 50 | 12.5 | 50 | 12.5 | 25 | 50 |
| PRT208 | 50 | 25 | 12.5 | 25 | 12.5 | 25 | 12.5 | 25 | 12.5 | 25 |
| PRT209 | 12.5 | 12.5 | 25 | 12.5 | 12.5 | 12.5 | 12.5 | 12.5 | 50 | 12.5 |
| PRT210 | 12.5 | 12.5 | 12.5 | 12.5 | 12.5 | 12.5 | 12.5 | 12.5 | 25 | 12.5 |
| PRT211 | 12.5 | 25 | 12.5 | 25 | 50 | 25 | 12.5 | 25 | 50 | 25 |
| PRT212 | 50 | 12.5 | 50 | 12.5 | 25 | 12.5 | 25 | 12.5 | 12.5 | 12.5 |
| PRT213 | 12.5 | 12.5 | 12.5 | 50 | 12.5 | 50 | 12.5 | 25 | 50 | 25 |
| PRT214 | 25 | 12.5 | 25 | 12.5 | 25 | 12.5 | 25 | 12.5 | 25 | 12.5 |
| PRT215 | 12.5 | 25 | 100 | 25 | 12.5 | 25 | 12.5 | 25 | 12.5 | 12.5 |
| PRT216 | 12.5 | 12.5 | 50 | 12.5 | 50 | 12.5 | 50 | 25 | 12.5 | 25 |
| PRT217 | 25 | 12.5 | 25 | 12.5 | 25 | 12.5 | 12.5 | 12.5 | 12.5 | 50 |
| PRT218 | 50 | 50 | 50 | 25 | 12.5 | 25 | 50 | 25 | 50 | 25 |
| PRT219 | 25 | 50 | 12.5 | 12.5 | 12.5 | 12.5 | 12.5 | 12.5 | 25 | 12.5 |
| PRT220 | 25 | 12.5 | 25 | 12.5 | 25 | 12.5 | 12.5 | 12.5 | 12.5 | 50 |
| PRT221 | 50 | 50 | 12.5 | 25 | 50 | 25 | 12.5 | 25 | 50 | 12.5 |
| PRT222 | 12.5 | 12.5 | 12.5 | 25 | 12.5 | 25 | 12.5 | 25 | 12.5 | 25 |
| PRT223 | 25 | 12.5 | 25 | 12.5 | 25 | 12.5 | 25 | 12.5 | 25 | 12.5 |
| PRT224 | 12.5 | 25 | 12.5 | 12.5 | 12.5 | 12.5 | 12.5 | 12.5 | 12.5 | 50 |
| PRT225 | 50 | 12.5 | 50 | 25 | 12.5 | 25 | 50 | 25 | 12.5 | 25 |
| PRT226 | 25 | 12.5 | 25 | 50 | 12.5 | 50 | 12.5 | 12.5 | 12.5 | 12.5 |
| PRT227 | 12.5 | 12.5 | 12.5 | 12.5 | 12.5 | 50 | 25 | 12.5 | 25 | 50 |
| PRT228 | 12.5 | 25 | 50 | 25 | 12.5 | 25 | 50 | 25 | 12.5 | 25 |
| PRT229 | 25 | 12.5 | 12.5 | 12.5 | 12.5 | 12.5 | 12.5 | 12.5 | 25 | 12.5 |
| PRT230 | 12.5 | 25 | 12.5 | 25 | 12.5 | 25 | 12.5 | 50 | 12.5 | 50 |
| PRT231 | 50 | 12.5 | 50 | 12.5 | 25 | 12.5 | 25 | 12.5 | 25 | 12.5 |
| PRT232 | 12.5 | 25 | 12.5 | 25 | 12.5 | 25 | 12.5 | 25 | 12.5 | 25 |
| PRT233 | 25 | 12.5 | 25 | 12.5 | 25 | 12.5 | 25 | 100 | 25 | 12.5 |
| PRT234 | 50 | 25 | 12.5 | 25 | 12.5 | 25 | 12.5 | 25 | 12.5 | 25 |
| PRT235 | 25 | 12.5 | 25 | 12.5 | 25 | 12.5 | 12.5 | 12.5 | 12.5 | 12.5 |
| PRT236 | 12.5 | 100 | 12.5 | 12.5 | 25 | 12.5 | 25 | 12.5 | 25 | 12.5 |
| PRT237 | 12.5 | 25 | 12.5 | 25 | 12.5 | 25 | 12.5 | 25 | 25 | 50 |
| PRT238 | 12.5 | 25 | 50 | 25 | 12.5 | 25 | 12.5 | 12.5 | 25 | 12.5 |
| PRT239 | 12.5 | 12.5 | 12.5 | 12.5 | 12.5 | 100 | 25 | 12.5 | 12.5 | 12.5 |
| PRT240 | 12.5 | 25 | 12.5 | 25 | 12.5 | 25 | 12.5 | 100 | 100 | 12.5 |
| PRT241 | 12.5 | 12.5 | 12.5 | 12.5 | 12.5 | 12.5 | 25 | 12.5 | 25 | 50 |
| PRT242 | 12.5 | 50 | 50 | 12.5 | 12.5 | 12.5 | 12.5 | 12.5 | 12.5 | 12.5 |
| PRT243 | 12.5 | 12.5 | 12.5 | 12.5 | 25 | 12.5 | 25 | 12.5 | 25 | 12.5 |
| PRT244 | 12.5 | 12.5 | 12.5 | 12.5 | 25 | 12.5 | 25 | 12.5 | 25 | 12.5 |
| PRT245 | 50 | 12.5 | 12.5 | 12.5 | 12.5 | 25 | 12.5 | 25 | 12.5 | 25 |
| PRT246 | 12.5 | 12.5 | 12.5 | 12.5 | 12.5 | 12.5 | 25 | 12.5 | 25 | 12.5 |
| PRT247 | 12.5 | 12.5 | 12.5 | 25 | 12.5 | 25 | 100 | 25 | 12.5 | 25 |
| PRT248 | 25 | 12.5 | 25 | 12.5 | 25 | 12.5 | 25 | 12.5 | 25 | 12.5 |
| PRT249 | 12.5 | 12.5 | 12.5 | 25 | 12.5 | 25 | 12.5 | 12.5 | 12.5 | 12.5 |
| PRT250 | 12.5 | 12.5 | 12.5 | 12.5 | 25 | 12.5 | 25 | 12.5 | 25 | 12.5 |
| PRT251 | 12.5 | 25 | 12.5 | 25 | 12.5 | 25 | 12.5 | 12.5 | 12.5 | 12.5 |
| PRT252 | 12.5 | 25 | 12.5 | 25 | 12.5 | 25 | 12.5 | 25 | 12.5 | 25 |
| PRT253 | 25 | 12.5 | 25 | 12.5 | 25 | 12.5 | 25 | 12.5 | 25 | 12.5 |
| PRT254 | 12.5 | 12.5 | 12.5 | 12.5 | 25 | 12.5 | 25 | 12.5 | 12.5 | 12.5 |
| PRT255 | 12.5 | 12.5 | 12.5 | 12.5 | 25 | 12.5 | 25 | 100 | 25 | 12.5 |
| PRT256 | 12.5 | 25 | 12.5 | 25 | 12.5 | 25 | 12.5 | 25 | 12.5 | 25 |
| PRT257 | 25 | 12.5 | 25 | 12.5 | 25 | 12.5 | 25 | 12.5 | 12.5 | 12.5 |
| PRT258 | 12.5 | 50 | 12.5 | 50 | 12.5 | 25 | 12.5 | 25 | 50 | 25 |
| PRT259 | 25 | 50 | 12.5 | 50 | 12.5 | 50 | 12.5 | 25 | 50 | 25 |
| PRT260 | 25 | 50 | 25 | 12.5 | 25 | 50 | 25 | 12.5 | 12.5 | 12.5 |
| PRT261 | 12.5 | 12.5 | 12.5 | 50 | 12.5 | 25 | 50 | 25 | 12.5 | 50 |
| PRT262 | 25 | 50 | 25 | 12.5 | 25 | 50 | 25 | 12.5 | 25 | 12.5 |
| PRT263 | 25 | 12.5 | 25 | 12.5 | 25 | 12.5 | 12.5 | 12.5 | 12.5 | 50 |
| PRT264 | 50 | 12.5 | 50 | 12.5 | 25 | 50 | 25 | 12.5 | 25 | 12.5 |
| PRT265 | 12.5 | 25 | 12.5 | 25 | 12.5 | 25 | 25 | 25 | 50 | 25 |
| PRT266 | 25 | 50 | 25 | 12.5 | 25 | 50 | 25 | 12.5 | 50 | 12.5 |
| PRT267 | 100 | 50 | 12.5 | 50 | 12.5 | 50 | 12.5 | 25 | 50 | 25 |
| PRT268 | 25 | 12.5 | 25 | 50 | 25 | 12.5 | 25 | 50 | 12.5 | 12.5 |
| PRT269 | 12.5 | 12.5 | 12.5 | 12.5 | 50 | 12.5 | 50 | 25 | 12.5 | 25 |
| PRT270 | 25 | 12.5 | 25 | 12.5 | 25 | 12.5 | 12.5 | 12.5 | 12.5 | 12.5 |
| PRT271 | 50 | 12.5 | 50 | 12.5 | 50 | 12.5 | 50 | 12.5 | 25 | 50 |
| PRT272 | 12.5 | 12.5 | 12.5 | 12.5 | 25 | 12.5 | 25 | 12.5 | 25 | 50 |
| PRT273 | 50 | 12.5 | 50 | 25 | 12.5 | 25 | 50 | 12.5 | 12.5 | 25 |
| PRT274 | 25 | 12.5 | 25 | 12.5 | 25 | 12.5 | 25 | 12.5 | 25 | 12.5 |
| PRT275 | 12.5 | 25 | 50 | 25 | 12.5 | 50 | 12.5 | 50 | 12.5 | 50 |
| PRT276 | 50 | 12.5 | 50 | 25 | 12.5 | 25 | 12.5 | 25 | 12.5 | 25 |

TABLE 3-continued

MIC (μg/mL) of the human-originated EGF domain proteins against various Gram-negative bacteria

| Protein | E. coli BL21 | P. aeruginosa | K. pneumonia | E. cloacae | A. hydrophila | C. diversus | M. catarrhalis | P. mirabilis | P. vulgaris | S. marcescens |
|---|---|---|---|---|---|---|---|---|---|---|
| PRT277 | 12.5 | 25 | 12.5 | 25 | 12.5 | 25 | 50 | 12.5 | 50 | 12.5 |
| PRT278 | 12.5 | 50 | 12.5 | 50 | 100 | 50 | 25 | 12.5 | 25 | 12.5 |
| PRT279 | 12.5 | 50 | 25 | 12.5 | 25 | 50 | 12.5 | 50 | 12.5 | 50 |
| PRT280 | 50 | 12.5 | 25 | 50 | 25 | 12.5 | 50 | 12.5 | 50 | 12.5 |
| PRT281 | 12.5 | 12.5 | 25 | 12.5 | 25 | 12.5 | 12.5 | 12.5 | 12.5 | 50 |
| PRT282 | 50 | 12.5 | 12.5 | 25 | 12.5 | 25 | 12.5 | 12.5 | 12.5 | 12.5 |
| PRT283 | 12.5 | 50 | 25 | 12.5 | 25 | 50 | 25 | 12.5 | 50 | 12.5 |
| PRT284 | 12.5 | 50 | 12.5 | 25 | 50 | 25 | 12.5 | 25 | 12.5 | 25 |
| PRT285 | 100 | 50 | 12.5 | 50 | 12.5 | 25 | 50 | 25 | 12.5 | 25 |
| PRT286 | 25 | 25 | 50 | 12.5 | 50 | 12.5 | 12.5 | 50 | 12.5 | 50 |
| PRT287 | 50 | 12.5 | 50 | 12.5 | 25 | 12.5 | 25 | 12.5 | 12.5 | 12.5 |
| PRT288 | 12.5 | 12.5 | 12.5 | 50 | 12.5 | 25 | 50 | 25 | 12.5 | 12.5 |
| PRT289 | 12.5 | 50 | 12.5 | 50 | 12.5 | 50 | 12.5 | 50 | 25 | 12.5 |
| PRT290 | 12.5 | 50 | 12.5 | 12.5 | 12.5 | 25 | 12.5 | 25 | 12.5 | 25 |
| PRT291 | 12.5 | 12.5 | 12.5 | 12.5 | 25 | 50 | 25 | 12.5 | 50 | 12.5 |
| PRT292 | 12.5 | 50 | 25 | 12.5 | 25 | 50 | 100 | 50 | 12.5 | 25 |
| PRT293 | 25 | 50 | 25 | 12.5 | 25 | 50 | 12.5 | 50 | 12.5 | 50 |
| PRT294 | 50 | 25 | 12.5 | 25 | 50 | 12.5 | 50 | 12.5 | 50 | 12.5 |
| PRT295 | 50 | 12.5 | 50 | 12.5 | 25 | 50 | 25 | 12.5 | 50 | 12.5 |
| PRT296 | 12.5 | 12.5 | 12.5 | 12.5 | 12.5 | 12.5 | 25 | 12.5 | 25 | 12.5 |
| PRT297 | 12.5 | 50 | 12.5 | 50 | 12.5 | 50 | 12.5 | 50 | 25 | 12.5 |
| PRT298 | 50 | 12.5 | 50 | 12.5 | 50 | 12.5 | 50 | 12.5 | 25 | 50 |
| PRT299 | 12.5 | 50 | 12.5 | 50 | 12.5 | 50 | 12.5 | 12.5 | 12.5 | 25 |
| PRT300 | 25 | 12.5 | 12.5 | 12.5 | 12.5 | 12.5 | 25 | 12.5 | 25 | 12.5 |
| PRT301 | 12.5 | 50 | 25 | 12.5 | 25 | 50 | 12.5 | 50 | 12.5 | 12.5 |
| PRT302 | 25 | 12.5 | 25 | 12.5 | 12.5 | 12.5 | 12.5 | 12.5 | 50 | 12.5 |
| PRT303 | 25 | 12.5 | 25 | 50 | 12.5 | 50 | 12.5 | 50 | 100 | 50 |
| PRT304 | 50 | 12.5 | 25 | 50 | 25 | 12.5 | 25 | 50 | 12.5 | 50 |
| PRT305 | 50 | 12.5 | 50 | 12.5 | 25 | 50 | 25 | 12.5 | 50 | 12.5 |
| PRT306 | 25 | 12.5 | 25 | 12.5 | 25 | 12.5 | 12.5 | 50 | 12.5 | 50 |
| PRT307 | 12.5 | 25 | 12.5 | 25 | 12.5 | 12.5 | 12.5 | 12.5 | 12.5 | 50 |
| PRT308 | 50 | 12.5 | 50 | 25 | 12.5 | 25 | 50 | 12.5 | 25 | 50 |
| PRT309 | 12.5 | 25 | 50 | 25 | 12.5 | 25 | 50 | 25 | 12.5 | 25 |
| PRT310 | 25 | 12.5 | 25 | 50 | 25 | 12.5 | 25 | 50 | 12.5 | 50 |
| PRT311 | 25 | 50 | 25 | 12.5 | 50 | 12.5 | 50 | 25 | 12.5 | 25 |
| PRT312 | 12.5 | 50 | 25 | 12.5 | 25 | 50 | 25 | 12.5 | 25 | 50 |
| PRT313 | 12.5 | 50 | 25 | 12.5 | 25 | 50 | 100 | 50 | 12.5 | 50 |
| PRT314 | 50 | 25 | 12.5 | 25 | 50 | 25 | 12.5 | 50 | 12.5 | 50 |
| PRT315 | 50 | 12.5 | 50 | 12.5 | 50 | 12.5 | 50 | 12.5 | 50 | 12.5 |
| PRT316 | 12.5 | 50 | 12.5 | 50 | 12.5 | 50 | 12.5 | 50 | 12.5 | 50 |
| PRT317 | 50 | 12.5 | 50 | 12.5 | 25 | 12.5 | 25 | 12.5 | 12.5 | 12.5 |
| PRT318 | 12.5 | 12.5 | 50 | 12.5 | 50 | 12.5 | 50 | 12.5 | 25 | 50 |
| PRT319 | 12.5 | 12.5 | 12.5 | 12.5 | 50 | 12.5 | 25 | 50 | 25 | 12.5 |
| PRT320 | 12.5 | 50 | 25 | 12.5 | 25 | 12.5 | 50 | 12.5 | 50 | 12.5 |
| PRT321 | 12.5 | 50 | 12.5 | 50 | 25 | 100 | 25 | 50 | 25 | 12.5 |
| PRT322 | 50 | 25 | 12.5 | 50 | 12.5 | 50 | 12.5 | 50 | 12.5 | 50 |
| PRT323 | 12.5 | 25 | 50 | 12.5 | 50 | 12.5 | 50 | 12.5 | 25 | 50 |
| PRT324 | 25 | 12.5 | 25 | 50 | 25 | 50 | 50 | 12.5 | 50 | 12.5 |
| PRT325 | 12.5 | 50 | 12.5 | 50 | 12.5 | 25 | 50 | 25 | 12.5 | 25 |
| PRT326 | 25 | 12.5 | 25 | 50 | 25 | 12.5 | 25 | 50 | 25 | 12.5 |
| PRT327 | 12.5 | 12.5 | 12.5 | 12.5 | 12.5 | 50 | 12.5 | 50 | 12.5 | 50 |
| PRT328 | 50 | 12.5 | 50 | 100 | 50 | 12.5 | 50 | 12.5 | 12.5 | 50 |
| PRT329 | 12.5 | 25 | 50 | 25 | 12.5 | 50 | 12.5 | 50 | 12.5 | 50 |
| PRT330 | 50 | 12.5 | 50 | 25 | 12.5 | 25 | 50 | 25 | 12.5 | 25 |
| PRT331 | 12.5 | 50 | 12.5 | 50 | 12.5 | 50 | 12.5 | 50 | 12.5 | 50 |
| PRT332 | 12.5 | 25 | 50 | 25 | 50 | 25 | 50 | 12.5 | 12.5 | 12.5 |
| PRT333 | 12.5 | 12.5 | 12.5 | 12.5 | 12.5 | 12.5 | 25 | 12.5 | 25 | 25 |
| PRT334 | 25 | 12.5 | 25 | 12.5 | 12.5 | 12.5 | 12.5 | 12.5 | 12.5 | 12.5 |
| PRT335 | 12.5 | 12.5 | 12.5 | 12.5 | 50 | 25 | 50 | 25 | 12.5 | 25 |
| PRT336 | 25 | 12.5 | 50 | 12.5 | 50 | 12.5 | 50 | 12.5 | 50 | 12.5 |
| PRT337 | 12.5 | 50 | 50 | 12.5 | 50 | 12.5 | 50 | 12.5 | 50 | 12.5 |
| PRT338 | 12.5 | 50 | 12.5 | 50 | 25 | 12.5 | 25 | 50 | 25 | 12.5 |
| PRT339 | 12.5 | 12.5 | 12.5 | 12.5 | 12.5 | 12.5 | 50 | 12.5 | 50 | 12.5 |
| PRT340 | 50 | 25 | 12.5 | 25 | 50 | 25 | 12.5 | 25 | 50 | 12.5 |
| PRT341 | 12.5 | 50 | 12.5 | 50 | 12.5 | 50 | 25 | 12.5 | 50 | 12.5 |
| PRT342 | 100 | 25 | 25 | 50 | 12.5 | 50 | 12.5 | 50 | 12.5 | 12.5 |
| PRT343 | 25 | 25 | 12.5 | 12.5 | 12.5 | 12.5 | 12.5 | 12.5 | 12.5 | 12.5 |
| PRT344 | 12.5 | 50 | 12.5 | 50 | 12.5 | 50 | 12.5 | 50 | 12.5 | 50 |
| PRT345 | 50 | 12.5 | 50 | 12.5 | 50 | 12.5 | 50 | 12.5 | 50 | 12.5 |
| PRT346 | 12.5 | 12.5 | 12.5 | 50 | 25 | 50 | 12.5 | 50 | 12.5 | 12.5 |
| PRT347 | 12.5 | 50 | 25 | 12.5 | 50 | 50 | 12.5 | 50 | 12.5 | 12.5 |
| PRT348 | 12.5 | 12.5 | 12.5 | 12.5 | 5 | 50 | 12.5 | 50 | 50 | 50 |
| PRT349 | 50 | 25 | 25 | 50 | 50 | 12.5 | 50 | 12.5 | 25 | 50 |

TABLE 3-continued

MIC (μg/mL) of the human-originated EGF domain proteins against various Gram-negative bacteria

| Protein | E. coli BL21 | P. aeruginosa | K. pneumonia | E. cloacae | A. hydrophila | C. diversus | M. catarrhalis | P. mirabilis | P. vulgaris | S. marcescens |
|---|---|---|---|---|---|---|---|---|---|---|
| PRT350 | 12.5 | 50 | 12.5 | 50 | 12.5 | 50 | 25 | 50 | 12.5 | 50 |
| PRT351 | 50 | 12.5 | 25 | 50 | 25 | 50 | 50 | 12.5 | 50 | 25 |
| PRT352 | 25 | 12.5 | 12.5 | 25 | 12.5 | 12.5 | 25 | 12.5 | 12.5 | 12.5 |
| PRT353 | 12.5 | 50 | 25 | 12.5 | 25 | 50 | 12.5 | 50 | 12.5 | 25 |
| PRT354 | 12.5 | 50 | 12.5 | 50 | 12.5 | 50 | 12.5 | 25 | 50 | 50 |
| PRT355 | 50 | 25 | 12.5 | 25 | 25 | 25 | 50 | 12.5 | 50 | 25 |
| PRT356 | 12.5 | 50 | 12.5 | 50 | 25 | 12.5 | 25 | 50 | 12.5 | 25 |
| PRT357 | 12.5 | 50 | 25 | 12.5 | 25 | 50 | 12.5 | 50 | 12.5 | 50 |
| PRT358 | 12.5 | 50 | 12.5 | 12.5 | 12.5 | 12.5 | 25 | 12.5 | 50 | 50 |
| PRT359 | 25 | 50 | 25 | 12.5 | 25 | 50 | 25 | 12.5 | 50 | 12.5 |
| PRT360 | 12.5 | 50 | 12.5 | 50 | 12.5 | 50 | 12.5 | 12.5 | 25 | 25 |
| PRT361 | 25 | 25 | 25 | 50 | 12.5 | 50 | 12.5 | 50 | 100 | 50 |
| PRT362 | 12.5 | 25 | 50 | 25 | 12.5 | 25 | 12.5 | 12.5 | 12.5 | 12.5 |
| PRT363 | 25 | 12.5 | 50 | 25 | 12.5 | 50 | 12.5 | 50 | 12.5 | 50 |
| PRT364 | 12.5 | 12.5 | 12.5 | 50 | 12.5 | 50 | 12.5 | 25 | 50 | 25 |
| PRT365 | 25 | 50 | 25 | 12.5 | 25 | 50 | 25 | 12.5 | 12.5 | 50 |
| PRT366 | 50 | 12.5 | 50 | 12.5 | 50 | 12.5 | 25 | 50 | 25 | 12.5 |
| PRT367 | 25 | 50 | 25 | 12.5 | 25 | 12.5 | 12.5 | 50 | 12.5 | 50 |
| PRT368 | 50 | 12.5 | 50 | 12.5 | 50 | 12.5 | 50 | 25 | 12.5 | 25 |
| PRT369 | 25 | 12.5 | 50 | 25 | 12.5 | 25 | 50 | 12.5 | 50 | 12.5 |
| PRT370 | 12.5 | 50 | 12.5 | 50 | 25 | 12.5 | 25 | 50 | 25 | 12.5 |
| PRT371 | 12.5 | 50 | 12.5 | 50 | 12.5 | 50 | 12.5 | 50 | 12.5 | 50 |
| PRT372 | 50 | 12.5 | 25 | 50 | 25 | 12.5 | 50 | 12.5 | 50 | 12.5 |
| PRT373 | 12.5 | 50 | 12.5 | 50 | 50 | 12.5 | 50 | 12.5 | 25 | 50 |
| PRT374 | 12.5 | 50 | 12.5 | 50 | 12.5 | 50 | 12.5 | 50 | 12.5 | 50 |
| PRT375 | 50 | 12.5 | 50 | 12.5 | 50 | 12.5 | 50 | 12.5 | 50 | 12.5 |
| PRT376 | 12.5 | 50 | 12.5 | 50 | 12.5 | 50 | 12.5 | 50 | 12.5 | 50 |
| PRT377 | 25 | 12.5 | 25 | 50 | 25 | 12.5 | 25 | 50 | 25 | 12.5 |
| PRT378 | 12.5 | 25 | 50 | 25 | 12.5 | 25 | 50 | 25 | 12.5 | 50 |
| PRT379 | 50 | 12.5 | 50 | 12.5 | 50 | 100 | 50 | 12.5 | 50 | 12.5 |
| PRT380 | 12.5 | 50 | 12.5 | 50 | 12.5 | 50 | 12.5 | 25 | 50 | 25 |
| PRT381 | 50 | 12.5 | 50 | 12.5 | 50 | 12.5 | 50 | 25 | 12.5 | 25 |
| PRT382 | 12.5 | 50 | 12.5 | 50 | 12.5 | 50 | 12.5 | 50 | 25 | 12.5 |
| PRT383 | 50 | 12.5 | 50 | 12.5 | 25 | 50 | 25 | 12.5 | 50 | 12.5 |
| PRT384 | 12.5 | 50 | 25 | 12.5 | 25 | 50 | 25 | 12.5 | 25 | 50 |
| PRT385 | 12.5 | 25 | 50 | 25 | 12.5 | 25 | 50 | 12.5 | 25 | 50 |
| PRT386 | 12.5 | 50 | 12.5 | 50 | 100 | 50 | 12.5 | 50 | 12.5 | 50 |
| PRT387 | 50 | 25 | 12.5 | 25 | 50 | 25 | 12.5 | 25 | 50 | 25 |
| PRT388 | 50 | 12.5 | 12.5 | 50 | 12.5 | 50 | 12.5 | 25 | 50 | 25 |
| PRT389 | 25 | 50 | 25 | 12.5 | 25 | 50 | 25 | 12.5 | 25 | 50 |
| PRT390 | 50 | 12.5 | 50 | 12.5 | 50 | 12.5 | 50 | 25 | 12.5 | 25 |
| PRT391 | 25 | 12.5 | 25 | 50 | 12.5 | 50 | 12.5 | 50 | 12.5 | 50 |
| PRT392 | 50 | 12.5 | 50 | 12.5 | 50 | 12.5 | 50 | 12.5 | 50 | 12.5 |
| PRT393 | 12.5 | 50 | 25 | 12.5 | 25 | 50 | 12.5 | 50 | 12.5 | 12.5 |
| PRT394 | 12.5 | 50 | 12.5 | 50 | 12.5 | 50 | 12.5 | 50 | 25 | 12.5 |
| PRT395 | 50 | 12.5 | 50 | 12.5 | 50 | 12.5 | 50 | 12.5 | 50 | 12.5 |
| PRT396 | 12.5 | 25 | 50 | 25 | 12.5 | 50 | 12.5 | 50 | 12.5 | 50 |
| PRT397 | 50 | 12.5 | 50 | 25 | 12.5 | 25 | 50 | 12.5 | 50 | 12.5 |
| PRT398 | 12.5 | 50 | 12.5 | 50 | 12.5 | 50 | 12.5 | 12.5 | 12.5 | 100 |
| PRT399 | 50 | 12.5 | 50 | 12.5 | 50 | 12.5 | 50 | 12.5 | 50 | 12.5 |
| PRT400 | 12.5 | 50 | 12.5 | 50 | 12.5 | 25 | 50 | 25 | 12.5 | 25 |
| PRT401 | 12.5 | 50 | 12.5 | 50 | 12.5 | 50 | 12.5 | 50 | 12.5 | 12.5 |
| PRT402 | 12.5 | 50 | 12.5 | 50 | 12.5 | 50 | 12.5 | 25 | 50 | 25 |
| PRT403 | 25 | 50 | 25 | 12.5 | 25 | 50 | 25 | 12.5 | 25 | 50 |
| PRT404 | 12.5 | 25 | 50 | 12.5 | 50 | 12.5 | 50 | 12.5 | 50 | 12.5 |
| PRT405 | 12.5 | 12.5 | 12.5 | 12.5 | 12.5 | 12.5 | 12.5 | 12.5 | 50 | 12.5 |
| PRT406 | 12.5 | 50 | 25 | 12.5 | 25 | 12.5 | 25 | 12.5 | 25 | 12.5 |
| PRT407 | 12.5 | 25 | 12.5 | 25 | 12.5 | 25 | 12.5 | 12.5 | 12.5 | 12.5 |
| PRT408 | 50 | 12.5 | 50 | 12.5 | 50 | 100 | 50 | 25 | 12.5 | 25 |
| PRT409 | 25 | 12.5 | 25 | 50 | 12.5 | 50 | 12.5 | 50 | 12.5 | 50 |
| PRT410 | 50 | 12.5 | 50 | 12.5 | 12.5 | 12.5 | 50 | 12.5 | 25 | 50 |
| PRT411 | 12.5 | 25 | 50 | 25 | 12.5 | 50 | 12.5 | 50 | 12.5 | 50 |
| PRT412 | 50 | 12.5 | 25 | 50 | 25 | 12.5 | 25 | 12.5 | 25 | 12.5 |
| PRT413 | 12.5 | 12.5 | 50 | 12.5 | 50 | 12.5 | 50 | 12.5 | 12.5 | 12.5 |
| PRT414 | 12.5 | 12.5 | 12.5 | 12.5 | 25 | 12.5 | 25 | 12.5 | 25 | 50 |
| PRT415 | 12.5 | 25 | 50 | 25 | 12.5 | 25 | 50 | 25 | 12.5 | 25 |
| PRT416 | 25 | 12.5 | 25 | 50 | 25 | 12.5 | 25 | 50 | 25 | 12.5 |
| PRT417 | 50 | 25 | 12.5 | 25 | 12.5 | 25 | 12.5 | 12.5 | 12.5 | 12.5 |
| PRT418 | 12.5 | 12.5 | 50 | 12.5 | 25 | 50 | 25 | 12.5 | 25 | 50 |
| PRT419 | 12.5 | 25 | 50 | 25 | 12.5 | 25 | 50 | 25 | 12.5 | 25 |
| PRT420 | 25 | 12.5 | 25 | 50 | 12.5 | 50 | 12.5 | 50 | 100 | 50 |
| PRT421 | 50 | 12.5 | 50 | 12.5 | 50 | 12.5 | 50 | 25 | 12.5 | 25 |
| PRT422 | 25 | 12.5 | 25 | 12.5 | 25 | 12.5 | 12.5 | 25 | 12.5 | 25 |

TABLE 3-continued

MIC (μg/mL) of the human-originated EGF domain proteins against various Gram-negative bacteria

| Protein | E. coli BL21 | P. aeruginosa | K. pneumonia | E. cloacae | A. hydrophila | C. diversus | M. catarrhalis | P. mirabilis | P. vulgaris | S. marcescens |
|---|---|---|---|---|---|---|---|---|---|---|
| PRT423 | 25 | 12.5 | 25 | 50 | 25 | 12.5 | 25 | 50 | 25 | 12.5 |
| PRT424 | 50 | 25 | 12.5 | 25 | 50 | 25 | 12.5 | 25 | 50 | 25 |
| PRT425 | 25 | 50 | 25 | 12.5 | 25 | 50 | 12.5 | 50 | 12.5 | 50 |
| PRT426 | 50 | 50 | 50 | 50 | 12.5 | 12.5 | 12.5 | 12.5 | 25 | 50 |
| PRT427 | 12.5 | 25 | 50 | 25 | 12.5 | 25 | 50 | 25 | 12.5 | 25 |
| PRT428 | 25 | 12.5 | 25 | 50 | 25 | 12.5 | 50 | 12.5 | 50 | 12.5 |
| PRT429 | 12.5 | 50 | 12.5 | 50 | 12.5 | 50 | 12.5 | 25 | 50 | 25 |
| PRT430 | 25 | 50 | 25 | 12.5 | 25 | 50 | 25 | 12.5 | 50 | 12.5 |
| PRT431 | 12.5 | 50 | 12.5 | 50 | 12.5 | 50 | 12.5 | 50 | 25 | 12.5 |
| PRT432 | 50 | 25 | 12.5 | 25 | 50 | 25 | 12.5 | 25 | 50 | 25 |
| PRT433 | 25 | 12.5 | 12.5 | 50 | 12.5 | 50 | 12.5 | 50 | 12.5 | 50 |
| PRT434 | 50 | 12.5 | 50 | 12.5 | 50 | 12.5 | 50 | 25 | 12.5 | 25 |
| PRT435 | 25 | 12.5 | 25 | 12.5 | 25 | 12.5 | 25 | 12.5 | 25 | 50 |
| PRT436 | 25 | 50 | 25 | 12.5 | 50 | 12.5 | 50 | 12.5 | 50 | 100 |
| PRT437 | 12.5 | 50 | 25 | 12.5 | 25 | 50 | 25 | 12.5 | 25 | 50 |
| PRT438 | 12.5 | 50 | 12.5 | 50 | 12.5 | 50 | 12.5 | 50 | 12.5 | 50 |
| PRT439 | 12.5 | 25 | 50 | 25 | 12.5 | 25 | 50 | 12.5 | 50 | 12.5 |
| PRT440 | 12.5 | 50 | 12.5 | 50 | 12.5 | 50 | 12.5 | 25 | 50 | 25 |
| PRT441 | 25 | 50 | 25 | 12.5 | 25 | 50 | 12.5 | 50 | 12.5 | 50 |
| PRT442 | 50 | 25 | 12.5 | 25 | 50 | 25 | 12.5 | 12.5 | 12.5 | 25 |
| PRT443 | 25 | 12.5 | 12.5 | 12.5 | 12.5 | 25 | 12.5 | 25 | 12.5 | 50 |
| PRT444 | 12.5 | 25 | 50 | 12.5 | 50 | 12.5 | 50 | 12.5 | 50 | 12.5 |
| PRT445 | 12.5 | 50 | 25 | 12.5 | 25 | 50 | 12.5 | 12.5 | 12.5 | 12.5 |
| PRT446 | 12.5 | 12.5 | 50 | 12.5 | 50 | 12.5 | 50 | 25 | 12.5 | 25 |
| PRT447 | 25 | 12.5 | 25 | 50 | 25 | 12.5 | 25 | 50 | 12.5 | 50 |
| PRT448 | 50 | 100 | 50 | 12.5 | 50 | 25 | 12.5 | 25 | 50 | 12.5 |
| PRT449 | 12.5 | 50 | 12.5 | 50 | 25 | 12.5 | 25 | 50 | 12.5 | 50 |
| PRT450 | 12.5 | 12.5 | 50 | 12.5 | 50 | 12.5 | 50 | 12.5 | 50 | 12.5 |
| PRT451 | 50 | 25 | 12.5 | 25 | 50 | 12.5 | 50 | 12.5 | 50 | 12.5 |
| PRT452 | 12.5 | 12.5 | 12.5 | 50 | 12.5 | 50 | 25 | 12.5 | 25 | 50 |
| PRT453 | 12.5 | 25 | 50 | 25 | 12.5 | 25 | 50 | 25 | 12.5 | 25 |
| PRT454 | 12.5 | 25 | 50 | 25 | 12.5 | 25 | 50 | 12.5 | 50 | 12.5 |
| PRT455 | 12.5 | 50 | 12.5 | 50 | 12.5 | 50 | 12.5 | 50 | 100 | 50 |
| PRT456 | 12.5 | 50 | 12.5 | 12.5 | 12.5 | 50 | 12.5 | 50 | 12.5 | 25 |
| PRT457 | 25 | 12.5 | 50 | 25 | 12.5 | 25 | 50 | 12.5 | 50 | 12.5 |
| PRT458 | 12.5 | 12.5 | 12.5 | 12.5 | 25 | 12.5 | 25 | 12.5 | 25 | 12.5 |
| PRT459 | 12.5 | 25 | 50 | 25 | 12.5 | 25 | 50 | 25 | 12.5 | 25 |
| PRT460 | 25 | 12.5 | 25 | 50 | 12.5 | 50 | 25 | 12.5 | 50 | 12.5 |
| PRT461 | 12.5 | 50 | 12.5 | 50 | 12.5 | 50 | 25 | 12.5 | 25 | 12.5 |
| PRT462 | 12.5 | 100 | 12.5 | 12.5 | 12.5 | 12.5 | 50 | 25 | 12.5 | 25 |
| PRT463 | 12.5 | 50 | 12.5 | 50 | 12.5 | 50 | 12.5 | 12.5 | 12.5 | 50 |
| PRT464 | 50 | 12.5 | 50 | 12.5 | 25 | 50 | 25 | 12.5 | 50 | 12.5 |
| PRT465 | 12.5 | 50 | 12.5 | 50 | 12.5 | 50 | 12.5 | 50 | 12.5 | 50 |
| PRT466 | 50 | 12.5 | 50 | 12.5 | 50 | 12.5 | 50 | 12.5 | 50 | 12.5 |
| PRT467 | 12.5 | 12.5 | 25 | 12.5 | 25 | 50 | 25 | 12.5 | 25 | 50 |
| PRT468 | 12.5 | 25 | 50 | 25 | 12.5 | 50 | 12.5 | 50 | 12.5 | 50 |
| PRT469 | 25 | 12.5 | 25 | 50 | 25 | 12.5 | 50 | 12.5 | 50 | 12.5 |
| PRT470 | 12.5 | 50 | 12.5 | 50 | 25 | 12.5 | 25 | 50 | 12.5 | 50 |
| PRT471 | 12.5 | 12.5 | 12.5 | 12.5 | 12.5 | 12.5 | 12.5 | 12.5 | 25 | 12.5 |
| PRT472 | 12.5 | 25 | 50 | 25 | 12.5 | 25 | 50 | 12.5 | 50 | 12.5 |
| PRT473 | 12.5 | 25 | 50 | 12.5 | 50 | 25 | 12.5 | 25 | 50 | 25 |
| PRT474 | 25 | 25 | 25 | 25 | 50 | 12.5 | 50 | 12.5 | 50 | 12.5 |
| PRT475 | 12.5 | 50 | 25 | 25 | 25 | 25 | 12.5 | 50 | 12.5 | 50 |
| PRT476 | 12.5 | 50 | 12.5 | 50 | 12.5 | 50 | 25 | 25 | 12.5 | 50 |
| PRT477 | 50 | 12.5 | 50 | 25 | 12.5 | 25 | 50 | 25 | 12.5 | 25 |
| PRT478 | 25 | 12.5 | 25 | 50 | 25 | 100 | 25 | 50 | 25 | 12.5 |
| PRT479 | 50 | 25 | 12.5 | 25 | 50 | 25 | 12.5 | 25 | 50 | 25 |
| PRT480 | 25 | 50 | 25 | 12.5 | 25 | 50 | 25 | 12.5 | 25 | 50 |
| PRT481 | 12.5 | 25 | 50 | 12.5 | 50 | 12.5 | 50 | 12.5 | 50 | 12.5 |
| PRT482 | 12.5 | 50 | 12.5 | 25 | 50 | 25 | 12.5 | 25 | 50 | 25 |
| PRT483 | 25 | 50 | 25 | 12.5 | 25 | 50 | 25 | 12.5 | 25 | 50 |
| PRT484 | 12.5 | 25 | 50 | 12.5 | 50 | 12.5 | 50 | 12.5 | 50 | 12.5 |
| PRT485 | 12.5 | 50 | 25 | 12.5 | 25 | 50 | 25 | 12.5 | 25 | 50 |
| PRT486 | 50 | 12.5 | 50 | 12.5 | 50 | 12.5 | 50 | 12.5 | 50 | 25 |
| PRT487 | 25 | 12.5 | 25 | 12.5 | 25 | 12.5 | 25 | 12.5 | 50 | 12.5 |
| PRT488 | 12.5 | 50 | 12.5 | 50 | 12.5 | 50 | 12.5 | 50 | 12.5 | 50 |
| PRT489 | 12.5 | 12.5 | 25 | 12.5 | 25 | 12.5 | 25 | 50 | 25 | 12.5 |
| PRT490 | 50 | 25 | 12.5 | 25 | 50 | 25 | 12.5 | 25 | 50 | 25 |
| PRT491 | 25 | 50 | 12.5 | 50 | 100 | 50 | 12.5 | 50 | 25 | 12.5 |
| PRT492 | 50 | 25 | 12.5 | 25 | 50 | 25 | 12.5 | 50 | 12.5 | 50 |
| PRT493 | 50 | 12.5 | 50 | 25 | 12.5 | 25 | 50 | 25 | 12.5 | 25 |
| PRT494 | 25 | 12.5 | 25 | 50 | 25 | 12.5 | 25 | 50 | 25 | 12.5 |
| PRT495 | 50 | 25 | 12.5 | 25 | 50 | 25 | 12.5 | 25 | 12.5 | 25 |

TABLE 3-continued

MIC (μg/mL) of the human-originated EGF domain proteins against various Gram-negative bacteria

| Protein | E. coli BL21 | P. aeruginosa | K. pneumonia | E. cloacae | A. hydrophila | C. diversus | M. catarrhalis | P. mirabilis | P. vulgaris | S. marcescens |
|---|---|---|---|---|---|---|---|---|---|---|
| PRT496 | 12.5 | 50 | 12.5 | 50 | 12.5 | 50 | 12.5 | 25 | 50 | 25 |
| PRT497 | 25 | 50 | 12.5 | 25 | 50 | 25 | 25 | 50 | 12.5 | 50 |
| PRT498 | 50 | 12.5 | 12.5 | 12.5 | 12.5 | 25 | 12.5 | 25 | 12.5 | 25 |
| PRT499 | 25 | 100 | 25 | 12.5 | 25 | 12.5 | 25 | 50 | 25 | 12.5 |
| PRT500 | 50 | 25 | 12.5 | 25 | 50 | 25 | 12.5 | 25 | 50 | 25 |
| PRT501 | 25 | 50 | 25 | 12.5 | 25 | 12.5 | 25 | 12.5 | 25 | 12.5 |
| PRT502 | 12.5 | 12.5 | 12.5 | 12.5 | 12.5 | 12.5 | 12.5 | 12.5 | 50 | 25 |
| PRT503 | 25 | 50 | 25 | 12.5 | 25 | 50 | 12.5 | 50 | 12.5 | 50 |
| PRT504 | 50 | 12.5 | 50 | 12.5 | 25 | 50 | 25 | 12.5 | 50 | 12.5 |
| PRT505 | 12.5 | 50 | 12.5 | 50 | 12.5 | 50 | 25 | 12.5 | 25 | 50 |
| PRT506 | 12.5 | 25 | 50 | 25 | 12.5 | 25 | 50 | 25 | 12.5 | 12.5 |
| PRT507 | 50 | 12.5 | 50 | 12.5 | 50 | 12.5 | 50 | 12.5 | 50 | 25 |
| PRT508 | 25 | 50 | 25 | 12.5 | 50 | 100 | 50 | 12.5 | 12.5 | 25 |
| PRT509 | 25 | 12.5 | 25 | 12.5 | 12.5 | 12.5 | 12.5 | 12.5 | 12.5 | 25 |
| PRT510 | 25 | 12.5 | 25 | 50 | 25 | 12.5 | 25 | 50 | 25 | 12.5 |
| PRT511 | 12.5 | 50 | 12.5 | 50 | 12.5 | 25 | 50 | 25 | 12.5 | 25 |
| PRT512 | 25 | 12.5 | 25 | 50 | 25 | 12.5 | 25 | 50 | 25 | 12.5 |
| PRT513 | 12.5 | 50 | 12.5 | 25 | 50 | 25 | 12.5 | 50 | 12.5 | 12.5 |
| PRT514 | 12.5 | 50 | 25 | 12.5 | 25 | 12.5 | 25 | 12.5 | 25 | 12.5 |
| PRT515 | 12.5 | 25 | 12.5 | 25 | 50 | 25 | 100 | 50 | 12.5 | 50 |
| PRT516 | 50 | 12.5 | 50 | 12.5 | 25 | 50 | 25 | 12.5 | 25 | 50 |
| PRT517 | 12.5 | 25 | 50 | 25 | 12.5 | 25 | 50 | 25 | 12.5 | 25 |
| PRT518 | 25 | 12.5 | 25 | 50 | 25 | 12.5 | 25 | 12.5 | 25 | 12.5 |
| PRT519 | 12.5 | 12.5 | 25 | 12.5 | 25 | 12.5 | 25 | 12.5 | 25 | 12.5 |
| PRT520 | 12.5 | 25 | 12.5 | 25 | 12.5 | 25 | 50 | 25 | 12.5 | 25 |
| PRT521 | 25 | 12.5 | 25 | 50 | 25 | 12.5 | 25 | 50 | 25 | 12.5 |
| PRT522 | 50 | 25 | 12.5 | 25 | 50 | 25 | 12.5 | 25 | 50 | 25 |
| PRT523 | 25 | 50 | 25 | 12.5 | 25 | 50 | 12.5 | 50 | 12.5 | 12.5 |
| PRT524 | 12.5 | 12.5 | 25 | 12.5 | 25 | 100 | 25 | 12.5 | 25 | 50 |
| PRT525 | 12.5 | 25 | 50 | 25 | 12.5 | 25 | 50 | 25 | 12.5 | 25 |
| PRT526 | 25 | 12.5 | 25 | 50 | 25 | 12.5 | 50 | 12.5 | 50 | 12.5 |
| PRT527 | 12.5 | 50 | 12.5 | 25 | 50 | 25 | 12.5 | 25 | 50 | 25 |
| PRT528 | 25 | 50 | 25 | 12.5 | 25 | 50 | 25 | 12.5 | 25 | 50 |
| PRT529 | 12.5 | 25 | 50 | 25 | 12.5 | 25 | 50 | 25 | 12.5 | 25 |
| PRT530 | 12.5 | 25 | 50 | 25 | 12.5 | 25 | 50 | 25 | 12.5 | 25 |
| PRT531 | 25 | 12.5 | 25 | 50 | 12.5 | 50 | 12.5 | 50 | 12.5 | 50 |
| PRT532 | 50 | 12.5 | 12.5 | 12.5 | 12.5 | 12.5 | 50 | 12.5 | 50 | 12.5 |
| PRT533 | 25 | 100 | 25 | 50 | 25 | 12.5 | 25 | 50 | 25 | 12.5 |
| PRT534 | 12.5 | 50 | 12.5 | 50 | 12.5 | 50 | 12.5 | 25 | 50 | 25 |
| PRT535 | 25 | 50 | 12.5 | 50 | 12.5 | 50 | 12.5 | 50 | 12.5 | 50 |
| PRT536 | 50 | 12.5 | 50 | 12.5 | 50 | 12.5 | 50 | 12.5 | 50 | 12.5 |
| PRT537 | 25 | 12.5 | 25 | 50 | 25 | 12.5 | 25 | 12.5 | 25 | 12.5 |
| PRT538 | 12.5 | 25 | 12.5 | 25 | 12.5 | 25 | 12.5 | 12.5 | 12.5 | 50 |
| PRT539 | 50 | 12.5 | 25 | 50 | 25 | 12.5 | 25 | 50 | 12.5 | 50 |
| PRT540 | 50 | 12.5 | 12.5 | 50 | 12.5 | 25 | 50 | 25 | 12.5 | 50 |
| PRT541 | 50 | 100 | 50 | 12.5 | 50 | 12.5 | 50 | 12.5 | 25 | 50 |
| PRT542 | 12.5 | 25 | 50 | 25 | 12.5 | 50 | 12.5 | 50 | 12.5 | 50 |
| PRT543 | 50 | 12.5 | 50 | 12.5 | 50 | 25 | 12.5 | 25 | 50 | 25 |
| PRT544 | 25 | 12.5 | 25 | 12.5 | 12.5 | 12.5 | 12.5 | 12.5 | 12.5 | 12.5 |
| PRT545 | 12.5 | 12.5 | 25 | 12.5 | 25 | 12.5 | 12.5 | 12.5 | 12.5 | 50 |
| PRT546 | 50 | 12.5 | 50 | 12.5 | 50 | 12.5 | 50 | 12.5 | 25 | 50 |
| PRT547 | 12.5 | 25 | 50 | 25 | 12.5 | 25 | 50 | 25 | 12.5 | 25 |
| PRT548 | 25 | 50 | 25 | 12.5 | 25 | 50 | 25 | 12.5 | 25 | 50 |
| PRT549 | 50 | 12.5 | 50 | 12.5 | 50 | 12.5 | 25 | 12.5 | 25 | 12.5 |
| PRT550 | 12.5 | 25 | 12.5 | 25 | 12.5 | 25 | 12.5 | 25 | 12.5 | 25 |
| PRT551 | 25 | 50 | 25 | 12.5 | 25 | 50 | 25 | 12.5 | 25 | 50 |
| PRT552 | 100 | 50 | 12.5 | 50 | 12.5 | 50 | 25 | 12.5 | 25 | 12.5 |
| PRT553 | 50 | 25 | 12.5 | 25 | 50 | 25 | 12.5 | 25 | 50 | 25 |
| PRT554 | 50 | 12.5 | 50 | 25 | 12.5 | 25 | 50 | 25 | 12.5 | 25 |
| PRT555 | 25 | 12.5 | 25 | 50 | 25 | 12.5 | 25 | 50 | 25 | 12.5 |
| PRT556 | 50 | 12.5 | 50 | 12.5 | 50 | 25 | 25 | 25 | 12.5 | 25 |
| PRT557 | 25 | 12.5 | 25 | 12.5 | 25 | 12.5 | 25 | 12.5 | 25 | 12.5 |
| PRT558 | 25 | 12.5 | 25 | 50 | 25 | 12.5 | 25 | 50 | 25 | 12.5 |
| PRT559 | 50 | 25 | 12.5 | 25 | 50 | 25 | 12.5 | 25 | 50 | 25 |
| PRT560 | 25 | 50 | 25 | 50 | 25 | 50 | 25 | 50 | 50 | 50 |
| PRT561 | 50 | 25 | 50 | 25 | 50 | 25 | 50 | 25 | 50 | 25 |
| PRT562 | 25 | 50 | 25 | 50 | 25 | 50 | 25 | 12.5 | 25 | 50 |
| PRT563 | 12.5 | 25 | 50 | 25 | 12.5 | 25 | 50 | 25 | 12.5 | 25 |
| PRT564 | 12.5 | 50 | 12.5 | 25 | 50 | 25 | 12.5 | 50 | 12.5 | 50 |
| PRT565 | 12.5 | 50 | 50 | 100 | 50 | 12.5 | 50 | 12.5 | 50 | 12.5 |
| PRT566 | 12.5 | 50 | 12.5 | 50 | 12.5 | 25 | 50 | 25 | 12.5 | 25 |
| PRT567 | 25 | 12.5 | 25 | 50 | 25 | 12.5 | 50 | 12.5 | 12.5 | 12.5 |
| PRT568 | 12.5 | 12.5 | 50 | 12.5 | 25 | 50 | 25 | 12.5 | 25 | 50 |

TABLE 3-continued

MIC (μg/mL) of the human-originated EGF domain proteins against various Gram-negative bacteria

| Protein | E. coli BL21 | P. aeruginosa | K. pneumonia | E. cloacae | A. hydrophila | C. diversus | M. catarrhalis | P. mirabilis | P. vulgaris | S. marcescens |
|---|---|---|---|---|---|---|---|---|---|---|
| PRT569 | 12.5 | 25 | 12.5 | 12.5 | 25 | 100 | 25 | 12.5 | 25 | 12.5 |
| PRT570 | 12.5 | 25 | 50 | 25 | 12.5 | 25 | 50 | 25 | 12.5 | 50 |
| PRT571 | 50 | 12.5 | 50 | 12.5 | 50 | 12.5 | 50 | 25 | 12.5 | 50 |
| PRT572 | 50 | 12.5 | 50 | 12.5 | 50 | 12.5 | 50 | 12.5 | 25 | 12.5 |
| PRT573 | 12.5 | 25 | 12.5 | 25 | 12.5 | 12.5 | 50 | 12.5 | 50 | 12.5 |
| PRT574 | 12.5 | 50 | 12.5 | 50 | 25 | 12.5 | 25 | 50 | 25 | 12.5 |
| PRT575 | 12.5 | 50 | 12.5 | 50 | 12.5 | 50 | 12.5 | 50 | 12.5 | 12.5 |
| PRT576 | 12.5 | 12.5 | 12.5 | 12.5 | 12.5 | 12.5 | 50 | 12.5 | 50 | 25 |
| PRT577 | 25 | 50 | 25 | 12.5 | 25 | 50 | 12.5 | 50 | 12.5 | 50 |
| PRT578 | 50 | 12.5 | 50 | 12.5 | 50 | 12.5 | 50 | 12.5 | 50 | 12.5 |
| PRT579 | 12.5 | 12.5 | 12.5 | 25 | 12.5 | 25 | 12.5 | 25 | 100 | 25 |
| PRT580 | 25 | 12.5 | 25 | 12.5 | 25 | 12.5 | 50 | 12.5 | 50 | 12.5 |
| PRT581 | 12.5 | 50 | 12.5 | 12.5 | 50 | 25 | 12.5 | 25 | 50 | 25 |
| PRT582 | 50 | 12.5 | 50 | 12.5 | 12.5 | 12.5 | 25 | 50 | 25 | 12.5 |
| PRT583 | 50 | 12.5 | 50 | 12.5 | 12.5 | 12.5 | 50 | 50 | 50 | 50 |
| PRT584 | 50 | 25 | 50 | 25 | 50 | 25 | 50 | 25 | 50 | 25 |
| PRT585 | 50 | 50 | 50 | 50 | 50 | 50 | 12.5 | 50 | 12.5 | 50 |
| PRT586 | 50 | 12.5 | 50 | 12.5 | 50 | 12.5 | 25 | 50 | 25 | 12.5 |
| PRT587 | 50 | 25 | 12.5 | 25 | 50 | 25 | 12.5 | 25 | 50 | 25 |
| PRT588 | 25 | 50 | 25 | 12.5 | 25 | 12.5 | 25 | 12.5 | 25 | 12.5 |
| PRT589 | 12.5 | 12.5 | 12.5 | 12.5 | 12.5 | 12.5 | 12.5 | 12.5 | 12.5 | 25 |
| PRT590 | 25 | 12.5 | 25 | 50 | 25 | 12.5 | 25 | 50 | 25 | 12.5 |
| PRT591 | 50 | 25 | 12.5 | 25 | 50 | 12.5 | 50 | 12.5 | 50 | 12.5 |
| PRT592 | 12.5 | 50 | 12.5 | 50 | 12.5 | 50 | 100 | 50 | 25 | 12.5 |
| PRT593 | 50 | 25 | 12.5 | 25 | 50 | 25 | 12.5 | 25 | 50 | 25 |
| PRT594 | 25 | 50 | 12.5 | 50 | 12.5 | 50 | 12.5 | 50 | 12.5 | 50 |
| PRT595 | 50 | 12.5 | 50 | 12.5 | 50 | 12.5 | 50 | 12.5 | 50 | 25 |
| PRT596 | 25 | 50 | 25 | 12.5 | 25 | 50 | 25 | 12.5 | 25 | 50 |
| PRT597 | 12.5 | 50 | 12.5 | 25 | 50 | 25 | 12.5 | 50 | 25 | 12.5 |
| PRT598 | 50 | 12.5 | 50 | 12.5 | 25 | 50 | 25 | 12.5 | 50 | 25 |
| PRT599 | 25 | 50 | 12.5 | 50 | 12.5 | 50 | 12.5 | 50 | 12.5 | 50 |
| PRT600 | 12.5 | 25 | 50 | 25 | 12.5 | 25 | 50 | 25 | 12.5 | 25 |
| PRT601 | 25 | 12.5 | 25 | 50 | 25 | 12.5 | 50 | 100 | 50 | 12.5 |
| PRT602 | 12.5 | 50 | 12.5 | 50 | 12.5 | 50 | 12.5 | 50 | 25 | 12.5 |
| PRT603 | 50 | 25 | 12.5 | 25 | 50 | 12.5 | 50 | 12.5 | 50 | 12.5 |
| PRT604 | 12.5 | 25 | 50 | 25 | 12.5 | 25 | 12.5 | 25 | 12.5 | 25 |
| PRT605 | 25 | 50 | 25 | 12.5 | 25 | 50 | 25 | 12.5 | 25 | 50 |
| PRT606 | 12.5 | 25 | 50 | 25 | 12.5 | 25 | 50 | 25 | 12.5 | 25 |
| PRT607 | 25 | 12.5 | 25 | 50 | 12.5 | 50 | 12.5 | 50 | 12.5 | 50 |
| PRT608 | 50 | 12.5 | 50 | 25 | 12.5 | 25 | 50 | 25 | 12.5 | 25 |
| PRT609 | 25 | 12.5 | 25 | 50 | 25 | 12.5 | 25 | 50 | 25 | 12.5 |
| PRT610 | 25 | 12.5 | 25 | 50 | 12.5 | 50 | 12.5 | 50 | 12.5 | 50 |
| PRT611 | 25 | 50 | 25 | 12.5 | 25 | 50 | 25 | 12.5 | 25 | 50 |
| PRT612 | 12.5 | 25 | 50 | 25 | 12.5 | 25 | 50 | 25 | 12.5 | 25 |
| PRT613 | 12.5 | 25 | 50 | 25 | 12.5 | 25 | 50 | 25 | 12.5 | 50 |
| PRT614 | 50 | 50 | 50 | 12.5 | 12.5 | 25 | 12.5 | 25 | 12.5 | 25 |
| PRT615 | 25 | 12.5 | 25 | 12.5 | 25 | 50 | 25 | 12.5 | 25 | 50 |
| PRT616 | 12.5 | 25 | 50 | 12.5 | 25 | 12.5 | 25 | 12.5 | 25 | 12.5 |
| PRT617 | 12.5 | 25 | 12.5 | 25 | 12.5 | 25 | 12.5 | 25 | 12.5 | 25 |
| PRT618 | 25 | 12.5 | 50 | 12.5 | 50 | 12.5 | 50 | 12.5 | 50 | 25 |
| PRT619 | 25 | 50 | 25 | 12.5 | 25 | 50 | 25 | 12.5 | 25 | 50 |
| PRT620 | 12.5 | 25 | 50 | 12.5 | 50 | 12.5 | 50 | 25 | 12.5 | 25 |
| PRT621 | 25 | 50 | 25 | 50 | 25 | 50 | 25 | 50 | 25 | 50 |
| PRT622 | 50 | 25 | 50 | 25 | 12.5 | 50 | 12.5 | 50 | 12.5 | 12.5 |
| PRT623 | 12.5 | 12.5 | 12.5 | 12.5 | 12.5 | 12.5 | 50 | 12.5 | 25 | 50 |
| PRT624 | 100 | 25 | 50 | 25 | 12.5 | 25 | 12.5 | 25 | 12.5 | 25 |
| PRT625 | 25 | 12.5 | 25 | 50 | 25 | 12.5 | 25 | 50 | 25 | 12.5 |
| PRT626 | 50 | 25 | 12.5 | 25 | 50 | 25 | 12.5 | 25 | 50 | 25 |
| PRT627 | 25 | 12.5 | 12.5 | 12.5 | 12.5 | 12.5 | 12.5 | 50 | 12.5 | 50 |
| PRT628 | 12.5 | 25 | 12.5 | 25 | 12.5 | 25 | 12.5 | 25 | 12.5 | 25 |
| PRT629 | 25 | 12.5 | 25 | 12.5 | 12.5 | 12.5 | 12.5 | 12.5 | 50 | 12.5 |
| PRT630 | 25 | 12.5 | 25 | 12.5 | 25 | 12.5 | 25 | 12.5 | 25 | 12.5 |
| PRT631 | 12.5 | 25 | 12.5 | 25 | 12.5 | 25 | 12.5 | 25 | 12.5 | 25 |
| PRT632 | 25 | 12.5 | 25 | 12.5 | 25 | 50 | 25 | 12.5 | 25 | 50 |
| PRT633 | 50 | 12.5 | 50 | 12.5 | 50 | 12.5 | 50 | 12.5 | 50 | 25 |
| PRT634 | 25 | 50 | 25 | 12.5 | 25 | 12.5 | 25 | 25 | 12.5 | 25 |
| PRT635 | 25 | 12.5 | 25 | 12.5 | 25 | 12.5 | 12.5 | 25 | 12.5 | 25 |
| PRT636 | 25 | 50 | 25 | 12.5 | 25 | 50 | 25 | 12.5 | 25 | 50 |
| PRT637 | 12.5 | 25 | 50 | 12.5 | 25 | 50 | 25 | 12.5 | 25 | 50 |
| PRT638 | 12.5 | 50 | 12.5 | 25 | 50 | 25 | 12.5 | 50 | 25 | 50 |
| PRT639 | 50 | 12.5 | 50 | 12.5 | 50 | 25 | 12.5 | 25 | 50 | 25 |
| PRT640 | 25 | 50 | 12.5 | 25 | 50 | 12.5 | 25 | 50 | 12.5 | 25 |
| PRT641 | 25 | 12.5 | 25 | 50 | 25 | 12.5 | 25 | 50 | 12.5 | 50 |

TABLE 3-continued

MIC (μg/mL) of the human-originated EGF domain proteins against various Gram-negative bacteria

| Protein | E. coli BL21 | P. aeruginosa | K. pneumonia | E. cloacae | A. hydrophila | C. diversus | M. catarrhalis | P. mirabilis | P. vulgaris | S. marcescens |
|---|---|---|---|---|---|---|---|---|---|---|
| PRT642 | 50 | 25 | 12.5 | 25 | 50 | 25 | 12.5 | 25 | 50 | 25 |
| PRT643 | 25 | 50 | 25 | 12.5 | 25 | 50 | 25 | 12.5 | 25 | 50 |
| PRT644 | 12.5 | 25 | 50 | 25 | 12.5 | 25 | 50 | 25 | 100 | 25 |
| PRT645 | 25 | 12.5 | 25 | 50 | 25 | 12.5 | 50 | 12.5 | 50 | 12.5 |
| PRT646 | 12.5 | 12.5 | 12.5 | 12.5 | 25 | 50 | 25 | 12.5 | 25 | 50 |
| PRT647 | 12.5 | 25 | 50 | 12.5 | 50 | 12.5 | 50 | 12.5 | 50 | 25 |
| PRT648 | 25 | 50 | 25 | 12.5 | 50 | 12.5 | 50 | 12.5 | 50 | 12.5 |
| PRT649 | 12.5 | 50 | 12.5 | 50 | 12.5 | 50 | 12.5 | 25 | 50 | 25 |
| PRT650 | 25 | 50 | 12.5 | 50 | 25 | 12.5 | 25 | 50 | 12.5 | 50 |
| PRT651 | 50 | 25 | 12.5 | 25 | 50 | 25 | 12.5 | 25 | 50 | 25 |
| PRT652 | 25 | 50 | 25 | 12.5 | 25 | 50 | 25 | 12.5 | 25 | 50 |
| PRT653 | 12.5 | 25 | 50 | 25 | 12.5 | 50 | 25 | 12.5 | 50 | 25 |
| PRT654 | 50 | 12.5 | 50 | 12.5 | 50 | 12.5 | 50 | 25 | 12.5 | 25 |
| PRT655 | 50 | 12.5 | 25 | 50 | 25 | 12.5 | 50 | 25 | 12.5 | 25 |
| PRT656 | 12.5 | 50 | 12.5 | 50 | 12.5 | 12.5 | 12.5 | 25 | 12.5 | 12.5 |
| PRT657 | 12.5 | 12.5 | 12.5 | 25 | 12.5 | 25 | 12.5 | 12.5 | 25 | 12.5 |
| PRT658 | 25 | 50 | 25 | 12.5 | 25 | 50 | 12.5 | 25 | 50 | 12.5 |
| PRT659 | 50 | 25 | 12.5 | 25 | 50 | 25 | 25 | 12.5 | 25 | 50 |
| PRT660 | 50 | 12.5 | 12.5 | 50 | 12.5 | 50 | 12.5 | 25 | 50 | 12.5 |
| PRT661 | 25 | 12.5 | 25 | 50 | 25 | 12.5 | 25 | 50 | 25 | 25 |
| PRT662 | 12.5 | 25 | 50 | 25 | 12.5 | 25 | 25 | 50 | 12.5 | 50 |
| PRT663 | 25 | 50 | 25 | 12.5 | 25 | 50 | 12.5 | 25 | 50 | 12.5 |
| PRT664 | 50 | 25 | 12.5 | 25 | 50 | 12.5 | 25 | 50 | 12.5 | 25 |
| PRT665 | 50 | 25 | 12.5 | 25 | 50 | 25 | 12.5 | 25 | 50 | 25 |
| PRT666 | 25 | 50 | 25 | 12.5 | 25 | 50 | 25 | 12.5 | 25 | 25 |
| PRT667 | 25 | 12.5 | 50 | 12.5 | 50 | 12.5 | 50 | 25 | 12.5 | 50 |
| PRT668 | 50 | 12.5 | 50 | 12.5 | 50 | 100 | 25 | 25 | 50 | 100 |
| PRT669 | 50 | 25 | 12.5 | 25 | 12.5 | 25 | 12.5 | 25 | 12.5 | 12.5 |
| PRT670 | 12.5 | 25 | 12.5 | 12.5 | 12.5 | 25 | 12.5 | 25 | 12.5 | 25 |
| PRT671 | 12.5 | 12.5 | 12.5 | 12.5 | 25 | 12.5 | 25 | 12.5 | 25 | 12.5 |
| PRT672 | 25 | 12.5 | 25 | 12.5 | 12.5 | 25 | 12.5 | 25 | 50 | 12.5 |
| PRT673 | 12.5 | 50 | 50 | 25 | 50 | 25 | 25 | 50 | 12.5 | 50 |
| PRT674 | 25 | 50 | 25 | 12.5 | 50 | 25 | 25 | 12.5 | 50 | 25 |
| PRT675 | 50 | 25 | 12.5 | 50 | 25 | 12.5 | 50 | 25 | 12.5 | 25 |
| PRT676 | 50 | 12.5 | 50 | 25 | 12.5 | 50 | 25 | 12.5 | 50 | 12.5 |
| PRT677 | 25 | 12.5 | 50 | 25 | 12.5 | 25 | 25 | 50 | 12.5 | 50 |
| PRT678 | 12.5 | 50 | 12.5 | 50 | 25 | 12.5 | 50 | 25 | 12.5 | 50 |
| PRT679 | 50 | 25 | 25 | 12.5 | 25 | 50 | 12.5 | 25 | 50 | 25 |
| PRT680 | 25 | 25 | 50 | 25 | 12.5 | 25 | 50 | 12.5 | 50 | 25 |
| PRT681 | 50 | 25 | 12.5 | 25 | 50 | 12.5 | 25 | 50 | 12.5 | 50 |
| PRT682 | 12.5 | 50 | 25 | 25 | 12.5 | 25 | 25 | 50 | 12.5 | 50 |
| PRT683 | 25 | 50 | 25 | 12.5 | 50 | 25 | 25 | 12.5 | 50 | 25 |
| PRT684 | 25 | 50 | 25 | 12.5 | 50 | 25 | 12.5 | 25 | 50 | 12.5 |
| PRT685 | 25 | 12.5 | 50 | 12.5 | 50 | 12.5 | 50 | 25 | 50 | 50 |
| PRT686 | 50 | 25 | 50 | 50 | 50 | 50 | 50 | 50 | 25 | 50 |
| PRT687 | 25 | 50 | 12.5 | 25 | 25 | 50 | 25 | 12.5 | 25 | 50 |
| PRT688 | 12.5 | 25 | 50 | 12.5 | 25 | 50 | 12.5 | 50 | 100 | 50 |
| PRT689 | 25 | 50 | 12.5 | 25 | 50 | 12.5 | 50 | 25 | 12.5 | 25 |
| PRT690 | 50 | 25 | 25 | 12.5 | 25 | 25 | 50 | 12.5 | 50 | 12.5 |
| PRT691 | 50 | 12.5 | 50 | 25 | 12.5 | 50 | 12.5 | 25 | 50 | 12.5 |
| PRT692 | 25 | 12.5 | 50 | 25 | 12.5 | 50 | 25 | 12.5 | 25 | 50 |
| PRT693 | 12.5 | 50 | 25 | 12.5 | 25 | 50 | 12.5 | 25 | 50 | 50 |
| PRT694 | 25 | 50 | 25 | 50 | 25 | 12.5 | 25 | 50 | 12.5 | 50 |
| PRT695 | 12.5 | 25 | 25 | 12.5 | 25 | 50 | 50 | 12.5 | 50 | 12.5 |
| PRT696 | 25 | 12.5 | 50 | 25 | 12.5 | 25 | 25 | 50 | 25 | 12.5 |
| PRT697 | 25 | 50 | 12.5 | 50 | 25 | 12.5 | 50 | 12.5 | 25 | 25 |
| PRT698 | 25 | 12.5 | 50 | 25 | 12.5 | 25 | 50 | 25 | 25 | 12.5 |
| PRT699 | 25 | 12.5 | 25 | 50 | 12.5 | 50 | 25 | 12.5 | 25 | 50 |
| PRT700 | 50 | 25 | 12.5 | 25 | 50 | 12.5 | 25 | 50 | 25 | 12.5 |
| PRT701 | 25 | 12.5 | 50 | 25 | 12.5 | 50 | 12.5 | 25 | 50 | 12.5 |
| PRT702 | 50 | 12.5 | 50 | 25 | 25 | 12.5 | 25 | 25 | 50 | 12.5 |
| PRT703 | 50 | 12.5 | 25 | 50 | 25 | 12.5 | 50 | 25 | 12.5 | 50 |
| PRT704 | 25 | 50 | 25 | 50 | 50 | 25 | 12.5 | 50 | 25 | 12.5 |
| PRT705 | 50 | 12.5 | 50 | 12.5 | 25 | 100 | 25 | 50 | 12.5 | 50 |
| PRT706 | 50 | 12.5 | 12.5 | 25 | 50 | 12.5 | 50 | 12.5 | 50 | 12.5 |
| PRT707 | 25 | 50 | 12.5 | 12.5 | 25 | 12.5 | 12.5 | 12.5 | 25 | 12.5 |
| PRT708 | 25 | 50 | 25 | 50 | 12.5 | 50 | 12.5 | 50 | 12.5 | 50 |
| PRT709 | 12.5 | 25 | 50 | 12.5 | 50 | 12.5 | 50 | 25 | 12.5 | 50 |
| PRT710 | 12.5 | 50 | 12.5 | 50 | 12.5 | 50 | 25 | 12.5 | 25 | 50 |
| PRT711 | 12.5 | 50 | 12.5 | 25 | 50 | 12.5 | 50 | 12.5 | 25 | 50 |
| PRT712 | 12.5 | 50 | 25 | 50 | 25 | 12.5 | 25 | 50 | 25 | 12.5 |
| PRT713 | 25 | 12.5 | 12.5 | 50 | 12.5 | 50 | 12.5 | 50 | 12.5 | 50 |
| PRT714 | 25 | 12.5 | 12.5 | 12.5 | 50 | 12.5 | 50 | 12.5 | 50 | 12.5 |

TABLE 3-continued

MIC (µg/mL) of the human-originated EGF domain proteins against various Gram-negative bacteria

| Protein | E. coli BL21 | P. aeruginosa | K. pneumonia | E. cloacae | A. hydrophila | C. diversus | M. catarrhalis | P. mirabilis | P. vulgaris | S. marcescens |
|---|---|---|---|---|---|---|---|---|---|---|
| PRT715 | 50 | 25 | 12.5 | 50 | 12.5 | 50 | 12.5 | 25 | 50 | 12.5 |
| PRT716 | 50 | 25 | 12.5 | 25 | 50 | 25 | 12.5 | 25 | 50 | 12.5 |
| PRT717 | 12.5 | 50 | 12.5 | 50 | 12.5 | 25 | 50 | 25 | 12.5 | 50 |
| PRT718 | 25 | 50 | 25 | 25 | 25 | 25 | 12.5 | 25 | 50 | 12.5 |
| PRT719 | 12.5 | 50 | 12.5 | 50 | 12.5 | 50 | 50 | 50 | 50 | 50 |
| PRT720 | 25 | 12.5 | 12.5 | 50 | 12.5 | 25 | 50 | 25 | 12.5 | 50 |
| PRT721 | 12.5 | 25 | 50 | 25 | 12.5 | 25 | 50 | 12.5 | 12.5 | 50 |
| PRT722 | 25 | 50 | 12.5 | 50 | 25 | 12.5 | 25 | 50 | 25 | 12.5 |
| PRT723 | 50 | 100 | 100 | 50 | 12.5 | 25 | 12.5 | 25 | 25 | 12.5 |
| PRT724 | 12.5 | 12.5 | 12.5 | 25 | 12.5 | 25 | 12.5 | 25 | 12.5 | 25 |
| PRT725 | 12.5 | 25 | 50 | 12.5 | 25 | 50 | 25 | 12.5 | 50 | 25 |
| PRT726 | 50 | 25 | 25 | 12.5 | 25 | 50 | 25 | 12.5 | 50 | 25 |
| PRT727 | 25 | 50 | 12.5 | 50 | 25 | 12.5 | 25 | 50 | 12.5 | 50 |
| PRT728 | 25 | 25 | 12.5 | 25 | 12.5 | 25 | 12.5 | 12.5 | 12.5 | 25 |
| PRT729 | 25 | 12.5 | 25 | 12.5 | 25 | 12.5 | 25 | 12.5 | 25 | 50 |
| PRT730 | 12.5 | 25 | 25 | 50 | 25 | 12.5 | 25 | 50 | 12.5 | 25 |
| PRT731 | 12.5 | 50 | 12.5 | 25 | 50 | 25 | 12.5 | 25 | 25 | 50 |
| PRT732 | 50 | 12.5 | 50 | 25 | 12.5 | 25 | 50 | 25 | 25 | 12.5 |
| PRT733 | 12.5 | 50 | 12.5 | 50 | 12.5 | 25 | 50 | 25 | 12.5 | 25 |
| PRT734 | 12.5 | 25 | 50 | 12.5 | 50 | 25 | 12.5 | 25 | 25 | 50 |
| PRT735 | 50 | 12.5 | 25 | 12.5 | 25 | 50 | 25 | 12.5 | 50 | 25 |
| PRT736 | 25 | 50 | 50 | 50 | 25 | 12.5 | 25 | 12.5 | 25 | 50 |
| PRT737 | 50 | 12.5 | 50 | 25 | 12.5 | 25 | 50 | 25 | 12.5 | 25 |
| PRT738 | 12.5 | 25 | 50 | 12.5 | 50 | 12.5 | 25 | 50 | 25 | 25 |
| PRT739 | 50 | 12.5 | 50 | 12.5 | 25 | 50 | 25 | 12.5 | 50 | 25 |
| PRT740 | 12.5 | 50 | 12.5 | 50 | 12.5 | 12.5 | 50 | 25 | 12.5 | 25 |
| PRT741 | 50 | 12.5 | 25 | 50 | 12.5 | 50 | 12.5 | 50 | 25 | 12.5 |
| PRT742 | 12.5 | 50 | 25 | 12.5 | 50 | 12.5 | 25 | 12.5 | 50 | 25 |
| PRT743 | 50 | 12.5 | 12.5 | 12.5 | 50 | 12.5 | 50 | 100 | 25 | 50 |
| PRT744 | 50 | 12.5 | 50 | 12.5 | 50 | 12.5 | 50 | 25 | 25 | 12.5 |
| PRT745 | 25 | 50 | 12.5 | 50 | 12.5 | 50 | 12.5 | 25 | 50 | 25 |
| PRT746 | 50 | 12.5 | 50 | 12.5 | 50 | 12.5 | 25 | 25 | 25 | 12.5 |
| PRT747 | 50 | 12.5 | 12.5 | 12.5 | 12.5 | 50 | 12.5 | 50 | 25 | 12.5 |
| PRT748 | 25 | 12.5 | 25 | 50 | 12.5 | 50 | 12.5 | 50 | 12.5 | 25 |
| PRT749 | 12.5 | 50 | 12.5 | 25 | 50 | 12.5 | 50 | 12.5 | 50 | 25 |
| PRT750 | 12.5 | 50 | 25 | 12.5 | 25 | 50 | 12.5 | 50 | 12.5 | 50 |
| PRT751 | 25 | 50 | 12.5 | 50 | 25 | 12.5 | 25 | 50 | 25 | 12.5 |
| PRT752 | 25 | 12.5 | 12.5 | 12.5 | 50 | 12.5 | 25 | 50 | 25 | 12.5 |
| PRT753 | 50 | 12.5 | 50 | 12.5 | 50 | 12.5 | 50 | 12.5 | 25 | 50 |
| PRT754 | 12.5 | 50 | 25 | 12.5 | 25 | 50 | 25 | 12.5 | 50 | 25 |
| PRT755 | 50 | 12.5 | 50 | 12.5 | 50 | 12.5 | 50 | 12.5 | 12.5 | 25 |
| PRT756 | 25 | 12.5 | 50 | 12.5 | 50 | 12.5 | 50 | 12.5 | 50 | 12.5 |
| PRT757 | 12.5 | 50 | 12.5 | 25 | 50 | 12.5 | 50 | 12.5 | 25 | 50 |
| PRT758 | 25 | 50 | 50 | 25 | 50 | 25 | 12.5 | 25 | 12.5 | 12.5 |
| PRT759 | 12.5 | 25 | 12.5 | 12.5 | 12.5 | 12.5 | 25 | 12.5 | 12.5 | 25 |
| PRT760 | 25 | 12.5 | 50 | 12.5 | 50 | 12.5 | 50 | 12.5 | 50 | 12.5 |
| PRT761 | 12.5 | 50 | 12.5 | 50 | 25 | 12.5 | 25 | 50 | 12.5 | 25 |
| PRT762 | 12.5 | 50 | 12.5 | 50 | 12.5 | 50 | 12.5 | 50 | 25 | 12.5 |
| PRT763 | 50 | 12.5 | 25 | 12.5 | 25 | 12.5 | 12.5 | 12.5 | 50 | 25 |
| PRT764 | 25 | 50 | 100 | 50 | 12.5 | 50 | 12.5 | 25 | 25 | 50 |
| PRT765 | 50 | 12.5 | 50 | 12.5 | 12.5 | 12.5 | 12.5 | 12.5 | 12.5 | 12.5 |
| PRT766 | 50 | 25 | 12.5 | 50 | 25 | 12.5 | 25 | 50 | 25 | 12.5 |
| PRT767 | 50 | 25 | 12.5 | 50 | 12.5 | 25 | 50 | 25 | 12.5 | 50 |
| PRT768 | 50 | 25 | 12.5 | 50 | 12.5 | 50 | 25 | 12.5 | 25 | 12.5 |
| PRT769 | 12.5 | 12.5 | 25 | 12.5 | 25 | 12.5 | 12.5 | 12.5 | 25 | 12.5 |
| PRT770 | 12.5 | 50 | 12.5 | 50 | 25 | 12.5 | 25 | 50 | 12.5 | 50 |
| PRT771 | 12.5 | 50 | 12.5 | 50 | 12.5 | 50 | 12.5 | 50 | 12.5 | 50 |
| PRT772 | 50 | 12.5 | 50 | 12.5 | 50 | 12.5 | 25 | 50 | 25 | 12.5 |
| PRT773 | 25 | 12.5 | 50 | 12.5 | 50 | 12.5 | 50 | 12.5 | 50 | 12.5 |
| PRT774 | 12.5 | 12.5 | 25 | 12.5 | 25 | 12.5 | 12.5 | 12.5 | 12.5 | 50 |
| PRT775 | 25 | 50 | 12.5 | 50 | 12.5 | 50 | 12.5 | 50 | 12.5 | 50 |
| PRT776 | 50 | 12.5 | 25 | 50 | 12.5 | 12.5 | 12.5 | 12.5 | 25 | 12.5 |
| PRT777 | 12.5 | 50 | 12.5 | 12.5 | 50 | 50 | 12.5 | 50 | 25 | 12.5 |
| PRT778 | 12.5 | 50 | 12.5 | 50 | 12.5 | 12.5 | 12.5 | 12.5 | 25 | 12.5 |
| PRT779 | 12.5 | 50 | 12.5 | 50 | 12.5 | 50 | 12.5 | 50 | 12.5 | 50 |
| PRT780 | 50 | 12.5 | 50 | 12.5 | 50 | 25 | 12.5 | 25 | 50 | 12.5 |
| PRT781 | 50 | 12.5 | 50 | 25 | 12.5 | 25 | 50 | 12.5 | 50 | 12.5 |
| PRT782 | 25 | 12.5 | 12.5 | 12.5 | 12.5 | 12.5 | 12.5 | 25 | 12.5 | 50 |
| PRT783 | 12.5 | 50 | 12.5 | 25 | 50 | 25 | 25 | 25 | 50 | 12.5 |
| PRT784 | 25 | 12.5 | 50 | 12.5 | 50 | 12.5 | 50 | 12.5 | 50 | 12.5 |
| PRT785 | 50 | 25 | 25 | 12.5 | 50 | 12.5 | 25 | 50 | 25 | 50 |
| PRT786 | 25 | 12.5 | 50 | 12.5 | 12.5 | 25 | 12.5 | 25 | 12.5 | 12.5 |
| PRT787 | 12.5 | 12.5 | 12.5 | 12.5 | 12.5 | 25 | 50 | 25 | 25 | 12.5 |

TABLE 3-continued

MIC (μg/mL) of the human-originated EGF domain proteins against various Gram-negative bacteria

| Protein | E. coli BL21 | P. aeruginosa | K. pneumonia | E. cloacae | A. hydrophila | C. diversus | M. catarrhalis | P. mirabilis | P. vulgaris | S. marcescens |
|---|---|---|---|---|---|---|---|---|---|---|
| PRT788 | 100 | 50 | 25 | 12.5 | 25 | 50 | 25 | 12.5 | 50 | 50 |
| PRT789 | 50 | 25 | 12.5 | 50 | 12.5 | 25 | 25 | 50 | 25 | 12.5 |
| PRT790 | 50 | 25 | 25 | 12.5 | 25 | 50 | 25 | 12.5 | 50 | 12.5 |
| PRT791 | 12.5 | 50 | 12.5 | 50 | 12.5 | 25 | 50 | 25 | 12.5 | 12.5 |
| PRT792 | 50 | 12.5 | 12.5 | 25 | 50 | 25 | 12.5 | 50 | 12.5 | 50 |
| PRT793 | 12.5 | 50 | 12.5 | 25 | 50 | 25 | 12.5 | 25 | 50 | 12.5 |
| PRT794 | 12.5 | 50 | 12.5 | 25 | 50 | 25 | 12.5 | 25 | 50 | 12.5 |
| PRT795 | 25 | 50 | 50 | 12.5 | 25 | 50 | 25 | 25 | 25 | 50 |
| PRT796 | 50 | 12.5 | 50 | 50 | 50 | 5 | 50 | 12.5 | 50 | 50 |
| PRT797 | 12.5 | 50 | 25 | 50 | 12.5 | 50 | 12.5 | 12.5 | 12.5 | 12.5 |
| PRT798 | 25 | 12.5 | 50 | 12.5 | 50 | 12.5 | 50 | 12.5 | 50 | 25 |
| PRT799 | 12.5 | 12.5 | 12.5 | 5 | 12.5 | 12.5 | 12.5 | 12.5 | 50 | 25 |
| PRT800 | 50 | 25 | 12.5 | 50 | 12.5 | 50 | 12.5 | 12.5 | 50 | 25 |
| PRT801 | 12.5 | 50 | 25 | 12.5 | 25 | 12.5 | 12.5 | 12.5 | 12.5 | 12.5 |
| PRT802 | 12.5 | 25 | 12.5 | 12.5 | 12.5 | 25 | 12.5 | 25 | 25 | 12.5 |
| PRT803 | 50 | 12.5 | 25 | 50 | 25 | 25 | 100 | 50 | 12.5 | 50 |
| PRT804 | 50 | 12.5 | 50 | 12.5 | 12.5 | 12.5 | 50 | 12.5 | 25 | 50 |
| PRT805 | 50 | 12.5 | 12.5 | 12.5 | 12.5 | 12.5 | 50 | 12.5 | 50 | 12.5 |
| PRT806 | 25 | 12.5 | 12.5 | 12.5 | 12.5 | 12.5 | 25 | 12.5 | 25 | 25 |
| PRT807 | 50 | 25 | 12.5 | 50 | 12.5 | 25 | 50 | 12.5 | 50 | 12.5 |
| PRT808 | 50 | 12.5 | 50 | 25 | 12.5 | 25 | 50 | 25 | 12.5 | 50 |
| PRT809 | 12.5 | 25 | 25 | 50 | 12.5 | 25 | 50 | 25 | 12.5 | 25 |
| PRT810 | 50 | 25 | 12.5 | 50 | 25 | 50 | 25 | 50 | 50 | 25 |
| PRT811 | 25 | 12.5 | 12.5 | 12.5 | 12.5 | 12.5 | 12.5 | 25 | 25 | 25 |
| PRT812 | 12.5 | 12.5 | 25 | 50 | 25 | 12.5 | 50 | 12.5 | 50 | 12.5 |
| PRT813 | 50 | 50 | 50 | 25 | 50 | 25 | 25 | 25 | 50 | 12.5 |
| PRT814 | 25 | 50 | 12.5 | 12.5 | 25 | 12.5 | 25 | 12.5 | 12.5 | 12.5 |
| PRT815 | 12.5 | 12.5 | 12.5 | 25 | 12.5 | 25 | 50 | 25 | 12.5 | 25 |
| PRT816 | 50 | 100 | 50 | 25 | 12.5 | 25 | 50 | 25 | 25 | 12.5 |
| PRT817 | 12.5 | 50 | 25 | 12.5 | 25 | 50 | 25 | 12.5 | 50 | 12.5 |
| PRT818 | 50 | 25 | 12.5 | 12.5 | 25 | 25 | 25 | 25 | 12.5 | 12.5 |
| PRT819 | 25 | 12.5 | 12.5 | 25 | 12.5 | 25 | 50 | 12.5 | 50 | 25 |
| PRT820 | 50 | 12.5 | 50 | 12.5 | 50 | 12.5 | 50 | 12.5 | 12.5 | 25 |
| PRT821 | 12.5 | 12.5 | 25 | 25 | 50 | 25 | 12.5 | 50 | 12.5 | 50 |
| PRT822 | 25 | 50 | 12.5 | 50 | 12.5 | 12.5 | 12.5 | 25 | 12.5 | 12.5 |
| PRT823 | 12.5 | 25 | 12.5 | 25 | 12.5 | 25 | 50 | 25 | 12.5 | 50 |
| PRT824 | 25 | 50 | 25 | 12.5 | 25 | 50 | 25 | 12.5 | 50 | 25 |
| PRT825 | 12.5 | 25 | 50 | 25 | 12.5 | 25 | 50 | 12.5 | 50 | 25 |
| PRT826 | 50 | 25 | 100 | 50 | 12.5 | 12.5 | 25 | 12.5 | 12.5 | 12.5 |
| PRT827 | 25 | 12.5 | 12.5 | 50 | 25 | 12.5 | 25 | 50 | 12.5 | 50 |
| PRT828 | 50 | 12.5 | 50 | 12.5 | 50 | 12.5 | 50 | 25 | 12.5 | 25 |
| PRT829 | 25 | 12.5 | 25 | 50 | 25 | 12.5 | 25 | 50 | 12.5 | 12.5 |
| PRT830 | 12.5 | 12.5 | 12.5 | 25 | 12.5 | 25 | 12.5 | 25 | 12.5 | 12.5 |
| PRT831 | 25 | 12.5 | 25 | 12.5 | 25 | 50 | 12.5 | 50 | 25 | 12.5 |
| PRT832 | 12.5 | 12.5 | 12.5 | 25 | 12.5 | 25 | 12.5 | 12.5 | 25 | 12.5 |
| PRT833 | 25 | 12.5 | 12.5 | 50 | 12.5 | 50 | 12.5 | 25 | 50 | 12.5 |
| PRT834 | 25 | 12.5 | 25 | 50 | 25 | 12.5 | 25 | 50 | 12.5 | 25 |
| PRT835 | 50 | 25 | 12.5 | 50 | 25 | 25 | 25 | 50 | 12.5 | 25 |
| PRT836 | 12.5 | 50 | 12.5 | 50 | 12.5 | 25 | 12.5 | 25 | 25 | 12.5 |
| PRT837 | 12.5 | 25 | 25 | 12.5 | 25 | 12.5 | 25 | 12.5 | 12.5 | 12.5 |
| PRT838 | 12.5 | 50 | 12.5 | 25 | 50 | 25 | 12.5 | 25 | 12.5 | 25 |
| PRT839 | 25 | 12.5 | 12.5 | 12.5 | 12.5 | 25 | 50 | 25 | 12.5 | 50 |
| PRT840 | 12.5 | 25 | 25 | 12.5 | 25 | 12.5 | 25 | 12.5 | 25 | 25 |
| PRT841 | 25 | 12.5 | 50 | 12.5 | 50 | 12.5 | 50 | 12.5 | 50 | 12.5 |
| PRT842 | 12.5 | 25 | 25 | 12.5 | 25 | 12.5 | 25 | 12.5 | 12.5 | 25 |
| PRT843 | 12.5 | 12.5 | 12.5 | 25 | 50 | 25 | 12.5 | 25 | 25 | 50 |
| PRT844 | 25 | 50 | 12.5 | 50 | 12.5 | 50 | 25 | 12.5 | 12.5 | 25 |
| PRT845 | 12.5 | 25 | 25 | 12.5 | 25 | 25 | 25 | 12.5 | 12.5 | 50 |
| PRT846 | 12.5 | 25 | 50 | 12.5 | 12.5 | 12.5 | 12.5 | 12.5 | 12.5 | 12.5 |
| PRT847 | 25 | 12.5 | 12.5 | 25 | 12.5 | 25 | 12.5 | 12.5 | 12.5 | 12.5 |
| PRT848 | 12.5 | 25 | 25 | 50 | 12.5 | 50 | 12.5 | 50 | 25 | 12.5 |
| PRT849 | 12.5 | 12.5 | 12.5 | 12.5 | 25 | 12.5 | 25 | 12.5 | 12.5 | 25 |
| PRT850 | 25 | 12.5 | 50 | 12.5 | 50 | 12.5 | 50 | 12.5 | 25 | 50 |
| PRT851 | 12.5 | 25 | 12.5 | 12.5 | 12.5 | 12.5 | 12.5 | 25 | 12.5 | 25 |
| PRT852 | 25 | 12.5 | 25 | 50 | 12.5 | 50 | 12.5 | 50 | 12.5 | 50 |
| PRT853 | 12.5 | 25 | 50 | 25 | 12.5 | 25 | 50 | 25 | 25 | 12.5 |
| PRT854 | 12.5 | 100 | 12.5 | 12.5 | 12.5 | 12.5 | 50 | 12.5 | 50 | 12.5 |
| PRT855 | 12.5 | 50 | 25 | 12.5 | 50 | 12.5 | 12.5 | 12.5 | 12.5 | 12.5 |
| PRT856 | 12.5 | 12.5 | 12.5 | 25 | 12.5 | 25 | 50 | 25 | 25 | 12.5 |
| PRT857 | 50 | 25 | 25 | 12.5 | 50 | 12.5 | 12.5 | 12.5 | 12.5 | 25 |
| PRT858 | 25 | 12.5 | 12.5 | 12.5 | 50 | 25 | 12.5 | 25 | 50 | 12.5 |
| PRT859 | 25 | 12.5 | 25 | 25 | 25 | 50 | 25 | 12.5 | 25 | 50 |
| PRT860 | 12.5 | 25 | 50 | 12.5 | 50 | 12.5 | 50 | 12.5 | 50 | 100 |

TABLE 3-continued

MIC (μg/mL) of the human-originated EGF domain proteins against various Gram-negative bacteria

| Protein | E. coli BL21 | P. aeruginosa | K. pneumonia | E. cloacae | A. hydrophila | C. diversus | M. catarrhalis | P. mirabilis | P. vulgaris | S. marcescens |
|---|---|---|---|---|---|---|---|---|---|---|
| PRT861 | 12.5 | 12.5 | 25 | 12.5 | 25 | 12.5 | 25 | 12.5 | 25 | 12.5 |
| PRT862 | 25 | 12.5 | 50 | 12.5 | 50 | 25 | 12.5 | 50 | 12.5 | 25 |
| PRT863 | 12.5 | 25 | 50 | 12.5 | 12.5 | 12.5 | 12.5 | 12.5 | 25 | 12.5 |
| PRT864 | 12.5 | 12.5 | 25 | 50 | 25 | 12.5 | 25 | 50 | 12.5 | 50 |
| PRT865 | 12.5 | 25 | 50 | 12.5 | 50 | 12.5 | 50 | 25 | 12.5 | 12.5 |
| PRT866 | 12.5 | 25 | 12.5 | 12.5 | 12.5 | 12.5 | 12.5 | 12.5 | 25 | 12.5 |
| PRT867 | 25 | 12.5 | 50 | 25 | 12.5 | 25 | 50 | 25 | 12.5 | 50 |
| PRT868 | 50 | 12.5 | 25 | 50 | 25 | 12.5 | 25 | 50 | 12.5 | 12.5 |
| PRT869 | 25 | 12.5 | 12.5 | 12.5 | 12.5 | 12.5 | 12.5 | 12.5 | 12.5 | 50 |
| PRT870 | 50 | 100 | 50 | 25 | 12.5 | 25 | 50 | 25 | 12.5 | 50 |
| PRT871 | 25 | 50 | 12.5 | 12.5 | 12.5 | 12.5 | 25 | 12.5 | 50 | 12.5 |
| PRT872 | 50 | 25 | 12.5 | 25 | 50 | 12.5 | 50 | 12.5 | 50 | 25 |
| PRT873 | 50 | 12.5 | 25 | 25 | 50 | 25 | 12.5 | 25 | 50 | 12.5 |
| PRT874 | 25 | 12.5 | 12.5 | 12.5 | 12.5 | 12.5 | 25 | 12.5 | 12.5 | 12.5 |
| PRT875 | 12.5 | 25 | 50 | 12.5 | 50 | 12.5 | 25 | 50 | 12.5 | 12.5 |
| PRT876 | 12.5 | 12.5 | 12.5 | 25 | 12.5 | 25 | 12.5 | 25 | 25 | 25 |
| PRT877 | 12.5 | 25 | 25 | 12.5 | 25 | 12.5 | 50 | 12.5 | 50 | 12.5 |
| PRT878 | 25 | 12.5 | 50 | 12.5 | 50 | 12.5 | 25 | 50 | 25 | 12.5 |
| PRT879 | 50 | 12.5 | 12.5 | 25 | 12.5 | 25 | 12.5 | 12.5 | 12.5 | 25 |
| PRT880 | 12.5 | 25 | 12.5 | 12.5 | 12.5 | 50 | 12.5 | 50 | 12.5 | 50 |
| PRT881 | 12.5 | 12.5 | 25 | 12.5 | 25 | 12.5 | 25 | 12.5 | 25 | 12.5 |
| PRT882 | 12.5 | 25 | 12.5 | 25 | 100 | 50 | 12.5 | 50 | 12.5 | 50 |
| PRT883 | 25 | 50 | 25 | 12.5 | 25 | 50 | 25 | 12.5 | 50 | 12.5 |
| PRT884 | 12.5 | 12.5 | 12.5 | 12.5 | 12.5 | 12.5 | 12.5 | 25 | 50 | 25 |
| PRT885 | 12.5 | 50 | 25 | 12.5 | 25 | 50 | 25 | 12.5 | 25 | 12.5 |
| PRT886 | 12.5 | 25 | 12.5 | 25 | 12.5 | 25 | 12.5 | 25 | 12.5 | 25 |
| PRT887 | 25 | 12.5 | 25 | 50 | 25 | 12.5 | 25 | 50 | 12.5 | 50 |
| PRT888 | 50 | 12.5 | 50 | 25 | 12.5 | 25 | 12.5 | 25 | 25 | 12.5 |
| PRT889 | 12.5 | 25 | 12.5 | 12.5 | 12.5 | 12.5 | 12.5 | 25 | 12.5 | 25 |
| PRT890 | 12.5 | 50 | 25 | 12.5 | 25 | 50 | 25 | 12.5 | 50 | 12.5 |
| PRT891 | 25 | 12.5 | 25 | 12.5 | 25 | 12.5 | 25 | 12.5 | 25 | 50 |
| PRT892 | 12.5 | 25 | 25 | 50 | 12.5 | 50 | 12.5 | 50 | 25 | 25 |
| PRT893 | 25 | 50 | 25 | 12.5 | 25 | 50 | 25 | 12.5 | 50 | 12.5 |
| PRT894 | 50 | 12.5 | 50 | 12.5 | 50 | 12.5 | 50 | 12.5 | 50 | 12.5 |
| PRT895 | 25 | 12.5 | 50 | 12.5 | 50 | 12.5 | 50 | 12.5 | 25 | 25 |
| PRT896 | 50 | 25 | 12.5 | 50 | 12.5 | 50 | 12.5 | 25 | 50 | 12.5 |
| PRT897 | 25 | 12.5 | 50 | 12.5 | 50 | 12.5 | 50 | 25 | 12.5 | 25 |
| PRT898 | 50 | 25 | 12.5 | 50 | 12.5 | 12.5 | 12.5 | 12.5 | 25 | 12.5 |
| PRT899 | 12.5 | 12.5 | 12.5 | 50 | 12.5 | 50 | 12.5 | 50 | 12.5 | 12.5 |
| PRT900 | 25 | 12.5 | 12.5 | 12.5 | 12.5 | 12.5 | 25 | 12.5 | 25 | 50 |
| PRT901 | 25 | 12.5 | 50 | 25 | 12.5 | 25 | 50 | 25 | 12.5 | 25 |
| PRT902 | 25 | 12.5 | 25 | 50 | 12.5 | 50 | 25 | 12.5 | 25 | 50 |
| PRT903 | 50 | 12.5 | 25 | 50 | 12.5 | 50 | 12.5 | 25 | 50 | 12.5 |
| PRT904 | 12.5 | 25 | 12.5 | 12.5 | 25 | 12.5 | 25 | 12.5 | 25 | 25 |
| PRT905 | 50 | 12.5 | 25 | 50 | 12.5 | 50 | 25 | 12.5 | 50 | 12.5 |
| PRT906 | 25 | 12.5 | 25 | 50 | 12.5 | 25 | 50 | 25 | 12.5 | 25 |
| PRT907 | 12.5 | 12.5 | 25 | 12.5 | 12.5 | 12.5 | 12.5 | 25 | 25 | 12.5 |
| PRT908 | 12.5 | 25 | 50 | 100 | 25 | 50 | 12.5 | 25 | 25 | 25 |
| PRT909 | 25 | 12.5 | 50 | 25 | 12.5 | 50 | 25 | 12.5 | 50 | 12.5 |
| PRT910 | 25 | 12.5 | 25 | 50 | 12.5 | 25 | 12.5 | 25 | 25 | 25 |
| PRT911 | 12.5 | 25 | 50 | 25 | 12.5 | 50 | 12.5 | 50 | 12.5 | 50 |
| PRT912 | 12.5 | 25 | 50 | 25 | 100 | 50 | 12.5 | 50 | 100 | 50 |
| PRT913 | 25 | 50 | 25 | 12.5 | 25 | 25 | 50 | 25 | 12.5 | 50 |
| PRT914 | 25 | 12.5 | 12.5 | 25 | 12.5 | 12.5 | 12.5 | 12.5 | 12.5 | 12.5 |
| PRT915 | 25 | 50 | 25 | 12.5 | 25 | 25 | 50 | 25 | 25 | 25 |
| PRT916 | 12.5 | 50 | 25 | 12.5 | 50 | 25 | 12.5 | 25 | 50 | 12.5 |
| PRT917 | 50 | 12.5 | 25 | 50 | 25 | 12.5 | 50 | 25 | 25 | 25 |
| PRT918 | 50 | 12.5 | 50 | 25 | 12.5 | 50 | 25 | 12.5 | 50 | 100 |
| PRT919 | 12.5 | 50 | 12.5 | 25 | 50 | 25 | 12.5 | 25 | 25 | 50 |
| PRT920 | 25 | 25 | 50 | 12.5 | 25 | 50 | 12.5 | 50 | 12.5 | 50 |
| PRT921 | 12.5 | 25 | 12.5 | 12.5 | 25 | 12.5 | 25 | 12.5 | 25 | 12.5 |
| PRT922 | 25 | 12.5 | 12.5 | 25 | 25 | 25 | 25 | 50 | 25 | 12.5 |
| PRT923 | 50 | 25 | 25 | 12.5 | 50 | 25 | 12.5 | 25 | 50 | 25 |
| PRT924 | 25 | 50 | 12.5 | 25 | 50 | 12.5 | 50 | 25 | 12.5 | 50 |
| PRT925 | 25 | 50 | 25 | 12.5 | 50 | 25 | 12.5 | 25 | 50 | 12.5 |
| PRT926 | 50 | 25 | 12.5 | 25 | 50 | 12.5 | 25 | 50 | 25 | 12.5 |
| PRT927 | 50 | 25 | 12.5 | 25 | 50 | 12.5 | 50 | 25 | 12.5 | 50 |
| PRT928 | 12.5 | 25 | 12.5 | 25 | 25 | 12.5 | 12.5 | 12.5 | 25 | 25 |
| PRT929 | 25 | 12.5 | 25 | 50 | 25 | 12.5 | 50 | 12.5 | 50 | 12.5 |
| PRT930 | 12.5 | 25 | 50 | 12.5 | 25 | 25 | 50 | 25 | 12.5 | 50 |
| PRT931 | 25 | 50 | 25 | 12.5 | 25 | 50 | 12.5 | 50 | 25 | 12.5 |
| PRT932 | 50 | 12.5 | 12.5 | 25 | 12.5 | 25 | 12.5 | 25 | 12.5 | 12.5 |
| PRT933 | 25 | 12.5 | 50 | 25 | 12.5 | 25 | 50 | 25 | 12.5 | 50 |

TABLE 3-continued

MIC (μg/mL) of the human-originated EGF domain proteins against various Gram-negative bacteria

| Protein | E. coli BL21 | P. aeruginosa | K. pneumonia | E. cloacae | A. hydrophila | C. diversus | M. catarrhalis | P. mirabilis | P. vulgaris | S. marcescens |
|---|---|---|---|---|---|---|---|---|---|---|
| PRT934 | 25 | 50 | 12.5 | 50 | 25 | 25 | 12.5 | 50 | 12.5 | 50 |
| PRT935 | 25 | 25 | 12.5 | 25 | 25 | 100 | 12.5 | 12.5 | 12.5 | 12.5 |
| PRT936 | 12.5 | 25 | 50 | 12.5 | 25 | 50 | 12.5 | 50 | 12.5 | 50 |
| PRT937 | 12.5 | 50 | 25 | 12.5 | 50 | 25 | 12.5 | 50 | 12.5 | 50 |
| PRT938 | 50 | 25 | 12.5 | 25 | 50 | 12.5 | 50 | 12.5 | 50 | 12.5 |
| PRT939 | 25 | 12.5 | 12.5 | 50 | 12.5 | 50 | 12.5 | 50 | 12.5 | 50 |
| PRT940 | 12.5 | 25 | 12.5 | 12.5 | 50 | 12.5 | 50 | 12.5 | 50 | 12.5 |
| PRT941 | 50 | 12.5 | 50 | 12.5 | 50 | 12.5 | 50 | 12.5 | 50 | 12.5 |
| PRT942 | 50 | 12.5 | 50 | 12.5 | 25 | 50 | 12.5 | 50 | 12.5 | 50 |
| PRT943 | 12.5 | 12.5 | 12.5 | 25 | 12.5 | 12.5 | 12.5 | 12.5 | 12.5 | 50 |
| PRT944 | 25 | 50 | 100 | 50 | 12.5 | 50 | 12.5 | 25 | 50 | 12.5 |
| PRT945 | 50 | 25 | 12.5 | 25 | 50 | 12.5 | 25 | 50 | 12.5 | 25 |
| PRT946 | 12.5 | 50 | 12.5 | 50 | 25 | 12.5 | 50 | 25 | 12.5 | 50 |
| PRT947 | 50 | 12.5 | 50 | 12.5 | 50 | 25 | 12.5 | 25 | 50 | 12.5 |
| PRT948 | 12.5 | 50 | 12.5 | 50 | 25 | 12.5 | 50 | 25 | 12.5 | 50 |
| PRT949 | 25 | 50 | 25 | 12.5 | 50 | 12.5 | 25 | 50 | 12.5 | 25 |
| PRT950 | 12.5 | 50 | 25 | 12.5 | 50 | 25 | 12.5 | 50 | 25 | 12.5 |
| PRT951 | 25 | 25 | 25 | 12.5 | 12.5 | 25 | 12.5 | 25 | 50 | 100 |
| PRT952 | 12.5 | 50 | 12.5 | 50 | 12.5 | 50 | 25 | 12.5 | 25 | 12.5 |
| PRT953 | 12.5 | 12.5 | 25 | 12.5 | 25 | 12.5 | 25 | 50 | 25 | 12.5 |
| PRT954 | 25 | 12.5 | 25 | 50 | 12.5 | 25 | 50 | 25 | 12.5 | 25 |
| PRT955 | 12.5 | 25 | 12.5 | 25 | 12.5 | 25 | 12.5 | 12.5 | 25 | 12.5 |
| PRT956 | 12.5 | 12.5 | 25 | 12.5 | 25 | 25 | 12.5 | 25 | 50 | 25 |
| PRT957 | 25 | 50 | 25 | 12.5 | 25 | 50 | 12.5 | 25 | 50 | 12.5 |
| PRT958 | 12.5 | 25 | 50 | 25 | 25 | 12.5 | 50 | 25 | 12.5 | 25 |
| PRT959 | 50 | 25 | 12.5 | 25 | 50 | 12.5 | 50 | 12.5 | 25 | 50 |
| PRT960 | 50 | 25 | 12.5 | 25 | 50 | 12.5 | 12.5 | 12.5 | 25 | 12.5 |
| PRT961 | 25 | 100 | 25 | 12.5 | 12.5 | 25 | 25 | 50 | 12.5 | 25 |
| PRT962 | 50 | 25 | 12.5 | 25 | 50 | 12.5 | 25 | 50 | 12.5 | 25 |
| PRT963 | 50 | 25 | 12.5 | 25 | 50 | 25 | 12.5 | 50 | 25 | 25 |
| PRT964 | 25 | 50 | 25 | 12.5 | 25 | 50 | 25 | 25 | 12.5 | 50 |
| PRT965 | 25 | 50 | 25 | 12.5 | 50 | 25 | 12.5 | 50 | 25 | 12.5 |
| PRT966 | 12.5 | 50 | 25 | 12.5 | 50 | 25 | 12.5 | 50 | 25 | 12.5 |
| PRT967 | 12.5 | 12.5 | 25 | 12.5 | 25 | 12.5 | 25 | 12.5 | 25 | 12.5 |
| PRT968 | 12.5 | 25 | 12.5 | 25 | 25 | 12.5 | 25 | 50 | 25 | 12.5 |
| PRT969 | 12.5 | 25 | 50 | 25 | 25 | 12.5 | 25 | 50 | 25 | 12.5 |
| PRT970 | 25 | 12.5 | 25 | 50 | 12.5 | 25 | 50 | 25 | 12.5 | 25 |
| PRT971 | 12.5 | 50 | 100 | 25 | 50 | 12.5 | 25 | 50 | 12.5 | 25 |
| PRT972 | 12.5 | 25 | 50 | 25 | 12.5 | 25 | 50 | 25 | 12.5 | 25 |
| PRT973 | 12.5 | 12.5 | 50 | 12.5 | 25 | 50 | 12.5 | 50 | 25 | 12.5 |
| PRT974 | 50 | 12.5 | 50 | 12.5 | 50 | 25 | 12.5 | 50 | 25 | 12.5 |
| PRT975 | 12.5 | 50 | 12.5 | 25 | 50 | 12.5 | 12.5 | 50 | 12.5 | 25 |
| PRT976 | 12.5 | 50 | 12.5 | 50 | 12.5 | 25 | 25 | 50 | 25 | 25 |
| PRT977 | 50 | 12.5 | 50 | 12.5 | 25 | 50 | 25 | 12.5 | 50 | 25 |
| PRT978 | 50 | 12.5 | 50 | 12.5 | 25 | 50 | 12.5 | 25 | 50 | 12.5 |
| PRT979 | 12.5 | 50 | 12.5 | 50 | 12.5 | 100 | 25 | 12.5 | 25 | 12.5 |
| PRT980 | 50 | 12.5 | 50 | 12.5 | 50 | 25 | 12.5 | 50 | 12.5 | 50 |
| PRT981 | 12.5 | 50 | 12.5 | 50 | 12.5 | 25 | 25 | 12.5 | 50 | 12.5 |
| PRT982 | 25 | 12.5 | 50 | 12.5 | 25 | 50 | 12.5 | 50 | 12.5 | 50 |
| PRT983 | 12.5 | 25 | 50 | 12.5 | 25 | 50 | 12.5 | 50 | 12.5 | 25 |
| PRT984 | 12.5 | 25 | 50 | 25 | 12.5 | 12.5 | 12.5 | 50 | 25 | 12.5 |
| PRT985 | 12.5 | 50 | 12.5 | 25 | 50 | 25 | 12.5 | 50 | 12.5 | 50 |
| PRT986 | 50 | 12.5 | 50 | 12.5 | 25 | 50 | 25 | 12.5 | 25 | 50 |
| PRT987 | 12.5 | 25 | 50 | 25 | 12.5 | 50 | 12.5 | 50 | 12.5 | 50 |
| PRT988 | 50 | 12.5 | 50 | 12.5 | 50 | 12.5 | 50 | 12.5 | 50 | 12.5 |
| PRT989 | 12.5 | 50 | 12.5 | 12.5 | 12.5 | 100 | 100 | 12.5 | 12.5 | 25 |
| PRT990 | 25 | 12.5 | 12.5 | 50 | 12.5 | 25 | 50 | 25 | 12.5 | 25 |
| PRT991 | 25 | 12.5 | 25 | 50 | 12.5 | 50 | 12.5 | 25 | 12.5 | 25 |
| PRT992 | 12.5 | 12.5 | 12.5 | 25 | 25 | 25 | 25 | 25 | 12.5 | 25 |
| PRT993 | 50 | 12.5 | 50 | 12.5 | 50 | 12.5 | 50 | 12.5 | 50 | 12.5 |
| PRT994 | 12.5 | 25 | 50 | 25 | 12.5 | 50 | 25 | 25 | 50 | 25 |
| PRT995 | 50 | 12.5 | 50 | 12.5 | 50 | 25 | 12.5 | 25 | 50 | 12.5 |
| PRT996 | 12.5 | 25 | 12.5 | 12.5 | 100 | 12.5 | 25 | 12.5 | 25 | 12.5 |
| PRT997 | 12.5 | 12.5 | 12.5 | 50 | 12.5 | 50 | 12.5 | 25 | 50 | 25 |
| PRT998 | 50 | 12.5 | 50 | 12.5 | 50 | 25 | 25 | 25 | 50 | 25 |
| PRT999 | 50 | 25 | 12.5 | 25 | 50 | 12.5 | 25 | 50 | 25 | 12.5 |
| PRT1000 | 12.5 | 50 | 25 | 12.5 | 25 | 50 | 25 | 12.5 | 25 | 50 |
| PRT1001 | 50 | 12.5 | 50 | 25 | 12.5 | 50 | 25 | 12.5 | 25 | 50 |
| PRT1002 | 12.5 | 25 | 50 | 12.5 | 50 | 25 | 12.5 | 25 | 50 | 12.5 |
| PRT1003 | 12.5 | 25 | 50 | 25 | 25 | 12.5 | 25 | 50 | 25 | 12.5 |
| PRT1004 | 100 | 50 | 12.5 | 50 | 25 | 12.5 | 25 | 50 | 25 | 12.5 |
| PRT1005 | 12.5 | 50 | 12.5 | 25 | 50 | 25 | 12.5 | 25 | 50 | 25 |
| PRT1006 | 50 | 12.5 | 50 | 12.5 | 50 | 25 | 12.5 | 25 | 50 | 25 |

TABLE 3-continued

MIC (μg/mL) of the human-originated EGF domain proteins against various Gram-negative bacteria

| Protein | E. coli BL21 | P. aeruginosa | K. pneumonia | E. cloacae | A. hydrophila | C. diversus | M. catarrhalis | P. mirabilis | P. vulgaris | S. marcescens |
|---|---|---|---|---|---|---|---|---|---|---|
| PRT1007 | 12.5 | 25 | 50 | 12.5 | 50 | 12.5 | 50 | 25 | 12.5 | 25 |
| PRT1008 | 12.5 | 12.5 | 12.5 | 50 | 12.5 | 50 | 12.5 | 25 | 50 | 25 |
| PRT1009 | 12.5 | 50 | 12.5 | 50 | 25 | 12.5 | 25 | 50 | 25 | 100 |
| PRT1010 | 12.5 | 50 | 12.5 | 50 | 12.5 | 50 | 25 | 12.5 | 25 | 50 |
| PRT1011 | 50 | 12.5 | 50 | 12.5 | 50 | 25 | 12.5 | 25 | 50 | 25 |
| PRT1012 | 50 | 12.5 | 12.5 | 50 | 12.5 | 50 | 12.5 | 12.5 | 25 | 12.5 |
| PRT1013 | 12.5 | 12.5 | 25 | 12.5 | 12.5 | 12.5 | 25 | 12.5 | 25 | 50 |
| PRT1014 | 25 | 50 | 25 | 12.5 | 50 | 12.5 | 50 | 12.5 | 50 | 25 |
| PRT1015 | 50 | 12.5 | 50 | 12.5 | 25 | 50 | 12.5 | 50 | 12.5 | 50 |
| PRT1016 | 25 | 50 | 25 | 12.5 | 25 | 50 | 100 | 50 | 25 | 12.5 |
| PRT1017 | 12.5 | 12.5 | 12.5 | 12.5 | 12.5 | 12.5 | 12.5 | 50 | 12.5 | 50 |
| PRT1018 | 12.5 | 50 | 12.5 | 25 | 50 | 12.5 | 50 | 12.5 | 50 | 25 |
| PRT1019 | 50 | 12.5 | 25 | 50 | 12.5 | 50 | 12.5 | 50 | 12.5 | 25 |
| PRT1020 | 12.5 | 12.5 | 25 | 12.5 | 12.5 | 12.5 | 12.5 | 12.5 | 50 | 25 |
| PRT1021 | 12.5 | 25 | 50 | 25 | 12.5 | 50 | 12.5 | 50 | 12.5 | 50 |
| PRT1022 | 50 | 12.5 | 25 | 25 | 25 | 50 | 12.5 | 50 | 12.5 | 12.5 |
| PRT1023 | 12.5 | 25 | 12.5 | 25 | 12.5 | 25 | 12.5 | 12.5 | 50 | 12.5 |
| PRT1024 | 12.5 | 50 | 25 | 12.5 | 25 | 50 | 25 | 12.5 | 50 | 12.5 |
| PRT1025 | 25 | 12.5 | 25 | 50 | 100 | 50 | 25 | 12.5 | 25 | 50 |
| PRT1026 | 25 | 50 | 25 | 12.5 | 50 | 12.5 | 50 | 12.5 | 25 | 50 |
| PRT1027 | 25 | 12.5 | 25 | 50 | 12.5 | 50 | 12.5 | 50 | 12.5 | 50 |
| PRT1028 | 50 | 25 | 50 | 25 | 25 | 12.5 | 25 | 50 | 25 | 50 |
| PRT1029 | 12.5 | 50 | 12.5 | 50 | 12.5 | 50 | 12.5 | 50 | 12.5 | 50 |
| PRT1030 | 12.5 | 50 | 12.5 | 50 | 25 | 50 | 12.5 | 50 | 12.5 | 50 |
| PRT1031 | 50 | 12.5 | 50 | 12.5 | 50 | 25 | 12.5 | 12.5 | 50 | 12.5 |
| PRT1032 | 12.5 | 50 | 12.5 | 50 | 12.5 | 25 | 50 | 25 | 12.5 | 25 |
| PRT1033 | 12.5 | 50 | 25 | 50 | 12.5 | 50 | 100 | 50 | 25 | 50 |
| PRT1034 | 50 | 25 | 12.5 | 50 | 50 | 50 | 12.5 | 50 | 12.5 | 50 |
| PRT1035 | 50 | 12.5 | 25 | 25 | 50 | 12.5 | 25 | 12.5 | 25 | 50 |
| PRT1036 | 50 | 25 | 25 | 50 | 12.5 | 50 | 12.5 | 50 | 50 | 50 |
| PRT1037 | 50 | 50 | 12.5 | 25 | 25 | 50 | 25 | 12.5 | 50 | 50 |
| PRT1038 | 12.5 | 50 | 50 | 50 | 12.5 | 25 | 50 | 50 | 12.5 | 25 |
| PRT1039 | 50 | 50 | 12.5 | 25 | 50 | 50 | 12.5 | 50 | 12.5 | 50 |
| PRT1040 | 50 | 50 | 25 | 50 | 12.5 | 50 | 25 | 50 | 25 | 50 |
| PRT1041 | 25 | 50 | 25 | 50 | 50 | 12.5 | 50 | 25 | 50 | 25 |
| PRT1042 | 50 | 12.5 | 25 | 50 | 50 | 50 | 12.5 | 50 | 25 | 50 |
| PRT1043 | 12.5 | 25 | 50 | 25 | 25 | 50 | 25 | 12.5 | 50 | 50 |
| PRT1044 | 50 | 50 | 12.5 | 50 | 50 | 50 | 25 | 12.5 | 25 | 50 |
| PRT1045 | 50 | 25 | 50 | 12.5 | 50 | 50 | 50 | 12.5 | 50 | 50 |
| PRT1046 | 25 | 50 | 25 | 25 | 12.5 | 50 | 50 | 50 | 25 | 12.5 |
| PRT1047 | 50 | 25 | 50 | 25 | 12.5 | 50 | 12.5 | 12.5 | 12.5 | 12.5 |
| PRT1048 | 25 | 50 | 25 | 12.5 | 25 | 50 | 25 | 12.5 | 50 | 12.5 |
| PRT1049 | 25 | 12.5 | 25 | 12.5 | 12.5 | 12.5 | 12.5 | 50 | 12.5 | 50 |
| PRT1050 | 12.5 | 25 | 12.5 | 25 | 25 | 12.5 | 12.5 | 12.5 | 50 | 12.5 |
| PRT1051 | 12.5 | 25 | 12.5 | 25 | 12.5 | 12.5 | 12.5 | 50 | 12.5 | 50 |
| PRT1052 | 25 | 50 | 25 | 12.5 | 50 | 12.5 | 50 | 12.5 | 12.5 | 12.5 |
| PRT1053 | 12.5 | 12.5 | 50 | 12.5 | 50 | 12.5 | 12.5 | 100 | 12.5 | 100 |
| PRT1054 | 25 | 12.5 | 25 | 12.5 | 12.5 | 12.5 | 12.5 | 25 | 50 | 25 |
| PRT1055 | 50 | 12.5 | 50 | 12.5 | 50 | 25 | 12.5 | 25 | 50 | 12.5 |
| PRT1056 | 25 | 12.5 | 25 | 50 | 12.5 | 50 | 12.5 | 50 | 12.5 | 25 |
| PRT1057 | 50 | 25 | 12.5 | 25 | 50 | 25 | 12.5 | 25 | 50 | 25 |
| PRT1058 | 25 | 50 | 25 | 12.5 | 50 | 12.5 | 50 | 12.5 | 50 | 12.5 |
| PRT1059 | 12.5 | 50 | 12.5 | 25 | 25 | 50 | 12.5 | 12.5 | 25 | 12.5 |
| PRT1060 | 12.5 | 25 | 50 | 25 | 12.5 | 50 | 12.5 | 25 | 12.5 | 25 |
| PRT1061 | 12.5 | 12.5 | 12.5 | 12.5 | 12.5 | 12.5 | 50 | 25 | 12.5 | 25 |
| PRT1062 | 50 | 25 | 12.5 | 25 | 25 | 50 | 25 | 12.5 | 25 | 50 |
| PRT1063 | 25 | 50 | 25 | 12.5 | 50 | 12.5 | 50 | 25 | 25 | 12.5 |
| PRT1064 | 50 | 25 | 12.5 | 50 | 25 | 12.5 | 25 | 50 | 25 | 12.5 |
| PRT1065 | 25 | 12.5 | 25 | 12.5 | 50 | 12.5 | 50 | 25 | 12.5 | 25 |
| PRT1066 | 12.5 | 12.5 | 12.5 | 12.5 | 50 | 25 | 100 | 25 | 50 | 12.5 |
| PRT1067 | 50 | 25 | 12.5 | 25 | 25 | 25 | 12.5 | 25 | 50 | 25 |
| PRT1068 | 50 | 25 | 12.5 | 25 | 50 | 25 | 12.5 | 25 | 50 | 25 |
| PRT1069 | 50 | 12.5 | 25 | 50 | 12.5 | 50 | 25 | 12.5 | 25 | 25 |
| PRT1070 | 12.5 | 25 | 12.5 | 25 | 12.5 | 12.5 | 12.5 | 12.5 | 12.5 | 12.5 |
| PRT1071 | 25 | 12.5 | 25 | 50 | 25 | 12.5 | 50 | 12.5 | 50 | 12.5 |
| PRT1072 | 12.5 | 12.5 | 25 | 50 | 12.5 | 50 | 12.5 | 12.5 | 12.5 | 12.5 |
| PRT1073 | 12.5 | 25 | 12.5 | 25 | 12.5 | 25 | 12.5 | 12.5 | 50 | 12.5 |
| PRT1074 | 12.5 | 50 | 12.5 | 12.5 | 12.5 | 12.5 | 12.5 | 12.5 | 12.5 | 12.5 |
| PRT1075 | 12.5 | 25 | 50 | 25 | 25 | 50 | 25 | 50 | 12.5 | 50 |
| PRT1076 | 25 | 12.5 | 25 | 12.5 | 12.5 | 12.5 | 12.5 | 25 | 12.5 | 25 |
| PRT1077 | 12.5 | 12.5 | 50 | 25 | 25 | 25 | 25 | 25 | 50 | 12.5 |
| PRT1078 | 50 | 25 | 12.5 | 25 | 50 | 12.5 | 50 | 12.5 | 50 | 12.5 |
| PRT1079 | 12.5 | 50 | 12.5 | 50 | 12.5 | 50 | 12.5 | 50 | 50 | 12.5 |

TABLE 3-continued

MIC (μg/mL) of the human-originated EGF domain proteins against various Gram-negative bacteria

| Protein | E. coli BL21 | P. aeruginosa | K. pneumonia | E. cloacae | A. hydrophila | C. diversus | M. catarrhalis | P. mirabilis | P. vulgaris | S. marcescens |
|---|---|---|---|---|---|---|---|---|---|---|
| PRT1080 | 25 | 12.5 | 25 | 50 | 12.5 | 12.5 | 12.5 | 12.5 | 25 | 50 |
| PRT1081 | 12.5 | 50 | 12.5 | 50 | 12.5 | 50 | 12.5 | 25 | 50 | 12.5 |
| PRT1082 | 12.5 | 25 | 50 | 25 | 12.5 | 25 | 50 | 25 | 12.5 | 25 |
| PRT1083 | 12.5 | 50 | 50 | 50 | 25 | 12.5 | 50 | 25 | 50 | 25 |
| PRT1084 | 12.5 | 50 | 50 | 50 | 12.5 | 12.5 | 25 | 12.5 | 25 | 12.5 |
| PRT1085 | 12.5 | 12.5 | 50 | 12.5 | 50 | 12.5 | 50 | 12.5 | 50 | 25 |
| PRT1086 | 25 | 50 | 25 | 12.5 | 25 | 50 | 25 | 12.5 | 50 | 12.5 |
| PRT1087 | 12.5 | 50 | 50 | 50 | 12.5 | 25 | 50 | 25 | 25 | 25 |
| PRT1088 | 50 | 50 | 12.5 | 50 | 50 | 50 | 25 | 12.5 | 25 | 50 |
| PRT1089 | 25 | 50 | 25 | 12.5 | 50 | 25 | 12.5 | 25 | 50 | 25 |
| PRT1090 | 12.5 | 50 | 12.5 | 50 | 12.5 | 25 | 50 | 25 | 12.5 | 25 |
| PRT1091 | 50 | 12.5 | 25 | 50 | 25 | 12.5 | 25 | 50 | 25 | 12.5 |
| PRT1092 | 50 | 25 | 12.5 | 25 | 12.5 | 12.5 | 25 | 50 | 25 | 25 |
| PRT1093 | 50 | 12.5 | 50 | 12.5 | 50 | 25 | 12.5 | 25 | 50 | 12.5 |
| PRT1094 | 50 | 25 | 12.5 | 25 | 50 | 12.5 | 50 | 12.5 | 50 | 12.5 |
| PRT1095 | 12.5 | 50 | 25 | 12.5 | 25 | 25 | 50 | 25 | 12.5 | 50 |
| PRT1096 | 50 | 50 | 50 | 12.5 | 50 | 50 | 12.5 | 12.5 | 12.5 | 25 |
| PRT1097 | 12.5 | 25 | 12.5 | 25 | 12.5 | 25 | 100 | 25 | 12.5 | 25 |
| PRT1098 | 12.5 | 12.5 | 12.5 | 12.5 | 25 | 12.5 | 25 | 12.5 | 25 | 50 |
| PRT1099 | 50 | 12.5 | 50 | 12.5 | 50 | 25 | 12.5 | 25 | 50 | 12.5 |
| PRT1100 | 25 | 100 | 25 | 12.5 | 100 | 12.5 | 12.5 | 12.5 | 25 | 12.5 |
| PRT1101 | 50 | 25 | 12.5 | 25 | 50 | 12.5 | 25 | 50 | 25 | 12.5 |
| PRT1102 | 12.5 | 12.5 | 12.5 | 12.5 | 12.5 | 12.5 | 12.5 | 12.5 | 12.5 | 25 |
| PRT1103 | 25 | 12.5 | 25 | 50 | 25 | 12.5 | 25 | 50 | 25 | 12.5 |
| PRT1104 | 12.5 | 50 | 12.5 | 25 | 50 | 25 | 12.5 | 25 | 50 | 25 |
| PRT1105 | 25 | 50 | 12.5 | 50 | 25 | 12.5 | 25 | 50 | 12.5 | 50 |
| PRT1106 | 25 | 12.5 | 25 | 50 | 12.5 | 25 | 50 | 25 | 12.5 | 50 |
| PRT1107 | 50 | 12.5 | 50 | 25 | 12.5 | 50 | 12.5 | 50 | 12.5 | 25 |
| PRT1108 | 12.5 | 12.5 | 12.5 | 25 | 25 | 12.5 | 25 | 12.5 | 25 | 12.5 |
| PRT1109 | 25 | 12.5 | 25 | 12.5 | 50 | 12.5 | 25 | 50 | 25 | 12.5 |
| PRT1110 | 50 | 25 | 12.5 | 50 | 12.5 | 50 | 12.5 | 25 | 50 | 25 |
| PRT1111 | 50 | 12.5 | 50 | 25 | 25 | 12.5 | 25 | 50 | 25 | 12.5 |
| PRT1112 | 25 | 12.5 | 25 | 50 | 12.5 | 25 | 12.5 | 25 | 12.5 | 25 |
| PRT1113 | 12.5 | 12.5 | 12.5 | 12.5 | 12.5 | 50 | 12.5 | 25 | 50 | 25 |
| PRT1114 | 12.5 | 25 | 50 | 25 | 25 | 12.5 | 25 | 50 | 25 | 12.5 |
| PRT1115 | 25 | 12.5 | 50 | 12.5 | 12.5 | 12.5 | 12.5 | 12.5 | 12.5 | 12.5 |
| PRT1116 | 12.5 | 25 | 12.5 | 25 | 25 | 12.5 | 25 | 50 | 25 | 12.5 |
| PRT1117 | 12.5 | 50 | 12.5 | 50 | 12.5 | 25 | 12.5 | 25 | 12.5 | 25 |
| PRT1118 | 12.5 | 25 | 12.5 | 25 | 12.5 | 12.5 | 50 | 12.5 | 25 | 50 |
| PRT1119 | 25 | 50 | 25 | 12.5 | 25 | 50 | 25 | 12.5 | 25 | 50 |
| PRT1120 | 12.5 | 25 | 50 | 25 | 12.5 | 50 | 12.5 | 50 | 12.5 | 12.5 |
| PRT1121 | 25 | 50 | 25 | 12.5 | 50 | 25 | 12.5 | 25 | 50 | 12.5 |
| PRT1122 | 12.5 | 50 | 12.5 | 50 | 25 | 12.5 | 50 | 12.5 | 50 | 12.5 |
| PRT1123 | 50 | 25 | 12.5 | 25 | 50 | 12.5 | 25 | 50 | 25 | 12.5 |
| PRT1124 | 50 | 25 | 12.5 | 25 | 50 | 12.5 | 50 | 12.5 | 50 | 12.5 |
| PRT1125 | 12.5 | 12.5 | 12.5 | 12.5 | 12.5 | 12.5 | 12.5 | 12.5 | 12.5 | 25 |
| PRT1126 | 50 | 25 | 12.5 | 25 | 25 | 50 | 12.5 | 50 | 12.5 | 50 |
| PRT1127 | 50 | 12.5 | 50 | 12.5 | 50 | 25 | 12.5 | 25 | 50 | 25 |
| PRT1128 | 50 | 12.5 | 50 | 12.5 | 50 | 12.5 | 50 | 12.5 | 50 | 12.5 |
| PRT1129 | 12.5 | 50 | 12.5 | 12.5 | 25 | 12.5 | 12.5 | 12.5 | 12.5 | 12.5 |
| PRT1130 | 12.5 | 50 | 12.5 | 50 | 12.5 | 25 | 50 | 25 | 12.5 | 25 |
| PRT1131 | 12.5 | 50 | 12.5 | 50 | 25 | 12.5 | 50 | 12.5 | 50 | 12.5 |
| PRT1132 | 12.5 | 50 | 12.5 | 50 | 12.5 | 50 | 12.5 | 25 | 50 | 25 |
| PRT1133 | 12.5 | 12.5 | 12.5 | 25 | 25 | 12.5 | 25 | 12.5 | 25 | 12.5 |
| PRT1134 | 25 | 12.5 | 25 | 12.5 | 12.5 | 12.5 | 12.5 | 12.5 | 50 | 12.5 |
| PRT1135 | 50 | 100 | 50 | 25 | 25 | 12.5 | 25 | 50 | 25 | 12.5 |
| PRT1136 | 12.5 | 50 | 12.5 | 50 | 12.5 | 50 | 12.5 | 25 | 50 | 12.5 |
| PRT1137 | 50 | 25 | 12.5 | 25 | 50 | 12.5 | 50 | 12.5 | 50 | 12.5 |
| PRT1138 | 50 | 25 | 12.5 | 25 | 25 | 50 | 25 | 12.5 | 25 | 50 |
| PRT1139 | 25 | 12.5 | 25 | 50 | 12.5 | 50 | 12.5 | 50 | 12.5 | 25 |
| PRT1140 | 50 | 12.5 | 50 | 12.5 | 50 | 12.5 | 50 | 12.5 | 50 | 100 |
| PRT1141 | 12.5 | 50 | 12.5 | 50 | 12.5 | 25 | 50 | 25 | 12.5 | 25 |
| PRT1142 | 50 | 25 | 12.5 | 25 | 25 | 50 | 25 | 12.5 | 25 | 50 |
| PRT1143 | 25 | 50 | 25 | 12.5 | 50 | 12.5 | 50 | 12.5 | 50 | 12.5 |
| PRT1144 | 12.5 | 50 | 12.5 | 50 | 12.5 | 25 | 50 | 25 | 12.5 | 25 |
| PRT1145 | 25 | 12.5 | 12.5 | 12.5 | 12.5 | 12.5 | 12.5 | 50 | 25 | 12.5 |
| PRT1146 | 25 | 12.5 | 25 | 50 | 12.5 | 25 | 50 | 12.5 | 50 | 12.5 |
| PRT1147 | 12.5 | 50 | 12.5 | 50 | 25 | 25 | 12.5 | 25 | 50 | 25 |
| PRT1148 | 25 | 12.5 | 25 | 12.5 | 12.5 | 12.5 | 12.5 | 12.5 | 25 | 12.5 |
| PRT1149 | 25 | 50 | 25 | 12.5 | 50 | 12.5 | 50 | 12.5 | 25 | 50 |
| PRT1150 | 50 | 12.5 | 50 | 12.5 | 50 | 25 | 12.5 | 25 | 50 | 25 |
| PRT1151 | 12.5 | 25 | 50 | 25 | 25 | 12.5 | 25 | 50 | 12.5 | 12.5 |
| PRT1152 | 25 | 12.5 | 25 | 12.5 | 12.5 | 12.5 | 12.5 | 12.5 | 25 | 50 |

TABLE 3-continued

MIC (μg/mL) of the human-originated EGF domain proteins against various Gram-negative bacteria

| Protein | E. coli BL21 | P. aeruginosa | K. pneumonia | E. cloacae | A. hydrophila | C. diversus | M. catarrhalis | P. mirabilis | P. vulgaris | S. marcescens |
|---|---|---|---|---|---|---|---|---|---|---|
| PRT1153 | 50 | 12.5 | 50 | 12.5 | 50 | 25 | 12.5 | 25 | 50 | 12.5 |
| PRT1154 | 12.5 | 50 | 12.5 | 25 | 100 | 12.5 | 12.5 | 12.5 | 12.5 | 12.5 |
| PRT1155 | 12.5 | 25 | 12.5 | 12.5 | 25 | 12.5 | 25 | 50 | 25 | 12.5 |
| PRT1156 | 25 | 12.5 | 25 | 25 | 50 | 25 | 12.5 | 50 | 12.5 | 50 |
| PRT1157 | 25 | 50 | 25 | 12.5 | 25 | 50 | 25 | 12.5 | 25 | 50 |
| PRT1158 | 12.5 | 25 | 50 | 12.5 | 50 | 12.5 | 50 | 12.5 | 50 | 25 |
| PRT1159 | 50 | 12.5 | 50 | 12.5 | 25 | 50 | 25 | 12.5 | 25 | 12.5 |
| PRT1160 | 25 | 12.5 | 25 | 12.5 | 12.5 | 25 | 12.5 | 25 | 12.5 | 25 |
| PRT1161 | 12.5 | 12.5 | 12.5 | 25 | 25 | 50 | 25 | 12.5 | 25 | 50 |
| PRT1162 | 50 | 12.5 | 50 | 12.5 | 50 | 25 | 12.5 | 25 | 50 | 25 |
| PRT1163 | 25 | 12.5 | 25 | 12.5 | 12.5 | 12.5 | 12.5 | 12.5 | 12.5 | 25 |
| PRT1164 | 12.5 | 12.5 | 12.5 | 12.5 | 25 | 12.5 | 25 | 50 | 25 | 12.5 |
| PRT1165 | 25 | 12.5 | 25 | 50 | 25 | 12.5 | 25 | 50 | 25 | 12.5 |
| PRT1166 | 12.5 | 25 | 50 | 25 | 25 | 12.5 | 50 | 12.5 | 50 | 12.5 |
| PRT1167 | 25 | 12.5 | 25 | 50 | 25 | 12.5 | 25 | 50 | 25 | 12.5 |
| PRT1168 | 12.5 | 25 | 50 | 12.5 | 50 | 12.5 | 50 | 12.5 | 50 | 12.5 |
| PRT1169 | 25 | 50 | 25 | 12.5 | 12.5 | 50 | 12.5 | 12.5 | 12.5 | 12.5 |
| PRT1170 | 12.5 | 25 | 12.5 | 100 | 50 | 12.5 | 50 | 12.5 | 12.5 | 25 |
| PRT1171 | 12.5 | 25 | 12.5 | 12.5 | 12.5 | 12.5 | 50 | 12.5 | 50 | 25 |
| PRT1172 | 25 | 50 | 25 | 12.5 | 12.5 | 12.5 | 12.5 | 12.5 | 12.5 | 12.5 |
| PRT1173 | 25 | 12.5 | 25 | 12.5 | 12.5 | 50 | 12.5 | 50 | 12.5 | 50 |
| PRT1174 | 50 | 12.5 | 50 | 12.5 | 50 | 12.5 | 50 | 12.5 | 25 | 50 |
| PRT1175 | 25 | 50 | 25 | 12.5 | 50 | 25 | 12.5 | 25 | 50 | 25 |
| PRT1176 | 50 | 12.5 | 50 | 12.5 | 25 | 50 | 12.5 | 50 | 25 | 12.5 |
| PRT1177 | 12.5 | 50 | 12.5 | 50 | 12.5 | 50 | 12.5 | 50 | 12.5 | 25 |
| PRT1178 | 12.5 | 25 | 50 | 12.5 | 25 | 12.5 | 25 | 12.5 | 25 | 12.5 |
| PRT1179 | 50 | 25 | 12.5 | 50 | 25 | 12.5 | 25 | 50 | 25 | 12.5 |
| PRT1180 | 12.5 | 50 | 25 | 12.5 | 50 | 25 | 12.5 | 25 | 50 | 25 |
| PRT1181 | 50 | 12.5 | 50 | 25 | 25 | 12.5 | 50 | 100 | 50 | 25 |
| PRT1182 | 25 | 50 | 25 | 25 | 12.5 | 50 | 12.5 | 50 | 12.5 | 25 |
| PRT1183 | 50 | 25 | 12.5 | 50 | 25 | 12.5 | 25 | 50 | 25 | 12.5 |
| PRT1184 | 25 | 12.5 | 25 | 50 | 12.5 | 25 | 50 | 25 | 12.5 | 25 |
| PRT1185 | 12.5 | 25 | 50 | 12.5 | 50 | 12.5 | 50 | 12.5 | 50 | 12.5 |
| PRT1186 | 25 | 12.5 | 25 | 50 | 25 | 12.5 | 50 | 12.5 | 50 | 12.5 |
| PRT1187 | 25 | 12.5 | 25 | 25 | 12.5 | 12.5 | 12.5 | 25 | 12.5 | 12.5 |
| PRT1188 | 12.5 | 25 | 12.5 | 12.5 | 50 | 12.5 | 25 | 50 | 12.5 | 25 |
| PRT1189 | 12.5 | 25 | 50 | 12.5 | 25 | 50 | 12.5 | 25 | 50 | 12.5 |
| PRT1190 | 12.5 | 25 | 12.5 | 50 | 12.5 | 25 | 50 | 25 | 12.5 | 50 |
| PRT1191 | 25 | 50 | 25 | 25 | 25 | 12.5 | 50 | 25 | 12.5 | 50 |
| PRT1192 | 12.5 | 25 | 50 | 25 | 12.5 | 50 | 25 | 12.5 | 50 | 25 |
| PRT1193 | 12.5 | 12.5 | 25 | 12.5 | 12.5 | 25 | 12.5 | 50 | 25 | 12.5 |
| PRT1194 | 12.5 | 50 | 12.5 | 25 | 50 | 25 | 100 | 25 | 50 | 12.5 |
| PRT1195 | 50 | 25 | 12.5 | 50 | 12.5 | 50 | 25 | 12.5 | 25 | 50 |
| PRT1196 | 50 | 12.5 | 25 | 25 | 25 | 50 | 25 | 12.5 | 25 | 50 |
| PRT1197 | 12.5 | 25 | 50 | 12.5 | 50 | 25 | 12.5 | 25 | 50 | 25 |
| PRT1198 | 12.5 | 25 | 50 | 12.5 | 50 | 25 | 12.5 | 50 | 25 | 12.5 |
| PRT1199 | 12.5 | 50 | 12.5 | 50 | 25 | 25 | 12.5 | 25 | 50 | 25 |
| PRT1200 | 12.5 | 12.5 | 12.5 | 25 | 25 | 12.5 | 50 | 25 | 12.5 | 50 |
| PRT1201 | 50 | 12.5 | 25 | 50 | 25 | 12.5 | 50 | 25 | 12.5 | 25 |
| PRT1202 | 12.5 | 25 | 50 | 12.5 | 50 | 12.5 | 50 | 12.5 | 25 | 50 |
| PRT1203 | 12.5 | 50 | 25 | 12.5 | 50 | 12.5 | 50 | 12.5 | 25 | 50 |
| PRT1204 | 25 | 50 | 25 | 12.5 | 50 | 25 | 25 | 12.5 | 50 | 25 |
| PRT1205 | 12.5 | 50 | 25 | 12.5 | 50 | 12.5 | 25 | 50 | 12.5 | 25 |
| PRT1206 | 12.5 | 25 | 50 | 12.5 | 50 | 25 | 12.5 | 50 | 25 | 25 |
| PRT1207 | 25 | 12.5 | 12.5 | 25 | 25 | 12.5 | 25 | 25 | 12.5 | 12.5 |
| PRT1208 | 25 | 12.5 | 25 | 12.5 | 50 | 25 | 12.5 | 50 | 25 | 12.5 |
| PRT1209 | 12.5 | 25 | 50 | 25 | 12.5 | 25 | 12.5 | 12.5 | 25 | 12.5 |
| PRT1210 | 12.5 | 25 | 12.5 | 25 | 25 | 12.5 | 25 | 12.5 | 25 | 12.5 |
| PRT1211 | 25 | 12.5 | 25 | 50 | 25 | 12.5 | 25 | 50 | 25 | 12.5 |
| PRT1212 | 25 | 12.5 | 50 | 25 | 25 | 12.5 | 25 | 50 | 25 | 12.5 |
| PRT1213 | 25 | 50 | 25 | 100 | 50 | 25 | 12.5 | 25 | 50 | 25 |
| PRT1214 | 12.5 | 50 | 25 | 12.5 | 50 | 12.5 | 25 | 50 | 12.5 | 25 |
| PRT1215 | 50 | 12.5 | 25 | 50 | 12.5 | 25 | 50 | 25 | 12.5 | 25 |
| PRT1216 | 12.5 | 50 | 12.5 | 25 | 25 | 50 | 12.5 | 50 | 25 | 12.5 |
| PRT1217 | 12.5 | 50 | 12.5 | 25 | 50 | 25 | 12.5 | 50 | 25 | 12.5 |
| PRT1218 | 25 | 25 | 12.5 | 12.5 | 12.5 | 25 | 12.5 | 12.5 | 12.5 | 25 |
| PRT1219 | 50 | 25 | 12.5 | 50 | 12.5 | 25 | 25 | 50 | 25 | 25 |
| PRT1220 | 25 | 50 | 12.5 | 25 | 25 | 50 | 25 | 12.5 | 50 | 25 |
| PRT1221 | 12.5 | 25 | 25 | 50 | 25 | 12.5 | 50 | 25 | 12.5 | 50 |
| PRT1222 | 25 | 50 | 12.5 | 25 | 50 | 12.5 | 25 | 50 | 25 | 12.5 |
| PRT1223 | 25 | 12.5 | 50 | 25 | 100 | 25 | 50 | 12.5 | 50 | 12.5 |
| PRT1224 | 50 | 25 | 12.5 | 25 | 50 | 12.5 | 25 | 50 | 12.5 | 50 |
| PRT1225 | 12.5 | 25 | 50 | 25 | 25 | 12.5 | 50 | 12.5 | 50 | 12.5 |

TABLE 3-continued

MIC (µg/mL) of the human-originated EGF domain proteins against various Gram-negative bacteria

| Protein | E. coli BL21 | P. aeruginosa | K. pneumonia | E. cloacae | A. hydrophila | C. diversus | M. catarrhalis | P. mirabilis | P. vulgaris | S. marcescens |
|---|---|---|---|---|---|---|---|---|---|---|
| PRT1226 | 50 | 25 | 12.5 | 25 | 25 | 50 | 12.5 | 50 | 12.5 | 25 |
| PRT1227 | 25 | 12.5 | 25 | 12.5 | 12.5 | 12.5 | 12.5 | 12.5 | 25 | 12.5 |
| PRT1228 | 25 | 50 | 25 | 12.5 | 25 | 50 | 25 | 12.5 | 25 | 50 |
| PRT1229 | 12.5 | 12.5 | 12.5 | 25 | 12.5 | 12.5 | 12.5 | 12.5 | 12.5 | 12.5 |
| PRT1230 | 25 | 12.5 | 12.5 | 25 | 12.5 | 12.5 | 12.5 | 50 | 12.5 | 50 |
| PRT1231 | 25 | 50 | 12.5 | 50 | 100 | 50 | 12.5 | 50 | 12.5 | 25 |
| PRT1232 | 25 | 25 | 12.5 | 25 | 50 | 25 | 12.5 | 25 | 50 | 25 |
| PRT1233 | 12.5 | 25 | 50 | 12.5 | 50 | 12.5 | 50 | 25 | 12.5 | 25 |
| PRT1234 | 50 | 12.5 | 25 | 50 | 25 | 25 | 25 | 25 | 12.5 | 25 |
| PRT1235 | 12.5 | 25 | 12.5 | 25 | 12.5 | 12.5 | 12.5 | 12.5 | 50 | 12.5 |
| PRT1236 | 25 | 12.5 | 50 | 12.5 | 50 | 12.5 | 12.5 | 25 | 12.5 | 25 |
| PRT1237 | 12.5 | 25 | 12.5 | 12.5 | 12.5 | 25 | 50 | 25 | 12.5 | 50 |
| PRT1238 | 12.5 | 50 | 12.5 | 50 | 12.5 | 50 | 25 | 12.5 | 25 | 50 |
| PRT1239 | 12.5 | 50 | 12.5 | 50 | 12.5 | 50 | 12.5 | 25 | 50 | 25 |
| PRT1240 | 50 | 12.5 | 12.5 | 25 | 12.5 | 25 | 50 | 25 | 12.5 | 25 |
| PRT1241 | 25 | 12.5 | 50 | 12.5 | 50 | 12.5 | 25 | 50 | 25 | 12.5 |
| PRT1242 | 50 | 25 | 12.5 | 25 | 25 | 50 | 25 | 12.5 | 25 | 50 |
| PRT1243 | 50 | 12.5 | 50 | 12.5 | 50 | 12.5 | 25 | 50 | 25 | 12.5 |
| PRT1244 | 12.5 | 50 | 12.5 | 12.5 | 50 | 25 | 12.5 | 25 | 50 | 12.5 |
| PRT1245 | 12.5 | 50 | 12.5 | 50 | 25 | 12.5 | 25 | 50 | 25 | 12.5 |
| PRT1246 | 25 | 12.5 | 25 | 50 | 25 | 12.5 | 25 | 50 | 25 | 12.5 |
| PRT1247 | 12.5 | 12.5 | 25 | 12.5 | 12.5 | 25 | 12.5 | 25 | 12.5 | 25 |
| PRT1248 | 25 | 25 | 25 | 12.5 | 12.5 | 25 | 12.5 | 25 | 12.5 | 25 |
| PRT1249 | 12.5 | 50 | 12.5 | 50 | 12.5 | 50 | 12.5 | 25 | 50 | 25 |
| PRT1250 | 50 | 12.5 | 25 | 50 | 12.5 | 50 | 12.5 | 25 | 50 | 25 |
| PRT1251 | 25 | 50 | 25 | 12.5 | 25 | 50 | 25 | 12.5 | 25 | 50 |
| PRT1252 | 50 | 25 | 12.5 | 25 | 50 | 12.5 | 25 | 50 | 25 | 12.5 |
| PRT1253 | 12.5 | 50 | 25 | 12.5 | 50 | 25 | 12.5 | 25 | 50 | 25 |
| PRT1254 | 25 | 50 | 25 | 12.5 | 50 | 12.5 | 50 | 12.5 | 25 | 50 |
| PRT1255 | 50 | 25 | 12.5 | 25 | 50 | 12.5 | 25 | 50 | 25 | 12.5 |
| PRT1256 | 12.5 | 25 | 12.5 | 25 | 50 | 12.5 | 50 | 12.5 | 50 | 25 |
| PRT1257 | 50 | 25 | 12.5 | 25 | 25 | 50 | 12.5 | 50 | 12.5 | 50 |
| PRT1258 | 25 | 50 | 25 | 12.5 | 25 | 50 | 12.5 | 50 | 25 | 12.5 |
| PRT1259 | 50 | 25 | 12.5 | 25 | 50 | 12.5 | 50 | 12.5 | 50 | 12.5 |
| PRT1260 | 50 | 25 | 12.5 | 25 | 50 | 12.5 | 50 | 12.5 | 50 | 25 |
| PRT1261 | 25 | 50 | 25 | 12.5 | 50 | 12.5 | 50 | 12.5 | 12.5 | 25 |
| PRT1262 | 25 | 12.5 | 25 | 12.5 | 50 | 12.5 | 50 | 12.5 | 50 | 25 |
| PRT1263 | 50 | 12.5 | 25 | 50 | 12.5 | 50 | 12.5 | 50 | 12.5 | 50 |
| PRT1264 | 50 | 12.5 | 25 | 12.5 | 25 | 12.5 | 50 | 12.5 | 50 | 12.5 |
| PRT1265 | 50 | 25 | 12.5 | 25 | 50 | 25 | 12.5 | 12.5 | 50 | 12.5 |
| PRT1266 | 12.5 | 25 | 50 | 25 | 25 | 12.5 | 25 | 50 | 12.5 | 50 |
| PRT1267 | 25 | 50 | 25 | 12.5 | 50 | 12.5 | 25 | 50 | 25 | 12.5 |
| PRT1268 | 12.5 | 50 | 12.5 | 25 | 50 | 12.5 | 50 | 12.5 | 25 | 50 |
| PRT1269 | 50 | 25 | 12.5 | 25 | 50 | 12.5 | 50 | 12.5 | 50 | 12.5 |
| PRT1270 | 12.5 | 50 | 12.5 | 50 | 25 | 12.5 | 25 | 50 | 25 | 12.5 |
| PRT1271 | 50 | 12.5 | 50 | 12.5 | 50 | 12.5 | 50 | 12.5 | 50 | 12.5 |
| PRT1272 | 50 | 100 | 50 | 25 | 12.5 | 50 | 12.5 | 50 | 12.5 | 50 |
| PRT1273 | 50 | 12.5 | 50 | 12.5 | 50 | 25 | 12.5 | 50 | 12.5 | 50 |
| PRT1274 | 50 | 12.5 | 50 | 12.5 | 50 | 25 | 12.5 | 25 | 50 | 25 |
| PRT1275 | 50 | 12.5 | 50 | 12.5 | 50 | 50 | 12.5 | 50 | 25 | 12.5 |
| PRT1276 | 12.5 | 50 | 12.5 | 50 | 12.5 | 50 | 12.5 | 50 | 12.5 | 50 |
| PRT1277 | 50 | 12.5 | 50 | 12.5 | 50 | 12.5 | 25 | 12.5 | 25 | 12.5 |
| PRT1278 | 12.5 | 12.5 | 12.5 | 12.5 | 12.5 | 12.5 | 12.5 | 12.5 | 12.5 | 12.5 |
| PRT1279 | 25 | 12.5 | 50 | 12.5 | 25 | 50 | 25 | 12.5 | 50 | 12.5 |
| PRT1280 | 50 | 25 | 12.5 | 50 | 12.5 | 50 | 12.5 | 50 | 12.5 | 25 |
| PRT1281 | 12.5 | 25 | 50 | 25 | 12.5 | 50 | 12.5 | 50 | 12.5 | 50 |
| PRT1282 | 50 | 12.5 | 50 | 25 | 12.5 | 50 | 25 | 12.5 | 25 | 50 |
| PRT1283 | 50 | 12.5 | 50 | 12.5 | 12.5 | 50 | 12.5 | 25 | 12.5 | 25 |
| PRT1284 | 50 | 25 | 12.5 | 25 | 12.5 | 12.5 | 50 | 12.5 | 25 | 12.5 |
| PRT1285 | 12.5 | 12.5 | 100 | 12.5 | 25 | 12.5 | 25 | 50 | 12.5 | 50 |
| PRT1286 | 50 | 12.5 | 50 | 12.5 | 50 | 12.5 | 25 | 50 | 25 | 12.5 |
| PRT1287 | 25 | 12.5 | 50 | 12.5 | 50 | 12.5 | 50 | 12.5 | 50 | 50 |
| PRT1288 | 25 | 12.5 | 25 | 50 | 12.5 | 12.5 | 50 | 12.5 | 25 | 12.5 |
| PRT1289 | 12.5 | 12.5 | 12.5 | 25 | 12.5 | 12.5 | 50 | 12.5 | 50 | 25 |
| PRT1290 | 12.5 | 50 | 12.5 | 50 | 25 | 12.5 | 25 | 50 | 12.5 | 12.5 |
| PRT1291 | 100 | 25 | 50 | 25 | 12.5 | 50 | 12.5 | 50 | 12.5 | 12.5 |
| PRT1292 | 12.5 | 12.5 | 12.5 | 50 | 25 | 12.5 | 50 | 12.5 | 50 | 12.5 |
| PRT1293 | 12.5 | 25 | 50 | 12.5 | 50 | 12.5 | 12.5 | 50 | 12.5 | 12.5 |
| PRT1294 | 12.5 | 50 | 12.5 | 50 | 12.5 | 50 | 12.5 | 50 | 12.5 | 50 |
| PRT1295 | 50 | 12.5 | 50 | 12.5 | 50 | 12.5 | 50 | 12.5 | 50 | 12.5 |

TABLE 3-continued

MIC (μg/mL) of the human-originated EGF domain proteins against various Gram-negative bacteria

| Protein | E. coli BL21 | P. aeruginosa | K. pneumonia | E. cloacae | A. hydrophila | C. diversus | M. catarrhalis | P. mirabilis | P. vulgaris | S. marcescens |
|---|---|---|---|---|---|---|---|---|---|---|
| PRT1296 | 12.5 | 25 | 50 | 25 | 100 | 50 | 12.5 | 25 | 50 | 25 |
| PRT1297 | 50 | 12.5 | 25 | 50 | 12.5 | 25 | 50 | 25 | 12.5 | 50 |
| PRT1298 | 50 | 12.5 | 50 | 25 | 12.5 | 50 | 12.5 | 50 | 12.5 | 25 |
| PRT1299 | 50 | 25 | 12.5 | 12.5 | 12.5 | 25 | 12.5 | 25 | 50 | 25 |
| PRT1300 | 50 | 25 | 12.5 | 25 | 50 | 12.5 | 12.5 | 12.5 | 12.5 | 12.5 |
| PRT1301 | 12.5 | 12.5 | 12.5 | 50 | 25 | 12.5 | 50 | 12.5 | 25 | 50 |
| PRT1302 | 50 | 12.5 | 50 | 25 | 12.5 | 50 | 12.5 | 25 | 50 | 25 |
| PRT1303 | 50 | 12.5 | 50 | 12.5 | 50 | 12.5 | 12.5 | 25 | 12.5 | 25 |
| PRT1304 | 12.5 | 25 | 12.5 | 12.5 | 25 | 12.5 | 25 | 12.5 | 25 | 12.5 |
| PRT1305 | 50 | 12.5 | 50 | 12.5 | 50 | 12.5 | 50 | 25 | 25 | 12.5 |
| PRT1306 | 50 | 12.5 | 50 | 12.5 | 25 | 50 | 25 | 12.5 | 25 | 50 |
| PRT1307 | 50 | 12.5 | 50 | 100 | 50 | 12.5 | 50 | 25 | 12.5 | 25 |
| PRT1308 | 12.5 | 50 | 12.5 | 50 | 12.5 | 25 | 50 | 25 | 12.5 | 50 |
| PRT1309 | 50 | 12.5 | 50 | 12.5 | 50 | 25 | 12.5 | 25 | 50 | 25 |
| PRT1310 | 50 | 12.5 | 25 | 50 | 12.5 | 25 | 50 | 25 | 12.5 | 25 |
| PRT1311 | 25 | 12.5 | 25 | 50 | 12.5 | 50 | 25 | 12.5 | 25 | 25 |
| PRT1312 | 12.5 | 50 | 12.5 | 50 | 12.5 | 50 | 12.5 | 50 | 12.5 | 50 |
| PRT1313 | 25 | 50 | 25 | 12.5 | 25 | 50 | 12.5 | 50 | 12.5 | 50 |
| PRT1314 | 50 | 12.5 | 50 | 12.5 | 50 | 12.5 | 12.5 | 12.5 | 12.5 | 12.5 |
| PRT1315 | 12.5 | 12.5 | 100 | 25 | 12.5 | 12.5 | 50 | 12.5 | 50 | 12.5 |
| PRT1316 | 12.5 | 50 | 25 | 12.5 | 50 | 12.5 | 50 | 12.5 | 50 | 12.5 |
| PRT1317 | 12.5 | 50 | 25 | 12.5 | 25 | 50 | 25 | 12.5 | 50 | 12.5 |
| PRT1318 | 12.5 | 25 | 50 | 25 | 12.5 | 50 | 12.5 | 25 | 50 | 25 |
| PRT1319 | 50 | 12.5 | 25 | 25 | 25 | 12.5 | 25 | 25 | 12.5 | 12.5 |
| PRT1320 | 12.5 | 25 | 12.5 | 25 | 12.5 | 12.5 | 12.5 | 12.5 | 50 | 12.5 |
| PRT1321 | 12.5 | 50 | 25 | 12.5 | 50 | 12.5 | 50 | 12.5 | 100 | 12.5 |
| PRT1322 | 25 | 12.5 | 25 | 50 | 12.5 | 50 | 12.5 | 12.5 | 25 | 12.5 |
| PRT1323 | 25 | 12.5 | 25 | 12.5 | 12.5 | 50 | 12.5 | 25 | 50 | 12.5 |
| PRT1324 | 25 | 50 | 25 | 12.5 | 50 | 25 | 12.5 | 25 | 12.5 | 25 |
| PRT1325 | 12.5 | 25 | 12.5 | 25 | 25 | 12.5 | 12.5 | 25 | 12.5 | 25 |
| PRT1326 | 12.5 | 50 | 12.5 | 50 | 12.5 | 50 | 25 | 12.5 | 25 | 50 |
| PRT1327 | 12.5 | 50 | 12.5 | 50 | 12.5 | 12.5 | 12.5 | 12.5 | 12.5 | 25 |
| PRT1328 | 12.5 | 50 | 12.5 | 50 | 25 | 12.5 | 25 | 50 | 12.5 | 50 |
| PRT1329 | 50 | 12.5 | 50 | 12.5 | 50 | 25 | 12.5 | 25 | 25 | 25 |
| PRT1330 | 12.5 | 12.5 | 12.5 | 50 | 12.5 | 50 | 25 | 12.5 | 25 | 50 |
| PRT1331 | 50 | 25 | 12.5 | 50 | 12.5 | 25 | 50 | 25 | 12.5 | 25 |
| PRT1332 | 12.5 | 50 | 25 | 12.5 | 50 | 25 | 12.5 | 25 | 12.5 | 25 |
| PRT1333 | 12.5 | 25 | 25 | 12.5 | 25 | 12.5 | 25 | 12.5 | 25 | 12.5 |
| PRT1334 | 12.5 | 50 | 12.5 | 50 | 12.5 | 50 | 25 | 100 | 25 | 25 |
| PRT1335 | 12.5 | 50 | 12.5 | 50 | 12.5 | 25 | 50 | 25 | 12.5 | 50 |
| PRT1336 | 50 | 12.5 | 50 | 25 | 12.5 | 50 | 12.5 | 50 | 12.5 | 50 |
| PRT1337 | 50 | 12.5 | 25 | 50 | 25 | 25 | 12.5 | 25 | 50 | 12.5 |
| PRT1338 | 25 | 12.5 | 25 | 50 | 12.5 | 12.5 | 12.5 | 12.5 | 12.5 | 25 |
| PRT1339 | 12.5 | 12.5 | 25 | 12.5 | 50 | 25 | 12.5 | 25 | 50 | 25 |
| PRT1340 | 50 | 25 | 12.5 | 25 | 25 | 50 | 25 | 12.5 | 25 | 50 |
| PRT1341 | 50 | 12.5 | 50 | 12.5 | 12.5 | 25 | 12.5 | 25 | 12.5 | 50 |
| PRT1342 | 12.5 | 25 | 50 | 12.5 | 50 | 12.5 | 50 | 12.5 | 25 | 50 |
| PRT1343 | 25 | 50 | 25 | 25 | 12.5 | 50 | 25 | 12.5 | 25 | 50 |
| PRT1344 | 50 | 25 | 12.5 | 25 | 50 | 12.5 | 50 | 12.5 | 50 | 25 |
| PRT1345 | 25 | 50 | 25 | 12.5 | 25 | 50 | 25 | 12.5 | 25 | 50 |
| PRT1346 | 25 | 50 | 25 | 12.5 | 50 | 25 | 12.5 | 25 | 50 | 25 |
| PRT1347 | 12.5 | 25 | 50 | 25 | 25 | 12.5 | 25 | 50 | 100 | 12.5 |
| PRT1348 | 12.5 | 25 | 12.5 | 25 | 50 | 25 | 12.5 | 25 | 50 | 12.5 |
| PRT1349 | 25 | 12.5 | 25 | 50 | 12.5 | 50 | 12.5 | 50 | 12.5 | 25 |
| PRT1350 | 12.5 | 50 | 12.5 | 50 | 25 | 12.5 | 25 | 50 | 25 | 12.5 |
| PRT1351 | 25 | 50 | 25 | 12.5 | 12.5 | 12.5 | 25 | 12.5 | 25 | 12.5 |
| PRT1352 | 12.5 | 12.5 | 12.5 | 12.5 | 12.5 | 50 | 12.5 | 25 | 50 | 25 |
| PRT1353 | 25 | 50 | 25 | 12.5 | 25 | 50 | 25 | 12.5 | 25 | 50 |
| PRT1354 | 12.5 | 25 | 50 | 25 | 12.5 | 25 | 50 | 25 | 12.5 | 25 |
| PRT1355 | 25 | 12.5 | 25 | 50 | 12.5 | 50 | 12.5 | 25 | 50 | 25 |
| PRT1356 | 50 | 12.5 | 50 | 25 | 25 | 12.5 | 25 | 50 | 25 | 12.5 |
| PRT1357 | 12.5 | 25 | 50 | 25 | 100 | 50 | 12.5 | 12.5 | 50 | 12.5 |
| PRT1358 | 12.5 | 50 | 12.5 | 12.5 | 25 | 12.5 | 25 | 12.5 | 25 | 12.5 |
| PRT1359 | 12.5 | 25 | 25 | 25 | 12.5 | 25 | 12.5 | 25 | 12.5 | 25 |
| PRT1360 | 25 | 50 | 25 | 12.5 | 50 | 12.5 | 50 | 12.5 | 25 | 50 |
| PRT1361 | 12.5 | 25 | 50 | 12.5 | 25 | 50 | 25 | 12.5 | 25 | 50 |
| PRT1362 | 25 | 50 | 25 | 12.5 | 50 | 12.5 | 50 | 12.5 | 12.5 | 12.5 |
| PRT1363 | 12.5 | 12.5 | 12.5 | 50 | 12.5 | 25 | 50 | 25 | 12.5 | 50 |
| PRT1364 | 12.5 | 25 | 50 | 25 | 25 | 12.5 | 12.5 | 12.5 | 12.5 | 12.5 |
| PRT1365 | 100 | 25 | 50 | 25 | 12.5 | 50 | 25 | 12.5 | 25 | 12.5 |

TABLE 3-continued

MIC (μg/mL) of the human-originated EGF domain proteins against various Gram-negative bacteria

| | MIC (μg/mL) | | | | | | | | | |
|---|---|---|---|---|---|---|---|---|---|---|
| Protein | E. coli BL21 | P. aeruginosa | K. pneumonia | E. cloacae | A. hydrophila | C. diversus | M. catarrhalis | P. mirabilis | P. vulgaris | S. marcescens |
| PRT1366 | 12.5 | 12.5 | 25 | 12.5 | 12.5 | 12.5 | 12.5 | 12.5 | 12.5 | 12.5 |
| PRT1367 | 50 | 25 | 12.5 | 25 | 50 | 12.5 | 50 | 12.5 | 50 | 25 |
| PRT1368 | 25 | 12.5 | 25 | 12.5 | 25 | 12.5 | 12.5 | 12.5 | 12.5 | 12.5 |
| PRT1369 | 12.5 | 12.5 | 12.5 | 25 | 12.5 | 12.5 | 12.5 | 25 | 12.5 | 25 |
| PRT1370 | 12.5 | 25 | 50 | 25 | 25 | 12.5 | 25 | 50 | 25 | 12.5 |
| PRT1371 | 12.5 | 12.5 | 12.5 | 12.5 | 12.5 | 100 | 12.5 | 12.5 | 12.5 | 12.5 |
| PRT1372 | 25 | 12.5 | 25 | 12.5 | 25 | 12.5 | 25 | 12.5 | 25 | 12.5 |
| PRT1373 | 12.5 | 12.5 | 12.5 | 12.5 | 12.5 | 50 | 12.5 | 25 | 50 | 12.5 |
| PRT1374 | 12.5 | 25 | 12.5 | 25 | 12.5 | 12.5 | 12.5 | 12.5 | 12.5 | 12.5 |
| PRT1375 | 12.5 | 12.5 | 12.5 | 12.5 | 25 | 12.5 | 25 | 50 | 25 | 12.5 |
| PRT1376 | 12.5 | 50 | 12.5 | 50 | 12.5 | 50 | 12.5 | 50 | 12.5 | 25 |
| PRT1377 | 50 | 12.5 | 50 | 12.5 | 50 | 12.5 | 50 | 12.5 | 50 | 12.5 |
| PRT1378 | 25 | 12.5 | 25 | 12.5 | 12.5 | 25 | 12.5 | 25 | 12.5 | 25 |
| PRT1379 | 12.5 | 50 | 12.5 | 50 | 25 | 12.5 | 25 | 50 | 25 | 12.5 |
| PRT1380 | 50 | 12.5 | 50 | 12.5 | 50 | 12.5 | 50 | 50 | 50 | 50 |
| PRT1381 | 25 | 50 | 25 | 12.5 | 50 | 25 | 12.5 | 25 | 50 | 25 |
| PRT1382 | 12.5 | 50 | 100 | 50 | 12.5 | 50 | 12.5 | 12.5 | 25 | 12.5 |
| PRT1383 | 12.5 | 12.5 | 25 | 12.5 | 50 | 25 | 12.5 | 50 | 12.5 | 50 |
| PRT1384 | 12.5 | 25 | 50 | 25 | 25 | 25 | 12.5 | 25 | 50 | 25 |
| PRT1385 | 50 | 12.5 | 50 | 12.5 | 50 | 12.5 | 50 | 12.5 | 25 | 50 |
| PRT1386 | 12.5 | 25 | 12.5 | 25 | 12.5 | 12.5 | 12.5 | 12.5 | 25 | 12.5 |
| PRT1387 | 12.5 | 50 | 25 | 12.5 | 50 | 25 | 12.5 | 25 | 12.5 | 25 |
| PRT1388 | 12.5 | 12.5 | 12.5 | 12.5 | 25 | 12.5 | 25 | 12.5 | 12.5 | 12.5 |
| PRT1389 | 12.5 | 25 | 12.5 | 25 | 12.5 | 12.5 | 12.5 | 12.5 | 25 | 12.5 |
| PRT1390 | 12.5 | 12.5 | 50 | 12.5 | 50 | 25 | 50 | 25 | 50 | 50 |
| PRT1391 | 12.5 | 12.5 | 12.5 | 12.5 | 12.5 | 12.5 | 12.5 | 12.5 | 12.5 | 12.5 |
| PRT1392 | 25 | 12.5 | 25 | 12.5 | 25 | 12.5 | 25 | 12.5 | 25 | 50 |
| PRT1393 | 12.5 | 25 | 50 | 25 | 12.5 | 25 | 50 | 12.5 | 50 | 12.5 |
| PRT1394 | 12.5 | 12.5 | 50 | 12.5 | 25 | 50 | 25 | 12.5 | 25 | 50 |
| PRT1395 | 25 | 12.5 | 25 | 12.5 | 100 | 12.5 | 12.5 | 12.5 | 12.5 | 25 |
| PRT1396 | 12.5 | 12.5 | 12.5 | 25 | 25 | 12.5 | 25 | 12.5 | 25 | 12.5 |
| PRT1397 | 25 | 12.5 | 50 | 12.5 | 50 | 25 | 12.5 | 25 | 50 | 25 |
| PRT1398 | 25 | 12.5 | 25 | 50 | 25 | 12.5 | 25 | 12.5 | 25 | 12.5 |
| PRT1399 | 12.5 | 12.5 | 12.5 | 25 | 12.5 | 25 | 12.5 | 25 | 12.5 | 25 |
| PRT1400 | 12.5 | 50 | 12.5 | 25 | 50 | 12.5 | 50 | 12.5 | 12.5 | 25 |
| PRT1401 | 25 | 12.5 | 25 | 12.5 | 25 | 12.5 | 25 | 12.5 | 25 | 12.5 |
| PRT1402 | 12.5 | 25 | 12.5 | 50 | 25 | 12.5 | 25 | 50 | 25 | 12.5 |
| PRT1403 | 12.5 | 50 | 12.5 | 25 | 25 | 50 | 12.5 | 50 | 12.5 | 50 |
| PRT1404 | 25 | 50 | 25 | 12.5 | 25 | 50 | 25 | 12.5 | 25 | 50 |
| PRT1405 | 12.5 | 12.5 | 12.5 | 12.5 | 12.5 | 12.5 | 12.5 | 12.5 | 50 | 12.5 |
| PRT1406 | 50 | 25 | 12.5 | 25 | 50 | 12.5 | 50 | 12.5 | 50 | 50 |
| PRT1407 | 25 | 12.5 | 12.5 | 12.5 | 50 | 12.5 | 50 | 12.5 | 12.5 | 25 |
| PRT1408 | 12.5 | 25 | 12.5 | 25 | 12.5 | 12.5 | 12.5 | 12.5 | 12.5 | 25 |
| PRT1409 | 12.5 | 12.5 | 12.5 | 12.5 | 12.5 | 12.5 | 12.5 | 50 | 12.5 | 50 |
| PRT1410 | 12.5 | 25 | 50 | 25 | 12.5 | 50 | 100 | 50 | 12.5 | 12.5 |
| PRT1411 | 25 | 12.5 | 25 | 12.5 | 12.5 | 12.5 | 12.5 | 12.5 | 25 | 12.5 |
| PRT1412 | 50 | 25 | 12.5 | 25 | 50 | 25 | 12.5 | 25 | 50 | 25 |
| PRT1413 | 25 | 50 | 25 | 12.5 | 25 | 50 | 12.5 | 50 | 25 | 12.5 |
| PRT1414 | 12.5 | 50 | 12.5 | 50 | 12.5 | 12.5 | 50 | 12.5 | 12.5 | 25 |
| PRT1415 | 12.5 | 25 | 12.5 | 25 | 25 | 50 | 25 | 12.5 | 25 | 50 |
| PRT1416 | 12.5 | 25 | 50 | 25 | 25 | 12.5 | 25 | 12.5 | 25 | 12.5 |
| PRT1417 | 12.5 | 12.5 | 50 | 12.5 | 50 | 25 | 12.5 | 25 | 50 | 25 |
| PRT1418 | 12.5 | 25 | 50 | 25 | 25 | 12.5 | 50 | 12.5 | 50 | 25 |
| PRT1419 | 50 | 100 | 50 | 12.5 | 50 | 12.5 | 50 | 12.5 | 12.5 | 25 |
| PRT1420 | 12.5 | 12.5 | 12.5 | 12.5 | 25 | 12.5 | 25 | 12.5 | 25 | 50 |
| PRT1421 | 50 | 12.5 | 50 | 12.5 | 50 | 25 | 12.5 | 25 | 12.5 | 25 |
| PRT1422 | 12.5 | 12.5 | 50 | 12.5 | 50 | 12.5 | 50 | 12.5 | 50 | 12.5 |
| PRT1423 | 12.5 | 12.5 | 12.5 | 12.5 | 12.5 | 25 | 50 | 12.5 | 50 | 12.5 |
| PRT1424 | 12.5 | 50 | 12.5 | 50 | 12.5 | 25 | 50 | 25 | 12.5 | 25 |
| PRT1425 | 50 | 12.5 | 50 | 25 | 12.5 | 50 | 12.5 | 12.5 | 12.5 | 12.5 |
| PRT1426 | 25 | 12.5 | 25 | 12.5 | 12.5 | 25 | 12.5 | 25 | 12.5 | 25 |
| PRT1427 | 12.5 | 12.5 | 12.5 | 25 | 25 | 25 | 12.5 | 25 | 12.5 | 25 |
| PRT1428 | 12.5 | 12.5 | 12.5 | 12.5 | 12.5 | 12.5 | 12.5 | 50 | 12.5 | 25 |
| PRT1429 | 50 | 25 | 12.5 | 25 | 25 | 50 | 25 | 12.5 | 25 | 12.5 |
| PRT1430 | 12.5 | 25 | 12.5 | 25 | 12.5 | 25 | 12.5 | 25 | 12.5 | 25 |
| PRT1431 | 25 | 12.5 | 25 | 50 | 12.5 | 50 | 12.5 | 50 | 12.5 | 50 |
| PRT1432 | 12.5 | 50 | 12.5 | 50 | 25 | 12.5 | 25 | 50 | 25 | 12.5 |
| PRT1433 | 12.5 | 12.5 | 12.5 | 12.5 | 25 | 12.5 | 25 | 12.5 | 12.5 | 12.5 |
| PRT1434 | 12.5 | 25 | 100 | 25 | 12.5 | 25 | 12.5 | 25 | 12.5 | 12.5 |
| PRT1435 | 25 | 12.5 | 25 | 50 | 25 | 12.5 | 50 | 25 | 12.5 | 12.5 |
| PRT1436 | 12.5 | 12.5 | 50 | 12.5 | 50 | 25 | 25 | 12.5 | 25 | 12.5 |
| PRT1437 | 25 | 12.5 | 12.5 | 12.5 | 12.5 | 12.5 | 12.5 | 25 | 12.5 | 50 |
| PRT1438 | 25 | 50 | 25 | 12.5 | 25 | 50 | 12.5 | 50 | 25 | 12.5 |

TABLE 3-continued

MIC (μg/mL) of the human-originated EGF domain proteins against various Gram-negative bacteria

| Protein | E. coli BL21 | P. aeruginosa | K. pneumonia | E. cloacae | A. hydrophila | C. diversus | M. catarrhalis | P. mirabilis | P. vulgaris | S. marcescens |
|---|---|---|---|---|---|---|---|---|---|---|
| PRT1439 | 12.5 | 50 | 12.5 | 50 | 12.5 | 50 | 12.5 | 50 | 12.5 | 50 |
| PRT1440 | 25 | 12.5 | 25 | 12.5 | 25 | 25 | 12.5 | 25 | 12.5 | 25 |
| PRT1441 | 25 | 12.5 | 25 | 12.5 | 25 | 100 | 12.5 | 12.5 | 25 | 12.5 |
| PRT1442 | 12.5 | 12.5 | 50 | 12.5 | 25 | 25 | 50 | 25 | 12.5 | 25 |
| PRT1443 | 50 | 25 | 12.5 | 25 | 50 | 25 | 25 | 12.5 | 25 | 50 |
| PRT1444 | 25 | 50 | 25 | 12.5 | 25 | 50 | 12.5 | 25 | 50 | 25 |
| PRT1445 | 12.5 | 50 | 50 | 50 | 50 | 25 | 25 | 50 | 25 | 50 |
| PRT1446 | 12.5 | 25 | 25 | 12.5 | 25 | 12.5 | 12.5 | 12.5 | 25 | 12.5 |
| PRT1447 | 25 | 12.5 | 12.5 | 12.5 | 50 | 12.5 | 50 | 25 | 12.5 | 25 |
| PRT1448 | 50 | 12.5 | 25 | 50 | 12.5 | 25 | 50 | 25 | 12.5 | 25 |
| PRT1449 | 25 | 12.5 | 50 | 12.5 | 25 | 50 | 12.5 | 50 | 12.5 | 50 |
| PRT1450 | 25 | 50 | 12.5 | 25 | 50 | 25 | 12.5 | 25 | 12.5 | 25 |
| PRT1451 | 12.5 | 25 | 12.5 | 25 | 12.5 | 25 | 12.5 | 12.5 | 12.5 | 12.5 |
| PRT1452 | 25 | 50 | 25 | 12.5 | 25 | 50 | 12.5 | 50 | 12.5 | 50 |
| PRT1453 | 12.5 | 25 | 50 | 25 | 12.5 | 25 | 50 | 12.5 | 25 | 12.5 |
| PRT1454 | 12.5 | 12.5 | 25 | 50 | 25 | 12.5 | 50 | 12.5 | 25 | 50 |
| PRT1455 | 12.5 | 25 | 25 | 12.5 | 25 | 12.5 | 12.5 | 12.5 | 12.5 | 25 |
| PRT1456 | 25 | 12.5 | 50 | 25 | 12.5 | 25 | 50 | 12.5 | 12.5 | 12.5 |
| PRT1457 | 25 | 12.5 | 100 | 12.5 | 12.5 | 12.5 | 12.5 | 25 | 12.5 | 25 |
| PRT1458 | 12.5 | 25 | 12.5 | 25 | 50 | 25 | 25 | 12.5 | 25 | 50 |
| PRT1459 | 50 | 25 | 25 | 12.5 | 25 | 50 | 12.5 | 25 | 50 | 25 |
| PRT1460 | 25 | 25 | 50 | 25 | 12.5 | 25 | 50 | 12.5 | 25 | 50 |
| PRT1461 | 12.5 | 50 | 12.5 | 25 | 12.5 | 25 | 12.5 | 25 | 12.5 | 25 |
| PRT1462 | 25 | 100 | 12.5 | 12.5 | 12.5 | 25 | 12.5 | 25 | 12.5 | 25 |
| PRT1463 | 25 | 12.5 | 25 | 50 | 12.5 | 50 | 25 | 12.5 | 25 | 12.5 |
| PRT1464 | 25 | 12.5 | 12.5 | 12.5 | 12.5 | 12.5 | 12.5 | 12.5 | 25 | 50 |
| PRT1465 | 25 | 50 | 12.5 | 25 | 50 | 25 | 12.5 | 50 | 25 | 12.5 |
| PRT1466 | 25 | 12.5 | 50 | 12.5 | 50 | 12.5 | 50 | 25 | 12.5 | 25 |
| PRT1467 | 50 | 25 | 12.5 | 50 | 25 | 12.5 | 25 | 50 | 25 | 12.5 |
| PRT1468 | 12.5 | 25 | 12.5 | 12.5 | 12.5 | 12.5 | 12.5 | 12.5 | 50 | 25 |
| PRT1469 | 12.5 | 25 | 25 | 50 | 25 | 12.5 | 50 | 100 | 50 | 12.5 |
| PRT1470 | 25 | 12.5 | 50 | 12.5 | 12.5 | 50 | 25 | 12.5 | 25 | 50 |
| PRT1471 | 25 | 50 | 12.5 | 50 | 25 | 50 | 25 | 25 | 50 | 25 |
| PRT1472 | 50 | 25 | 25 | 12.5 | 25 | 12.5 | 25 | 12.5 | 25 | 50 |
| PRT1473 | 25 | 25 | 50 | 12.5 | 50 | 12.5 | 25 | 50 | 25 | 12.5 |
| PRT1474 | 12.5 | 25 | 25 | 50 | 25 | 12.5 | 25 | 50 | 12.5 | 25 |
| PRT1475 | 12.5 | 12.5 | 12.5 | 25 | 12.5 | 25 | 12.5 | 25 | 12.5 | 12.5 |
| PRT1476 | 25 | 12.5 | 50 | 12.5 | 50 | 12.5 | 25 | 50 | 12.5 | 25 |
| PRT1477 | 12.5 | 50 | 12.5 | 25 | 50 | 25 | 12.5 | 25 | 50 | 12.5 |
| PRT1478 | 12.5 | 50 | 25 | 12.5 | 50 | 12.5 | 25 | 50 | 25 | 12.5 |
| PRT1479 | 12.5 | 50 | 100 | 50 | 12.5 | 50 | 12.5 | 25 | 50 | 12.5 |
| PRT1480 | 12.5 | 25 | 12.5 | 25 | 12.5 | 25 | 12.5 | 50 | 12.5 | 50 |
| PRT1481 | 25 | 50 | 12.5 | 50 | 25 | 12.5 | 50 | 12.5 | 50 | 25 |
| PRT1482 | 50 | 12.5 | 50 | 12.5 | 50 | 12.5 | 25 | 50 | 25 | 25 |
| PRT1483 | 25 | 50 | 25 | 12.5 | 25 | 50 | 25 | 12.5 | 25 | 25 |
| PRT1484 | 12.5 | 50 | 12.5 | 25 | 50 | 25 | 12.5 | 50 | 12.5 | 50 |
| PRT1485 | 50 | 12.5 | 12.5 | 12.5 | 50 | 12.5 | 50 | 12.5 | 12.5 | 12.5 |
| PRT1486 | 12.5 | 25 | 25 | 12.5 | 25 | 12.5 | 25 | 12.5 | 12.5 | 12.5 |
| PRT1487 | 12.5 | 25 | 50 | 25 | 12.5 | 25 | 50 | 12.5 | 50 | 12.5 |
| PRT1488 | 50 | 25 | 12.5 | 50 | 12.5 | 50 | 12.5 | 25 | 50 | 12.5 |
| PRT1489 | 50 | 25 | 25 | 12.5 | 25 | 50 | 25 | 100 | 50 | 25 |
| PRT1490 | 50 | 12.5 | 50 | 25 | 12.5 | 25 | 50 | 12.5 | 50 | 25 |
| PRT1491 | 12.5 | 25 | 50 | 25 | 12.5 | 25 | 50 | 25 | 12.5 | 50 |
| PRT1492 | 50 | 50 | 25 | 12.5 | 25 | 50 | 25 | 12.5 | 12.5 | 12.5 |
| PRT1493 | 25 | 12.5 | 12.5 | 12.5 | 50 | 50 | 25 | 50 | 25 | 50 |
| PRT1494 | 12.5 | 25 | 12.5 | 25 | 12.5 | 25 | 25 | 12.5 | 12.5 | 12.5 |
| PRT1495 | 12.5 | 25 | 25 | 12.5 | 12.5 | 50 | 50 | 50 | 25 | 25 |
| PRT1496 | 25 | 12.5 | 12.5 | 100 | 50 | 50 | 12.5 | 50 | 100 | 25 |
| PRT1497 | 25 | 12.5 | 50 | 25 | 12.5 | 25 | 50 | 25 | 50 | 12.5 |
| PRT1498 | 25 | 12.5 | 12.5 | 50 | 12.5 | 50 | 12.5 | 50 | 12.5 | 12.5 |

Conclusion: It can be known from the above table that: all of the recombinant human-originated EGF domain proteins (PRT1 to PRT1498 in Table 1) set forth in the present invention exhibit inhibitory effects on various Gram-negative bacteria, such as, E. coli, Pseudomonas aeruginosa, Klebsiella pneumonia, Enterobacter cloacae, Aeromonas hydrophila, Citrobacter diversus, Moraxella catarrhalis, Proteus mirabilis, Proteus vulgaris, Serratia marcescens, etc.

Example 17: Silver Staining Detection of Endotoxin (LPS) Hydrolyzed by the Human-Originated EGF Domain Proteins (PRT1 to PRT1498 in Table 1) Such as the Recombination Protein hF VII-EGF1, Etc.

1. The E. coli EH100 LPS (Sigma) samples were respectively incubated with the obtained human-originated EGF domain proteins (PRT1 to PRT1498 in Table 1) such as the recombination protein hF VII-EGF1, etc.; and the control group was the LPS sample incubated with TB S buffer. The incubation lasted overnight. Then, the centrifugation was performed to collect the pellet.

2. The 1×loading buffer for LPS (0.05 mol/L Tris-HCl, containing 10 g/L SDS, 100 g/L sucrose, 0.5% β-mercaptoethanol, 10 mg/L Bromophenol Blue, pH 6.8) was mixed with the sample of the treated pellet and incubated on a metal bath at 100° C. for 5 min.

3. 15% separating gel (containing 4 mol/L urea, Bio-Rad with a thickness of 1.0 mm, the detailed composition as follows: 1.15 mL of deionized water, 2.5 mL of 30% acrylamide, 1.3 mL of 1.5 mol/L Tris-HCl (pH 8.8, containing 10% SDS), 50 µl of 10% ammonium persulfate, 4 µl of TEMED) was mixed well and prepared. The top of the separating gel was overlaid with water.

4. 5% stacking gel was prepared as follows: 1.42 mL of deionized water, 0.33 mL of 30% acrylamide, 0.25 mL of 1 mol/L Tris-HCl (pH 6.8, containing 10% SDS), 20 µL of 10% ammonium persulfate, 2 µL of TEMED) were mixed well and poured. A ten-well comb was quickly inserted.

5. After the gel was prepared, the samples were loaded. Then, the gel was run at a voltage of 120 V to separate the samples. After running, the gel was taken to start silver staining. The gel was transferred into a tray washed thoroughly with deionized water, followed by washing the gel three times with deionized water.

6. After completion of the washing, the gel was fixed with 50 mL of fixation solution (30% alcohol, 10% glacial acetic acid, 7 g/L periodic acid) for oxidation at room temperature for 25 min After completion of the fixation, the gel was washed three times each time with deionized water for 5 min.

7. After completion of the washing, the gel was stained in 100 mL of 1 g/L $AgNO_3$ at room temperature for 40 min After completion of the staining, the gel was washed one time with $ddH_2O$.

8. The gel was transferred into 50 mL of 30 g/L $Na_2CO_3$ pre-chilled on ice, to which 0.02% formaldehyde was added just before visualization. When the band appeared or began to become dark, the reaction was stopped by adding 6 mL glacial acetic acid. The stopping solution was removed upon completion of the termination reaction and the gel was kept in deionized water.

The silver staining picture was exemplified by the protein hF VII-EGF1, as shown in FIG. 28. After treated with hF VII-EGF1, the LPS band is obviously decreased and becomes weak, indicating that the protein hF VII-EGF1 eliminates the majority of LPS. The silver staining pictures of PRT2 to PRT1498 in Table 1 are similar to that in FIG. 28. This indicated that the human-originated EGF domain proteins (PRT1 to PRT1498 in Table 1) described in the present invention can hydrolyze LPS and may be used in preparation of a medicament for treating endotoxemia caused by the Gram-negative bacteria.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09833497B2). An electronic copy of the "Sequence Listing" will also be available from the USPTO upon request and payment of the fee set forth in 37 CFR 1.19(b)(3).

The invention claimed is:

1. A method for treating a Gram-negative bacterial infection, said method comprises administering an effective amount of human-originated EGF domain protein or a composition thereof to a subject in need thereof.

2. The method of claim 1, wherein the Gram-negative bacterial infection causes endotoxemia.

3. The method of claim 1, wherein the human-originated EGF domain protein comprises the amino acid sequence of any one of SEQ ID NO:1-SEQ ID NO:1498 or any combination thereof.

4. The method of claim 2, wherein the human-originated EGF domain protein comprises the amino acid sequence of any one of SEQ ID NO:1-SEQ ID NO:1498 or any combination thereof.

5. The method of claim 3, wherein the human-originated EGF domain protein is a human coagulation factor EGF domain protein comprising the amino acid sequence of any one of SEQ ID NO:1, SEQ ID NO:2, SEQ ID NO:3, SEQ ID NO:4, SEQ ID NO:5, SEQ ID NO:6, SEQ ID NO:108, SEQ ID NO:109, SEQ ID NO:1472, SEQ ID NO:1473, SEQ ID NO:1474, SEQ ID NO:1475, SEQ ID NO:1476, SEQ ID NO:1477, SEQ ID NO:1478 or SEQ ID NO:1479.

6. The method of claim 4, wherein the human-originated EGF domain protein is a human coagulation factor EGF domain protein comprises the amino acid sequence of any one of SEQ ID NO:1, SEQ ID NO:2, SEQ ID NO:3, SEQ ID NO:4, SEQ ID NO:5, SEQ ID NO:6, SEQ ID NO:108, SEQ ID NO:109, SEQ ID NO:1472, SEQ ID NO:1473, SEQ ID NO:1474, SEQ ID NO:1475, SEQ ID NO:1476, SEQ ID NO:1477, SEQ ID NO:1478 or SEQ ID NO:1479.

7. The method of claim 1, wherein the Gram-negative bacteria is one or more of *Escherichia coli, Pseudomonas aeruginosa, Klebsiella pneumonia, Enterobacter cloacae, Aeromonas hydrophila, Citrobacter diversus, Moraxella catarrhalis, Proteus mirabilis, Proteus vulgaris* and *Serratia marcescens*.

8. The method of claim 2, wherein the Gram-negative bacteria is one or more of *Escherichia coli, Pseudomonas aeruginosa, Klebsiella pneumonia, Enterobacter cloacae, Aeromonas hydrophila, Citrobacter diversus, Moraxella catarrhalis, Proteus mirabilis, Proteus vulgaris* and *Serratia marcescens*.

9. The method of claim 3, wherein the Gram-negative bacteria is one or more of *Escherichia coli, Pseudomonas aeruginosa, Klebsiella pneumonia, Enterobacter cloacae, Aeromonas hydrophila, Citrobacter diversus, Moraxella catarrhalis, Proteus mirabilis, Proteus vulgaris* and *Serratia marcescens*.

10. The method of claim 4, wherein the Gram-negative bacteria is one or more of *Escherichia coli, Pseudomonas* aeruginosa, Klebsiella pneumonia, Enterobacter cloacae, Aeromonas hydrophila, Citrobacter diversus, Moraxella catarrhalis, Proteus mirabilis, Proteus vulgaris and Serratia marcescens.

11. The method of claim 5, wherein the Gram-negative bacteria is one or more of *Escherichia coli, Pseudomonas aeruginosa, Klebsiella pneumonia, Enterobacter cloacae, Aeromonas hydrophila, Citrobacter diversus, Moraxella catarrhalis, Proteus mirabilis, Proteus vulgaris* and *Serratia marcescens*.

12. The method of claim 6, wherein the Gram-negative bacteria is one or more of *Escherichia coli, Pseudomonas aeruginosa, Klebsiella pneumonia, Enterobacter cloacae, Aeromonas hydrophila, Citrobacter diversus, Moraxella catarrhalis, Proteus mirabilis, Proteus vulgaris* and *Serratia marcescens*.

13. A method for hydrolyzing a lipopolysaccharide of Gram-negative bacteria, said method comprising contacting the lipopolysaccharide with an effective amount of human-originated EGF domain protein or a composition containing human-originated EGF domain protein to hydrolyze the lipopolysaccharide.

14. The method of claim 13, wherein the Gram-negative bacteria is one or more of *Escherichia coli, Pseudomonas aeruginosa, Klebsiella pneumonia, Enterobacter cloacae, Aeromonas hydrophila, Citrobacter diversus, Moraxella catarrhalis, Proteus mirabilis, Proteus vulgaris* and *Serratia marcescens*.

15. The method of claim 13, wherein the human-originated EGF domain protein comprises the amino acid sequence of any one of SEQ ID NO:1-SEQ ID NO:1498 or any combination thereof.

16. The method of claim 14, wherein the human-originated EGF domain protein comprises the amino acid sequence of any one of SEQ ID NO:1-SEQ ID NO:1498 or any combination thereof.

17. The method of claim 13, wherein the human-originated EGF domain protein is a human coagulation factor EGF domain protein comprising the amino acid sequence of any one of SEQ ID NO:1, SEQ ID NO:2, SEQ ID NO:3, SEQ ID NO:4, SEQ ID NO:5, SEQ ID NO:6, SEQ ID NO:108, SEQ ID NO:109, SEQ ID NO:1472, SEQ ID NO:1473, SEQ ID NO:1474, SEQ ID NO:1475, SEQ ID NO:1476, SEQ ID NO:1477, SEQ ID NO:1478 or SEQ ID NO:1479.

18. The method of claim 15, wherein the human-originated EGF domain protein is a human coagulation factor EGF domain protein comprising the amino acid sequence of any one of SEQ ID NO:1, SEQ ID NO:2, SEQ ID NO:3, SEQ ID NO:4, SEQ ID NO:5, SEQ ID NO:6, SEQ ID NO:108, SEQ ID NO:109, SEQ ID NO:1472, SEQ ID NO:1473, SEQ ID NO:1474, SEQ ID NO:1475, SEQ ID NO:1476, SEQ ID NO:1477, SEQ ID NO:1478 or SEQ ID NO:1479.

\* \* \* \* \*